US011847532B2

(12) United States Patent
Drake et al.

(10) Patent No.: US 11,847,532 B2
(45) Date of Patent: *Dec. 19, 2023

(54) MACHINE LEARNING IMPLEMENTATION FOR MULTI-ANALYTE ASSAY DEVELOPMENT AND TESTING

(71) Applicant: Freenome Holdings, Inc., South San Francisco, CA (US)

(72) Inventors: Adam Drake, Pacifica, CA (US); Daniel Delubac, Leesburg, VA (US); Katherine Niehaus, South San Francisco, CA (US); Eric Ariazi, South San Francisco, CA (US); Imran Haque, South San Francisco, CA (US); Tzu-Yu Liu, South San Francisco, CA (US); Nathan Wan, South San Francisco, CA (US); Ajay Kannan, South San Francisco, CA (US); Brandon White, South San Francisco, CA (US)

(73) Assignee: Freenome Holdings, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/174,153

(22) Filed: Feb. 11, 2021

(65) Prior Publication Data

US 2021/0210205 A1 Jul. 8, 2021

Related U.S. Application Data

(63) Continuation of application No. 16/624,897, filed as application No. PCT/US2019/027565 on Apr. 15, 2019.
(Continued)

(51) Int. Cl.
*G01N 33/48* (2006.01)
*G01N 33/50* (2006.01)
(Continued)

(52) U.S. Cl.
CPC ............. *G06N 20/10* (2019.01); *G16B 20/00* (2019.02); *G16H 50/20* (2018.01); *G16H 50/70* (2018.01); *G06F 18/24* (2023.01); *G06N 20/20* (2019.01)

(58) Field of Classification Search
CPC ........ G16H 50/20; G06N 20/20; G06N 20/10; G06K 9/6267
See application file for complete search history.

(56) References Cited

U.S. PATENT DOCUMENTS

| 10,295,540 | B1 | 5/2019 | Buturovic et al. |
| 10,731,223 | B2 | 8/2020 | Kennedy et al. |

(Continued)

FOREIGN PATENT DOCUMENTS

| AU | 2006203948 A1 | 7/2006 |
| CN | 101268367 A | 9/2008 |

(Continued)

OTHER PUBLICATIONS

Singh et al. Gene expression correlates of clinical prostate cancer behavior. Cancer Cell, vol. 1, pp. 203-209. (Year: 2002).*
(Continued)

*Primary Examiner* — Russell S Negin
(74) *Attorney, Agent, or Firm* — Kilpatrick Townsend & Stockton LLP

(57) ABSTRACT

Systems and methods that analyze blood-based cancer diagnostic tests using multiple classes of molecules are described. The system uses machine learning (ML) to analyze multiple analytes, for example cell-free DNA, cell-free microRNA, and circulating proteins, from a biological sample. The system can use multiple assays, e.g., whole-genome sequencing, whole-genome bisulfite sequencing or EM-seq, small-RNA sequencing, and quantitative immunoassay. This can increase the sensitivity and specificity of (Continued)

diagnostics by exploiting independent information between signals. During operation, the system receives a biological sample, and separates a plurality of molecule classes from the sample. For a plurality of assays, the system identifies feature sets to input to a machine learning model. The system performs an assay on each molecule class and forms a feature vector from the measured values. The system inputs the feature vector into the machine learning model and obtains an output classification of whether the sample has a specified property.

7 Claims, 64 Drawing Sheets

Related U.S. Application Data

(60) Provisional application No. 62/824,709, filed on Mar. 27, 2019, provisional application No. 62/804,614, filed on Feb. 12, 2019, provisional application No. 62/767,369, filed on Nov. 14, 2018, provisional application No. 62/767,435, filed on Nov. 14, 2018, provisional application No. 62/749,955, filed on Oct. 24, 2018, provisional application No. 62/742,799, filed on Oct. 8, 2018, provisional application No. 62/731,557, filed on Sep. 14, 2018, provisional application No. 62/679,641, filed on Jun. 1, 2018, provisional application No. 62/679,587, filed on Jun. 1, 2018, provisional application No. 62/657,602, filed on Apr. 13, 2018.

(51) Int. Cl.
| | | |
|---|---|---|
| G06N 20/10 | (2019.01) | |
| G16H 50/20 | (2018.01) | |
| G16B 20/00 | (2019.01) | |
| G16H 50/70 | (2018.01) | |
| G06N 20/20 | (2019.01) | |
| G06F 18/24 | (2023.01) | |

(56) References Cited

U.S. PATENT DOCUMENTS

| | | | |
|---|---|---|---|
| 2006/0177837 A1 | 8/2006 | Borozan et al. | |
| 2010/0131286 A1* | 5/2010 | Houlgatte | G16H 50/20 705/2 |
| 2010/0151471 A1* | 6/2010 | Faham | C12Q 1/6886 435/6.16 |
| 2014/0234854 A1 | 8/2014 | Blue et al. | |
| 2014/0274767 A1 | 9/2014 | Yegnasubramanian et al. | |
| 2014/0365243 A1* | 12/2014 | Varadan | G16H 10/60 705/3 |
| 2015/0218646 A1 | 8/2015 | Haince et al. | |
| 2015/0324527 A1 | 11/2015 | Siegel et al. | |
| 2016/0068915 A1 | 3/2016 | Kennedy et al. | |
| 2017/0091637 A1 | 3/2017 | Chae et al. | |
| 2017/0261509 A1* | 9/2017 | Wang | G01N 33/57488 |
| 2017/0277844 A1 | 9/2017 | Apte et al. | |
| 2018/0037953 A1 | 2/2018 | Emerson et al. | |
| 2018/0068083 A1 | 3/2018 | Cohen et al. | |
| 2018/0102187 A1 | 4/2018 | Apte et al. | |
| 2018/0122508 A1 | 5/2018 | Wilde et al. | |
| 2018/0349548 A1 | 12/2018 | Walsh et al. | |
| 2018/0358132 A1 | 12/2018 | Bagaev et al. | |
| 2019/0196877 A1 | 6/2019 | Biener et al. | |
| 2019/0256924 A1 | 8/2019 | Vogelstein et al. | |
| 2019/0391151 A1 | 12/2019 | Gatto et al. | |
| 2020/0131582 A1 | 4/2020 | Zhou et al. | |
| 2020/0377956 A1 | 12/2020 | Vogelstein et al. | |
| 2021/0017609 A1 | 1/2021 | Gross et al. | |
| 2021/0020314 A1 | 1/2021 | Erich et al. | |

FOREIGN PATENT DOCUMENTS

| | | | | |
|---|---|---|---|---|
| CN | 104603292 A | 5/2015 | | |
| WO | 2006074360 A2 | 7/2006 | | |
| WO | 2013022995 A2 | 2/2013 | | |
| WO | WO-2016119190 A1 * | 8/2016 | | C12Q 1/689 |
| WO | 2017062867 A1 | 4/2017 | | |
| WO | 2018009723 A1 | 1/2018 | | |
| WO | 2018013865 A1 | 1/2018 | | |
| WO | WO-2019067092 A1 * | 4/2019 | | C12Q 1/6827 |

OTHER PUBLICATIONS

Golub et al. Molecular classification of cancer: Class discovery and class prediction by gene expression monitoring. Science, vol. 286, pp. 531-537. (Year: 1999).*

Ng et al. Differential expression of microRNAs in plasma of patients with colorectal cancer: a potential marker for colorectal cancer screening. Gut, vol. 58, pp. 1375-1381. (Year: 2009).*

Homilla et al. Targeted deep sequencing of plasma ciculating cell-free DNA reveals Vimentin and Fibulin 1 as potential epigenetic biomarkers for hepatocellular carcinoma. Plos One, vol. 12, Mar. 23, 2017, article e0174265, 15 pages.*

Zhang et al. Predicting essential genes and proteins based on machine learning and network topological features: a comprehensive review. Frontiers in Physiology, vol. 7, article 75, 11 pages. (Year: 2016).*

International Search report, dated Jul. 9, 2019, for corresponding International Patent Application No. PCT/US2019/027565, filed Apr. 15, 2019, 3 pages.

Written Opinion, dated Jul. 9, 2019, for corresponding International Patent Application No. PCT/US2019/027565, filed Apr. 15, 2019, 18 pages.

Liu, T. et al., *An Individualized Predictor of Health and Disease Using Paired Reference and Target Samples*, BMC Bioinformatics, Jan. 22, 2016, vol. 17, No. 47, pp. 1-15.

Kourou, K. et al., *Machine Learning Applications in Cancer Prognosis and Prediction*, Computational and Structural Biotechnology Journal, Nov. 15, 2014, vol. 13, pp. 8-17.

Manghnani, K. et al., *METric Learning for Confounder Control Making Distance Matter in High Dimensional Biological Analysis*, ArXiv 2018, Research paper [online], Dec. 7, 2018 [Retrieved from the internet on Dec. 19, 2019 at https://arxiv.org/pdf/1812.03188. pdf, pp. 1-10.

Wan, N. et al., *Machine Learning Enables Detection of Early-Stage Colorectal Cancer by Whole-Genome Sequencing of Plasma Cell-Free DNA*, BMC Cancer, Aug. 23, 2019, vol. 19, Article 832, pp. 1-10.

Church, Timothy Robert et al.; "Prospective evaluation of methylated SEPT9 in plasma for detection of asymptomatic colorectal cancer"; Gut; 2014; vol. 63, No. 2; pp. 317-325.

Warren, Jorja D. et al.; "Septin 9 methylated DNA is a sensitive and specific blood test for colorectal cancer"; BMC Medicine; 2011; vol. 9, No. 133; 9 pages.

Potter, Nicholas T. et al.; "Validation of a Real-Time PCR-Based Qualitative Assay for the Detection of Methylated SEPT9 DNA in Human Plasma"; Clinical Chemistry; 2014; vol. 60, No. 9; pp. 1183-1191.

Ahlquist, David A. et al.; "The Stool DNA Test Is More Accurate Than the Plasma Septin 9 Test in Detecting Colorectal Neoplasia"; Clinical Gastroenterology and Hepatology; 2012; vol. 10, No. 3; pp. 272-277 (7 total pages).

International Preliminary Report on Patentability dated Oct. 13, 2020 in International Patent Application No. PCT/US2019/027565. 19 pages.

Non-Final Office Action dated Nov. 16, 2021 in U.S. Appl. No. 16/624,897, filed Dec. 19, 2019. 34 pages.

Glaab, Enrico et al.; "Using Rule-Based Machine Learning for Candidate Disease Gene Prioritization and Sample Classification of Cancer Gene Expression Data"; PLOS One; Jul. 2012; vol. 7, No. 7; e39932; pp. 1-18.

(56) References Cited

OTHER PUBLICATIONS

Hasan, Mohammad R. et al.; "Classification of cancer cells using computational analysis of dynamic morphology"; Computer Methods and Programs in Biomedicine; 2018; vol. 156; pp. 105-112.
Huang, Shujun et al.; "Applications of Support Vector Machine (SVM) Learning in Cancer Genomics"; Cancer Genomics & Proteomics; 2018; vol. 15, No. 1; pp. 41-51.
Ko, Jina et al.; "Combining Machine Learning and Nanofluidic Technology To Diagnose Pancreatic Cancer Using Exosomes"; ACS Nano; vol. 11; pp. 11182-11193.
Libbrecht, Maxwell W. et al.; "Machine learning applications in genetics and genomics"; Nature Reviews Genetics; Jun. 2015; vol. 16, No. 6; pp. 321-332.
Way, Gregory P. et al.; "A machine learning classifier trained on cancer transcriptomes detects NF1 inactivation signal in glioblastoma"; BMC Genomics; 2017; vol. 18, No. 127; pp. 1-11.
Extended European Search Report dated Dec. 2, 2021 in EP Patent Application No. 19785375.7. 12 pages.
Cohen, Joshua D. et al.; "Detection and localization of surgically resectable cancers with a multi-analyte blood test"; Science; HHS Public Access Author Manuscript; Feb. 2018 (Epub Jan. 18, 2018); Science; vol. 359, No. 6378; pp. 926-930 (manuscript: 12 pages).
Cohen, Joshua D. et al.; Supplementary Material for "Detection and localization of surgically resectable cancers with a multi-analyte blood test"; Science; HHS Public Access Author Manuscript; Feb. 2018 (Epub Jan. 18, 2018); Science; vol. 359, No. 6378; 21 pages.
Non-Final Office Action dated Mar. 25, 2022 in U.S. Appl. No. 16/624,897, filed Dec. 19, 2019. 22 pages.
Written Opinion dated Aug. 4, 2022 in SG Patent Application No. 11202009696W. 9 pages.
Non-Final Office Action dated Aug. 9, 2022 in U.S. Appl. No. 16/624,897, filed Dec. 19, 2019. 24 pages.
Notice of Allowance dated Dec. 22, 2022 in U.S. Appl. No. 16/624,897, filed Dec. 19, 2019. 14 pages.
Ko, Jina et al.; "Combining Machine Learning and Nanofluidic Technology To Diagnose Pancreatic Cancer Using Exosomes"; ACS Nano; vol. 11; pp. 11182-11193. 2017.
English translation of Office Action dated Apr. 25, 2023 in JP Patent Application No. 2020-556286. 8 pages.

* cited by examiner

Classification performance

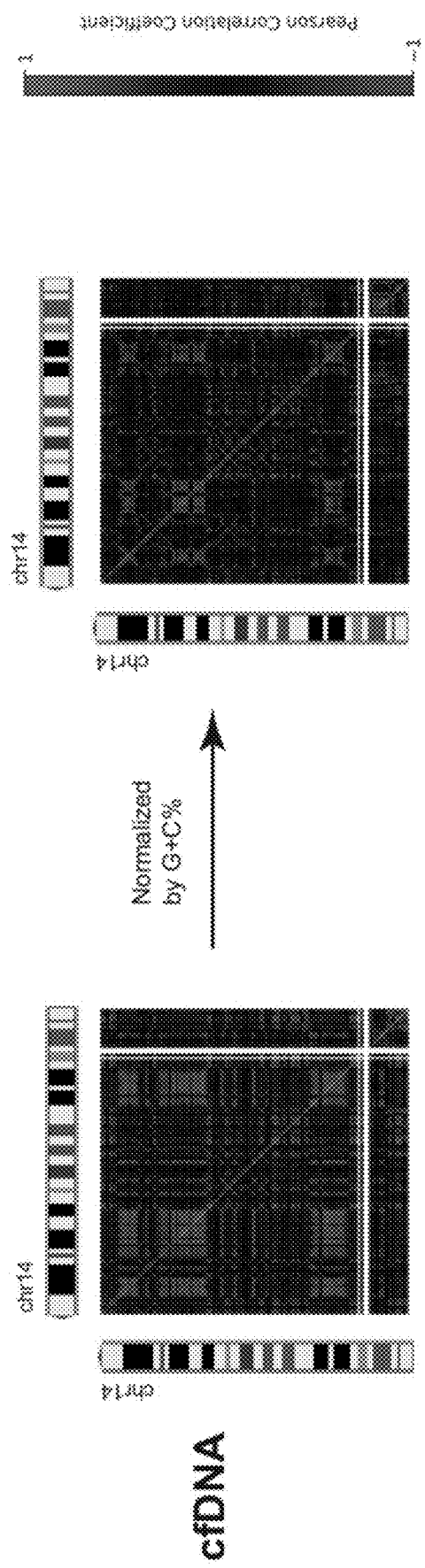
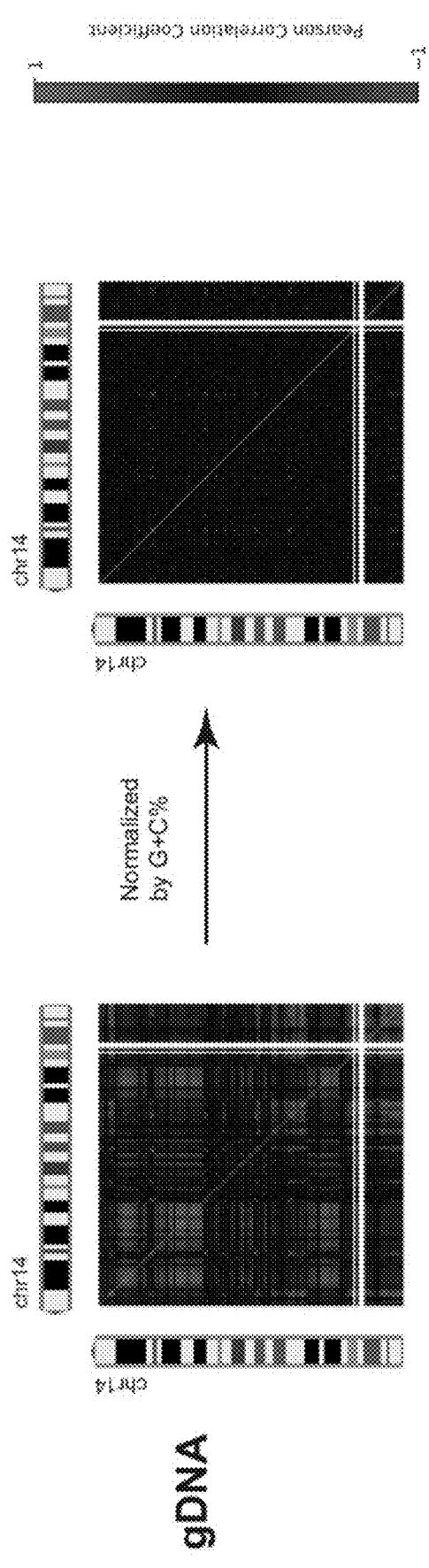
FIG. 17A  FIG. 17B  FIG. 17C  FIG. 17D

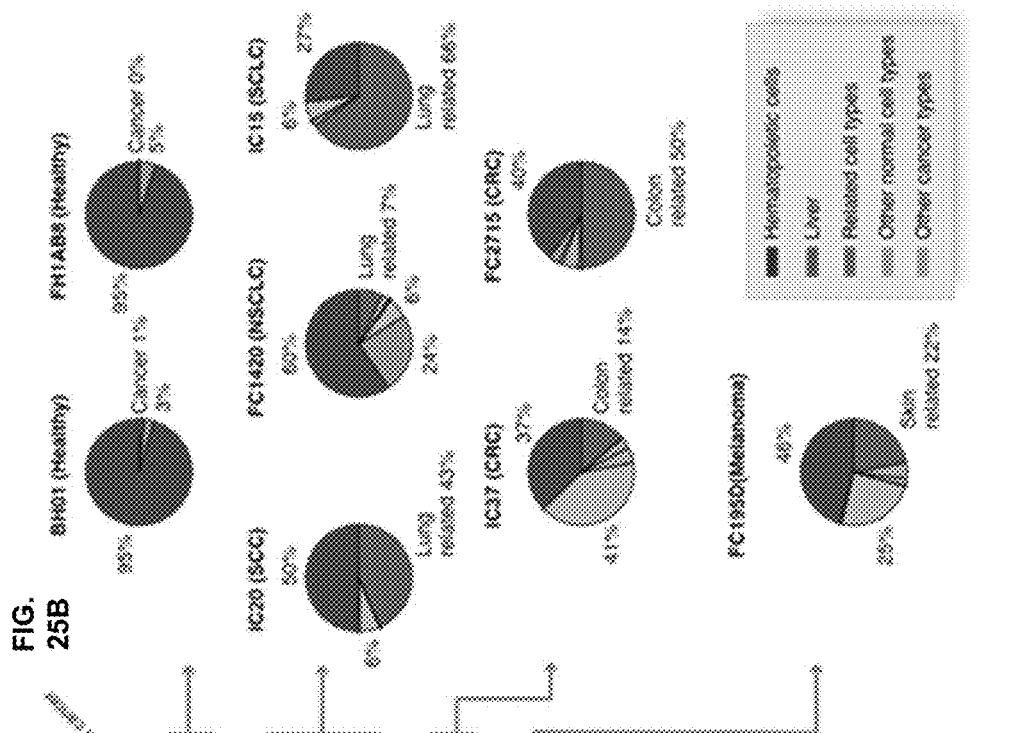
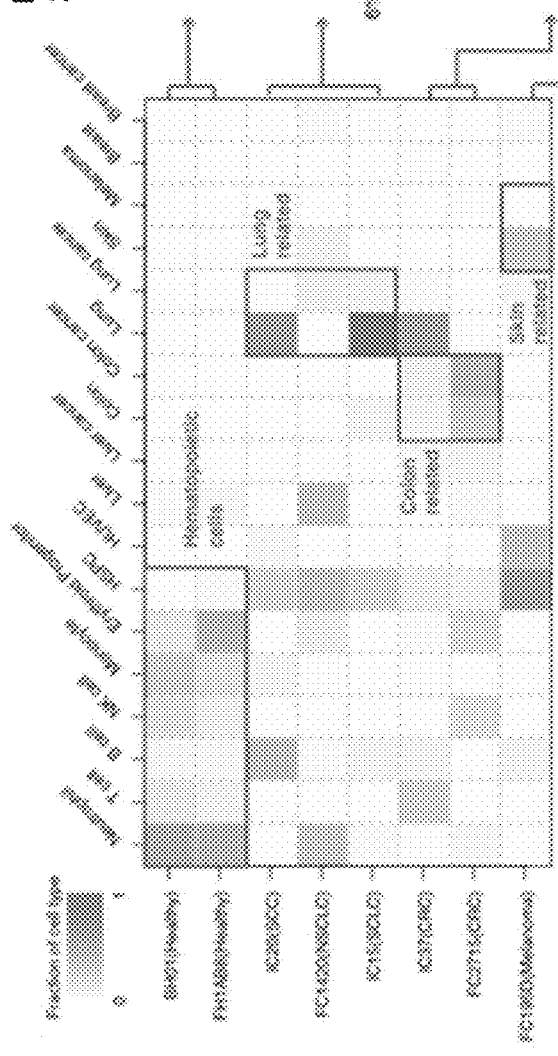
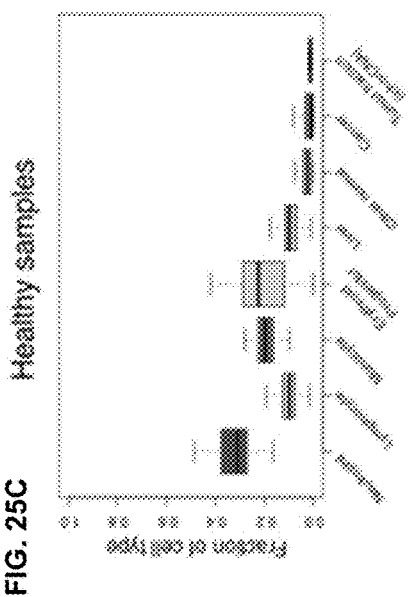
FIG. 25A
FIG. 25B
FIG. 25C

TSS A

TSS B

P(on | TSS A) = 0.83

P(on | TSS B) = 0.01

MACHINE LEARNING IMPLEMENTATION FOR MULTI-ANALYTE ASSAY DEVELOPMENT AND TESTING

CROSS REFERENCE TO RELATED APPLICATIONS

This application is a continuation application of U.S. patent application Ser. No. 16/624,897 entitled "MACHINE LEARNING IMPLEMENTATION FOR MULTI-ANALYTE ASSAY DEVELOPMENT AND TESTING," filed on Dec. 19, 2019, which is a U.S. 371 national phase application of International Patent Application No. PCT/US2019/027565, filed on Apr. 15, 2019, which claims the benefit of U.S. Provisional Patent Application Nos.
62/824,709 filed Mar. 27, 2019,
62/804,614 filed Feb. 2, 2019,
62/767,369 filed Nov. 14, 2018,
62/767,435 filed Nov. 14, 2018,
62/749,955 filed Oct. 24, 2018,
62/742,799 filed Oct. 8, 2018,
62/731,557 filed Sep. 14, 2018,
62/679,641 filed Jun. 1, 2018,
62/679,587 filed Jun. 1, 2018, and
62/657,602 filed Apr. 13, 2018, the contents of which are incorporated by reference in their entirety.

BACKGROUND

Cancer screening is complex and various cancer types require different approaches for screening and early detection. Patient compliance remains an issue—screening methods that require non-serum analytes frequently result in low participation. Screening rates for breast cancer, cervical and colorectal cancer with mammogram, pap tests, and sigmoidoscopy/FOBT respectively are far from 100% compliance recommended by the US Preventative Services Task Force (USPSTF) (Sabatino et al, Cancer Screening Test Use—United States, 2013, MMWR, 2015 64(17):464-468, Adler et al. BMC Gastroenterology 2014, 14:183). A recent report found that the percentage of eligible adults who were up to date with colorectal cancer screening by state ranged from 58.5% (New Mexico) to 75.9% (Maine) in 2016 with a mean of 67.3%. (Joseph D A, et al. Use of Colorectal Cancer Screening Tests by State. Prev Chronic Dis 2018; 15:170535).

Blood-based tests hold great promise as cancer diagnostics and in precision medicine. However, most current tests are restricted to the analysis of a single class of molecules (e.g., circulating tumor DNA, platelet mRNA, circulating proteins). There is a broad complement of biological analytes in blood for potential analysis and the associated data generation is significant. However, analysis of the totality of analytes is laborious, not economical, and may inject tremendous biological noise relative to the useful signal and confound useful analysis for diagnostic or precision medicine applications.

Even with early detection and genomic characterization, there remain a significant number of cases where genomic analysis fails to nominate effective drugs or applicable clinical trials. Even when targetable genomic alterations are discovered, patients do not always respond to therapy. (Pauli et al., Cancer Discov. 2017, 7(5): 462-477). Furthermore, there exists a sensitivity barrier for the use of circulating tumor DNA (ctDNA) for detection methods. ctDNA has recently been evaluated as a prospective analyte to detect early-stage cancer and it has been found to require significant volumes of blood to detect ctDNA at requisite specificity and sensitivity. (Aravanis, A. et al., Next-Generation Sequencing of Circulating Tumor DNA for Early Cancer Detection, Cell, 168:571-574). As such, a simple, readily-available, single-analyte test remains elusive.

In the field of cancer diagnostics, machine learning may enable large-scale statistical approaches and automated characterization of signal strength. Yet machine learning applied to biology in the molecular diagnostics context remains a largely unexplored field and has not previously been applied to aspects of diagnosis and precision medicine such as analyte selection, assay selection, and overall optimization.

What is therefore needed are methods of analyzing biological analytes that are readily obtained to stratify individuals at risk of or who have cancer and to provide effective characterization of early stage cancer to guide treatment decisions. What is also needed are methods of incorporating machine learning approaches with analyte data sets to develop and refine classifiers for use in stratifying individual populations and detecting disease such as cancer.

BRIEF SUMMARY

Described herein are methods and systems that incorporate machine learning approaches with one or more biological analytes in a biological sample for various applications to stratify individual populations. In particular examples, the methods and systems are useful for predicting disease, treatment efficacy, and guiding treatment decisions for affected individuals.

The present approach differs from other methods and systems in that the present methods focus on approaches to characterize the non-cellular portion of the circulation that includes analytes derived from tumor cells, healthy non-tumor cells induced or educated by the microenvironment, and circulating immune cells that may have been educated by tumor cells that are present in an individual.

While other approaches have been directed to characterizing the cellular portion of the immune systems, the present methods and systems interrogate the cancer-educated, non-cellular portion of the circulation to provide informed biological information that is then combined with machine learning tools for useful applications. The study of non-cellular analytes in a liquid biological sample (e.g., plasma) permits deconvolution of the sample to recapitulate the molecular state of the individual's tissue and immune cells in a living cellular state. Studying the non-cellular portion of the immune system provides a surrogate indicator of cancer status and preempts the requirement for significant blood volume to detect cancer cells and associated biological markers when screening with ctDNA alone.

In a first aspect, the disclosure provides a method of using a classifier capable of distinguishing a population of individuals comprising:

a) assaying a plurality of classes of molecules in the biological sample, wherein the assaying provides a plurality of sets of measured values representative of the plurality of classes of molecules, b) identifying a set of features corresponding to properties of each of the plurality of classes of molecules to be input to a machine learning or statistical model, c) preparing a feature vector of feature values from each of the plurality of sets of measured values, each feature value corresponding to a feature of the set of features and including one or more measured values, wherein the feature vector includes at least one feature value obtained using each set of the plurality of sets of measured values, d) loading, into a memory of a computer system, the machine learning model comprising the classifier, the machine learning model trained using training vectors obtained from training biological samples, a first subset of the training biological samples identified as having a specified property and a second subset of the training biological samples identified as not having the specified property, e) inputting the feature vector into the machine learning model to obtain an output classification of whether the biological sample has the specified property, thereby distinguishing a population of individuals having the specified property.

As examples, the classes of molecules can be selected from nucleic acid, polyamino acids, carbohydrates, or metabolites. As further examples, the classes of molecules can include nucleic acids comprising deoxyribonucleic acid (DNA), genomic DNA, plasmid DNA, complementary DNA (cDNA), cell-free (e.g., non-encapsulated) DNA (cfDNA), circulating tumor DNA (ctDNA), nucleosomal DNA, chromatosomal DNA, mitochondrial DNA (miDNA), an artificial nucleic acid analog, recombinant nucleic acid, plasmids, viral vectors, and chromatin. In one example, the sample comprises cfDNA. In one example, the sample comprises peripheral blood mononuclear cell-derived (PBMC-derived) genomic DNA.

As further examples, the classes of molecules can include nucleic acids comprising ribonucleic acid (RNA), messenger RNA (mRNA), transfer RNA (tRNA), micro RNA (mitoRNA), ribosomal RNA (rRNA), circulating RNA (cRNA), alternatively spliced mRNAs, small nuclear RNAs (snRNAs), antisense RNA, short hairpin RNA (shRNA), or small interfering RNA (siRNA).

As further examples, the classes of molecules can include polyamino acids comprising polyamino acid, peptide, protein, autoantibody or a fragment thereof.

As further examples, the classes of molecules can include sugars, lipids, amino acids, fatty acids, phenolic compounds, or alkaloids.

In various examples, the plurality of classes of molecules includes at least two of: cfDNA molecules, cfRNA molecules, circulating proteins, antibodies, and metabolites.

As with aspects of the disclosure, various examples for the systems and methods herein, the plurality of classes of molecules can be selected from: 1) cfDNA, cfRNA, polyamino acid, and small chemical molecules, or 2) cfDNA and cfRNA, and polyamino acids, 3) cfDNA and cfRNA and small chemical molecules, or 4) cfDNA, polyamino acid, and small chemical molecules, or 5) cfRNA, polyamino acid, and small chemical molecules, or 6) cfDNA and cfRNA, or 7) cfDNA and polyamino acid, or 8) cfDNA and small chemical molecules, or 9) cfRNA and polyamino acid, or 10) cfRNA and small chemical molecules, or 11) polyamino acid and small chemical molecules.

In one example, the plurality of classes of molecules is cfDNA, protein, and autoantibodies.

In various examples, the plurality of assays can include at least two of: whole-genome sequencing (WGS), whole-genome bisulfite sequencing (WGSB), small-RNA sequencing, quantitative immunoassay, enzyme-linked immunosorbent assay (ELISA), proximity extension assay (PEA), protein microarray, mass spectrometry, low-coverage Whole-Genome Sequencing (lcWGS); selective tagging 5mC sequencing (WO2019/051484), CNV calling; tumor fraction (TF) estimation; Whole Genome Bisulfite Sequencing; LINE-1 CpG methylation; 56 genes CpG methylation; cf-Protein Immuno-Quant ELISAs, SIMOA; and cf-miRNA sequencing, and cell type or cell phenotype mixture proportions derived from any of the above assays.

In one example, the whole-genome bisulfite sequencing includes a methylation analysis.

In various examples, the classifying of the biological sample is performed by a classifier trained and constructed according to one or more of: linear discriminant analysis (LDA); partial least squares (PLS); random forest; k-nearest neighbor (KNN); support vector machine (SVM) with radial basis function kernel (SVMRadial); SVM with linear basis function kernel (SVMLinear); SVM with polynomial basis function kernel (SVMPoly), decision trees, multilayer perceptron, mixture of experts, sparse factor analysis, hierarchical decomposition and combinations of linear algebra routines and statistics.

In various examples, the specified property can be a clinically-diagnosed disorder. The clinically-diagnosed disorder may be cancer. As examples, the cancer can be selected from colorectal cancer, liver cancer, lung cancer, pancreatic cancer, or breast cancer. In some examples, the specified property is responsiveness to a treatment. In one example the specified property may be a continuous measurement of a patient trait or phenotype.

In a second aspect, the present disclosure provides a system for performing classifications of biological samples comprising:

a) a receiver to receive a plurality of training samples, each of the plurality of training samples having a plurality of classes of molecules, wherein each of the plurality of training samples comprises one or more known labels b) a feature module to identify a set of features corresponding to an assay that are operable to be input to the machine learning model for each of the plurality of training samples, wherein the set of features correspond to properties of molecules in the plurality of training samples, wherein for each of the plurality of training samples, the system is operable to subject a plurality of classes of molecules in the training sample to a plurality of different assays to obtain sets of measured values, wherein each set of measured values is from one assay applied to a class of molecules in the training sample, wherein a plurality of sets of measured values are obtained for the plurality of training samples, c) an analysis module to analyze the sets of measured values to obtain a training vector for the training sample, wherein the training vector comprises feature values of the N set of features of the corresponding assay, each feature value corresponding to a feature and including one or more measured values, wherein the training vector is formed using at least one feature from at least two of the N sets of features corresponding to a first subset of the plurality of different assays, d) a labeling module to inform the system on the training vectors using parameters of the machine learning model to obtain output labels for the plurality of training samples, e) a comparator module to compare the output labels to the known labels of the training samples, f) a training module to iteratively search for optimal values of the parameters as part of training the machine learning model based on the comparing the output labels to the known labels of the training samples, and g) an output module to provide the parameters of the machine learning model and the set of features for the machine learning model.

In a third aspect, the disclosure provides a system for classifying subjects based on multi-analyte analysis in a biological sample composition comprising: (a) a computer-readable medium comprising a classifier operable to classify the subjects based on the multi-analyte analysis; and (b) one or more processors for executing instructions stored on the computer-readable medium.

In one example, the system comprises a classification circuit that is configured as a machine learning classifier selected from a linear discriminant analysis (LDA) classifier, a quadratic discriminant analysis (QDA) classifier, a support vector machine (SVM) classifier, a random forest (RF) classifier, a linear kernel support vector machine classifier, a first or second order polynomial kernel support vector machine classifier, a ridge regression classifier, an elastic net algorithm classifier, a sequential minimal optimization algorithm classifier, a naive Bayes algorithm classifier, and a NMF predictor algorithm classifier.

In one example, the system comprises means for performing any of the preceding methods. In one example, the system comprises one or more processors configured to perform any of the preceding methods. In one example, the system comprises modules that respectively perform the steps of any of the preceding methods.

Another aspect of the present disclosure provides a non-transitory computer-readable medium comprising machine-executable code that, upon execution by one or more computer processors, implements any of the methods above or elsewhere herein.

Another aspect of the present disclosure provides a system comprising one or more computer processors and computer memory coupled thereto. The computer memory comprises machine-executable code that, upon execution by the one or more computer processors, implements any of the methods above or elsewhere herein.

In a fourth aspect, the present disclosure provides a method of detecting presence of cancer in an individual comprising:

a) assaying a plurality of classes of molecules in a biological sample obtained from the individual wherein the assaying provides a plurality of sets of measured values representative of the plurality of classes of molecules, b) identifying a set of features corresponding to properties of each of the plurality of classes of molecules to be input to a machine learning model, c) preparing a feature vector of feature values from each of the plurality of sets of measured values, each feature value corresponding to a feature of the set of features and including one or more measured values, wherein the feature vector includes at least one feature value obtained using each set of the plurality of sets of measured values, d) loading into a memory of a computer system a machine learning model that is trained using training vectors obtained from training biological samples, a first subset of the training biological samples identified from individuals with cancer and a second subset of the training biological samples identified from individuals not having cancer, e) inputting the feature vector into the machine learning model to obtain an output classification of whether the biological sample is associated with the cancer, thereby detecting the presence of the cancer in the individual.

In one example, the method comprises combining the classification data from classifier analysis to provide a detection value, wherein the detection value indicates presence of cancer in an individual.

In one example, the method comprises combining the classification data from classifier analysis to provide a detection value, wherein the detection value indicates stage of cancer in an individual.

As examples, the cancer can be selected from colorectal cancer, liver cancer, lung cancer, pancreatic cancer or breast cancer. In one example, the cancer is colorectal cancer In a fifth aspect, the present disclosure provides a method of determining the prognosis of an individual with cancer comprising:

a) assaying a plurality of classes of molecules in the biological sample wherein the assaying provides a plurality of sets of measured values representative of the plurality of classes of molecules, b) identifying a set of features corresponding to properties of the plurality of classes of molecules to be input to a machine learning model, preparing a feature vector of feature values from each of the plurality of sets of measured values, each feature value corresponding to a feature of the set of features and including one or more measured values, wherein the feature vector includes at least one feature value obtained using each set of the plurality of sets of measured values, c) loading into memory of a computer system a machine learning model that is trained using training vectors obtained from training biological samples, a first subset of the training biological samples identified from individuals with good cancer prognosis and a second subset of the training biological samples identified from individuals not having good cancer prognosis, d) inputting the feature vector into the machine learning model to obtain an output classification of whether the biological sample is associated with the good cancer prognosis, thereby determining the prognosis of the individual with cancer.

As examples, the cancer can be selected from colorectal cancer, liver cancer, lung cancer, pancreatic cancer or breast cancer.

In a sixth aspect, the present disclosure provides a method of determining responsiveness to a cancer treatment comprising:

a) assaying a plurality of classes of molecules in the biological sample wherein the assaying provides a plurality of sets of measured values representative of the plurality of classes of molecules, b) identifying a set of features corresponding to properties of each of the plurality of classes of molecules to be input to a machine learning model, preparing a feature vector of feature values from each of the plurality of sets of measured values, each feature value corresponding to a feature of the set of features and including one or more measured values, wherein the feature vector includes at least one feature value obtained using each set of the plurality of sets of measured values, c) loading into memory of a computer system a machine learning model that is trained using training vectors obtained from training biological samples, a first subset of the training biological samples identified from individuals responding to a treatment and a second subset of the training biological samples identified from individuals not responding to a treatment, d) inputting the feature vector into the machine learning model to obtain an output classification of whether the biological sample is associated with treatment response thereby determining the responsiveness to the cancer treatment.

In one example, the cancer treatment is selected from alkylating agents, plant alkaloids, antitumor antibiotics, antimetabolites, topoisomerase inhibitors, retinoids, checkpoint inhibitor therapy, or VEGF inhibitors.

In one example, the method comprises combining the classification data from classifier analysis to provide a detection value wherein the detection value indicates response to treatment in an individual.

These and other example are described in detail below. For example, other examples are directed to systems, devices, and computer readable media associated with methods described herein.

A better understanding of the nature and advantages of examples of the present disclosure may be gained with reference to the following detailed description and the accompanying drawings.

BRIEF DESCRIPTION OF THE DRAWINGS

FIG. 17A shows a heatmap of cfHi-C before G+C % is regressed out by LOWESS from fragment length in each bin on chr1. FIG. 17B shows a heatmap of cfHi-C after G+C % is regressed out by LOWESS from fragment length in each bin on chr1. FIG. 17C shows a heatmap of gDNA before G+C % is regressed out by LOWESS from fragment length in each bin on chr1. FIG. 17D shows a heatmap of gDNA after G+C % is regressed out by LOWESS from fragment length in each bin on chr1.

FIG. 25A shows a heatmap of cell composition inferred from single-sample cfDNA of healthy, colorectal cancer, lung cancer, and melanoma samples. FIG. 25B shows a pie chart of cell composition inferred from single-sample cfDNA of healthy, colorectal cancer, lung cancer, and melanoma samples. FIG. 25C shows a boxplot of white blood cell fraction and tumor fraction inferred from single-sample cfDNA from 100 healthy individuals.

TERMS

Figure 1:
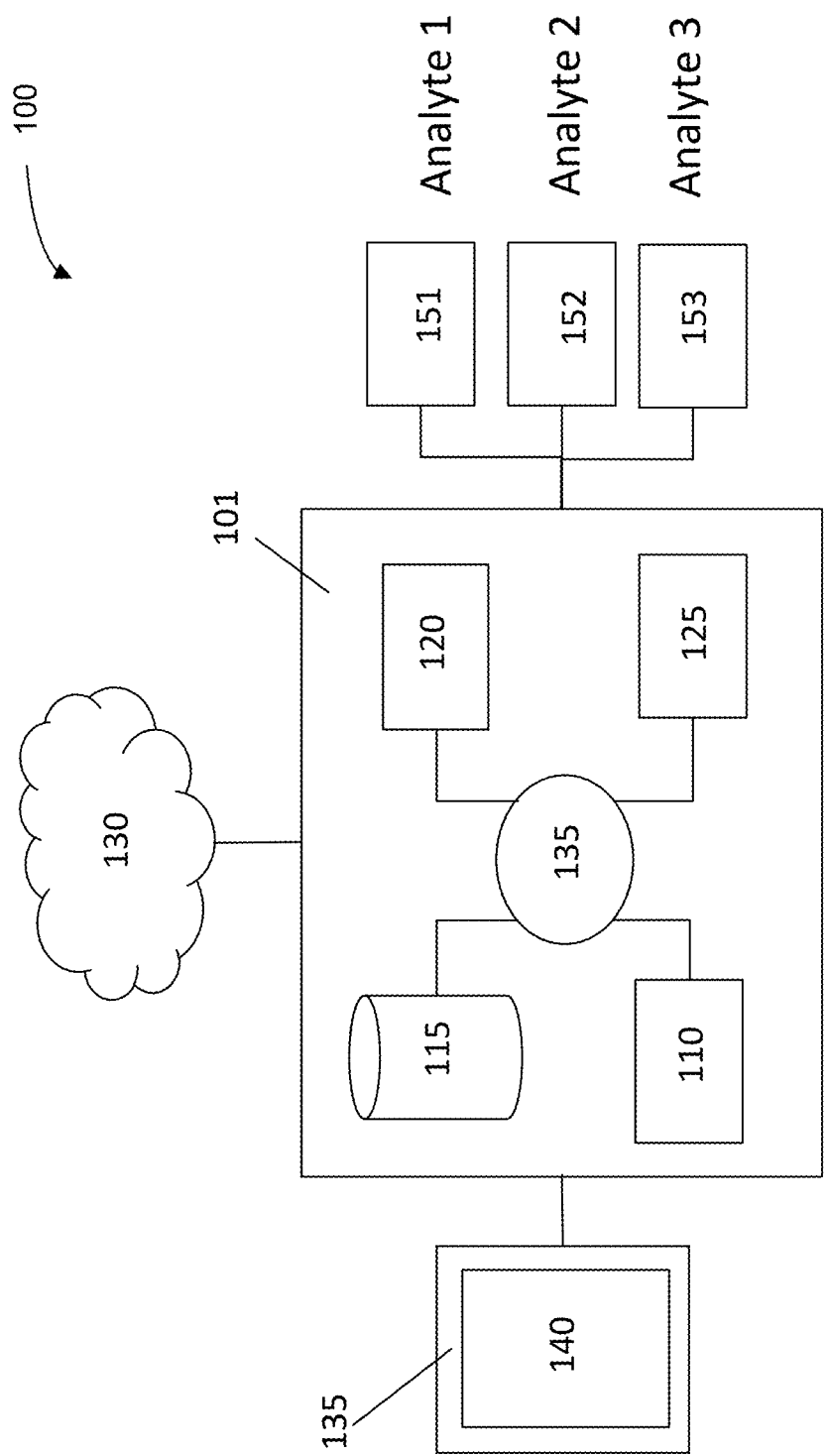
FIG. 1 shows an example system that is programmed or otherwise configured to implement methods provided herein.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

The term "area under the curve" or "AUC" refers to the area under the curve of a receiver operating characteristic (ROC) curve. AUC measures are useful for comparing the accuracy of a classifier across the complete data range. Classifiers with a greater AUC have a greater capacity to classify unknowns correctly between two groups of interest (e.g., cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature may be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

The term "biological sample" (or just "sample") refers to any substance obtained from a subject. A sample may contain or be presumed to contain analytes for example those described herein (nucleic acids, polyamino acids, carbohydrates, or metabolites) from a subject. In some aspects, a sample can include cells and/or cell-free material obtained in vivo, cultured in vitro, or processed in situ, as well as lineages including pedigree and phylogeny. In various aspects, the biological sample can be tissue (e.g., solid tissue or liquid tissue), such as normal or healthy tissue from the subject. Examples of solid tissue include a primary tumor, a metastasis tumor, a polyp, or an adenoma. Examples of a liquid sample (e.g., a bodily fluid) include whole blood, buffy coat from blood (which can include lymphocytes), urine, saliva, cerebrospinal fluid, plasma, serum, ascites, sputum, sweat, tears, buccal sample, cavity rinse, or organ rinse. In some cases, the liquid is a cell-free liquid that is an essentially cell-free liquid sample or comprises cell-free nucleic acid, e.g., cell-freeDNA in some cases, cells, including circulating tumor cells, can be enriched for or isolated from the liquid.

The terms "cancer" and "cancerous" refer to or describe the physiological condition in mammals that is typically characterized by unregulated cell growth. Neoplasia, malignancy, cancer and tumor are often used interchangeably and refer to abnormal growth of a tissue or cells that results from excessive cell division.

The term "cancer-free" refers to a subject who has not been diagnosed with a cancer of that organ or does not have detectable cancer.

The term "genetic variant" (or "variant") refers to a deviation from one or more expected values. Examples include a sequence variant or a structural variation. In various examples, a variant can refer to a variant already known, such as scientifically confirmed and reported in literature, a putative variant associated with a biological change, a putative variant reported in literature but not yet biologically confirmed, or a putative variant never reported in literature but inferred based on a computational analysis.

The term "germline variant" refers to nucleic acids inducing natural or normal variations (e.g., skin colors, hair colors, and normal weights). A somatic mutation can refer to nucleic acids inducing acquired or abnormal variations (e.g., cancers, obesity, symptoms, diseases, disorders, etc.). Germline variants are inherited, and thus correspond to an individual's genetic differences that he or she is born relative to a canonical human genome. Somatic variants are variants that occur in the zygote or later on at any point in cell division, development, and aging. In some examples, an analysis can distinguish between germline variants, e.g., private variants, and somatic mutations.

The term "input features" (or "features") refers to variables that are used by the model to predict an output classification (label) of a sample, e.g., a condition, sequence content (e.g., mutations), suggested data collection operations, or suggested treatments. Values of the variables can be determined for a sample and used to determine a classification. Example of input features of genetic data include: aligned variables that relate to alignment of sequence data (e.g., sequence reads) to a genome and non-aligned variables, e.g., that relate to the sequence content of a sequence read, a measurement of protein or autoantibody, or the mean methylation level at a genomic region.

The term "machine learning model" (or "model") refers to a collection of parameters and functions, where the parameters are trained on a set of training samples. The parameters and functions may be a collection of linear algebra operations, non-linear algebra operations, and tensor algebra operations. The parameters and functions may include statistical functions, tests, and probability models. The training samples can correspond to samples having measured properties of the sample (e.g., genomic data and other subject data, such as images or health records), as well as known classifications/labels (e.g., phenotypes or treatments) for the subject. The model can learn from the training samples in a training process that optimizes the parameters (and potentially the functions) to provide an optimal quality metric (e.g., accuracy) for classifying new samples. The training function can include expectation maximization, maximum likelihood, Bayesian parameter estimation methods such as markov chain monte carlo, gibbs sampling, hamiltonian monte carlo, and variational inference, or gradient based methods such as stochastic gradient descent and the Broyden-Fletcher-Goldfarb-Shanno (BFGS) algorithm. Example parameters include weights (e.g., vector or matrix transformations) that multiply values, e.g., in regression or neural networks, families of probability distributions, or a loss, cost or objective function that assigns scores and guides model training. Example parameters include weights that multiple values, e.g., in regression or neural networks. A model can include multiple submodels, which may be different layers of a model or independent model, which may have a different structural form, e.g., a combination of a neural network and a support vector machine (SVM). Examples of machine learning models include deep learning models, neural networks (e.g., deep learning neural networks), kernel-based regressions, adaptive basis regression or classification, Bayesian methods, ensemble methods, logistic regression and extensions, Gaussian processes, support vector machines (SVMs), a probabilistic model, and a probabilistic graphical model. A machine learning model can further include feature engineering (e.g., gathering of features into a data structure such as a 1, 2, or greater dimensional vector) and feature representation (e.g., processing of data structure of features into transformed features to use in training for inference of a classification).

"Marker" or "marker proteins" are diagnostic indicators found in a patient and are detected, directly or indirectly by the inventive methods. Indirect detection is preferred. In particular, all of the inventive markers have been shown to cause the production of (auto)antigens in cancer patients or patients with a risk of developing cancer. A simple way to detect these markers is thus to detect these (auto)antibodies in a blood or serum sample from the patient. Such antibodies can be detected by binding to their respective antigen in an assay. Such antigens are in particular the marker proteins themselves or antigenic fragments thereof. Suitable methods may be used to specifically detect such antibody-antigen reactions and can be used according to the systems and methods of the present disclosure. Preferably the entire antibody content of the sample is normalized (e.g. diluted to a pre-set concentration) and applied to the antigens. Preferably the IgG, IgM, IgD, IgA or IgE antibody fraction, is exclusively used. Preferred antibodies are IgG.

The term "non-cancerous tissue" refers to a tissue from the same organ wherein the malignant neoplasm formed but does not have the characteristic pathology of the neoplasm. Generally, noncancerous tissue appears histologically normal. A "normal tissue" or "healthy tissue" as used herein refers to tissue from an organ, wherein the organ is not cancerous.

The terms "polynucleotides", "nucleotide", "nucleic acid", and "oligonucleotides" are used interchangeably. They refer to a polymeric form of nucleotides of any length, only minimally bounded at length 1, either deoxyribonucleotides or ribonucleotides, or analogs thereof. In some examples, polynucleotides have any three-dimensional structure, and can perform any function, known or unknown. Nucleic acids can comprise RNA, DNA, e.g., genomic DNA, mitochondrial DNA, viral DNA, synthetic DNA, cDNA that is reverse transcribed from RNA, bacterial DNA, viral DNA, and chromatin. Non-limiting examples of polynucleotides include coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, and can also be a single base of nucleotide. In some examples, a polynucleotide comprises modified nucleotides, such as methylated or glycosylated nucleotides and nucleotideanalogs. If present, modifications to the nucleotide structure can be imparted before or after assembly of the polymer. In some examples, a sequence of nucleotides is interrupted by non-nucleotide components. In certain examples, a polynucleotide is further modified after polymerization, such as by conjugation with a labeling component.

The term "polypeptide" or "protein" or "peptide" is specifically intended to cover naturally occurring proteins, as well as those which are recombinantly or synthetically produced. It should be noted that the term "polypeptide" or "protein" may include naturally occurring modified forms of the proteins, such as glycosylated forms. The terms "polypeptide" or "protein" or "peptide" as used herein are intended to encompass any amino acid sequence and include modified sequences such as glycoproteins.

The term "prediction" is used herein to refer to the likelihood, probability or score that a patient will respond either favorably or unfavorably to a drug or set of drugs, and also the extent of those responses, and detection of disease. Example predictive methods of the present disclosure can be used clinically to make treatment decisions by choosing the most appropriate treatment modalities for any particular patient. The predictive methods of the present disclosure are valuable tools in predicting if a patient is likely to respond favorably to a treatment regimen, such as surgical intervention, chemotherapy with a given drug or drug combination, and/or radiation therapy.

The term "prognosis" as used herein refers to the likelihood of the clinical outcome for a subject afflicted with a specific disease or disorder. With regard to cancer, the prognosis is a representation of the likelihood (probability) that the subject will survive (such as for one, two, three, four or five years) and/or the likelihood (probability) that the tumor will metastasize.

The term "specificity" (also called the true negative rate) refers to a measure of the proportion of actual negatives that are correctly identified as such (e.g., the percentage of healthy people who are correctly identified as not having the condition). Specificity is a function of the number of true negative calls (TN), and false positive calls (FP). Specificity is measured as (TN)/(TN+FP).

The term "sensitivity" (also called the true positive rate, or probability of detection) refers to a measure of the proportion of actual positives that are correctly identified as such (e.g., the percentage of sick people who are correctly identified as having the condition). Sensitivity is a function of the number of true positive calls (TP), and false negative calls (FN) Sensitivity is measured as (TP)/(TP+FN).

The term "structural variation (SV)" refers to a region of DNA that differs from the reference genome that is approximately 50 bp and larger in size. Examples of SVs include inversions, translocations, and copy number variants (CNVs), e.g., insertions, deletions, and amplifications.

The term "subject" refers to a biological entity containing genetic materials. Examples of a biological entity include a plant, animal, or microorganism, including, e.g., bacteria, viruses, fungi, and protozoa. In some examples, a subject is a mammal, e.g., a human that can be male or female. Such a human can be of various ages, e.g., from 1 day to about 1 year old, about 1 year old to about 3 years old, about 3 years old to about 12 years old, about 13 years old to about 19 years old, about 20 years old to about 40 years old, about 40 years old to about 65 years old, or over 65 years old. In various examples, a subject can be healthy or normal, abnormal, or diagnosed or suspected of being at a risk for a disease. In various examples, a disease comprises a cancer, a disorder, a symptom, a syndrome, or any combination thereof.

The term "training sample" refers to samples for which a classification may be known. Training samples can be used to train the model. The values of the features for a sample can form an input vector, e.g., a training vector for a training sample. Each element of a training vector (or other input vector) can correspond to a feature that includes one or more variables. For example, an element of a training vector can correspond to a matrix. The value of the label of a sample can form a vector that contains strings, numbers, bytecode, or any collection of the aforementioned datatypes in any size, dimension, or combination.

The terms "tumor", "neoplasia", "malignancy" or "cancer" as used herein refer generally to neoplastic cell growth and proliferation, whether malignant or benign, and all pre-cancerous and cancerous cells and tissues and the result of abnormal and uncontrolled growth of cells.

The term "tumor burden" refers to the amount of a tumor in an individual which can be measured as the number, volume, or weight of the tumor. A tumor that does not metastasize is referred to as "benign." A tumor that invades the surrounding tissue and/or can metastasize is referred to as "malignant."

The term nucleic acid sample encompasses "nucleic acid library" or "library" which, as used herein, includes a nucleic acid library that has been prepared by any suitable method. The adaptors may anneal to PCR primers to facilitate amplification by PCR or may be universal primer regions such as, for example, sequencing tail adaptors. The adaptors may be universal sequencing adaptors. As used herein, the term "efficiency," may refer to a measurable metric calculated as the division of the number of unique molecules for which sequences may be available after sequencing over the number of unique molecules originally present in the primary sample. Additionally, the term "efficiency" may also refer to reducing initial nucleic acid sample material required, decreasing sample preparation time, decreasing amplification processes, and/or reducing overall cost of nucleic acid library preparation.

As used herein, the term "barcode" may be a known sequence used to associate a polynucleotide fragment with the input polynucleotide or target polynucleotide from which it is produced. A barcode sequence may be a sequence of synthetic nucleotides or natural nucleotides. A barcode sequence may be contained within adapter sequences such that the barcode sequence is contained in the sequencing reads. Each barcode sequence may include at least 4, 5, 6, 7, 8, 9, 10, 11, 12, 13, 14, 15, 16, or more nucleotides in length. In some cases, barcode sequences may be of sufficient length and may be sufficiently different from one another to allow the identification of samples based on barcode sequences with which they are associated. In some cases, barcode sequences are used to tag and subsequently identify an "original" nucleic acid molecule (a nucleic acid molecule present in a sample from a subject). In some cases, a barcode sequence, or a combination of barcode sequences, is used in conjunction with endogenous sequence information to identify an original nucleic acid molecule. For example, a barcode sequence (or combination of barcode sequences)

can be used with endogenous sequences adjacent to the barcodes (e.g., the beginning and end of the endogenous sequences) and/or with the length of the endogenous sequence.

In some examples, nucleic acid molecules used herein can be subjected to a "tagmentation" or "ligation" reaction. "Tagmentation" combines the fragmentation and ligation reactions into a single step of the library preparation process. The tagged polynucleotide fragment is "tagged" with transposon end sequences during tagmentation and may further include additional sequences added during extension during a few cycles of amplification. Alternatively, the biological fragment can directly be "tagged," for processing a nucleic acid molecule or fragment thereof may comprise performing nucleic acid amplification. For example, any type of nucleic acid amplification reaction can be used to amplify a target nucleic acid molecule or fragment thereof and generate an amplified product.

DETAILED DESCRIPTION

Methods and systems are provided that detect analytes in a biological sample, measure various metrics of the analytes, and enter the metrics as features into a machine learning model to train a classifier for medical diagnostic use. The trained classifiers produced using the methods described herein are useful for multiple approaches including disease detection and staging, identification of treatment responders, and stratification on patient populations in need thereof.

Provided herein are methods and systems that incorporate machine learning approaches with one or more biological analytes in a biological sample for various applications to stratify individual populations. Methods and systems are provided that detect analytes in a biological sample, measure various metrics of the analytes, and enter the metrics as features into a machine learning model to train a classifier for medical diagnostic use. The trained classifiers produced using the methods described herein are useful for multiple approaches including disease detection and staging, identification of treatment responders, and stratification on patient populations in need thereof. In particular examples, the methods and systems are useful for predicting disease, treatment efficacy and guiding treatment decisions for affected individuals.

The present approach differs from other methods and systems in that the present methods focus on approaches to characterize the non-cellular portion of the circulating immune system, although cellular portions may also be used. The process of hematopoietic turnover is the natural death and lysis of circulating immune cells. The plasma fraction of blood contains a fragment-enriched sample of the immune system at the time where cells die and release the intracellular contents into the circulation. Specifically, plasma provides an information-rich sample of biological analytes that reflects the population of immune cells that have been educated by the presence of cancer cells before presentation of clinical symptoms. While other approaches have been directed to characterizing the cellular portion of the immune systems, the present methods interrogate the cancer-educated, non-cellular portion of the immune system to provide biological information that is then combined with machine learning tools for useful applications. The study of non-cellular analytes in a liquid such as plasma permits deconvolution of the liquid sample to recapitulate the molecular state of the immune cells when they were alive. Studying the non-cellular portion of the immune system provides a surrogate indicator of cancer status and preempts the requirement for significant blood volume to detect cancer cells and associated biological markers.

I. CIRCULATING ANALYTES AND CELLULAR DECONSTRUCTION WITH BIOLOGICAL ASSAYS

For health-related or biological predictions (e.g., predicting drug resistance/sensitivity) based entirely, or partly, on bodily fluid diagnostics, it is important to develop a cost-effective and quality assay for each question. It is imperative to be able to quickly and efficiently generate data representative of the different analytes that may carry the strongest signal required to successfully learn high performance (precision) predictive models.

A. Analytes

In various examples, a biological sample includes different analytes that provide a source of feature information for the models, methods and systems described herein. Analytes may be derived from apoptosis, necrosis and secretion from tumor, non-tumor or immune cells. Four highly informative classes of molecular biomarkers include: 1) genomic biomarkers based on the analysis of DNA profiles, sequences or modifications; 2) transcriptomic biomarkers based on the analysis of RNA expression profiles, sequences or modifications; 3) proteomic or protein biomarkers based on the analysis of protein profiles, sequences or modifications and 4) metabolomic biomarkers based on the analysis of metabolites abundance.

1. DNA

Examples of nucleic acids include, but are not limited to, deoxyribonucleic acid (DNA), genomic DNA, plasmid DNA, complementary DNA (cDNA), cell-free (e.g., non-encapsulated) DNA (cfDNA), circulating tumor DNA (ctDNA), nucleosomal DNA, chromatosomal DNA, mitochondrial DNA (miDNA), an artificial nucleic acid analog, recombinant nucleic acid, plasmids, viral vectors, and chromatin. In one example, the sample comprises cfDNA. In one example, the sample comprises PBMC-derived genomic DNA.

2. RNA

In various examples, the biological sample includes coding and non-coding transcripts that include ribonucleic acid (RNA), messenger RNA (mRNA), transfer RNA (tRNA), micro RNA (miRNA), ribosomal RNA (rRNA), circulating RNA (cRNA), alternatively spliced mRNAs, small nuclear RNAs (snRNAs), antisense RNA, short hairpin RNA (shRNA), small interfering RNA (siRNA), A nucleic acid molecule or fragment thereof may comprise a single strand or can be double-stranded. A sample may comprise one or more types of nucleic acid molecules or fragments thereof.

A nucleic acid molecule or fragment thereof may comprise any number of nucleotides. For example, a single-stranded nucleic acid molecule or fragment thereof may comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 220, at least 240, at least 260, at least 280, at least 300, at least 350, at least 400, or more nucleotides. In the instance of a double-stranded nucleic acid molecule or fragment thereof, the nucleic acid molecule or fragment thereof may comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 220, at least 240, at least 260, at least 280, at least 300, at least 350, at least 400, or more basepairs (bp), e.g. pairs of nucleotides. In some cases, a double-stranded nucleic acid molecule or fragment thereof may comprise between 100 and 200 bp, such as between 120 and 180 bp. For example, the sample may comprise a cfDNA molecule that comprises between 120 and 180 bp.

3. Polyamino Acids, Peptides, and Proteins

In various examples, the analyte is a polyamino acid, peptide, protein or fragment thereof. As used herein the term polyamino acid refers to a polymer in which the monomers are amino acid residues which are joined together through amide bonds. When the amino acids are alpha-amino acids, either the L-optical isomer or the D-optical isomer can be used, the L-isomers being preferred. In one example, the analyte is an autoantibody.

In cancer-patients serum-antibody profiles change, as well as autoantibodies against the cancerous tissue are generated. Those profile-changes provide much potential for tumour associated antigens as markers for early diagnosis of cancer. The immunogenicity of tumour associated antigens is conferred to mutated amino acid sequences, which expose an altered non-self-epitope. Other explanations are also implicated of this immunogenicity, including alternative splicing, expression of embryonic proteins in adulthood (e.g. ectopic expression), deregulation of apoptotic or necrotic processes (e.g. overexpression), abnormal cellular localizations (e.g. nuclear proteins being secreted). Examples of epitopes of the tumour-restricted antigens, encoded by intron sequences (e.g. partially unspliced RNA were translated) have been shown to make the tumour associated antigen highly immunogenic.

Example inventive markers are suitable protein antigens that are overexpressed in tumours. The markers usually cause an antibody reaction in a patient. Therefore, the most convenient method to detect the presence of these markers in a patient is to detect (auto) antibodies against these marker proteins in a sample from the patient, especially a body fluid sample, such as blood, plasma or serum.

4. Other Analytes

In various examples, the biological sample includes small chemical molecules such as, but not limited to, sugars, lipids, amino acids, fatty acids, phenolic compounds, and alkaloids.

In one example, the analyte is a metabolite. In one example, the analyte is a carbohydrate. In one example, the analyte is a carbohydrate antigen. In one example, the carbohydrate antigen is attached to an O-glycan. In one example, the analyte is a mono- di-, tri- or tetra-saccharide. In one example, the analyte is a tetra-saccharide. In one example, the tetra-saccharide is CA19-9. In one example, the analyte is a nucleosome. In one example, the analyte is a platelet-rich plasma (PRP). In one example, the analyte is a cellular element such as lymphocytes (Neutrophils, Eosinophils, Basophils, Lymphocytes, PBMCs and Monocytes), or platelets.

In one example, the analyte is a cellular element such as lymphocytes (Neutrophils, Eosinophils, Basophils, Lymphocytes, PBMCs and Monocytes), or platelets.

In various examples a combination of analytes is assayed to obtain information useful for the methods described herein. In various examples, the combination of analytes assayed differs for the cancer type or for the classification need.

In various examples, the combination of analytes is selected from: 1) cfDNA, cfRNA, polyamino acid, and small chemical molecules, or 2) cfDNA and cfRNA, and polyamino acids, 3) cfDNA and cfRNA and small chemical molecules, or 4) cfDNA, polyamino acid, and small chemical molecules, or 5) cfRNA, polyamino acid, and small chemical molecules, or 6) cfDNA and cfRNA, or 7) cfDNA and polyamino acid, or 8) cfDNA and small chemical molecules, or 9) cfRNA and polyamino acid, or 10) cfRNA and small chemical molecules, or 11) polyamino acid and small chemical molecules.

II. SAMPLE PREPARATION

In some examples, a sample is obtained, e.g., from a tissue or a bodily fluid or both, from a subject. In various examples, the biological sample is a liquid sample such as plasma, or serum, buffy coat, mucous, urine, saliva, or cerebrospinal fluid. In one example, the liquid sample is a cell-free liquid. In various examples, the sample includes cell-free nucleic acid, (e.g., cfDNA or cfRNA).

A sample comprising one or more analytes can be processed to provide or purify a particular nucleic acid molecule or a fragment thereof or a collection thereof. For example, a sample comprising one or more analytes can be processed to separate one type of analyte (e.g., cfDNA) from other types of analytes. In another example, the sample is separated into aliquots for analysis of a different analyte in each aliquot from the sample. In one example, a sample comprising one or more nucleic acid molecules or fragments thereof of different sizes (e.g., lengths) can be processed to remove higher molecular weight and/or longer nucleic acid molecules or fragments thereof or lower molecular weight and/or shorter nucleic acid molecules or fragments thereof.

The methods described herein may comprise processing or modifying a nucleic acid molecule or fragment thereof. For example, a nucleotide of a nucleic acid molecule or fragment thereof can be modified to include a modified nucleobase, sugar, and/or linker. Modification of a nucleic acid molecule or fragment thereof may comprise oxidation, reduction, hydrolysis, tagging, barcoding, methylation, demethylation, halogenation, deamination, or any other process. Modification of a nucleic acid molecule or fragment thereof can be achieved using an enzyme, a chemical reaction, physical process, and/or exposure to energy. For example, deamination of unmethylated cytosine can be achieved through the use of bisulfite for methylation analysis.

Sample processing may comprise, for example, one or more processes such as centrifugation, filtration, selective precipitation, tagging, barcoding, and partitioning. For example, cellular DNA can be separated from cfDNA by a selective polyethylene glycol and bead-based precipitation process such as a centrifugation or filtration process. Cells included in a sample may or may not be lysed prior to separation of different types of nucleic acid molecules or fragments thereof. In one example, the sample is substantially free of cells. In one examples, cellular components are assayed for measurements that may be inputted as features into a machine learning method or model. In various examples cellular components such as PBMC, lymphocytes may be detected (for example by flow cytometry, mass spectrometry or immunopanning) A processed sample may comprise, for example, at least 1 femtogram (fg), 10 fg, 100 fg, 1 picogram (pg), 10 pg, 100 pg, 1 nanogram (ng), 10 ng, 50 ng, 100 ng, 500 ng, 1 microgram (µg), or more of a particular size or type of nucleic acid molecules or fragments thereof.

In some examples, blood samples are obtained from healthy individuals and individuals with cancer, e.g., individuals with stage I, II, III, or IV cancer. In one example, blood samples are obtained from healthy individuals and individuals with benign polyps, advanced adenomas (AAs), and stage I-IV colorectal cancer (CRC). The systems and methods described herein are useful for detecting presence of AA and CRC and differentiating between stages and sizes thereof. Such differentiation is useful to stratify individuals in a population for changes in behavior and/or treatment decisions.

A. Library Preparation and Sequencing

Purified nucleic acid (e.g. cfDNA) may be used to prepare a library for sequencing. A library can be prepared using platform-specific library preparation method or kit. The method or kit can be commercially available and can generate a sequencer-ready library. Platform-specific library preparation methods can add a known sequence to the end of nucleic acid molecules; the known sequence can be referred to as an adapter sequence. Optionally, the library preparation method can incorporate one or more molecular barcodes.

To sequence a population of double-stranded DNA fragments using massively parallel sequencing systems, the DNA fragments must be flanked by known adapter sequences. A collection of such DNA fragments with adapters at either end is called a sequencing library. Two examples of suitable methods for generating sequencing libraries from purified DNA are (1) ligation-based attachment of known adapters to either end of fragmented DNA, and (2) transposase-mediated insertion of adapter sequences. Any suitable massively parallel sequencing techniques may be used for sequencing.

For methylation analysis, nucleic acid molecules are treated prior to sequencing. Treatment of a nucleic acid molecule (e.g., a DNA molecule) with bisulfite, enzymatic methyl-seq or hydroxymethyl-seq deaminates unmethylated cytosine bases and converts them to uracil bases. This bisulfite conversion process does not deaminate cytosines that are methylated or hydroxymethylated at the 5' position (5mC or 5hmC). When used in conjunction with a sequencing analysis, a process involving bisulfite conversion of a nucleic acid molecule or a fragment thereof can be referred to as bisulfite sequencing (BS-seq). In some cases, a nucleic acid molecule can be oxidized before undergoing bisulfite conversion. Oxidation of a nucleic acid molecule may convert 5hmC to 5-formylcytosine and 5-carboxlcytosine, both of which are sensitive to bisulfite conversion to uracil. When used in conjunction with a sequencing analysis, oxidation of a nucleic acid molecule or fragment thereof prior to subjecting the nucleic acid molecule or fragment thereof to bisulfite sequencing can be referred to as oxidative bisulfite sequencing (oxBS-seq).

1. Sequencing

Nucleic acids may be sequenced using sequencing methods such as next-generation sequencing, high-throughput sequencing, massively parallel sequencing, sequencing-by-synthesis, paired-end sequencing, single-molecule sequencing, nanopore sequencing, pyrosequencing, semiconductor sequencing, sequencing-by-ligation, sequencing-by-hybridization, RNA-Seq, Digital Gene Expression, Single Molecule Sequencing by Synthesis (SMSS), Clonal Single Molecule Array (Solexa), shotgun sequencing, Maxim-Gilbert sequencing, primer walking, and Sanger sequencing.

Sequencing methods may comprise targeted sequencing, whole-genome sequencing (WGS), lowpass sequencing, bisulfite sequencing, whole-genome bisulfite sequencing (WGBS), or a combination thereof. Sequencing methods may include preparation of suitable libraries. Sequencing methods may include amplification of nucleic acids (e.g., by targeted or universal amplification, such as PCR). Sequencing methods may be performed at a desired depth, such as at least about 5×, at least about 10×, at least about 15×, at least about 20×, at least about 25×, at least about 30×, at least about 35×, at least about 40×, at least about 45×, at least about 50×, at least about 60×, at least about 70×, at least about 80×, at least about 90×, at least about 100×. For targeted sequencing methods may be performed at a desired depth, such as at least about 500×, at least about 1000×, at least about 1500×, at least about 2000×, at least about 2500×, at least about 3000×, at least about 3500×, at least about 4000×, at least about 4500×, at least about 5000×, at least about 6000×, at least about 7000×, at least about 8000×, at least about 9000×, at least about 10000×.

Biological information can be prepared using any useful method. The biological information may comprise sequencing information. The sequencing information may be prepared using, for example, an assay for transposase-accessible chromatin using sequencing (ATAC-seq) method, a micrococcal nuclease sequencing (MNase-seq) method, a deoxyribonuclease hypersensitive sites sequencing (DNase-seq) method, or a chromatin immunoprecipitation sequencing (ChIP-seq) method.

Sequencing reads can be obtained from various sources including, for example, whole genome sequencing, whole exome-sequencing, targeted sequencing, next-generation sequencing, pyrosequencing, sequencing-by-synthesis, ion semiconductor sequencing, tag-based next generation sequencing semiconductor sequencing, single-molecule sequencing, nanopore sequencing, sequencing-by-ligation, sequencing-by-hybridization, Digital Gene Expression (DGE), massively parallel sequencing, Clonal Single Molecule Array (Solexa/Illumina), sequencing using PacBio, and Sequencing by Oligonucleotide Ligation and Detection (SOLiD).

In some examples, sequencing comprises modification of a nucleic acid molecule or fragment thereof, for example, by ligating a barcode, a unique molecular identifier (UMI), or another tag to the nucleic acid molecule or fragment thereof. Ligating a barcode, UMI, or tag to one end of a nucleic acid molecule or fragment thereof may facilitate analysis of the nucleic acid molecule or fragment thereof following sequencing. In some examples, a barcode is a unique barcode (i.e., a UMI). In some examples, a barcode is non-unique, and barcode sequences can be used in connection with endogenous sequence information such as the start and stop sequences of a target nucleic acid (e.g., the target nucleic acid is flanked by the barcode and the barcode sequences, in connection with the sequences at the beginning and end of the target nucleic acid, creates a uniquely tagged molecule).

Sequencing reads may be processed using methods such as de-multiplexing, de-deduplication (e.g., using unique molecular identifiers, UMIs), adapter-trimming, quality filtering, GC correction, amplification bias correction, correction of batch effects, depth normalization, removal of sex chromosomes, and removal of poor-quality genomic bins.)

In various examples, sequencing reads may be aligned to a reference nucleic acid sequence. In one example, the reference nucleic acid sequence is a human reference genome. As examples, the human reference genome can be hg19, hg38, GrCH38, GrCH37, NA12878, or GM12878.

2. Assays

The selection of which assays to use is integrated based on the results of training the machine learning model, given the clinical goal of the system. As used herein the term "assay" includes known biological assays and may also include computational biology approaches for transforming biological information into useful features as inputs for machine learning analysis and modeling. Various pre-processing computational tools may be included with the assays described herein and the term "assay" is not intended to be limiting. Various classes of samples, fractions of samples, portions of those fractions/samples with different classes of molecules, and types of assays can be used to generate feature data for use in computational methods and models to inform a classifier useful in the methods described herein. In one example, the sample is separated into aliquots for performing biological assays.

In various examples, biological assays are performed on different portions of the biological sample to provide a data set corresponding to the biological assay for an analyte in the portion. Various assays are known to those of skill in the art and are useful to interrogate a biological sample. Examples of such assays include but are not limited to: whole-genome sequencing (WGS), whole-genome bisulfite sequencing (WGSB), small-RNA sequencing, quantitative immunoassay, enzyme-linked immunosorbent assay (ELISA), proximity extension assay (PEA), protein microarray, mass spectrometry, low-coverage Whole-Genome Sequencing (lcWGS); selective tagging 5mC sequencing (WO2019/051484), CNV calling; tumor fraction (TF) estimation; Whole Genome Bisulfite Sequencing; LINE-1 CpG methylation; 56 genes CpG methylation; cf-Protein Immuno-Quant ELISAs, SIMOA; and cf-miRNA sequencing, and cell type or cell phenotype mixture proportions derived from any of the above assays. This ability to analyze multiple analytes (such as but not limited to DNA, RNA, proteins, autoantibodies, metabolites, or combinations thereof) simultaneously from the same biological sample, or fractions thereof can increase the sensitivity and specificity of such bodily fluid diagnostic tests by exploiting independent information between signals.

In one example, cell-free DNA (cfDNA) content is assessed by low-coverage whole-genome sequencing (lcWGS) or targeted sequencing, or whole-genome bisulfite sequencing (WGBS) or whole-genome enzymatic methyl sequencing, cell-free microRNA (cf-miRNA) is assessed by small-RNA sequencing or PCR (digital droplet or quatitative), and levels of circulating proteins are measured by quantitative immunoassay. In one example, cell-free DNA (cfDNA) content is assessed by whole-genome bisulfite sequencing (WGBS), proteins are measured by quantitative immunoassay (including ELISA or proximity extension assay), and autoantibodies are measured by protein microarrays.

B. cf-DNA Assays using WGS

In various examples, assays that profile the characteristics of cfDNA are used to generate features useful in the computational applications. In one example, characteristics of cf-DNA are used in machine learning models and to generate classifiers to stratify individuals or detect disease as described herein. Exemplary features include but are not limited to those that provide biological information regarding gene expression, 3D chromatin, chromatin states, copy number variants, tissue of origin and cell composition in cfDNA samples. Metrics of cfDNA concentration that may be used as input features for machine learning methods and models may be obtained by methods that include but are not limited to methods that quantitate dsDNA within specified size ranges (e.g., Agilent TapeStation, Bioanalyzer, Fragment Analyzer), methods that quantitate all dsDNA using dsDNA-binding dyes (e.g., QuantiFluor, PicoGreen, SYBR Green), and methods quantify DNA fragments (either dsDNA or ssDNA) at or below specific sizes (e.g., short fragment qPCR, long fragment qPCR, and long/short qPCR ratio).

Biological information may also include information regarding transcription start sites, transcription factor binding sites, assay for transposase-accessible chromatin using sequencing (ATAC-seq) data, histone marker data, DNAse hypersensitivity sites (DHSs), or combinations thereof.

In one example, the sequencing information includes information regarding a plurality of genetic features such as, but not limited to, transcription start sites, transcription factor binding sites, chromatin open and closed states, nucleosomal positioning or occupancy, and the like.

1. cfDNA Plasma Concentration

The plasma concentration of cfDNA may be assayed as a feature that in various examples indicates the presence of cancer. In various examples, both the total quantity of cfDNA in the circulation and estimates of the tumor-derived contribution to cfDNA (also referred to as "tumor fraction") are used as prognostic biomarkers and indicators of response and resistance to therapy. Sequencing fragments that aligned within annotated genomic regions were counted and normalized for depth of sequencing to produce a 30,000-dimensional vector per sample, each element correspond to a count for a gene (e.g., number of reads aligning to that gene in a reference genome). In one example, a sequence read count is determined for a list of known genes having annotated regions for each of those annotated regions by counting the number of fragments aligned to that region. The read count for the genes is normalized in various ways, e.g., using a global expectation that the genome is deployed; within-sample normalization; and a cross feature normalization. The cross-feature normalization refers to every one of those features averaging to specified value, e.g., 0, different negative values, one, or the range is 0 to 2. For cross feature normalization, the total reads from the sample is variable, and can thus depend on the preparation process and the sequencer loading process. The normalization can be to a constant number of reads, as part of a global normalization.

For a within-sample normalization, it is possible to normalize by some of the features or qualifying characteristics of some regions, in particular, for GC bias. Thus, the base pair makeup of each region can be different and used for normalization. And in some cases, the number of GCs is significantly higher or lower than 50% and that has thermodynamic impact because the bases are more energetic, and the processes are biased. Some regions provide more reads than expected because of biology artifacts of sample preparation in the lab. Thus, it may be necessary to correct for such biases by applying another kind of feature/feature transformation/normalization method when modeling.

In one example, the software tool ichorCNA is used to identify the tumor fraction component of cfDNA through copy number alterations detected by sparse (~0.1× coverage) to deep (~30× coverage) whole genome sequencing (WGS). In another example, measuring tumor content through quantification of the presence of individual alleles is used to assess response or resistance to therapy in cancers where those alleles are known clonal drivers.

Copy number variation (CNV) can be amplified or deleted in regions of the genome that are recognized as a primary source of average human genome viability and contribute significantly to phenotype variation. Tumor-derived cfDNA carries genomic alterations corresponding to copy number alterations. Copy number alterations plays a role in carcinogenesis in many cancers including CRC. Genome-wide detection of copy number alterations can be characterized in cfDNA, acting as tumour biomarkers. In one example, detection uses deep WGS. In another example, chromosomal instability analysis in cell-free DNA by low-coverage whole-genome sequencing can be used as an assay of cfDNA. Other examples of cfDNA assays useful for detection of tumor DNA fragments include Length Mixture Model (LMM), and Fragment Endpoint Analysis, In one example, samples with high (>20%) tumor fraction are identified via manual inspection of large-scale CNV.

In one example, changes in gene expression are also reflected in plasma cfDNA concentration levels and methods such as microarray analysis may be used to assay changes in gene expression levels in a cfDNA sample. Metrics of cfDNA concentration that may be used as input features for machine learning methods and models include but are not limited to Tape Station, short qPCR, long qPCR, and long/short qPCR ratio.

2. Somatic Mutation Analysis

In one example, low-coverage whole genome sequencing (lcWGS) can be used to sequence the cf-DNA in a sample and then interrogated for somatic mutations associated with a particular cancer type. Using somatic mutations from lcWGS, deep WGS, or targeted sequencing (by NGS or other techniques) may generate features which may be inputted into the machine learning methods and models described herein.

Somatic mutation analysis has matured to include highly complex technologies such as microarrays and next-generation sequencing (NGS) or massively parallel sequencing. This approach may permit extensive multiplexing capabilities in a single test. These types of hot-spot panels can range in gene number from several to several hundred in a single assay. Other types of gene panels include whole-exon or whole-gene sequencing and offer the advantage of identifying novel mutations in a specific gene set.

3. Transcription Factor Profiling

The inference of transcription factor binding from cfDNA has tremendous diagnostic potential in cancer. The constituents involved in nucleosome signatures at Transcription Factor Binding Sites (TFBSs) are assayed to assess and to compare transcription factor binding sites accessibility in different plasma samples. In one example, deep whole-genome sequencing (WGS) data obtained from blood samples taken from plasma samples from healthy donors and cancer patients with metastasized prostate, colon or breast cancer, is used where cfDNA also comprises circulating tumor DNA (ctDNA). Shallow WGS data profiles individual transcription factors, instead of establishing general tissue-specific patterns using mixtures of cfDNA signals resulting from multiple cell types and analyses by Fourier transformation and statistical summarization. The approach provided herein thus provides a more nuanced view of both tissue contributions and biological processes, which allows identification of lineage-specific transcription factors suitable for both tissue-of-origin and tumor-of-origin analyses. In one example, transcription factor binding site plasticity in cfDNA from patients with cancer is used for classifying cancer subtypes, stages and response to treatment.

In one example, cfDNA fragmentation patterns are used to detect non-hematopoietic signatures. In order to identify transcription factor-nucleosome interactions mapped from cfDNA, hematopoietic transcription factor-nucleosome footprints in plasma samples from healthy controls are first identified. The curated list of transcription factor binding sites from publically-accessible databases (for example the Gene Transcription Regulation Database (GTRD)) may be used to generate comprehensive transcription factor binding site-nucleosome occupancy maps from cfDNA. Different stringency criteria are used to measure nucleosome signatures at transcription factor binding sites, and establish a metric termed "accessibility score", and a z-score statistic to objectively compare in different plasma samples significant changes in transcription factor binding site accessibility. For clinical purposes, a set of lineage-specific transcription factors can be identified that is suitable for identifying the tissue-of-origin of cfDNA or in patients with cancer the tumor-of-origin. The accessibility score and z-score statistics are used to elucidate changing transcription factor binding site accessibilities from cfDNA of patients with cancer.

In an aspect, the present disclosure provides a method for diagnosing a disease in a subject, the method comprising: (a) providing sequence reads from deoxyribonucleic acid (DNA) extracted from the subject; (b) generating a coverage pattern for a transcription factor; (c) processing the coverage pattern to provide a signal; (d) comparing the signal to a reference signal, wherein the signal and the reference signal have different frequencies; and (e) based on the signal, diagnosing the disease in the subject.

In some examples, (b) comprises aligning the sequence reads to a reference sequence to provide an aligned sequence pattern, selecting regions of the aligned sequence pattern that correspond to binding sites of the transcription factor, and normalizing the aligned sequence pattern in the regions.

In some examples, the transcription factor is selected from the group consisting of GRH-L2, ASH-2, HOX-B13, EVX2, PU.1, Lyl-1, Spi-B, and FOXA1.

In some examples, (e) comprises identifying a sign of higher accessibility of the transcription factor. In some examples, the transcription factor is an epithelial transcription factor. In some examples, the transcription factor is GRHH-L2.

4. Inferring Chromosome Structure/Chromatin State

In other examples, assays are used to infer the three-dimensional structure of a genome using cell-free DNA (cfDNA). In particular, the present disclosure provides methods and systems for detecting chromatin abnormalities associated with diseases or conditions, such as cancer. While not to be bound by any specific mechanism, it is believed that DNA fragments are released from cells into, for example, the blood stream. The half-life of released DNA fragments, known as cell-free DNA (cfDNA) once released from cells can depend on chromatin remodeling states. Thus, the abundance of a cfDNA fragment in a biological sample can be indicative of the chromatin state of the gene from which the cfDNA fragment originated (known as the cfDNA's "position"). Chromatin states of genes can change in diseases. Identifying changes in the chromatin state of genes can serve as a method to identify the presence of a disease in a subject. The chromatin state of genes can be predicted from the abundance and position of cfDNA fragments in biological samples using computer-aided techniques. The chromatin state may also be useful in inferring gene expression in a sample. A non-limiting example of a computer-aided technique that can be used to predict chromatin state is a probabilistic graphical model (PGM). PGMs can be estimated using statistical techniques such as expectation maximization or gradient methods to identify the cfDNA profiles for open and closed TSSs (or in-between states) by fitting the parameters of the PGM with training sets and a statistical technique to estimate those parameters. Training sets can be cfDNA profiles for known open and closed transcription start sites. Once trained, PGMs can predict the chromatin state of one or more genes in naive (never before seen) samples. Predictions can be analyzed and quantified. By comparing predictions in the chromatin state of one or more genes from healthy and diseased samples, biomarker or diagnostic tests can be developed. PGMs can include varied information, measurements, and mathematical objects that contribute to a model that can be made more accurate. These objects can include other measured covariates such as the biological context of the data and the lab process conditions of the sample.

In one example where the genetic feature is chromatin state, the first array provides a measure of constitutive openness of a plurality of cell types as a reference, the second array provides relative proportions for cell types in a sample, and the third array provides a measure of chromatin state in the sample.

The expression of a gene can be controlled by access of the cellular machinery to the transcription start site. Access to the transcription start site can be determined the state of the chromatin on which the transcription start site is located. Chromatin state can be controlled through chromatin remodeling, which can condense (close) or loosen (open) transcription start site. A closed transcription start site results in decreased gene expression while an open transcription start site results in increased gene expression. Also, the length of cfDNA fragments may depend on chromatin state. Chromatin remodeling can occur through the modification of histone and other related proteins. Non-limiting examples of histone modifications that can control the state of chromatin and transcription start sites include, for example, methylation, acetylation, phosphorylation, and ubiquitination.

Expression of genes is also controlled by more distal elements such as enhancers, which interact with transcriptional machinery in the 3D space of the physical genome. ATAC-seq and DNAse-seq provide measurements of open chromatin, which correlate with the binding of these more distal elements which may not be obviously associated with a particular gene. For example, ATAC-seq data can be obtained for a multitude of cell types and states and be used to identify regions of the genome with open chromatin for a variety of underlying regions such as active transcription start sites or bound enhancers or repressors.

The half-life of cfDNA once released from cells can depend on chromatin remodeling states. Thus, the abundance of a cfDNA fragment in a biological sample can be indicative of the chromatin state of the gene from which the cfDNA fragment originated (referred to herein as a cfDNA's "position"). Chromatin states of genes can change in diseases. Identifying changes in the chromatin state of genes can serve as a method to identify the presence of a disease in a subject. When comparing expressed and unexpressed genes, there is a quantitative shift in both the number and positional distribution of cell-free DNA (cfDNA) fragments. More specifically, there is a strong depletion of reads within a ~1000-3000 bp region surrounding a transcription start site (TSS), and the nucleosomes downstream of the TSS become strongly positioned (the positions become much more predictable). The present disclosure provides a way to solve the inverse relationship: starting from cfDNA, the expression or chromatin openness of a gene can be inferred. In one example, this assay in used in the multi-analyte methods described herein.

The present disclosure also provides a way to generate predictions for other chromatin states as well, for example, in repressed regions, active or poised promoters, and more. These predictions can quantify differences between different individuals (or samples), e.g. healthy, colorectal cancer (CRC) patients, or other disease- or cancer-diagnosed samples.

Because the presence of open chromatin is broadly also captured by the absence of nucleosomes, or through the presence of strongly positioned nucleosomes flanking an inner region of open chromatin, the methods described herein can also be used on enhancers, repressors, or naively on regions of open chromatin identified by other means in reference samples.

The position of cfDNA sequence reads within the genome can be determined by "mapping" the sequence to a reference genome. Mapping can be performed with the aid of computer algorithms including, for example, the Needleman-Wunsch algorithm, the BLAST algorithm, the Smith-Waterman algorithm, a Burrows-wheeler alignment, a suffix tree, or a custom-developed algorithm.

The three-dimensional conformation of chromosomes is involved in compartmentalizing the nucleus and joining spatially separated functional elements into close proximity. Analysis of the spatial disposition of chromosomes and understanding how chromosomes fold can provide insight into the relationship between chromatin structure, gene activity, and biological state of the cell.

Detection of DNA interactions and modeling of three-dimensional chromatin structure can be accomplished using chromosome conformation technologies. Such technologies include, for example, 3C (Chromosome Conformation Capture), 4C (Circularized Chromosome Conformation Capture), 5C (Chromosome Conformation Capture Carbon Copy), Hi-C (3C with high-throughput sequencing), ChIP-loop (3C with ChIP-seq), and ChIA-PET (Hi-C with ChIP-seq).

Hi-C sequencing is used to probe the three-dimensional structure of whole genomes by coupling proximity-based ligation with massively parallel sequencing. Hi-C sequencing utilizes high-throughput, next-generation sequencing to unbiasedly quantify the interactions across an entire genome. In Hi-C sequencing, DNA are crosslinked with formaldehyde; the crosslinked DNA is digested with a restriction enzyme to yield a 5'-overhang, which is then filled with a biotinylated residue; and the resulting blunt-end fragments are ligated under conditions that favor ligation between crosslinked DNA fragments. The resulting DNA sample contains ligation products consisting of fragments that were close in spatial proximity in the nucleus, marked with biotin at the junction. A Hi-C library can be created by shearing the DNA and selecting the biotinylated products with streptavidin beads. The library can be analyzed by using massively parallel, paired-end DNA sequencing. Using this technique, all pairwise interactions in the genome can be calculated to infer a potential chromosomal structural.

In one example, the nucleosome occupancy of the cfDNA provides an indication of openness of the DNA and the ability to infer transcription factor binding. In certain examples, nucleosome occupancy is associated with tumor cell phenotype.

cfDNA represents a unique analyte generated by endogenous physiological processes to generate in vivo maps of nucleosomal occupancy by whole-genome sequencing. Nucleosomal occupancy at transcription start sites has been leveraged to infer expressed genes from cells releasing their DNA into the circulation. cfDNA nucleosome occupancy may reflect footprints of transcription factors.

In various examples, cfDNA includes non-encapsulated DNA in, e.g., a blood or plasma sample and can include ctDNA and/or cffDNA. cfDNA can be, for example, less than 200 base pairs (bp) long, such as between 120 and 180 bp long. cfDNA fragmentation patterns generated by mapping cfDNA fragment ends to a reference genome can include regions of increased read depth (e.g., fragment pileups). These regions of increased read depth can be approximately 120-180 bp in size, which reflects the size of nucleosomal DNA. A nucleosome is a core of 8 histone proteins that are wrapped by about 147 bp of DNA. A chromatosome includes a nucleosome plus a histone (e.g., histone H1) and about 20 bp of associated DNA tethered to the outside of a nucleosome. Regions of increased read depth of a cfDNA may correlate with nucleosome positioning. Accordingly, a method of analyzing cfDNA, as disclosed herein, may facilitate the mapping of a nucleosome. Fragment pileups seen when cfDNA reads are mapped to a reference genome may reflect nucleosomal binding that protects certain regions from nuclease digestion during the process of cell death (apoptosis) or systemic clearance of circulating cfDNA by the liver and kidneys. A method of analyzing cfDNA, as disclosed herein, can be complemented by, for example, digestion of a DNA or chromatin with MNase and subsequent sequencing (MNase sequencing). This method may reveal regions of DNA protected from MNase digestion due to binding of nucleosomal histones at regular intervals with intervening regions preferentially degraded, thus reflecting a footprint of nucleosomal positioning.

5. Tissue of Origin Assay

The plurality of nucleic acid molecules in a cfDNA sample derives from one or more cell types. In various examples, assays are used to identify tissue of origin of nucleic acid sequences in the sample. Inferring cellular-derived contribution of analytes in a sample is useful in deconstructing analyte information in a biological sample. In various examples, methods such as Learning of Regulatory Regions (LRR), and immune DHS signatures are useful in methods of determining cell-type-of-origin and cell-type-contribution of analytes in a biological sample. In various examples, genetic features such as, V-plot measures, FREE-C, the cfDNA measurement over a transcription start site and DNA methylation levels over cfDNA fragments are used as input features into machine learning methods and models.

In one example, a first array of values corresponding to a state of the plurality of genetic features for a plurality of cell types may be prepared. In one example, the values corresponding to the state of the plurality of genetic features are obtained for a reference population. The reference population provides values that are used to provide an indication of the constitutive state for the plurality of genetic features.

In one example, a second array of values corresponding to the plurality of genetic features for the plurality of nucleic acid molecules of a nucleic acid sample may also be prepared. The first and second arrays may then be used to prepare a third array of values.

In one example, the first and second arrays are matrices and are used to prepare a third array of values by matrix multiplication and parameter optimization. In one example, the third array of values corresponds to the estimated proportion of a plurality of cell types for a plurality of nucleic acid molecules of the sample. The nucleic acid data from the sample in combination with the reference population of information is used to estimate a mixture of the reference population that best fits the plurality of nucleic acids of the sample. This mixture could be normalized to 1 and used to represent the proportion or score of those reference populations in the sample.

The type and proportion of the one or more cell types from which the plurality of nucleic acid molecules is derived may thus be determined.

In a first aspect, the present disclosure provides a method of processing a sample comprising a plurality of nucleic acid molecules, comprising:
(a) providing sequencing information for the sample comprising the plurality of nucleic acid molecules, which sequencing information includes information regarding a plurality of genetic features, and which plurality of nucleic acid molecules derive from one or more cell types;
(b) preparing a first array of values corresponding to an aspect of the plurality of genetic features for a plurality of cell types, which plurality of cell types comprises the one or more cell types;
(c) preparing a second array of values corresponding to the aspect of the plurality of genetic features for the plurality of nucleic acid molecules of the sample; and
(d) using the first array of values and the second array of values to prepare a third array of values corresponding to the plurality of cell types for the plurality of nucleic acid molecules of the sample, thereby determining the type and proportion of the one or more cell types from which the plurality of nucleic acid molecules are derived.

C. cfDNA Assays of Methylation using WGBS

1. Methylation Sequencing

Assays are used to sequence the whole genome (e.g. via WGBS), enzymatic methyl sequencing ("EMseq")), which is capable of providing the ultimate resolution by characterizing DNA methylation of nearly every nucleotide in the genome. Other targeted methods may be useful for methylation analysis for example high-throughput sequencing, pyrosequencing, Sanger sequencing, qPCR, or ddPCR. DNA methylation, which refers to the addition of the methyl group to DNA, is one of the most extensively characterized epigenetic modification with important functional consequences. Typically, DNA methylation occurs at cytosine bases of nucleic acid sequences. Enzymatic methyl sequencing is especially useful since it uses a three step conversion requiring lower volume of sample for analysis.

In some examples of any of the foregoing aspects, subjecting the DNA or the barcoded DNA to conditions sufficient to convert cytosine nucleobases of the DNA or the barcoded DNA into uracil nucleobases comprises performing bisulfite conversion. In some examples, performing bisulfite conversion comprises oxidizing the DNA or the barcoded DNA. In some examples, oxidizing the DNA or the barcoded DNA comprises oxidizing 5-hydroxymethylcytosine to 5-formylcytosine or 5-carboxlcytosine. In some examples, the bisulfite conversion comprises reduced representation bisulfite sequencing.

In other examples, the assay that is used for methylation analysis is selected from mass spectrometry, methylation-Specific PCR (MSP), reduced representation bisulfite sequencing, (RRBS), HELP assay, GLAD-PCR assay, ChIP-on-chip assays, restriction landmark genomic scanning, methylated DNA immunoprecipitation (MeDIP), pyrosequencing of bisulfite treated DNA, molecular break light assay, methyl Sensitive Southern Blotting, High Resolution Melt Analysis (HRM or HRMA, ancient DNA methylation reconstruction, or Methylation Sensitive Single Nucleotide Primer Extension Assay (msSNuPE).

In one example, the assay used for methylation analysis is whole genome bisulfite sequencing (WGB S). Modification of a nucleic acid molecule or fragment thereof can be achieved using an enzyme or other reaction. For example, deamination of cytosine can be achieved through the use of bisulfite. Treatment of a nucleic acid molecule (e.g., a DNA molecule) with bisulfite deaminates unmethylated cytosine bases and converts them to uracil bases. This bisulfite conversion process does not deaminate cytosines that are methylated or hydroxymethylated at the 5 position (5mC or 5hmC). When used in conjunction with a sequencing analysis, a process involving bisulfite conversion of a nucleic acid molecule or a fragment thereof can be referred to as bisulfite sequencing (BS-seq). In some cases, a nucleic acid molecule can be oxidized before undergoing bisulfite conversion. Oxidation of a nucleic acid molecule may convert 5hmC to 5-formylcytosine and 5-carboxlcytosine, both of which are sensitive to bisulfite conversion to uracil. When used in conjunction with a sequencing analysis, oxidation of a nucleic acid molecule or fragment thereof prior to subjecting the nucleic acid molecule or fragment thereof to bisulfite sequencing can be referred to as oxidative bisulfite sequencing (oxBS-seq).

Methylation of cytosine at CpG sites can be greatly enriched in nucleosome-spanning DNA compared to flanking DNA. Therefore, CpG methylation patterns may also be employed to infer nucleosomal positioning using a machine learning approach. Matched nucleosome positioning and 5mC datasets from the same cfDNA samples generated by micrococcal nuclease-seq (MNase-seq) and WGBS, respectively, can be used to train machine learning models. The BS-seq or EM-seq datasets may also be analyzed according to the same methods used for WGS to generate features for input into machine learning methods and models regardless of methylation conversion. Then, 5mC patterns can be used to predict nucleosome positioning, which may aid in inferring gene expression and/or classification of disease and cancer. In another example, features may be obtained from a combination of methylation state and nucleosome positioning information.

Metrics that are used in methylation analysis include, but are not limited to, M-bias (base wise methylation % for CpG, CHG, CHH), conversion efficiency (100-Mean methylation % for CHH), hypomethylated blocks, methylation levels (global mean methylation for CPG, CHH, CHG, chrM, LINE1, ALU), dinucleotide coverage (normalized coverage of di-nucleotide), evenness of coverage (unique CpG sites at 1× and 10× mean genomic coverage (for S4 runs), mean CpG coverage (depth) globally and mean coverage at CpG islands, CGI shelves, CGI shores. These metrics may be used as feature inputs for machine learning methods and models.

In an aspect, the present disclosure provides a method, comprising: (a) providing a biological sample comprising deoxyribonucleic acid (DNA) from a subject; (b) subjecting the DNA to conditions sufficient to convert unmethylated cytosine nucleobases of the DNA into uracil nucleobases, wherein the conditions at least partially degrade the DNA; (c) sequencing the DNA, thereby generating sequence reads; (d) computer processing the sequence reads to (i) determine a degree of methylation of the DNA based on a presence of the uracil nucleobases and (ii) model the at least partial degradation of the DNA, thereby generating degradation parameters; and (e) using the degradation parameters and the degree of methylation to determine a genetic sequence feature.

In another aspect, the present disclosure provides a method, comprising: (a) providing a biological sample comprising deoxyribonucleic acid (DNA) from a subject; (b) subjecting the DNA to conditions sufficient for optional enrichment of methylated DNA in the sample; (c) and convert unmethylated cytosine nucleobases of the DNA into uracil nucleobases; (d) sequencing the DNA, thereby generating sequence reads; (e) computer processing the sequence reads to (i) determine a degree of methylation of the DNA based on a presence of the uracil nucleobases and (ii) model the at least partial degradation of the DNA, thereby generating degradation parameters; and (f) using the degradation parameters and the degree of methylation to determine a genetic sequence feature.

In some examples, (d) comprises determining a degree of methylation of the DNA based on a ratio of unconverted cytosine nucleobases to converted cytosine nucleobases. In some examples, the converted cytosine nucleobases are detected as uracil nucleobases. In some examples, the uracil nucleobases are observed as thymine nucleobases in sequence reads.

In some examples, generating degradation parameters comprises using a Bayesian model.

In some examples, the Bayesian model is based on strand bias or bisulfite conversion or over-conversion. In some examples, (e) comprises using the degradation parameters under the framework of a paired HMM or Naive Bayesian model.

In certain examples, methylation of specific gene markers is assayed for use in informing the classifiers described herein. In various examples, the methylation of a promoter such as APC, IGF2, MGMT, RASSF1A, SEPT9, NDRG4 and BMP3 or combinations thereof is assayed. In various examples methylation of 2, 3, 4, or 5 of these markers is assayed.

2. Differentially Methylated Regions (DMRs)

In one example, the methylation analysis is Differentially Methylated Region (DMR) analysis. DMRs are used to quantitate CpG methylation over regions of the genome. The regions are dynamically assigned by discovery. A number of samples from different classes can be analyzed and regions that are the most differentially methylated between the different classifications can be identified. A subset may be selected to be differentially methylated and used for classification. The number of CpGs captured in the region may be used for the analysis. The regions may tend to be variable size. In one example, a prediscovery process is performed that bundles a number of CpG sites together as a region. In one example, DMRs are used as input features for machine learning methods and models.

3. Haplotype Blocks

In one example, a haplotype block assay is applied to the samples. Identification of methylation haplotype blocks aids in deconvolution of heterogeneous tissue samples and tumor tissue-of-origin mapping from plasma DNA. Tightly coupled CpG sites, known as methylation haplotype blocks (MHBs) can be identified in WGBS data. A metric called methylation haplotype load (MHL) is used to perform tissue-specific methylation analysis at the block level. This method provides informative blocks useful for deconvolution of heterogeneous samples. This method is useful for quantitative estimation of tumor load and tissue-of-origin mapping in circulating cf DNA. In one example, haplotype blocks are used as input features for machine learning methods and models.

cfRNA Assays

In various example, assaying cfRNA may be accomplished using methods such as RNA sequencing, whole transcriptome shotgun sequencing, northern blot, in situ hybridization, hybridization array, serial analysis of gene expression (SAGE), reverse transcription PCR, real-time PCR, real-time reverse transcription PCR, quantitative PCR, digital droplet PCR, or microarray, Nanostring, FISH assays or a combination thereof.

When using small cfRNA (including one-RNA and miRNA) as an analyte, the measured values relate to the abundance for these cfRNAs. Their transcripts are of a certain size, and each transcript is stored, and the number of cfRNAs found for each can be counted. RNA sequences can be aligned to a reference cfRNA database, such as for example a set of sequences corresponding to the known cfRNA in the human transcriptome. Each cfRNA found can be used as its own feature and the plurality of cfRNA found across all samples can become a feature set. In one example, RNA fragments that aligned to annotated cfRNA genomic regions are counted and normalized for depth of sequencing to produce a multi-dimensional vector for a biological sample.

In various example, every measurable cfRNA (cfRNA) is used as a feature. Some samples have feature values that are 0, in which there is no expression detected for that cfRNA.

In an example, every sample is taken, and the reads are aggregated together. For each microRNA found in a sample, there may be numerous aggregate reads found. Note that micro RNA with high expression rank may provide better markers, as a larger absolute change may result in a more reliable signal.

In one example, cfRNA may be detected in a sample with direct detection methods such as nCounter Analysis System® (nanoString, South Lake Union, Wash.) to molecular "barcodes" and microscopic imaging to detect and count up to several hundred unique transcripts in one hybridization reaction.

In various examples, assaying mRNA levels comprises contacting the biological sample with polynucleotide probes capable of specifically hybridizing to mRNA of one or more sequences and thereby forming probe-target hybridization complexes. Hybridization-based RNA assays include, but are not limited to, traditional "direct probe" methods such as, northern blot or in situ hybridization. The methods can be used in a wide variety of formats including, but not limited to, substrate (e.g. membrane or glass) bound methods or array-based approaches. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. Preferred probes are sufficiently long so as to specifically hybridize with the target nucleic acid(s) under stringent conditions. In one example the size range is from about 200 bases to about 1000 bases. In another example for small RNAs, shorter probes are used in the size range from about 20 bases to about 200 bases. Hybridization protocols suitable for use with the methods of the invention are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In situ Hybridization Protocols, Choo, ed., Humana Press, Totowa, N.J. (1994), Pinkel, et al. (1998) Nature Genetics 20: 207-211, and/or Kallioniemi (1992) Proc. Natl Acad Sci USA 89:5321-5325 (1992). In some applications, it is necessary to block the hybridization capacity of repetitive sequences. Thus, in some examples, tRNA, human genomic DNA, or Cot-I DNA is used to block non-specific hybridization.

In various examples, assaying mRNA levels comprises contacting the biological sample with polynucleotide primers capable of specifically hybridizing to mRNAs of single exon genes (SEGs), forming primer-template hybridization complexes, and performing a PCR reaction. In some examples, the polynucleotide primers comprises about 15-45, 20-40, or 25-35 bp sequences that are identical (for forward primers) or complementary (for reverse primers) to sequences of SEGs listed in Table 1. As a non-liming example, the polynucleotide primers for STMN1 (e.g., NM_203401, Homo sapiens stathmin 1 (STMN1), transcript variant 1, mRNA, 1730 bp) can comprise sequences that are identical (for forward primers) or complementary (for reverse primers) to STMN1's bp 1-20, 5-25, 10-30, 15-35, 20-40, 25-45, 30-50, so on and so forth, until the end of STMN, by 1690-1710, 1695-1715, 1700-1720, 1705-1725, 1710-1730. While not listed here exhaustively because of the space, all these polynucleotide primers for STMN1 and other SEGs listed in Table 1 can be used in the systems and methods of this disclosure. In various examples, the polynucleotide primers are labeled with radioisotopes or fluorescent molecules. As the labeled primers emit radio or fluorescent signals, the PCR products containing the labeled primers can be detected and analyzed with a variety of imaging equipment.

Methods of "quantitative" amplification are a variety of suitable methods. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, A Guide to Methods and Applications, Academic Press, Inc. N.Y.). Measurement of DNA copy number at microsatellite loci using quantitative PCR anlaysis is described in Ginzonger, et al. (2000) Cancer Research 60:5405-5409. The known nucleic acid sequence for the genes is sufficient to enable one to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green. Other suitable amplification methods include, but are not limited to, ligase chain reaction (LCR) (see Wu and Wallace (1989) Genomics 4: 560, Landegren, et al. (1988) Science 241:1077, and Barringer et al. (1990) Gene 89: 117), transcription amplification (Kwoh, et al. (1989) Proc. Natl. Acad. Sci. USA 86: 1173), self-sustained sequence replication (Guatelli, et al. (1990) Proc. Nat. Acad. Sci. USA 87: 1874), dot PCR, and linker adapter PCR, etc.

In various examples, the RNA markers associated with cancer are selected from miR-125b-5p, miR-155, miR-200, miR21-5pm, miR-210, miR-221, miR-222 or combinations thereof.

Poly-Amino Acid and Autoantibody Assays

1. Proteins and Peptides

In various examples, proteins are assayed using immunoassay or mass spectrometry. For example, proteins may be measured by liquid chromatography-tandem mass spectrometry (LC-MS/MS).

In various examples, proteins are measured by affinity reagents or immunoassays such as protein arrays, SIMOA (antibodies; Quanterix), ELISA (Abcam), O-link (DNA-conjugated antibodies; O-link Proteomics), or SOMASCAN (aptamers; SomaLogic), Luminex and Meso Scale Discovery.

In one examples, the protein data is normalized by a standard curve. In various examples, each protein is treated as an essentially unique immunoassays, each with a standard curve that can be calculated in various ways. The concentration relationship is typically non-linear. Then the sample may be run. and calculated based on the expected fluorescence concentration in the primary sample.

A number of cancer-associated peptide and protein sequences are known and in various examples are useful in the systems and methods described herein.

In one example, the assay includes a combination of detecting at least 2, 3, 4, 5, 6 or more of the markers.

In various examples, the cancer associated peptide or protein markers are selected from oncofetal antigens (e.g. CEA, AFP), glycoprotein antigens or carbohydrate antigens (e.g. CA125, CA 19.9, CA 15-3), enzymes (e.g. PSA, ALP, NSE), hormone receptors (ER, PR), hormones (b-hCG, calcitonin), or other known biomolecules (VMA, 5HIAA).

In various examples, the cancer associated peptide or protein markers are selected from 1p/19q deletion, HIAA, ACTH, AE1,3, ALK(D5F3), AFP, APC, ATRX, BOB-1, BCL-6, BCR-ABL1, beta-hCG, BF-1, BTAA, BRAF, GCDFP-15, BRCA1, BRCA2, b72.3, c-MET, calcitonin, CALR, calretinin, CA125, CA27.29, CA 19-9, CEA M, CEA P, CEA, CBFB-MYH11, CALA, c-Kit, syndical-1, CD14, CD15, CD19, CD2, CD20, CD200, CD23, CD3, CD30, CD33, CD4, CD45, CD5, CD56, CD57, CD68, CD7, CD79A, CD8, CDK4, CDK2, chromogranin A, creatine kinase isoenzymes, Cox-2, CXCL 13, cyclin D, CK 19, CYFRA 21-1, CK 20, CK5,6, CK 7, CAM 5.2, DCC, des-gamma-carboxy prothrombin, E-cadherin, EGFR T790M, EML4-ALK, ERBB2, ER, ESR1, FAP, gastrin, glucagon, HER-2/neu, SDHB, SDHC, SDHD, HMB45, HNPCC, HVA, beta-hCG, HE4, FBXW7, IDH1 R132H, IGH-CCND1, IGHV, IMP3, LOH, MUM1/IRF4, JAK exon 12, JAK2 V617F, Ki-67, KRAS, MCC, MDM2, MGMT, melan A, MET, metanephrines, MSI, MPL codon 515, Muc-1, Muckiest-4, MEN2, MYC, MYCN, MPO, myf4, myoglobin, myosin, napsin A, neurofilament, NSE P, NMP22, NPM1, NRAS, Oct 2, p16, p21, p53, pancreatic polypeptide, PTH, Pax-5, PAX8, PCA3, PD-L1 28-8, PIK3CA, PTEN, ERCC-1, Ezrin, STK11, PLAP, PML/RARa translocation, PR, proinsulin, prolactin, PSA, PAP, PGP, RAS, ROS1, S-100, S100A2, S100B, SDHB, serotonin, SAMD4, MESOMARK, squamous cell carcinoma antigen, SS18 SYT 18q11, synaptophysin, TIA-1, TdT, thyroglobulin, TNIK, TP53, TTF-1, TNF-alpha, TRAFF2, urovysion, VEGF, or combinations thereof.

In one example, the cancer is colorectal cancer and the CRC-associated markers are selected from APC, BRAF, DPYD, ERBB2, KRAS, NRAS, RET, TP53, UGT1A1 and combinations thereof.

In one example, the cancer is lung cancer and the lung cancer-associated markers are selected from ALK, BRAF, EGFR, ERBB2, KRAS, MET, NRAS, RET, ROS1, TP53 and combinations thereof. In one example, the cancer is breast and the breast cancer-associated markers are selected from BRCA1, BRCA2, ERBB2, TP53 and combinations thereof. In one example, the cancer is gastric cancer and the gastric cancer-associated markers are selected from APC, ERBB2, KRAS, ROS1, TP53 and combinations thereof. In one example, the cancer is glioma and the glioma-associated markers are selected from APCAPC, BRAF, BRCA2, EGFR, ERBB2, ROS1, TP53 and combinations thereof. In one example, the cancer is melanoma and the melanoma-associated markers are selected from BRAF, KIT, NRAS and combinations thereof. In one example, the cancer is ovarian cancer and the ovarian cancer-associated markers are selected from BRAF, BRCA1, BRCA2, ERBB2, KRAS, TP53 and combinations thereof. In one example, the cancer is thyroid cancer and the thyroid cancer-associated markers are selected from BRAF, KRAS, NRAS, RET and combinations thereof. In one example, the cancer is pancreatic cancer and the pancreatic cancer-associated markers are selected from APC, BRCA1, BRCA2, KRAS, TP53 and combinations thereof.

2. Autoantibodies

In another example, antibodies (for example autoantibodies) are detected in the sample and are markers of early tumorigenesis. Autoantibodies are produced early in tumorigenesis and have demonstrated the possibility of being detected from several months or years before clinical symptoms develop. In one example, plasma samples are screened with a mini-APS array (ITSI-Biosciences, Johnstown, Pa., USA) using the protocol described in Somiari R I, et al. (Somiari R I, et al., A low-density antigen array for detection of disease-associated autoantibodies in human plasma. Cancer Genom Proteom 13: 13-19, 2016). Autoantibody markers may be used as input features in machine learning methods or models.

Assays to detect autoantibodies include an immunosorbent assay, such as ELISA or PEA. When detecting autoantibodies, preferably the marker protein or at least an epitope containing fragment thereof, is bound to a solid support, e.g. a microtiter well. The autoantibody of a sample is bound to this antigen or fragment. Bound autoantibodies can be detected by secondary antibodies with a detectable label, e.g. a fluorescence label. The label is then used to generate a signal in dependence of binding to the autoantibodies. The secondary antibody may be an antihuman antibody if the patient is human or be directed against any other organism in dependence of the patient sample to be analyzed. The kit may comprise means for such an assay, such as the solid support and preferably also the secondary antibody. Preferably the secondary antibody binds to the Fc part of the (auto) antibodies of the patient. Also possible is the addition of buffers and washing or rinsing solutions. The solid support may be coated with a blocking compound to avoid unspecific binding.

In one example, autoantibodies are assayed with protein microarrays, or other immunoassay.

Metrics for autoantibody assay that may be used as input features include but are not limited to, adjusted quantile normalized z-scores for all autoantibodies, Binary 0/1, or absence/presence for each autoantibody based on a specific z-score cutoff.

In various examples, autoantibody markers are associated with different subtype or stages of cancer. In various examples, autoantibody markers are directed to, or capable of binding with high affinity to tumor associated antigens. In various examples, the tumor associated antigens are selected from Oncofetal Antigen/immature Laminin Receptor Protein (OFA/iLRP), Alphafetoprotein (AFP), Carcinoembryonic antigen (CEA), CA-125, MUC-1, Epithelial tumor antigen (ETA), Tyrosinase, Melanoma-associated antigen (MAGE), abnormal products of ras, abnormal products of p53, wild-type forms of ras, wild-type forms of p53, or fragments thereof.

In one example ZNF700 was shown to be a capture antigen for the detection of autoantibodies in colorectal cancer. In a panel with other zinc finger proteins, ZNF-specific autoantibody detection allowed the detection of colorectal cancer (O'Reilly et al., 2015). In one example anti-p53 antibodies are assayed as such antibodies may develop months to years before a clinical diagnosis of cancer.

F. Carbohydrates

Assays exist for measuring carbohydrates in a biological sample. Thin layer chromatography (TLC), Gas chromatography (GC) and High-Performance Liquid chromatography (HPLC) may be used to separate and identify carbohydrates. The concentration of carbohydrate may be determined gravimetrically (Munson and Walker method), spectrophotometrically or by titration (e.g. Lane-Eynon method). Also, calorimetric methods of analyzing carbohydrates (Anthrone method, Phenol—Sulfuric Acid method). Other physical methods of characterizing carbohydrates include polarimetry, refractive index, IR, and density. In one example, metrics from carbohydrate assays are used as input features for machine learning methods and models.

III. EXAMPLE SYSTEMS

In some examples, the present disclosure provides systems, methods, or kits that can include data analysis realized in measurement devices (e.g., laboratory instruments, such as a sequencing machine), software code that executes on computing hardware. The software can be stored in memory and execute on one or more hardware processors. The software can be organized into routines or packages that can communicate with each other. A module can comprise one or more devices/computers, and potentially one or more software routines/packages that execute on the one or more devices/computers. For example, an analysis application or system can include at least a data receiving module, a data pre-processing module, a data analysis module (which can operate on one or more types of genomic data), a data interpretation module, or a data visualization module.

The data receiving module can connect laboratory hardware or instrumentation with computer systems that process laboratory data. The data pre-processing module can perform operations on the data in preparation for analysis. Examples of operations that can be applied to the data in the pre-processing module include affine transformations, denoising operations, data cleaning, reformatting, or subsampling. The data analysis module, which can be specialized for analyzing genomic data from one or more genomic materials, can, for example, take assembled genomic sequences and perform probabilistic and statistical analysis to identify abnormal patterns related to a disease, pathology, state, risk, condition, or phenotype. The data interpretation module can use analysis methods, for example, drawn from statistics, mathematics, or biology, to support understanding of the relation between the identified abnormal patterns and health conditions, functional states, prognoses, or risks. The data analysis module and/or the data interpretation module can include one or more machine learning models, which can be implemented in hardware, e.g., which executes software that embodies a machine learning model. The data visualization module can use methods of mathematical modeling, computer graphics, or rendering to create visual representations of data that can facilitate the understanding or interpretation of results. The present disclosure provides computer systems that are programmed to implement methods of the disclosure.

In some examples, the methods disclosed herein can include computational analysis on nucleic acid sequencing data of samples from an individual or from a plurality of individuals. An analysis can identify a variant inferred from sequence data to identify sequence variants based on probabilistic modeling, statistical modeling, mechanistic modeling, network modeling, or statistical inferences. Non-limiting examples of analysis methods include principal component analysis, autoencoders, singular value decomposition, Fourier bases, wavelets, discriminant analysis, regression, support vector machines, tree-based methods, networks, matrix factorization, and clustering. Non-limiting examples of variants include a germline variation or a somatic mutation. In some examples, a variant can refer to an already-known variant. The already-known variant can be scientifically confirmed or reported in literature. In some examples, a variant can refer to a putative variant associated with a biological change. A biological change can be known or unknown. In some examples, a putative variant can be reported in literature, but not yet biologically confirmed. Alternatively, a putative variant is never reported in literature, but can be inferred based on a computational analysis disclosed herein. In some examples, germline variants can refer to nucleic acids that induce natural or normal variations.

Natural or normal variations can include, for example, skin color, hair color, and normal weight. In some examples, somatic mutations can refer to nucleic acids that induce acquired or abnormal variations. Acquired or abnormal variations can include, for example, cancer, obesity, conditions, symptoms, diseases, and disorders. In some examples, the analysis can include distinguishing between germline variants. Germline variants can include, for example, private variants and somatic mutations. In some examples, the identified variants can be used by clinicians or other health professionals to improve health care methodologies, accuracy of diagnoses, and cost reduction.

FIG. 1 shows a system 100 that is programmed or otherwise configured to perform methods described herein. As various examples, system 100 can process and/or assay a sample, perform sequencing analysis, measure sets of values representative of classes of molecules, identify sets of features and feature vectors from assay data, process feature vectors using a machine learning model to obtain output classifications, and train a machine learning model (e.g., iteratively search for optimal values of parameters of the machine learning model). System 100 includes a computer system 101 and one or more measurement devices 151, 152, or 153 that can measure various analytes. As shown, measurements devices 151-153 measure respective analytes 1-3.

The computer system 101 can regulate various aspects of sample processing and assaying of the present disclosure, such as, for example, activation of a valve or pump to transfer a reagent or sample from one chamber to another or application of heat to a sample (e.g., during an amplification reaction), other aspects of processing and/or assaying a sample, performing sequencing analysis, measuring sets of values representative of classes of molecules, identifying sets of features and feature vectors from assay data, processing feature vectors using a machine learning model to obtain output classifications, and training a machine learning model (e.g., iteratively searching for optimal values of parameters of the machine learning model). The computer system 101 can be an electronic device of a user or a computer system that is remotely located with respect to the electronic device.

The computer system 101 includes a central processing unit (CPU, also "processor" and "computer processor" herein) 105, which can be a single core or multi core processor, or a plurality of processors for parallel processing; memory 110 (e.g., cache, random-access memory, read-only memory, flash memory, or other memory); electronic storage unit 115 (e.g., hard disk), communication interface 120 (e.g., network adapter) for communicating with one or more other systems; and peripheral devices 125, such as adapters for cache, other memory, data storage and/or electronic display. The memory 110, storage unit 115, interface 120 and peripheral devices 125 may be in communication with the CPU 105 through a communication bus (solid lines), such as a motherboard. The storage unit 115 can be a data storage unit (or data repository) for storing data. One or more analyte feature inputs can be entered from the one or more measurement devices 151, 152, or 153. Example analytes and measurement devices are described herein.

The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing over the network 130 ("the cloud") to perform various aspects of analysis, calculation, and generation of the present disclosure, such as, for example, activation of a valve or pump to transfer a reagent or sample from one chamber to another or application of heat to a sample (e.g., during an amplification reaction), other aspects of processing and/or assaying a sample, performing sequencing analysis, measuring sets of values representative of classes of molecules, identifying sets of features and feature vectors from assay data, processing feature vectors using a machine learning model to obtain output classifications, and training a machine learning model (e.g., iteratively searching for optimal values of parameters of the machine learning model). Such cloud computing may be provided by cloud computing platforms such as, for example, Amazon Web Services (AWS), Microsoft Azure, Google Cloud Platform, and IBM cloud. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions can be stored in a memory location, such as the memory 110. The instructions can be directed to the CPU 105, which can subsequently program or otherwise configure the CPU 105 to implement methods of the present disclosure. The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine-readable code can be provided in the form of software. During use, the code can be executed by the CPU 105. In some cases, the code can be retrieved from the storage unit 115 and stored on the memory 110 for ready access by the CPU 105. In some situations, the electronic storage unit 115 can be precluded, and machine-executable instructions are stored on memory 110.

The code can be pre-compiled and configured for use with a machine having a processer adapted to execute the code or can be compiled during runtime. The code can be supplied in a programming language that can be selected to enable the code to execute in a pre-compiled or as—compiled fashion.

Aspects of the systems and methods provided herein, such as the computer system 101, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium, or physical transmission medium. Non-volatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system.

Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media can be involved in carrying one or more sequences of one or more instructions to a processor for execution.

The computer system 101 can include or be in communication with an electronic display 135 that comprises a user interface (UI) 140 for providing, for example, a current stage of processing or assaying of a sample (e.g., a particular step, such as a lysis step, or sequencing step that is being performed). Inputs are received by the computer system from one or more measurement devices 151, 152 or 153. Examples of UIs include, without limitation, a graphical user interface (GUI) and web-based user interface. The algorithm can, for example, process and/or assay a sample, perform sequencing analysis, measure sets of values representative of classes of molecules, identify sets of features and feature vectors from assay data, process feature vectors using a machine learning model to obtain output classifications, and train a machine learning model (e.g., iteratively search for optimal values of parameters of the machine learning model).

IV. MACHINE LEARNING TOOLS

To determine a set of assays to be used in an experimental test, machine learning systems can be leveraged to assess the effectiveness of a given dataset generated from a given assay or plurality of assays and run on a given analyte to add to the overall prediction accuracy of classification. In this manner, a new biological/health/diagnostics question can be tackled to design a new assay.

Machine learning can be used to reduce a set of data generated from all (primary sample/analytes/test) combinations into an optimal predictive set of features, e.g., which satisfy specified criteria. In various examples statistical learning, and/or regression analysis can be applied. Simple to complex and small to large models making a variety of modeling assumptions can be applied to the data in a cross-validation paradigm. Simple to complex includes considerations of linearity to non-linearity and non-hierarchical to hierarchical representations of the features. Small to large models includes considerations of the size of basis vector space to project the data onto as well as the number of interactions between features that are included in the modelling process.

Machine learning techniques can be used to assess the commercial testing modalities most optimal for cost/performance/commercial reach as defined in the initial question. A threshold check can be performed: If the method applied to a hold-out dataset that was not used in cross validation surpasses the initialized constraints, then the assay is locked, and production initiated. For example, a threshold for assay performance may include a desired minimum accuracy, positive predictive value (PPV), negative predictive value (NPV), clinical sensitivity, clinical specificity, area under the curve (AUC), or a combination thereof. For example, a desired minimum accuracy, PPV, NPV, clinical sensitivity, clinical specificity, or combination thereof may be at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%. As another example, a desired minimum AUC may be at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, or at least about 0.99. A subset of assays may be selected from a set of assays to be performed on a given sample based on the total cost of performing the subset of assays, subject to the threshold for assay performance, such as desired minimum accuracy, positive predictive value (PPV), negative predictive value (NPV), clinical sensitivity, clinical specificity, area under the curve (AUC), and a combination thereof. If the thresholds are not met, then the assay engineering procedure can loop back to either the constraint setting for possible relaxation or to the wet lab to change the parameters in which data was acquired. Given the clinical question, biological constraints, budget, lab machines, etc., can constrain the problem.

In various examples, the computer processing of a machine learning technique can include method(s) of statistics, mathematics, biology, or any combination thereof. In various examples, any one of the computer processing methods can include a dimension reduction method, logistic regression, dimension reduction, principal component analysis, autoencoders, singular value decomposition, Fourier bases, singular value decomposition, wavelets, discriminant analysis, support vector machine, tree-based methods, random forest, gradient boost tree, logistic regression, matrix factorization, network clustering, statistical testing and neural network.

In various examples, the computer processing of a machine learning technique can include logistic regression, multiple linear regression (MLR), dimension reduction, partial least squares (PLS) regression, principal component regression, autoencoders, variational autoencoders, singular value decomposition, Fourier bases, wavelets, discriminant analysis, support vector machine, decision tree, classification and regression trees (CART), tree-based methods, random forest, gradient boost tree, logistic regression, matrix factorization, multidimensional scaling (MDS), dimensionality reduction methods, t-distributed stochastic neighbor embedding (t-SNE), multilayer perceptron (MLP), network clustering, neuro-fuzzy, neural networks (shallow and deep), artificial neural networks, Pearson product-moment correlation coefficient, Spearman's rank correlation coefficient, Kendall tau rank correlation coefficient, or any combination thereof.

In some examples, the computer processing method is a supervised machine learning method including, for example, a regression, support vector machine, tree-based method, and neural network. In some examples, the computer processing method is an unsupervised machine learning method including, for example, clustering, network, principal component analysis, and matrix factorization.

For supervised learning, training samples (e.g., in thousands) can include measured data (e.g., of various analytes) and known labels, which may be determined via other time-consuming processes, such as imaging of the subject and analysis by a trained practitioner. Example labels can include classification of a subject, e.g., discrete classification of whether a subject has cancer or not or continuous classifications providing a probability (e.g., a risk or a score) of a discrete value. A learning module can optimize parameters of a model such that a quality metric (e.g., accuracy of prediction to known label) is achieved with one or more specified criteria. Determining a quality metric can be implemented for any arbitrary function including the set of all risk, loss, utility, and decision functions. A gradient can be used in conjunction with a learning step (e.g., a measure of how much the parameters of the model should be updated for a given time step of the optimization process).

As described above, examples can be used for a variety of purposes. For example, plasma (or other sample) can be collected from subjects symptomatic with a condition (e.g., known to have the condition) and healthy subjects. Genetic data (e.g., cfDNA) can be acquired analyzed to obtain a variety of different features, which can include features based on a genome wide analysis. These features can form a feature space that is searched, stretched, rotated, translated, and linearly or non-linearly transformed to generate an accurate machine learning model, which can differentiate between healthy subjects and subjects with the condition (e.g., identify a disease or non-disease status of a subject). Output derived from this data and model (which may include probabilities of the condition, stages (levels) of the condition, or other values), can be used to generate another model that can be used to recommend further procedures, e.g., recommend a biopsy or keep monitoring the subject condition.

V. SELECTION OF INPUT FEATURES

As described above, a large set of features can be generated to provide a feature space from which a feature vector can be determined. This feature vector from each of a set of training samples can then be used for training a current version of the machine learning model. The types of features used can depend on the types of analytes used.

Examples of features can include variables related to structural variations (SVs), such as a copy number variation and translocations; fusions; mutations (e.g., SNPs or other single nucleotide variations (SNVs), or slightly larger sequence variations); telomere attrition; and nucleosome occupancy and distribution. These features can be calculated genomewide. Example classes (types) of features are provided below. When genetic sequence data is obtained from at least one of the analytes, example features can include aligned features (e.g., a comparison with one or more reference genomes) and non-aligned features. Example aligned features can include sequence variations and sequence counts in a genomic window. Example non-aligned features can include kmers from sequence reads and biological derived information from the reads.

In some examples, at least one of the features is a genetic sequence feature. As examples, a genetic sequence feature can be selected from a methylation status of the DNA, a single nucleotide polymorphism, a copy number variation, an indel, and a structural variant. In various examples, the methylation status can be used to determine nucleosomal occupancy and/or to determine a methylation density in a CpG island of the DNA or the barcoded DNA.

Ideally, the feature selection can select features that are invariant or have low variation within samples that have a same classification (e.g., have a same probability or associated risk of particular phenotype), but where such features vary among groups of samples that have different classifications. Procedures can be implemented to identify what features appear to be the most invariant within a particular population (e.g., one that shares a classification or lease has a similar classification when the classification is a real number). Procedures can also identify features that vary among populations. For example, read counts of sequence reads that partially or entirely overlap with various genomic regions of a genome can be analyzed to determine how they change within a population, and such read counts can be compared to those of separate populations (e.g., subjects known to have a disease or disorder or who are asymptomatic for a disease or disorder).

Various statistical metrics can be used to analyze the variation in a feature across populations for the purpose of selecting features that may be predictive of a classification, and thus may be advantageous for training. Further examples can also select a particular type of model based on the analysis of the feature space, and the selected features to be used in the feature vector.

A. Creation of Feature Vector

The feature vector can be created as any data structure that can be reproduced for each training sample, so that corresponding data appears in the same place in the data structure across the training samples. For example, the feature vector can be associated with indices, where a particular value exists at each index. As explained above, a matrix can be stored at a particular index of the feature vector, and the matrix elements can have further sub-indices. Other elements of the feature vector can be generated from summary statistics of such a matrix.

As another example, a single element of a feature vector can correspond to the set of sequence reads across a set of windows of a genome. Thus, an element or the feature vector can itself be a vector. Such counts of reads can be of all reads or certain group (class) of reads, e.g., reads having a particular sequence complexity or entropy. A set of sequence reads can be filtered or normalized, such as for GC bias and/or mappability bias.

In some examples, an element of the feature vector can be the result of a concatenation of multiple features. This can differ from other examples where an element is itself an array (e.g., a vector or matrix) in that the concatenation value can be treated as a single value, as opposed to a collection of values. Thus, features can be concatenated, merged, and combined to be used as engineered features or feature representations for the machine learning model.

Multiple combinations and approaches to merging the features can be performed. For example, when different measures are counted over the same window (bin), ratios between those bins, such as inversions divided by deletions, may be a useful feature. Further, ratios of bins that are proximal in space and whose merging may convey biological information, such as dividing a transcript start site count by a gene body count, can also serve as a useful feature.

Features can also be engineered, e.g., by setting up a multi-task unsupervised learning problem where the joint probability of all feature vectors given a set of parameters and latent vectors is maximized. The latent vectors of this probabilistic procedure often serve as excellent features when trying to predict phenotype (or other classifications) from biological sequence data.

B. Weights Used in Training

Weights can be applied to features when they are added to a feature vector. Such weights can be based on elements within the feature vector, or specific values within an element of the feature vector. For example, every region (window) in the genome can have a different weight. Some windows can have a weight of zero meaning that the window does not contribute to classification. Other windows can have larger weights, e.g., between 0 and 1. Thus, a weighting mask can be applied to the values for the features used to create the feature vector, e.g., different values of the mask to be applied to features for count, sequence complexity, frequency, sequence similarity in the population, etc.

In some examples, the training process can learn the weights to be applied. In this manner, one does not need to know any prior knowledge or biological insight into the data before the training process. The weights initially applied to features can be considered as part of a first layer of the model. Once a model has been trained and satisfies one or more specified criteria, (e.g., a desired minimum accuracy, positive predictive value (PPV), negative predictive value (NPV), clinical sensitivity, clinical specificity, area under the curve (AUC), or a combination thereof), the model can be used in a production run to classify a new sample. In such production runs, any features that have an initial weight of zero do not need to be calculated. Thus, the size of the feature vector can be reduced from training to production. In some examples, principal component analysis (PCA) may be used to train the machine learning model. For the machine learning model, in various examples, each principal component can be a feature, or all the principal components concatenated together can be a feature. Based on the outputs of the PCA for each of these for analytes, a model can be created. Models can be updated based on the raw features before PCA (not necessarily the PCA output). In various approaches, the raw features can be used every single bit of data; a random selection of each batch of data can be taken and run through; a random forest can be performed; or other trees or random data sets can be created. Features may also be the measured values themselves, as opposed to the results of any dimensionality reduction, but both can also be used.

C. Selecting Features between Training Iterations

As mentioned above, a training process may not produce a model that satisfies desired criteria. At such a point, feature selection may be performed again. The feature space may be quite large (e.g., 35 or 100 thousand) so the number of different possible permutations of difference features to use in the feature vector can be enormous. Certain features (potentially many) may belong to a same class (type), e.g., read counts in windows, ratios of counts from different regions, variants at different sites, etc. Further, the concatenation of features into a single element can further increase the number of permutations.

The new set of features can be selected based on information from the previous iteration of the training process. For example, weights associated with the features can be analyzed. These weights can be used to determine whether a feature should be kept or discarded. A feature associated with a weight or average weight greater than a threshold can be kept. A feature associated with a weight or average weight less than a threshold (same or different than for keeping) can be removed.

The selection of features and creation of a feature vector for training the model can repeat until one or more desired criteria are satisfied, e.g., a suitable quality metric for the model (e.g., a desired minimum accuracy, positive predictive value (PPV), negative predictive value (NPV), clinical sensitivity, clinical specificity, area under the curve (AUC), or a combination thereof). Other criteria may be selecting a model with the best quality metric out of a set of models generated with different feature vectors. Accordingly, a model with the best statistical performance and generalizability in the ability to detect a phenotype from the data can be chosen. Further, a set of training samples can be used for training various models for different purposes, e.g., a classification of a condition (e.g., an individual having cancer or not having cancer), of a treatment (e.g., an individual having treatment response or not having treatment response), of a prognosis (e.g., an individual having a good prognosis or not having a good prognosis), etc. A good cancer prognosis can correspond to when the individual is has the potential for symptom resolution or improvement or is expected to recover after treatment (e.g., a tumor is shrinking, or cancer is not expected to return) as used herein refers to prognosis associated with disease forms that are less aggressive and/or more treatable. For example, less aggressive more treatable forms of cancer have higher expected survival than more aggressive and/or less treatable forms. In various examples, a good prognosis refers to a tumor staying the same size or decreasing in response to treatment, remission or improved overall survival.

Similarly, a poor prognosis (or an individual not having a good prognosis) as used herein refers to prognosis associated with disease forms that are more aggressive and/or less treatable. For example, aggressive less treatable forms have poorer survival than less aggressive and/or treatable forms. In various examples, a poor prognosis refers to a tumor staying the same size or increasing, or the cancer returning or not decreasing.

VI. USE OF MACHINE LEARNING MODEL FOR MULTI-ANALYTE ASSAYS

Figure 2:
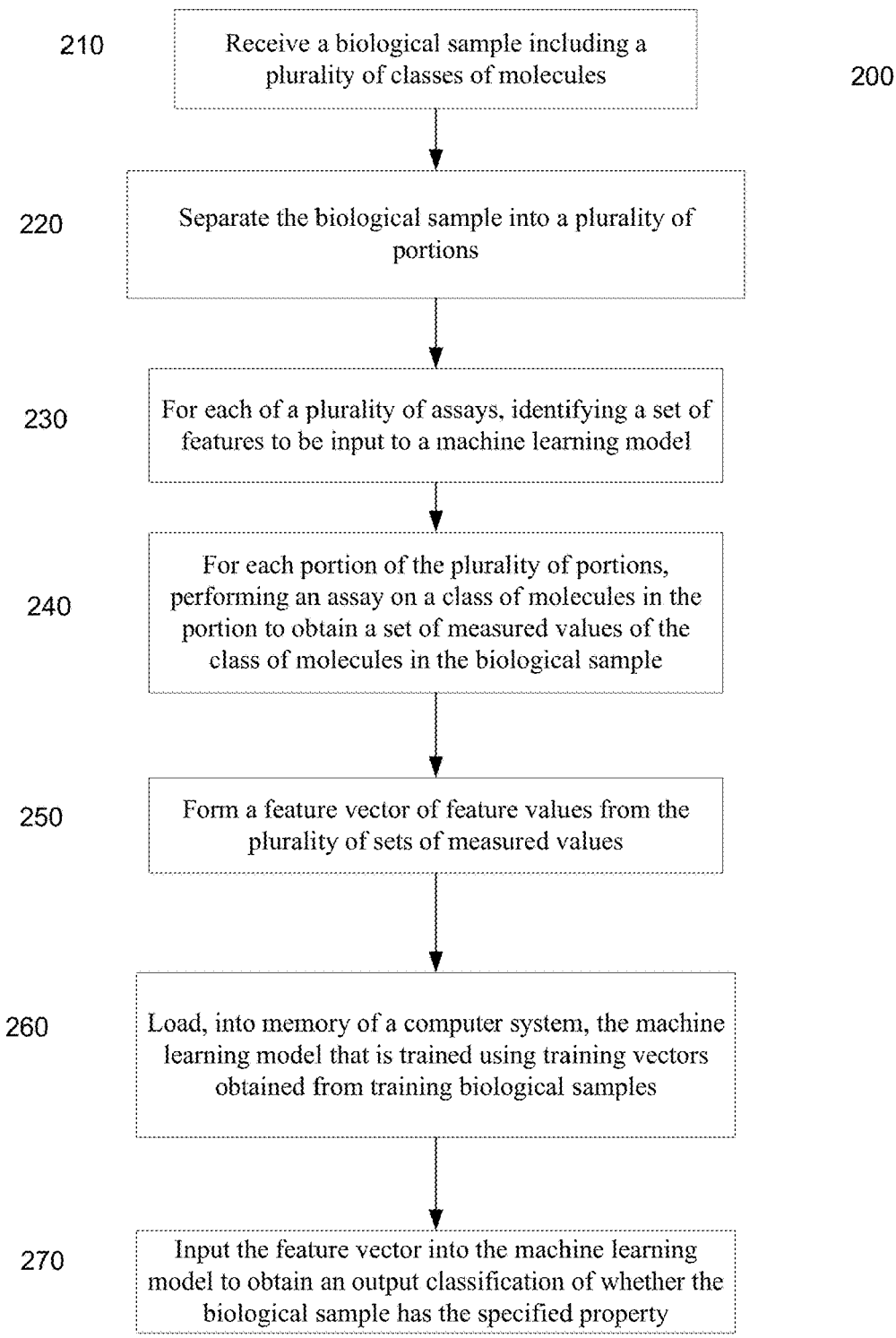
FIG. 2 is a flowchart illustrating a method for analyzing a biological sample.

FIG. 2 illustrates an example method 200 for analyzing a biological sample, according to an example. Method 200 may be implemented by any of the systems described herein. In one example, the method uses a machine learning model capable of class distinction in a population of individuals. In various examples, this model capable of class distinction (e.g. a classifier) is used to distinguish between health and disease populations, treatment responders/non-responders and stage of disease to provide information useful to guide treatment decisions.

At block 210, the system receives the biological sample including a plurality of classes of molecules. Example biological samples are described herein, e.g., blood, plasma, or urine. Separate samples can also be received. A single sample (e.g., of blood) may be collected into multiple containers, e.g., a set of vials.

At block 220, the system separates the biological sample into a plurality of portions, each of the plurality of classes of molecules being in one of the plurality of portions. The sample could already be a fraction of a larger sample, e.g., plasma obtained from a blood sample. And, the portions can then be obtained from such a fraction. In some examples, a portion can include multiple classes of molecules. An assay on a portion might only test one class of molecules, and thus a class of molecules in one portion might not get measured but can be measured in a different portion. As examples, measurement devices 151, 152 and 153 can perform respective assays on different portions of the sample. Computer system 101 can analyze measured data from the various assays.

At block 230, for each of a plurality of assays, the system identifies a set of features to be input to a machine learning model. The set of features can correspond to properties of one of the plurality of classes of molecules in the biological sample. The definition of the set of features to use can be stored in memory of a computer system. The set of features can be previously identified, e.g., using machine learning techniques described herein. When a particular assay is to be used, the corresponding set of features can be retrieved from memory. Each assay can have an identifier that is used to retrieve the corresponding set of features, along with any particular software code for creating the features. Such code can be modular so that section can be updated independently, with a final collection of features being defined based on the assays used and the stored definitions for the various sets of features.

At block 240, for each portion of the plurality of portions, the system performs an assay on a class of molecules in the portion to obtain a set of measured values of the class of molecules in the biological sample. The system can obtain a plurality of sets of measured values for the biological sample from the plurality of assays. Depending on which assays are specified (e.g., via an input file or measurement configuration specified by a user), a particular set of measurement devices can be used to provide particular measurements to the computer system.

At block 250, the system forms a feature vector of feature values from the plurality of sets of measured values. Each feature value can correspond to a feature and including one or more measured values. The feature vector can include at least one feature value formed using each set of the plurality of sets of measured values. Thus, the feature vector can be determined using values measured from each of the assays on the different classes of molecules. Other details for the formation of a feature vector and extraction of a feature vector are described in other section but apply to all instances for the formation of a feature vector.

The features for a given analyte may be determined using a principal component analysis. For the machine learning model, in various examples, each principal component can be a feature, or all the principal components concatenated together can be a feature. Based on the outputs of the PCA for each of these for analytes, a model can be created. In other examples, models can also be updated based on the raw features before any PCA, and thus the features may not necessarily include any PCA output. In various approaches, the raw features can include every single bit of data; a random selection of each batch of data for an analyte can be used; a random forest can be performed; or other trees or random data sets can be created. Features may also be the measured values themselves, as opposed to the results of any dimensionality reduction (e.g., PCA), but both can also be used.

At block 260, the system loads, into memory of a computer system, the machine learning model that is trained using training vectors obtained from training biological samples. The training samples can have the same measurements performed, and thus the same feature vector can be generated. The training samples can be selected based on the desired classification, e.g., as indicated by a clinical question. Different subsets can have different properties, e.g., as determined by labels assigned to them. A first subset of the training biological samples can be identified as having a specified property and a second subset of the training biological samples can be identified as not having the specified property. Examples of properties are various diseased or disorders but could be intermediate classifications or measurements as well. Examples of such properties include existence of cancer or a stage of cancer, or a prognosis of cancer, e.g., for treatment of the cancer. As examples, the cancer can be colorectal cancer, liver cancer, lung cancer, pancreatic cancer or breast cancer.

At block 270, the system inputs the feature vector into the machine learning model to obtain an output classification of whether the biological sample has the specified property. The classification can be provided in various ways, e.g., as a probability for each of one or more classifications. For instance, the existence of cancer can be assigned a probability and output. Similarly, the absence of cancer can be assigned a probability and output. The classification with the highest probability can be used, e.g., subject to one or more criteria, such one classification having a sufficiently higher probability than a second highest classification. The difference can be required to be above a threshold. If the one or more criteria are not satisfied, the output classification can be indeterminate. Accordingly, the output classification can include a detection value (e.g., a probability) that indicates the presence of cancer in the individual. And, the machine learning model can further output another classification that provides a probability of the biological sample not having cancer.

After such a classification, treatment may be provided to the subject. Example treatment regimens can include surgical intervention, chemotherapy with a given drug or drug combination, and/or radiation therapy.

VII. CLASSIFIER GENERATION

The methods and systems of the present disclosure may relate to identifying a set of informative features (e.g., genomic loci) that correlate with a class distinction between samples, comprising sorting features (e.g., genes) by degree to which their presence in the samples correlate with a class distinction, and determining whether said correlation is stronger than expected by chance. Machine learning techniques can implicitly use such informative features from the input feature vector. In one example, the class distinction is a known class, and in one example the class distinction is a disease class distinction. In particular, the disease class distinction can be a cancer class distinction. In various examples, the cancer is colorectal cancer, lung cancer, liver cancer, or pancreatic cancer.

Some examples of the present disclosure can also be directed to ascertaining at least one previously unknown class (e.g., a disease class, proliferative disease class, cancer stage or treatment response) into which at least one sample to be tested is classified, wherein the sample is obtained from an individual. In an aspect, the disclosure provides a classifier capable of distinguishing individuals within a population of individuals. The classifier may be part of a machine learning model. The machine learning model may receive as inputs a set of features corresponding to properties of each of a plurality of classes of molecules of a biological sample. A plurality of classes of molecules in the biological sample may be assayed to be obtained a plurality of sets of measured values representative of the plurality of classes of molecules. A set of features corresponding to properties of each of the plurality of classes of molecules may be identified and to be input to a machine learning model. A feature vector of feature values from each of the plurality of sets of measured values may be generated, such that each feature value corresponds to a feature of the set of features and includes one or more measured values. The feature vector may include at least one feature value obtained using each set of the plurality of sets of measured values. The machine learning model comprising the classifier may be loaded into computer memory. The machine learning model may be trained using training vectors obtained from training biological samples, such that a first subset of the training biological samples is identified as having a specified property and a second subset of the training biological samples is identified as not having the specified property. The feature vector may be inputted into the machine learning model to obtain an output classification of whether the biological sample has the specified property, thereby distinguishing a population of individuals having the specified property. As an example, the specified property is whether an individual has cancer or not.

In one aspect, the disclosure provides a system for classifying subjects based on multi-analyte analysis of a biological sample comprising: (a) a computer-readable medium comprising the classifier operable to classify the subjects based on the multi-analyte analysis; and (b) one or more processors for executing instructions stored on the computer-readable medium.

In one example, the system comprises a classification circuit that is configured as a machine learning classifier selected from a linear discriminant analysis (LDA) classifier, a quadratic discriminant analysis (QDA) classifier, a support vector machine (SVM) classifier, a random forest (RF) classifier, a linear kernel support vector machine classifier, a first or second order polynomial kernel support vector machine classifier, a ridge regression classifier, an elastic net algorithm classifier, a sequential minimal optimization algorithm classifier, a naive Bayes algorithm classifier, and a NMF predictor algorithm classifier.

In one example, the informative features (e.g., genomic loci) of biomarkers in a cancer sample (e.g., tissue) are assayed to form a profile. The threshold of the linear classifier scalar output is optimized to maximize accuracy, positive predictive value (PPV), negative predictive value (NPV), clinical sensitivity, clinical specificity, area under the curve (AUC), or a combination thereof, such as the sum of sensitivity and specificity under cross-validation as observed within the training dataset.

The overall multi-analyte assay data (e.g., expression data or sequence data) for a given sample may be normalized using methods known to those skilled in the art in order to correct for differing amounts of starting material, varying efficiencies of the extraction and amplification reactions, etc. Using a linear classifier on the normalized data to make a diagnostic or prognostic call (e.g. responsiveness or resistance to agent) effectively means to split the data space, e.g. all possible combinations of expression values for all features (e.g. genes) in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which may automatically define a threshold value for this remaining biomarker where the decision may change from, for example, responsiveness or resistance to a therapeutic agent. Expression values above this dynamic threshold may then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, e.g. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

In one example, the biomarker profile (e.g. expression profile) of a patient biological (e.g. tissue) sample is evaluated by a linear classifier. As used herein, a linear classifier refers to a weighted sum of the individual biomarker features into a compound decision score ("decision function"). The decision score is then compared to a pre-defined cut-off score threshold, corresponding to a certain set-point in terms of accuracy, positive predictive value (PPV), negative predictive value (NPV), clinical sensitivity, clinical specificity, area under the curve (AUC), or a combination thereof, which indicates if a sample is above the score threshold (decision function positive) or below (decision function negative). Effectively, this means that the data space, e.g. the set of all possible combinations of biomarker feature values, is split into two mutually exclusive halves corresponding to different clinical classifications or predictions, e.g. one corresponding to responsiveness to a therapeutic agent and the other to resistance.

The interpretation of this quantity, i.e. the cut-off threshold responsiveness or resistance to a therapeutic agent, is derived in the development phase ("training") from a set of patients with known outcome. The corresponding weights and the responsiveness/resistance cut-off threshold for the decision score are fixed a priori from training data by methods known to those skilled in the art. In one example, Partial Least Squares Discriminant Analysis (PLS-DA) is used for determining the weights. (L. Stale, S. Wold, J. Chemom. 1 (1987) 185-196; D. V. Nguyen, D. M. Rocke, Bioinformatics 18 (2002) 39-50). Other methods for performing the classification, known to those skilled in the art, may also be with the methods described herein when applied to the assay data (e.g. transcripts) of a cancer classifier.

Different methods can be used to convert quantitative assay data measured on these biomarkers into a prognosis or other predictive use. These methods include, but not limited to methods from the fields of pattern recognition (Duda et al. Pattern Classification, 2.sup.nd ed., John Wiley, New York 2001), machine learning (Scholkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, N.Y. 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998).

In a training step, a set of patient samples for both responsiveness and resistance cases (e.g., including patients showing responsiveness to a treatment, patients not showing responsiveness to a treatment, patients showing resistance to a treatment, and/or patients not showing resistance to a treatment) are measured and the prediction method is optimized using the inherent information from this training data to optimally predict the training set or a future sample set. In this training step, the method is trained or parameterized to predict from a specific assay data profile to a specific predictive call. Suitable transformation or pre-processing steps may be performed with the measured data before it is subjected to the classification (e.g., diagnostic or prognostic) method or algorithm.

A weighted sum of the pre-processed feature (e.g., intensity) values for each of the assay data (e.g., transcript) is formed and compared with a threshold value optimized on the training set (Duda et al. Pattern Classification, $2^{nd}$ ed., John Wiley, New York 2001). The weights can be derived by a multitude of linear classification methods, including but not limited to Partial Least Squares (PLS, (Nguyen et al., 2002, Bioinformatics 18 (2002) 39-50)) or Support Vector Machines (SVM, (Scholkopf et al. Learning with Kernels, MIT Press, Cambridge 2002)).

The data may be transformed non-linearly before applying a weighted sum as described above. This non-linear transformation may include increasing the dimensionality of the data. The non-linear transformation and weighted summation may also be performed implicitly, e.g. through the use of a kernel function. (Scholkopf et al. Learning with Kernels, MIT Press, Cambridge 2002).

In another example, decision trees (Hastie et al., The Elements of Statistical Learning, Springer, New York 2001) or random forests (Breiman, Random Forests, Machine Learning 45:5 2001) are used to make a classification (e.g., diagnostic or prognostic call) from the measured values (e.g., intensity data) for the assay data (e.g., transcript set) or their products.

In another example, neural networks (Bishop, Neural Networks for Pattern Recognition, Clarendon Press, Oxford 1995) are used to make a classification (e.g., diagnostic or prognostic call) from the measured values (e.g., intensity data) for the assay data (e.g., transcript set) or their products.

In another example, discriminant analysis (Duda et al., Pattern Classification, 2nd ed., John Wiley, New York 2001), comprising methods such as linear, diagonal linear, quadratic and logistic discriminant analysis, is used to make a classification (e.g., diagnostic or prognostic call) from the measured values (e.g., intensity data) for the assay data (e.g., transcript set) or their products.

In another example, Prediction Analysis for Microarrays (PAM, (Tibshirani et al., 2002, Proc. Natl. Acad. Sci. USA 99:6567-6572)) is used to make a classification (e.g., diagnostic or prognostic call) from the measured values (e.g., intensity data) for the assay data (e.g., transcript set) or their products.

In another example, Soft Independent Modelling of Class Analogy (SIMCA, (Wold, 1976, Pattern Recogn. 8:127-139)) is used to make a predictive call from the measured intensity data for the transcript set or their products.

Various types of signals can be processed and classifications (e.g., phenotypes or probabilities of phenotypes) inferred using a machine learning model. One type of classifications corresponds to conditions (e.g., diseases and/or stages or severity of diseases) of the subject. Thus, in some example, the model can classify a subject based on the type of conditions on which the model was trained. Such conditions may correspond to the labels, or a collection of categorical variables, of the training samples. As mentioned above, these labels can be determined through more intensive measurements or of patients at later stages of a condition, which made the condition more easily identified.

Such a model created using training samples having the prescribed conditions can provide certain advantages. Advantages of the technologies include: (a) advance screening of diseases or disorders (e.g., age-associated diseases before onset of symptoms or reliable detection via alternative methods, where applications may include but not limited to cancer, diabetes, Alzheimer's disease and other diseases that may have genetic signatures, e.g., somatic genetic signatures; (b) diagnostic confirmation or supplementary evidence to existing diagnostic methods (e.g., cancer biopsy/medical imaging scans); and (c) treatment and post-treatment monitoring for prognosis report, treatment response, treatment resistance, and recurrence detection.

In various examples, a biological condition can comprise a disease or disorder (e.g., an age-associated disease, a state in aging, a treatment effect, a drug effect, a surgical effect, a measureable trait, or a biological state after a lifestyle modification (e.g., a diet change, a smoking change, a sleeping pattern change, etc.). In some examples, a biological condition could be unknown, where the classification can be determined as the absence of another condition. Thus, the machine learning model can infer an unknown biological condition or interpret the unknown biological condition.

In some examples, there may be a gradual change of a classification, and thus there can be many levels of classification of a condition, e.g., corresponding to real numbers. Accordingly, the classification may be a probability, a risk, or a measure as to a subject having a condition or other biological state. Each of such values can correspond to a different classification.

In some examples, the classification can include recommendations, which may be based on a previous classification of a condition. The previous classification can be performed by a separate model that uses the same training data (although potentially different input features), or an earlier sub-model that is part of a larger model that includes various classifications, where an output classification of one model can be used as input to another model. For example, if a subject is classified as having a high risk of myocardial infarction, a model can recommend a change in lifestyle. e.g. exercise regularly, consume heathy dietary, maintain healthy weight, quit smoking, and lower LDL cholesterol. As another example, a model can recommend a clinical test for the subject to confirm a classification (e.g., diagnostic or prognostic call). This clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof. Such recommended actions can be performed as part of methods and system described herein.

Accordingly, examples can provide many different models, each one directed to a different type of classification. As another example, an initial model can determine whether the subject has cancer or not. A further model can determine whether the subject has a particular stage of the particular cancer or not. A further model can determine whether the subject has a particular cancer or not. A further model can classify a predicted response of a subject to a particular surgery, chemotherapy (e.g., drug), radiotherapy, immunotherapy, or other type of treatment. As another example, a model early in a chain of sub-models can determine whether certain genetic variations are accurate or not, or are relevant or not, and then use that information to generate input feature to a later sub-model (e.g. later in a pipeline).

In some examples, a classification of a phenotype is derived from a physiological process, such as changes in cell turnover due to infection or physiological stress that induces a change in the kinds and distributions of molecules an experimenter may observe in a patient's blood, plasma, urine, etc.

Accordingly, some examples can include active learning, where the machine learning procedure can suggest future experiments or data to acquire based on the probability of that data reducing uncertainty in the classification. Such issues may relate to sufficient coverage of the subject genome, lack of time point resolution, insufficient patient background sequences, or other reasons. In various examples, the model may suggest one of many follow-up steps based on the missing variables, including one or more of the following: (i) re-sequencing whole genome sequencing (WGS), (ii) re-sequencing whole chromosome sequencing (WES), (iii) targeted sequencing of a particular region of the subject's genome, (iv) specific primer or other approaches, and (v) other wet lab approaches. The recommendation can vary among patients (e.g., due to the subject's genetic data or non-genetic data). In some examples, the analysis aims to minimize some function such as the cost, risk, or morbidity to the patient, or maximize classification performance such as accuracy, positive predictive value (PPV), negative predictive value (NPV), clinical sensitivity, clinical specificity, area under the curve (AUC), or a combination thereof, while suggesting the best next steps to get the most accurate classification.

VIII. CANCER DIAGNOSIS AND DETECTION

The trained machine learning methods, models and discriminate classifiers described herein are useful for various medical applications including cancer detection, diagnosis and treatment responsiveness. As models are trained with individual metadata and analyte-derived features, the applications may be tailored to stratify individuals in a population and guide treatment decisions accordingly.

A. Diagnosis

Methods and systems provided herein may perform predictive analytics using artificial intelligence-based approaches to analyze acquired data from a subject (patient) to generate an output of diagnosis of the subject having a cancer (e.g., colorectal cancer, CRC). For example, the application may apply a prediction algorithm to the acquired data to generate the diagnosis of the subject having the cancer. The prediction algorithm may comprise an artificial intelligence-based predictor, such as a machine learning-based predictor, configured to process the acquired data to generate the diagnosis of the subject having the cancer.

The machine learning predictor may be trained using datasets e.g., datasets generated by performing multi-analyte assays of biological samples of individuals) from one or more sets of cohorts of patients having cancer as inputs and known diagnosis (e.g., staging and/or tumor fraction) outcomes of the subjects as outputs to the machine learning predictor.

Training datasets (e.g., datasets generated by performing multi-analyte assays of biological samples of individuals) may be generated from, for example, one or more sets of subjects having common characteristics (features) and outcomes (labels). Training datasets may comprise a set of features and labels corresponding to the features relating to diagnosis. Features may comprise characteristics such as, for example, certain ranges or categories of cfDNA assay measurements, such as counts of cfDNA fragments in a biological sample obtained from a healthy and disease samples that overlap or fall within each of a set of bins (genomic windows) of a reference genome. For example, a set of features collected from a given subject at a given time point may collectively serve as a diagnostic signature, which may be indicative of an identified cancer of the subject at the given time point. Characteristics may also include labels indicating the subject's diagnostic outcome, such as for one or more cancers.

Labels may comprise outcomes such as, for example, a known diagnosis (e.g., staging and/or tumor fraction) outcomes of the subject. Outcomes may include a characteristic associated with the cancers in the subject. For example, characteristics may be indicative of the subject having one or more cancers.

Training sets (e.g., training datasets) may be selected by random sampling of a set of data corresponding to one or more sets of subjects (e.g., retrospective and/or prospective cohorts of patients having or not having one or more cancers). Alternatively, training sets (e.g., training datasets) may be selected by proportionate sampling of a set of data corresponding to one or more sets of subjects (e.g., retrospective and/or prospective cohorts of patients having or not having one or more cancers). Training sets may be balanced across sets of data corresponding to one or more sets of subjects (e.g., patients from different clinical sites or trials). The machine learning predictor may be trained until certain predetermined conditions for accuracy or performance are satisfied, such as having minimum desired values corresponding to diagnostic accuracy measures. For example, the diagnostic accuracy measure may correspond to prediction of a diagnosis, staging, or tumor fraction of one or more cancers in the subject.

Examples of diagnostic accuracy measures may include sensitivity, specificity, positive predictive value (PPV), negative predictive value (NPV), accuracy, and area under the curve (AUC) of a Receiver Operating Characteristic (ROC) curve corresponding to the diagnostic accuracy of detecting or predicting the cancer (e.g., colorectal cancer).

In another aspect, the present disclosure provides a method for identifying a cancer in a subject, comprising: (a) providing a biological sample comprising cell-free nucleic acid (cfNA) molecules from said subject; (b) sequencing said cfNA molecules from said subject to generate a plurality of cfNA sequencing reads; (c) aligning said plurality of cfNA sequencing reads to a reference genome; (d) generating a quantitative measure of said plurality of cfNA sequencing reads at each of a first plurality of genomic regions of said reference genome to generate a first cfNA feature set, wherein said first plurality of genomic regions of said reference genome comprises at least about 10 distinct regions, each of said at least about 10 distinct regions comprising at least a portion of a gene selected from the group consisting of genes in Table 1; and (e) applying a trained algorithm to said first cfNA feature set to generate a likelihood of said subject having said cancer.

In some examples, said at least about 10 distinct regions comprises at least about 20 distinct regions, each of said at least about 20 distinct regions comprising at least a portion of a gene selected from the group in Table 1. In some examples, said at least about 10 distinct regions comprises at least about 30 distinct regions, each of said at least about 30 distinct regions comprising at least a portion of a gene selected from the group in Table 1. In some examples, said at least about 10 distinct regions comprises at least about 40 distinct regions, each of said at least about 40 distinct regions comprising at least a portion of a gene selected from the group in Table 1. In some examples, said at least about 10 distinct regions comprises at least about 50 distinct regions, each of said at least about 50 distinct regions comprising at least a portion of a gene selected from the group in Table 1. In some examples, said at least about 10 distinct regions comprises at least about 60 distinct regions, each of said at least about 60 distinct regions comprising at least a portion of a gene selected from the group in Table 1. In some examples, said at least about 10 distinct regions comprises at least about 70 distinct regions, each of said at least about 70 distinct regions comprising at least a portion of a gene selected from the group in Table 1.

TABLE 1

| Gene | Seq Name | CNV p-value | Feature p-value |
|---|---|---|---|
| CCR3 | chr3 | 4.59E−12 | 9.17E−11 |
| CD4 | chr12 | 1.68E−01 | 1.24E−05 |
| CTBP2 | chr10 | 1.70E+01 | 6.67E−11 |
| CTSD | chr11 | | 1.98E−01 |
| ENHO | chr21 | 1.91E+01 | 5.10E−10 |
| EVA1C | chr6 | 5.47E−01 | 4.38E−08 |
| GSTA3 | chr6 | 1.35E+01 | 1.78E−07 |
| HIST1H2AK | chr5 | 7.43E+00 | 2.04E−03 |
| IK | chr7 | 7.98E−01 | 2.28E−07 |
| IRF5 | chr7 | 5.46E−10 | 2.19E−09 |
| KLF14 | chr1 | 1.96E−12 | 1.41E−07 |
| KMO | chr3 | 1.79E+01 | 4.36E−07 |
| KY | chr3 | 7.13E−04 | 2.36E−20 |
| LGALS3 | chr14 | 1.75E−06 | 5.94E−13 |
| LOC100130520 | chr17 | 1.75E+00 | 1.08E−10 |
| LOC105376906 | chr19 | 5.76E−09 | 5.27E−08 |
| MCAT | chr22 | 2.48E−07 | 5.88E−11 |
| NEDD8 | chr14 | 2.19E−06 | 2.73E−11 |
| NSMCE1 | chr16 | 3.71E−01 | 1.27E−06 |

For example, such a predetermined condition may be that the sensitivity of predicting the cancer (e.g., colorectal cancer, breast cancer, pancreatic cancer, or liver cancer) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the specificity of predicting the cancer (e.g., colorectal cancer, breast cancer, pancreatic cancer, or liver cancer) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of predicting the cancer (e.g., colorectal cancer, breast cancer, pancreatic cancer, or liver cancer) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of predicting the cancer (e.g., colorectal cancer, breast cancer, pancreatic cancer, or liver cancer) comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve of predicting the cancer (e.g., colorectal cancer, breast cancer, pancreatic cancer, or liver cancer) comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

In some examples of any of the foregoing aspects, a method further comprises monitoring a progression of a disease in the subject, wherein the monitoring is based at least in part on the genetic sequence feature. In some examples, the disease is a cancer.

In some examples of any of the foregoing aspects, a method further comprises determining the tissue-of-origin of a cancer in the subject, wherein the determining is based at least in part on the genetic sequence feature.

In some examples of any of the foregoing aspects, a method further comprises estimating a tumor burden in the subject, wherein the estimating is based at least in part on the genetic sequence feature.

B. Treatment Responsiveness

The predictive classifiers, systems and methods described herein are useful for classifying populations of individuals for a number of clinical applications. (e.g., based on performing multi-analyte assays of biological samples of individuals). Examples of such clinical applications include, detecting early stage cancer, diagnosing cancer, classifying cancer to a particular stage of disease, determining responsiveness or resistance to a therapeutic agent for treating cancer.

The methods and systems described herein are applicable to various cancer types, similar to grade and stage, and as such, is not limited to a single cancer disease type. Therefore, combinations of analytes and assays may be used in the present systems and methods to predict responsiveness of cancer therapeutics across different cancer types in different tissues and classifying individuals based on treatment responsiveness. In one example, the classifiers described herein are capable of stratifying a group of individuals into treatment responders and non-responders.

The present disclosure also provides a method for determining a drug target of a condition or disease of interest (e.g., genes that are relevant/important for a particular class), comprising assessing a sample obtained from an individual for the level of gene expression for at least one gene; and using a neighborhood analysis routine, determining genes that are relevant for classification of the sample, to thereby ascertain one or more drug targets relevant to the classification.

The present disclosure also provides a method for determining the efficacy of a drug designed to treat a disease class, comprising obtaining a sample from an individual having the disease class; subjecting the sample to the drug; assessing the drug-exposed sample for the level of gene expression for at least one gene; and, using a computer model built with a weighted voting scheme, classifying the drug-exposed sample into a class of the disease as a function of relative gene expression level of the sample with respect to that of the model.

The present disclosure also provides a method for determining the efficacy of a drug designed to treat a disease class, wherein an individual has been subjected to the drug, comprises obtaining a sample from the individual subjected to the drug; assessing the sample for the level of gene expression for at least one gene; and using a model built with a weighted voting scheme, classifying the sample into a class of the disease including evaluating the gene expression level of the sample as compared to gene expression level of the model.

Yet another application is a method of determining whether an individual belongs to a phenotypic class (e.g., intelligence, response to a treatment, length of life, likelihood of viral infection or obesity) that comprises obtaining a sample from the individual; assessing the sample for the level of gene expression for at least one gene; and using a model built with a weighted voting scheme, classifying the sample into a class of the disease including evaluating the gene expression level of the sample as compared to gene expression level of the model.

There is a need to identify biomarkers useful for predicting prognosis of patients with colon cancer. The ability to classify patients as high risk (poor prognosis) or low risk (favorable prognosis) may enable selection of appropriate therapies for these patients. For example, high-risk patients are likely to benefit from aggressive therapy, whereas therapy may have no significant advantage for low risk patients. However, in spite of this need, a solution to this problem has not been available.

Predictive biomarkers that can guide treatment decision have been sought after to identify subsets of patients who may be "exceptional responders" to specific cancer therapies, or individuals who may benefit from alternative treatment modalities.

In one aspect, the systems and methods described herein that relate to classifying a population based on treatment responsiveness refer to cancers that are treated with chemotherapeutic agents of the classes DNA damaging agents, DNA repair target therapies, inhibitors of DNA damage signaling, inhibitors of DNA damage induced cell cycle arrest and inhibition of processes indirectly leading to DNA damage, but not limited to these classes. Each of these chemotherapeutic agents is considered a "DNA-damage therapeutic agent" as the term is used herein.

The patient's analyte data is classified in high risk and low risk patient groups, such as patient with a high or low risk of clinical relapse, and the results may be used to determine a course of treatment. For example, a patient determined to be a high-risk patient may be treated with adjuvant chemotherapy after surgery. For a patient deemed to be a low risk patient, adjuvant chemotherapy may be withheld after surgery. Accordingly, the present disclosure provides, in certain aspects, a method for preparing a gene expression profile of a colon cancer tumor that is indicative of risk of recurrence.

In various examples, the classifiers described herein are capable of stratifying a population of individuals between responders and non-responders to treatment.

In various examples, the treatment is selected from alkylating agents, plant alkaloids, antitumor antibiotics, antimetabolites, topoisomerase inhibitors, retinoids, checkpoint inhibitor therapy, or VEGF inhibitors.

Examples of treatments for which a population may be stratified into responders and non-responders include but are not limited to: chemotherapeutic agents including sorafenb, regorafenib, imatinib, eribulin, gemcitabine, capecitabine, pazopani, lapatinib, dabrafenib, sutinib malate, crizotinib, everolimus, torisirolimus, sirolimus, axitinib, gefitinib, anastrole, bicalutamide, fulvestrant, ralitrexed, pemetrexed, goserilin acetate, erlotininb, vemurafenib, visiodegib, tamoxifen citrate, paclitaxel, docetaxel, cabazitaxel, oxaliplatin, ziv-aflibercept, bevacizumab, trastuzumab, pertuzumab, pantiumumab, taxane, bleomycin, melphalen, plumbagin, camptosar, mitomycin-C, mitoxantrone, SMANCS, doxorubicin, pegylated doxorubicin, Folfori, 5-fluorouracil, temozolomide, pasireotide, tegafur, gimeracil, oteraci, itraconazole, bortezomib, lenalidomide, irinotecan, epirubicin, and romidepsin, resminostat, tasquinimod, refametinib, lapatinib, Tyverb, Arenegyr, pasireotide, Signifor, ticilimumab, tremelimumab, lansoprazole, PrevOnco, ABT-869, linifanib, vorolanib, tivantinib, Tarceva, erlotinib, Stivarga, regorafenib, fluoro-sorafenib, brivanib, liposomal doxorubicin, lenvatinib, ramucirumab, peretinoin, Ruchiko, muparfostat, Teysuno, tegafur, gimeracil, oteracil, and orantinib; and antibody therapies including Alemtuzumab, Atezolizumab, Ipilimumab, Nivolumab, Ofatumumab, Pembrolizumab, or Rituximab.

In other examples, a population may be stratified into responders and non-responders for checkpoint inhibitor therapies such as compounds that bind to PD-1 or CTLA4.

In other examples, a population may be stratified into responders and non-responders for anti-VEGF therapies that bind to VEGF pathway targets.

IX. INDICATIONS

In some examples, a biological condition can include a disease. In some examples, a biological condition can be a stage of a disease. In some examples, a biological condition can be a gradual change of a biological state. In some examples, a biological condition can be a treatment effect. In some examples, a biological condition can be a drug effect. In some examples, a biological condition can be a surgical effect. In some examples, a biological condition can be a biological state after a lifestyle modification. Non-limiting examples of lifestyle modifications include a diet change, a smoking change, and a sleeping pattern change.

In some examples, a biological condition is unknown. The analysis described herein can include machine learning to infer an unknown biological condition or to interpret the unknown biological condition.

In one example, the present systems and methods are particularly useful for applications related to colon cancer: Cancer that forms in the tissues of the colon (the longest part of the large intestine). Most colon cancers are adenocarcinomas (cancers that begin in cells that make line internal organs and have gland-like properties). Cancer progression is characterized by stages, or the extent of cancer in the body. Staging is usually based on the size of the tumor, whether lymph nodes contain cancer, and whether the cancer has spread from the original site to other parts of the body. Stages of colon cancer include stage I, stage II, stage III and stage IV. Unless otherwise specified, the term colon cancer refers to colon cancer at Stage 0, Stage I, Stage II (including Stage IIA or IIB), Stage III (including Stage IIIA, IIIB or IIIC), or Stage IV. In some examples herein, the colon cancer is from any stage. In one example the colon cancer is a stage I colorectal cancer. In one example the colon cancer is a stage II colorectal cancer. In one example the colon cancer is a stage III colorectal cancer. In one example the colon cancer is a stage IV colorectal cancer.

Conditions that can be inferred by the disclosed methods include, for example, cancer, gut-associated diseases, immune-mediated inflammatory diseases, neurological diseases, kidney diseases, prenatal diseases, and metabolic diseases.

In some examples, a method of the present disclosure can be used to diagnose a cancer.

Non-limiting examples of cancers include adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

Non-limiting examples of cancers that can be inferred by the disclosed methods and systems include acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CIVIL), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, and Wilms Tumor.

Non-limiting examples of gut-associated diseases that can be inferred by the disclosed methods and systems include Crohn's disease, colitis, ulcerative colitis (UC), inflammatory bowel disease (IBD), irritable bowel syndrome (IBS), and celiac disease. In some examples, the disease is inflammatory bowel disease, colitis, ulcerative colitis, Crohn's disease, microscopic colitis, collagenous colitis, lymphocytic colitis, diversion colitis, Behcet's disease, and indeterminate colitis.

Non-limiting examples of immune-mediated inflammatory diseases that can be inferred by the disclosed methods and systems include psoriasis, sarcoidosis, rheumatoid arthritis, asthma, rhinitis (hay fever), food allergy, eczema, lupus, multiple sclerosis, fibromyalgia, type 1 diabetes, and Lyme disease. Non-limiting examples of neurological diseases that can be inferred by the disclosed methods and systems include Parkinson's disease, Huntington's disease, multiple sclerosis, Alzheimer's disease, stroke, epilepsy, neurodegeneration, and neuropathy. Non-limiting examples of kidney diseases that can be inferred by the disclosed methods and systems include interstitial nephritis, acute kidney failure, and nephropathy. Non-limiting examples of prenatal diseases that can be inferred by the disclosed methods and systems include Down syndrome, aneuploidy, spina bifida, trisomy, Edwards syndrome, teratomas, sacrococcygeal teratoma (SCT), ventriculomegaly, renal agenesis, cystic fibrosis, and hydrops fetalis.Non-limiting examples of metabolic diseases that can be inferred by the disclosed methods and systems include cystinosis, Fabry disease, Gaucher disease, Lesch-Nyhan syndrome, Niemann-Pick disease, phenylketonuria, Pompe disease, Tay-Sachs disease, von Gierke disease, obesity, diabetes, and heart disease.

The specific details of particular examples may be combined in any suitable manner without departing from the spirit and scope of disclosed examples of the invention. However, other examples of the invention may be directed to specific examples relating to each individual aspect, or specific combinations of these individual aspects. All patents, patent applications, publications, and descriptions mentioned herein are incorporated by reference in their entirety for all purposes.

X. EXAMPLES

The above description and the Examples provided below of the invention have been presented for the purposes of illustration and description. It is not intended to be exhaustive or to limit the invention to the precise form described, and many modifications and variations are possible in light of the teaching above.

A. Example 1: Preparing a Multi-Analyte Assay of Biological Samples

This example provides a multi-analyte approach to exploit independent information between signals. A process diagram is described below for different components of a system for an assay with a corresponding machine learning model to perform an accurate classification. The selection of which assays to use can be integrated based on the results of training the machine learning model, given the clinical goal of the system. Various classes of samples, fractions of samples, portions of those fractions/samples with different classes of molecules, and types of assays can be used.

1. System Diagram

Figure 3:
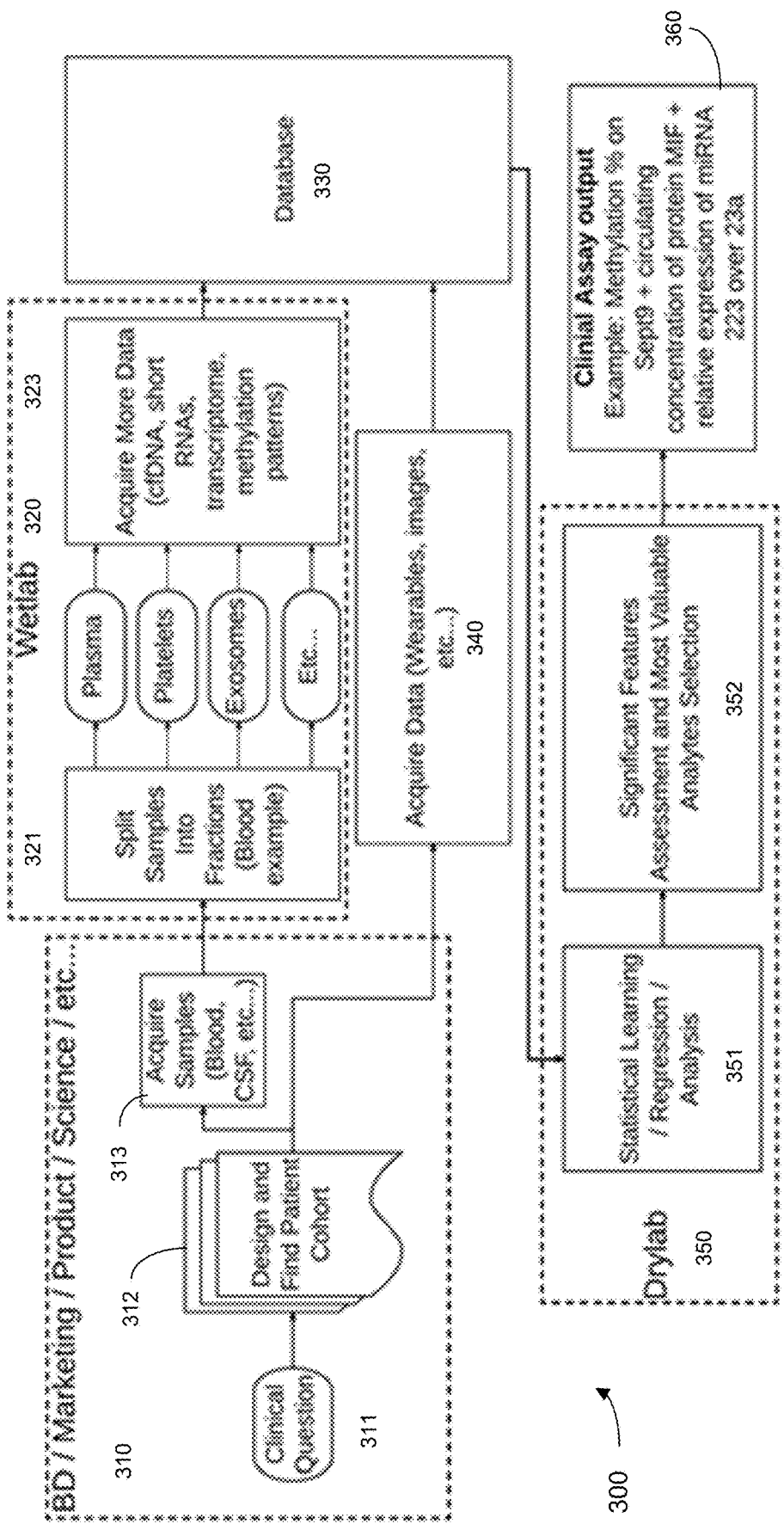
FIG. 3 shows an overall framework according to various aspects.

FIG. 3 shows an overall framework 300 for the disclosed system and methods. The framework 300 can use measurements of sample (wetlab 320) and other data about the subjects in combination with machine learning to identify a set of assays and features for classifying subjects, e.g., diagnosis or prognosis. In this example, the steps of the process may be as follows.

At block 311 of stage 310, a question with clinical, scientific and/or commercial relevance is asked, e.g., early colorectal cancer detection for actionable follow-ups. At block 312, subjects (new or previously tested) are identified. The subjects can have known classifications (labels) for use later in machine learning. Thus, different cohorts can be identified. At block 313, the analysis can select the types of samples that are going to be mined (i.e., the samples may not ultimately end up in the final assay) and determine the collection of biological molecules in each of the samples (e.g., blood) that can generate sufficient signal to assess the presence or absence of a condition/disorder (e.g., an early stage colorectal cancer malignancy). Constraints can be imposed on the assay/model, e.g., relating to accuracy. Example constraints include: the minimum sensitivity of the assay; the minimum specificity of the assay; the maximum cost of the assay; the time available to develop the assay; the available biological materials and expected rate of accrual; the available set of previously developed processes which determines the maximum set of experiments that can be done on those biological materials; and the available hardware which limits the number of processes that can be run on those biological materials to acquire data.

The cohort of patients can be designed and sampled to accurately represent the different classifications needed to appropriately achieve the clinical goal (healthy, colorectal other, advanced adenomas, colorectal cancer (CRC)). The patient cohort can be selected, where the selected cohort can be viewed as a constraint on the system. An example cohort is 100 CRC, 200 advanced adenomas, 200 non-advanced adenomas, and 200 healthy subjects. The selected cohort can correspond to an intended use population for the final assay, and the cohort can specify the number of samples on which to calculate assay performance.

Once the cohort is selected, samples can be collected to meet the cohort designs. Various samples can be collected, e.g., blood, cerebrospinal fluid (CSF), and others mentioned herein. Such analysis can occur in block 313 of FIG. 3.

In stage 320, wet lab experiments can be performed for an initial set of assays. For example, an unconstrained set of tests can be chosen (primary sample/analytes/test combination). Protocols and modalities for analyte isolation from the primary samples can be performed. Protocols and modalities for test execution can be generated. The performance of the wet lab activities can be performed using hardware devices including sequencers, fluorescence detectors, and centrifuges.

At block 321, samples are split into subcomponents (also called fractions or portions), e.g., by centrifugation. As an example, blood is split into fractions of plasma, buffy coat (white blood cells and platelets), serum, red blood cells, and extracellular vesicles, such as exosomes. A fraction (e.g., plasma) can be split into aliquots to assay different analytes. For instance, different aliquots are used to extract cfDNA and cfRNA. Accordingly, analytes can be isolated from fractions or aliquots of a fraction to permit multianalyte assay. A fraction (e.g., some plasma) can be kept for measuring protein concentration.

At block 323, experimental procedures are executed to measure characteristics and quantities of the above molecules in their respective fractions, e.g., (1) the sequence and imputed location along the genome of cell free DNA fragments found in plasma, (2) methylation patterns of cfDNA fragments found in plasma, (3) quantity and type of microRNAs found in plasma, and (4) the concentration of proteins known to be related to CRC from literature (CRP, CEA, FAP, FRIL, etc.).

The QC of each of the samples being processed on any given pipeline can be verified. cfDNA QCs include: insert size distribution, relative representation of GC bias, barcode sequence of spike-in (introduced for sample traceability), etc. Example methylation QCs include bisulfate conversion efficiency for control DNA, insert size distribution, average depth of sequencing, % duplication, etc. Example miRNA QCs include insert size distribution, relative representation of normalization spike-in, etc. Example proteins QCs include linearity of standard curve, control sample concentration, etc.

Next, samples are processed, and data acquired for all patients in the cohort. Raw data is indexed by patient metadata. Data from other sources can be obtained and stored in a database. The data can be curated from relevant open databases such as GTEX, TCGA, and ENCODE. This includes ChIP-seq, RNA-seq, and eQTL.

In stage 340, data from other sources can be obtained, e.g., wearables, images, etc. Such other data corresponds to data determined outside of a biological sample. Such measurements could be heart rate, activity measurements, or other such data available from wearable devices. The imaging data can provide information such as sizes of organs and locations, as well as identify unknown masses.

Database 330 can store the data. The data can be curated from relevant open databases such as GTEX, TCGA, and ENCODE. This includes ChIP-seq, RNA-seq, and eQTL. A record for each subject can include fields with the measured data and labels of the subjects, e.g., whether a condition exists, a severity (stage) of the condition, etc. A subject could have multiple labels.

At block 350, drylab operations can occur. The "drylab" work can initiate with a query to the database to generate a matrix of values of the relevant data and metadata to execute the prediction tasks. Features are generated by processing the incoming data and possibly selecting a subset of relevant inputs.

At block 351, machine learning can be used to reduce the entire set of data generated from all (primary sample/ analytes/test) combinations into the most predictive set of features, at block 352. Accuracy metrics of different sets of features can be compared against each other to determine the most predictive set of features. In some embodiments, a collection of features/models that satisfy an accuracy threshold can be identified, and then other constraints (e.g. cost and number of tests) can be used to select an optimal model/features grouping.

A variety of different features and models can be tested. Simple to complex and small to large models making a variety of modeling assumptions can be applied to the data in a cross-validation paradigm. Simple to complex includes considerations of linearity to non-linearity and non-hierarchical to hierarchical representations of the features. Small to large models includes considerations of the size of basis vector space to project the data onto as well as the number of interactions between features that are included in the modelling process.

Machine learning techniques can be used to assess the commercial testing modalities most optimal for cost/performance/commercial reach as defined in the initial question. A threshold check can be performed: If the method applied to a hold-out dataset that was not used in cross validation surpasses the initialized constraints, then the assay is locked and production initiated. Thus, the assay can be output at block 360.

If the thresholds are not met, then the assay engineering procedure loops back to either the constraint setting for possible relaxation or to the wet lab to change the parameters in which data was acquired.

Given the clinical question, biological constraints, budget, lab machines, etc., can constrain the problem. Then the cohort design can be based on clinical samples, which is actually based for the performance or prior knowledge base; statistical, informative nest of what can be done; and the sample accrual rate.

2. Hierarchy of Samples and Portions Thereof

In one example, multiple analytes are taken from a patient in the cohort and analyzed into multiple molecule types via multiple assays. The assay results are then analyzed by an ML model, and after significant feature and analyte selection, the relevant assay results for the clinically, scientifically, or commercially important question are output.

Figure 4:
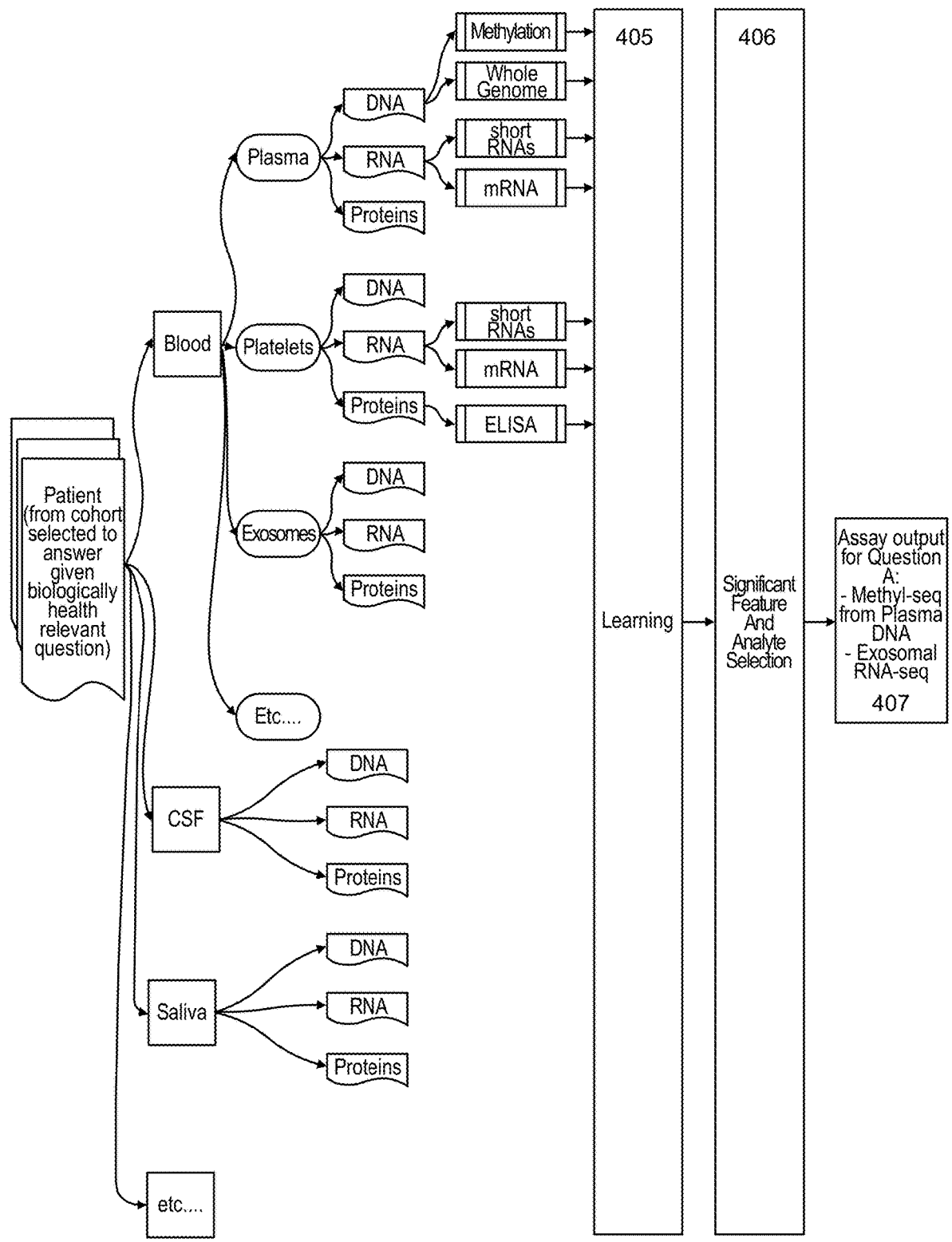
FIG. 4 shows an overview of a multi-analyte approach.

FIG. 4 shows a hierarchal overview of the multi-analyte approach as used for an exemplary 'liquid biopsy.' At stage 401, different samples are collected. As shown, blood, CSF, and saliva are collected. At stage 402, a sample can be split into fractions (portions), e.g., blood is shown being split into plasma, platelets, and exosomes. At stage 403, each of the fractions can be analyzed to measure one or more classes of molecules, e.g., DNA, RNA, and/or proteins. At stage 404, each of the classes of molecules can be subjected to one or more assays. For example, methylation and whole genome assays can be applied to DNA. For RNA, assays detecting mRNA or short RNAs can be applied. For proteins, enzyme-linked immunosorbent assay (ELISA) can be used.

In thoneis example, collected plasma was analyzed using multi-analyte assays, including: Low coverage Whole Genome Sequencing; CNV calling; Tumor fraction (TF) estimation; Whole Genome Bisulfite Sequencing; LINE-1 CpG methylation; 56 genes CpG methylation; cf-Protein Immuno-Quant ELISAs, SIMOA; and cf-miRNA sequencing. Whole blood can be collected in K3-EDTA tubes and double-spun to isolate plasma. Plasma can be split into aliquots for cfDNA lcWGS, WGS, WGBS, cf-miRNA sequencing, and quantitative immunoassays (either enzyme-linked immunosorbent assay [ELISA] or single molecule array [SIMOA]).

At stage 405, a learning module executing on computer hardware can receive the measured data from the various assays of various fraction(s) of various sample(s). The learning module can provide metrics for various groupings of models/features. For example, various sets of features can be identified for each of a plurality of models. Different models can use different techniques, such as neural networks or decision trees. Stage 406 can select the model/features grouping to use, or potentially to provide instructions (commands) to perform further measurements. Stage 407 can specify the samples, fractions, and individual assays to be used as part of the total assay that will be used to measure a new sample and perform a classification.

3. Iterative Flow between Modules

Figure 5:
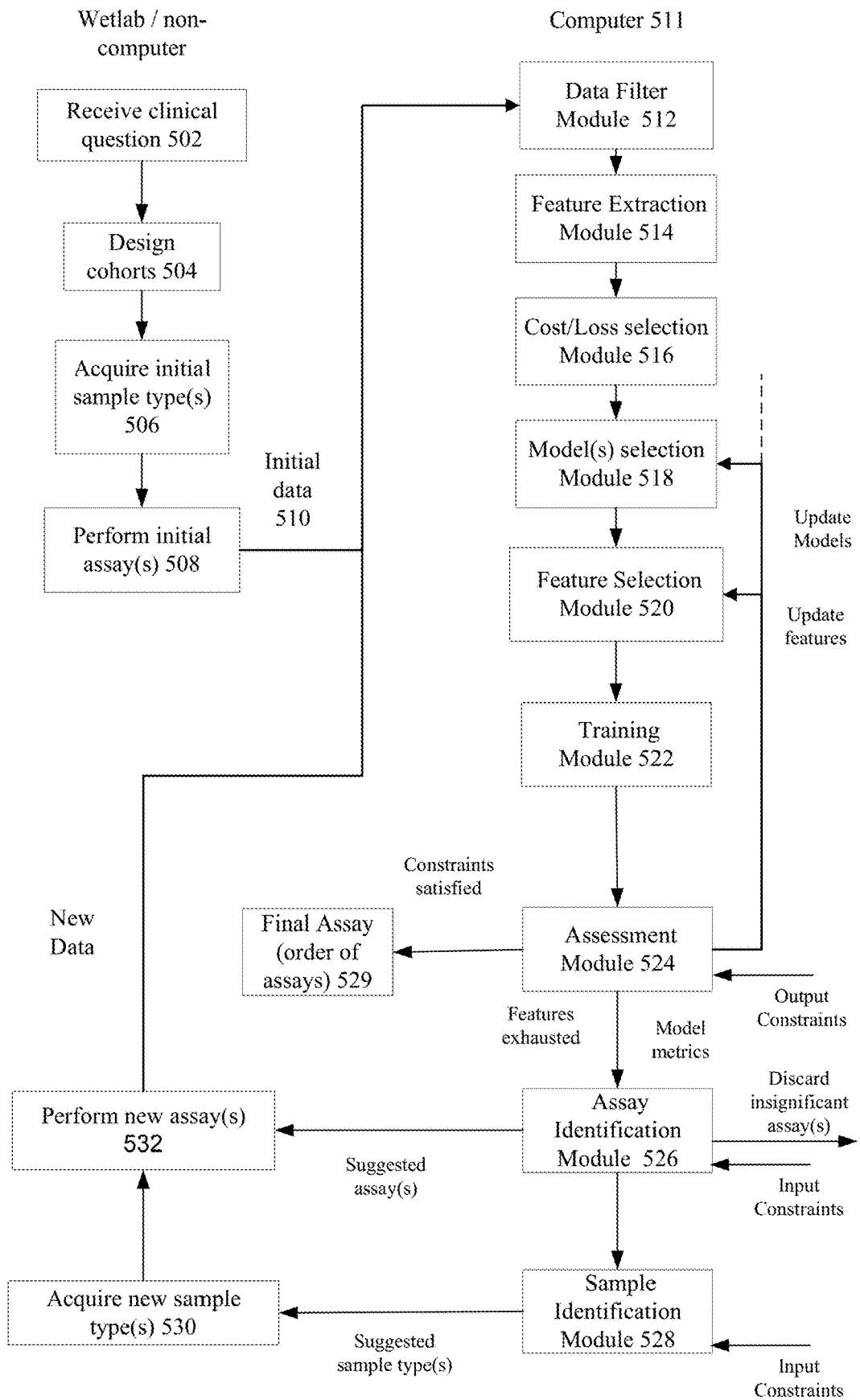
FIG. 5 shows an iterative process for designing an assay and corresponding machine learning model according to various aspects.

FIG. 5 shows an iterative process for designing an assay and corresponding machine learning model according to embodiments of the present invention. Wet lab components are shown on the left, and computer components are shown on the right. Omitted modules include external data, prior structure, clinical metadata . . . etc. These metacomponents can flow into both the wet and dry lab (computer) components. In general, the iterative process can include various phases, including initialization phase, exploratory phase, refinement phase, and validation/confirmation phase. The initialization phase can include blocks 502-508. The exploratory phase can include a first pass through blocks 512-528. The refinement phase can include additional passes through blocks 512-528 as well as blocks 530 and 532. The validation/confirmation phase can occur using blocks 524 and 529. Various blocks may be optional or be hardcoded to provide a specified result, e.g., a particular model may always be selected by module 518.

At block 502, a clinical question is received, e.g., to screen for the existence of colorectal cancer (CRC). Such a clinical question can also include the number of classifications that are needed. For example, the number of classifications can correspond to different stages of cancer.

At block 504, the cohort(s) are designed. For example, the number of cohorts can equal the number of classifications, with the subjects in a cohort having a same label. At later stages or phases of the process, additional cohorts could be added.

In an embodiment, there is an initialselection of sample and/or tests before any biochemical tests are performed. For example, genome wide sequencing may be chosen in order to obtain information for an initial sample, e.g., blood. Such an initial sample and initial assays can be selected based on the clinical question, e.g., based on a relevant organ.

At block 506, initial samples are acquired. The samples could be of various types, e.g., blood, urine, saliva, cerebrospinal fluid. As part of acquiring the initials samples, samples can be split into fractions (e.g., blood into plasma, buffy coat, exosomes, etc.), and those fractions can be further split into portions having a particular class of molecules, as described herein.

At block 508, one or more initial assays are performed. The initial assays can operate on individual classes of molecules. Some or all of the initial set of assays can be used as a default across various clinical questions. Initial data 510 can be transmitted to a computer 511 to assess the data and determine a machine learning model, and potentially to suggest further assays to be performed. Computer 511 can perform operations described in this section and other sections of the disclosure.

Data filter module 512 can filter the initial data 510 to provide one or more sets of filtered data. Such filtering may just identy the data from the different assays, but may be more complex, e.g., performing statistical analysis to provide measured values from the raw data, wherein initial data 510 is considered the raw data. The filtering can include dimensional reduction, e.g., a principal component analysis (PCA), Non-negative matrix factorization (NMF), Kernel PCA, graph-based kernel PCA, linear discriminant analysis (LDA), generalized discriminant analysis (GDA), or autoencoders. Multiple sets of filtered data can be determined from the raw data of a single assay. The different sets of filtered data can be used to determined different sets of features. [0097] In some embodiments, data filter module 512 can take into account processing performed by downstream modules. For example, the type of machine learning model may affect the type of dimensionality reduction used.

Feature extraction module 514 can extract features, e.g., using genetic data, non-genetic data, filtered data, and reference sequences. Feature extraction may also be referred to as feature engineering. The features for the data obtained from an assay would correspond to properties of the class of molecules obtained in that assay. As examples, the features (and their corresponding feature values) could be the measured values output from the filtering, only some of such measured values, a further statistical result of such measured values, or measured values appended to each other. The particular features are extracted with a goal that the some of the features have different values among different groups of subjects (e.g., different values among subjects with a condition and without the condition), thereby allowing discrimination between the different groups or inference of an extent of a property, state, or trait. Examples of features are provided in section V.

Cost/Loss selection module 516 can select a particular cost function (also referred to as loss function) to optimize in the training of the machine learning model. The cost function can have various terms for defining the accuracy of the current model. At this point, other constraints may be injected algorithmically. For example, the cost function can measure the number of misclassifications (e.g., false positives and false negatives) and have a scaling factor for each of the different types of misclassifications, thereby providing a score that can be compared to a threshold to determine whether a current model is satisfactory. Such a test of accuracy can also implicitly determine whether a set of features and set of assays can provide a satisfactory model; if the set of features and assays do not, then a different set of features can be selected.

In an example, the distribution of data can affect the choice of loss function, e.g., for the unsupervised task for having technical control of the system. In this case, the loss function can correspond to a distribution matching the incoming data.

Model selection module 518 can select which model(s) to use. Examples of such models include logistic regression, support vector machines with different kernels (e.g., linear or nonlinear kernels), neural networks (e.g., multilayer perceptrons), and various types a decision trees (e.g., random forest, gradient trees, or gradient boosting techniques). Multiple models can be used, e.g., where models can be used sequentially (e.g., output of one model that into input of another model) or used in parallel (e.g., using voting to determine final classification). If there is more than one model selected, these can be referred to as submodels.

The cost function is different than the model, which is different than the features. These different parts of the architecture can have significant effects on each other, but they are also defined by other components of the test design and its corresponding constraints. For example, the cost function can be defined by components including a distribution of the features, the numerics of the features, the diversity of the label distribution, the kinds of labels, the complexity of the labels, the risk associated with different error types, etc. Certain changes to features might change models and cost functions and vice versa.

Feature selection module 520 can select a set of features to be used for a current iteration in training the machine learning model. In various embodiments, all the features extracted by feature extraction module 514 can be used or only a portion of the features may be used. Feature values for the selected features can be determined and used as inputs for the training. As part of the selection, some or all extracted features may undergo a transformation. For example, weights may be applied to certain features, e.g., based on an expected importance (probability) of certain feature(s) relative to other feature(s). Other examples include dimensional reduction (e.g., of a matrix), distribution analysis, normalization or regularization, matrix decompositions (e.g., a kernel-based discriminant analyses and non-negative matrix factorization), which can provide a low dimensional manifold corresponding to the matrix. Another example is to transform the raw data or features from one type of instrument to another type of instrument, e.g., if different samples are measured using different instruments.

Training module 522 can perform an optimization of parameters of the machine learning model, which may include submodels. Various optimization techniques can be used, e.g., gradient descent or use of a second derivative (Hessian). In other embodiments, training can be implemented with methods that do not require a hessian or gradient calculation, such as dynamic programming or evolutionary algorithms.

Assessment module 524 can determine whether the current model (e.g., as defined by set of parameters) satisfy one or more criteria, included in output constraint(s). For instance, a quality metric can measure the predictive accuracy of the model with respect to the training set and/or a validation set of samples whose labels are known. Such an accuracy metric can include sensitivity and specificity. The quality metric may be determined using other values than accuracy, e.g., a number of assays, an expected cost of the assays, and a time to perform the measurements of the assays. If the constraints are satisfied, a final assay 529 can be provided. Final assay 529 can include a particular order for performing assays on a test sample, e.g., when an assay is selected that is not on a default list.

If the output constraints are not satisfied, various items can be updated. For example, the set of selected features can be updated, or the set of selected models can be updated. Some or all upstream modules can be assessed, checked, and alternatives proposed. Thus, feedback can be provided to anywhere in the upstream pipeline. If assessment module 524 determines that the space of features and models has been sufficiently searched without satisfying the constraints (e.g., exhausted), the process may flow to further modules to determine new assays and/or types of samples to obtain. Such a determination can be defined by constraints. For example, a user may only be willing to perform so many assays (and associated time and cost), have so many samples, or perform the iterative loop (or some loops) so many times. These constraints can contribute to the stopping of the test design for a current set of features, models, and assays in lieu of minimal metrics being surpassed.

Assay identification module 526 can identify new assays to perform. If a particular assay is determined to be insignificant, its data can be discarded. Assay identification module 526 can receive certain input constraints, which may be used to determine one or more assays to select, e.g., based on cost or timing of performing the assay.

Sample identification module 528 can determine new sample types (or portions thereof) to use. The selection can be dependent on which new assay(s) are to be performed. Input constraints can also be provided to sample identification module 528.

The assay identification module 526 and the sample identification module 528 can be used when the assessment is that the assays and model do not satisfy the output constraints (e.g., accuracy). The discarding of an assay can be implemented in a next round of assay design, where that assay or sample type is not used. The new assay or sample could be ones that were measured previously, but whose data was not used.

At block 530, new samples types are acquired, or potentially more samples of a same type, e.g., to increase the number of samples in a cohort.

At block 532, new assays can be performed, e.g., based on suggested assays from assay identification module 526.

The final assay 529 can specify, e.g., an order, data quantity, data quality, and data throughput for the assays in the set. The order of the assays can optimize cost and timing. Order and timing of assays can be a parameter that is optimized.

In some embodiments, the computer modules can inform other parts of the wet lab steps. For example, some computer module(s) might precede wet lab steps for some assay development procedures, such as when external data can be used to inform the starting point for the wet lab experimentation. Further, outputs of the wet lab experiments components might feed into the computer components such as cohort design and clinical question. On the other hand, computer results might feed back into the wet lab such as cost function choice's effects on cohort design.

4. Method for Designing Multi-Analyte Assay

Figure 6:
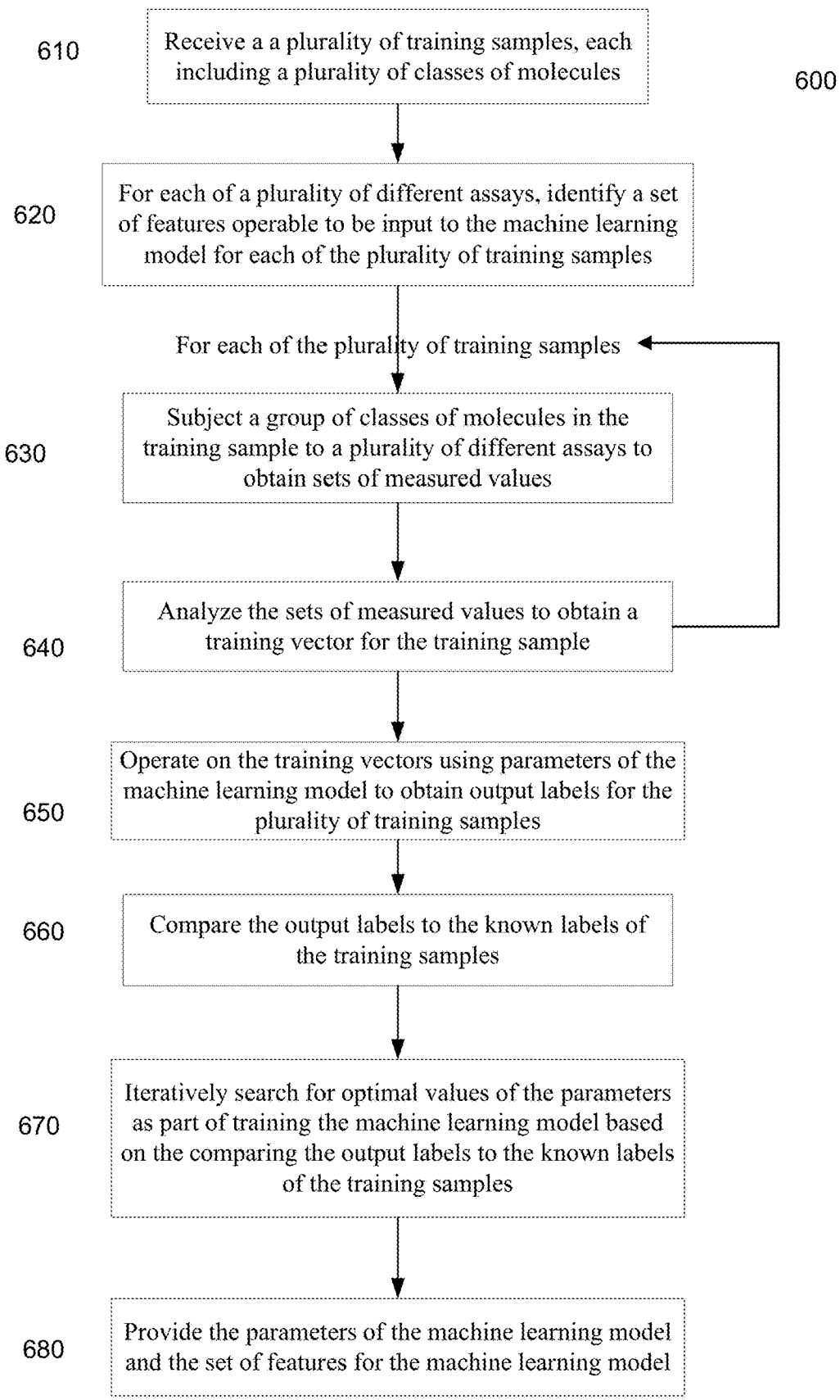
FIG. 6 is a flowchart illustrating a method for performing classifications of biological samples, according to an embodiment.

FIG. 6 shows an overall process flow for the disclosed methods. In this example, the steps of the process are as follows.

At block 610, during operation, the system receives a plurality of training samples, each including a plurality of classes of molecules, where one or more labels are known for each of the training samples. Examples of analytes are provided herein, such as cell-free DNA, cell-free RNA (e.g., miRNA or mRNA), proteins, carbohydrates, autoantibodies or metabolites. The labels may be for a particular condition (e.g., different classifications of cancer or a particular cancer), or treatment responsiveness. Block 610 may be performed by a receiver that includes one or more receiving devices, such as measurement devices, e.g., measurement devices 151-153 in FIG. 1. The measurement devices may implement different assays. The measurement devices can convert the samples into useable features (e.g., a library of volumes of information for each analyte from a sample) so that a computer can select a combination of input features needed for a particular ML model to classify a specific biological sample.

At block 620, for each of a plurality of different assays, the system identifies a set of features operable to be input to the machine learning model for each of the plurality of training samples. The set of features may correspond to properties of molecules in the training samples. For example, the features may be read counts in different regions, methylation percentage in regions, number of counts of different miRNA, or concentration of a set of proteins. Different assays can have different features. Block 620 may performed by feature selection module 520 of FIG. 5. In FIG. 5, feature selection may occur before or after feature extraction, e.g., if possible features are already known based on the types of assays performed. As part of an iterative procedure, new sets of features can be identified, e.g., based on a result from assessment module 524.

At block 630, for each of the plurality of training samples, the system subjects a group of classes of molecules in the training sample to a plurality of different assays to obtain sets of measured values. Each set of measured values may be from one assay applied to a class of molecules in the training sample. A plurality of sets of measured values may be obtained for the plurality of training samples. As examples, the different assays can be lcWGS, WGBS, cf-miRNA sequencing, and protein concentration measurements. In one example, one portion contains more than one class of molecules, but only one type of assay is applied to the portion. The measured value can correspond to values resulting from an analysis of the raw data (e.g., sequence reads). Examples of measured values are read counts of sequences that partially or entirely overlap with different genomic regions of a genome, methylation percentage in regions, number of counts of different miRNA, or concentration of a set of proteins. A feature can be determined from multiple measured values, e.g., a statistical value of a distribution of measured values or a concatenation of measured values appended to each other.

At block 640, the system analyzes the sets of measured values to obtain a training vector for the training sample. The training vector may comprise feature values of the set of features of the corresponding assay Each feature value may correspond to a feature and including one or more measured values. The training vector may be formed using at least one feature from at least two of the N sets of features corresponding to a first subset of the plurality of different assays, where N corresponds to the number of different assays. A training vector can be determined for each sample, with the training vector potentially including features from some or all of the assays, and thus all of the classes of molecules. Block 640 may be performed by feature extraction module 514 of FIG. 5.

At block 650, the system operates on the training vectors using parameters of the machine learning model to obtain output labels for the plurality of training samples. Block 650 may be performed by a machine learning module that implements the machine learning model.

At block 660, the system compares the output labels to the known labels of the training samples. A comparator module can perform such comparisons of the labels to form an error measurement of the current state of the machine learning model. The comparator module may be part of training module 522 of FIG. 5.

A first subset of the plurality of training samples can be identified as having a specified label, and a second subset of the plurality of training samples can be identified as not having the specified label. In one example, the specified label is a clinically-diagnosed disorder, e.g., colorectal cancer.

At block 670, the system iteratively searches for optimal values of the parameters as part of training the machine learning model based on the comparing the output labels to the known labels of the training samples. Various techniques for performing the iterative search are described herein, e.g., gradient techniques. Block 670 may be implemented by training module 522 of FIG. 5.

The training of the machine learning model can provide a first version of the machine learning model, e.g., after a refinement phase, which can include one or more additional passes through modules 512-528. A quality metric can be determined for the first version, and the quality metric can be compared to one or more criteria, e.g., a threshold. The quality metric may be composed of various metrics, e.g., an accuracy metric, a cost metric, a time metric, and the like, as described for FIG. 4. Each of these metrics can be individually compared to a threshold or other determine whether that metric satisfies one or more criteria. Based on the comparison(s), it can be determined whether to select a new subset of assays for determining sets of features, e.g., at blocks 526 and 532 if FIG. 5.

The new subset of assays can include at least one of the plurality of different assays that was not in the first subset, and/or potentially remove an assay. The new subset of assays can include at least one assay from the first subset, and a new set of features can be determined for the one assay from the first subset. When the quality metric for the new subset of assays satisfies the one or more criteria, the new subset of assays can be output, e.g., as the final assay 529 of FIG. 5.

If the new subset includes a new assay that had not been previously performed, the molecules in the training samples can be subjected to a new assay not in the plurality of different assays to obtain new sets of measured values based on the quality metric for the new subset of assays not satisfying the one or more criteria. The new assay can be performed on a new class of molecules not in the group of classes of molecules.

At block 680, the system provides the parameters of the machine learning model and the set of features for the machine learning model. The parameters of the machine learning model may be stored in a predefined format or stored with tags that identify the number and identity of each of the parameters. The definitions of the features can be obtained from settings used in feature extraction and selection, e.g., as specified by a current iteration through feature extraction module 514 and feature selection module 520. Block 680 may be performed by an output module.

5. Method for Identifying a Cancer

In an aspect, the present disclosure provides a method for identifying a cancer in a subject, comprising: (a) providing a biological sample comprising cell-free nucleic acid (cfNA) molecules from said subject; (b) sequencing said cfNA molecules from said subject to generate a plurality of cfNA sequencing reads; (c) aligning said plurality of cfNA sequencing reads to a reference genome; (d) generating a quantitative measure of said plurality of cfNA sequencing reads at each of a first plurality of genomic regions of said reference genome to generate a first cfNA feature set, wherein said first plurality of genomic regions of said reference genome comprises at least about 15 thousand distinct hypomethylated regions; and (e) applying a trained algorithm to said first cfNA feature set to generate a likelihood of said subject having said cancer.

In some examples, said trained algorithm comprises performing a dimensionality reduction by singular value decomposition. In some examples, the method further comprises generating a quantitative measure of said plurality of cfNA sequencing reads at each of a second plurality of genomic regions of said reference genome to generate a second cfNA feature set, wherein said second plurality of genomic regions of said reference genome comprises at least about 20 thousand distinct protein-encoding gene regions; and applying said trained algorithm to said second cfNA feature set to generate said likelihood of said subject having said cancer. In some examples, the method further comprises generating a quantitative measure of said plurality of cfNA sequencing reads at each of a third plurality of genomic regions of said reference genome to generate a third cfNA feature set, wherein said third plurality of genomic regions of said reference genome comprises consecutive non-overlapping genomic regions of equal size; and applying said trained algorithm to said third cfNA feature set to generate said likelihood of said subject having said cancer. In some examples, said third plurality of non-overlapping genomic regions of said reference genome comprises at least about 60 thousand distinct genomic regions. In some examples, the method further comprises generating a report comprising information indicative of said likelihood of said subject having said cancer. In some examples, the method further comprises generating one or more recommended steps for said subject to treat said cancer based at least in part on said generated likelihood of said subject having said cancer. In some examples, the method further comprises diagnosing said subject with said cancer when said likelihood of said subject having said cancer satisfies a predetermined criterion. In some examples, said predetermined criterion is said likelihood being greater than a predetermined threshold. In some examples, said predetermined criterion is determined based on an accuracy metric of said diagnosis. In some examples, said accuracy metric is selected from the group consisting of sensitivity, specificity, positive predictive value (PPV), negative predictive value (NPV), accuracy, and area under the curve (AUC).

In some examples, the computer modules may inform other parts of the wet lab steps. For example, some computer module(s) may precede wet lab steps for some assay development procedures, such as when external data may be used to inform the starting point for the wet lab experimentation. Further, outputs of the wet lab experiments components may feed into the computer components such as cohort design and clinical question. On the other hand, computer results may feed back into the wet lab such as cost function choice's effects on cohort design.

6. Results

Table 2 shows results for different analytes and corresponding best performing model according to examples of the present disclosure.

| | Feature | Test AUC Mean | Test AUC std | Model |
|---|---|---|---|---|
| 4 | Genes | 70.8 | 11.4 | SD LR |
| 6 | miRNA | 66 | 11.2 | PCA LR |
| 8 | Protein | 56.5 | 12.5 | LR |
| 7 | Methyl | 61.7 | 12.1 | PCA LR |
| 3 | Genes + Methyl | 72.8 | 11.9 | PCA LR Voting |
| 2 | Genes + Protein | 73.2 | 9.4 | SD LR Combining |
| 1 | Genes + RNA | 75.8 | 8.8 | SD LR Voting |
| 5 | All | 68.5 | 16 | LR Combining |

Samples that were in similar across the analytes were used.

In Table 2, SD refers to significant differences, as determined by comparing read counts for different genes among the different classified labels. This is part of dimensionality reduction. It is doing a filtering of the features of those that are significantly different between the two classifications and then taking those forwards into classification. While PCA looks at a collapsed group of features, but which correlate in a particular way, SD looks unilaterally at individual features. The features (e.g., read counts for genes) that have the highest SD can be used in the feature vector for the subject. PCA relates to the projection of the measured values through the first few components. It is a condensed representation of many features, e.g., in a smaller dimensional space.

The table was created by analyzing results of different models, with different dimensional reduction (including no reduction), for different combinations of analytes. The table includes the model that performed the best. As an example, for multi-analyte assay datasets that involve proteins, there may be no need for PCA because the dimensionality is small (14), and thus just logistic regression (LR) is used.

Of the models, LR was tried along, with PCA (top 5 components), and with feature selection by significant differences (keeping 10% of features). The PCA can be done across analytes or within just one analyte.

The feature column corresponds to different combinations of analytes, e.g., genes (cell-free DNA analysis) plus methylation. When more than one analyte was used, two options were to combine the features into a single set of features, or to run two models to output two classifications (e.g., probabilities for the classifications) and use those as votes, e.g., majority voting or some weighted average or probabilities to determine which classification has a highest score. As another example, a mean or mode of the prediction can be taken as opposed to looking at the scores.

Figure 7A:
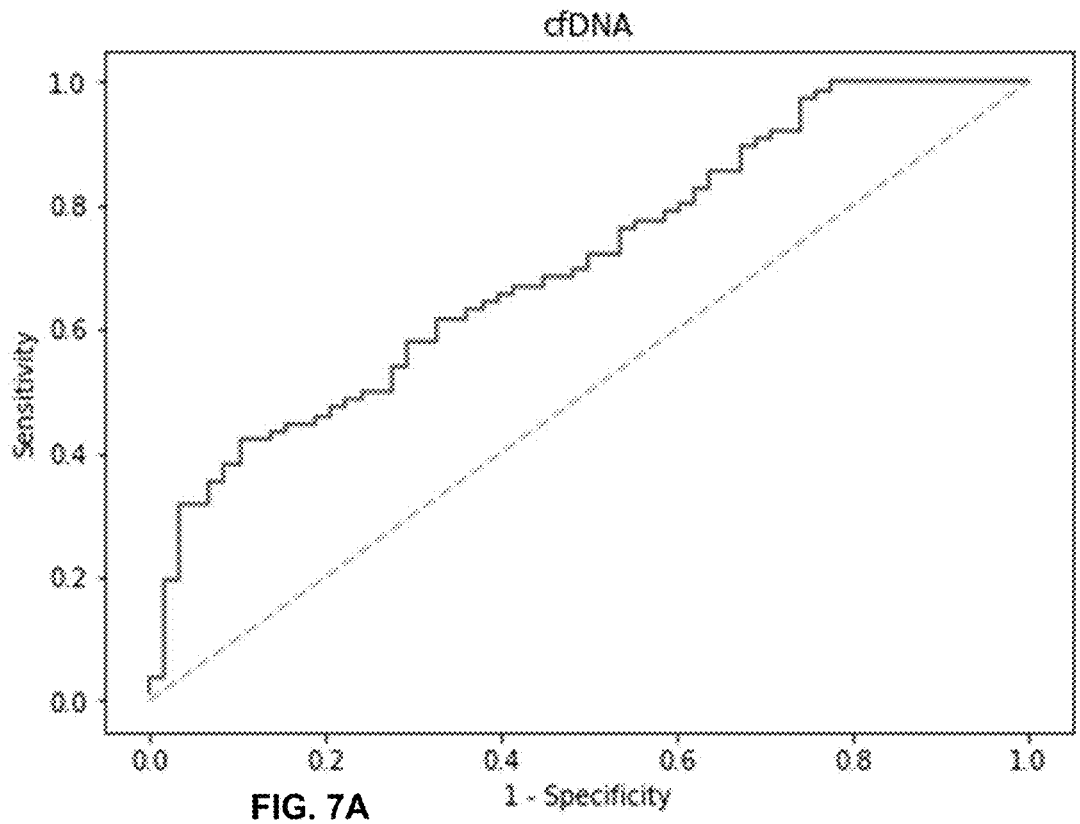
FIGS. 7A and 7B show classification performance for different analytes.
Figure 7B:
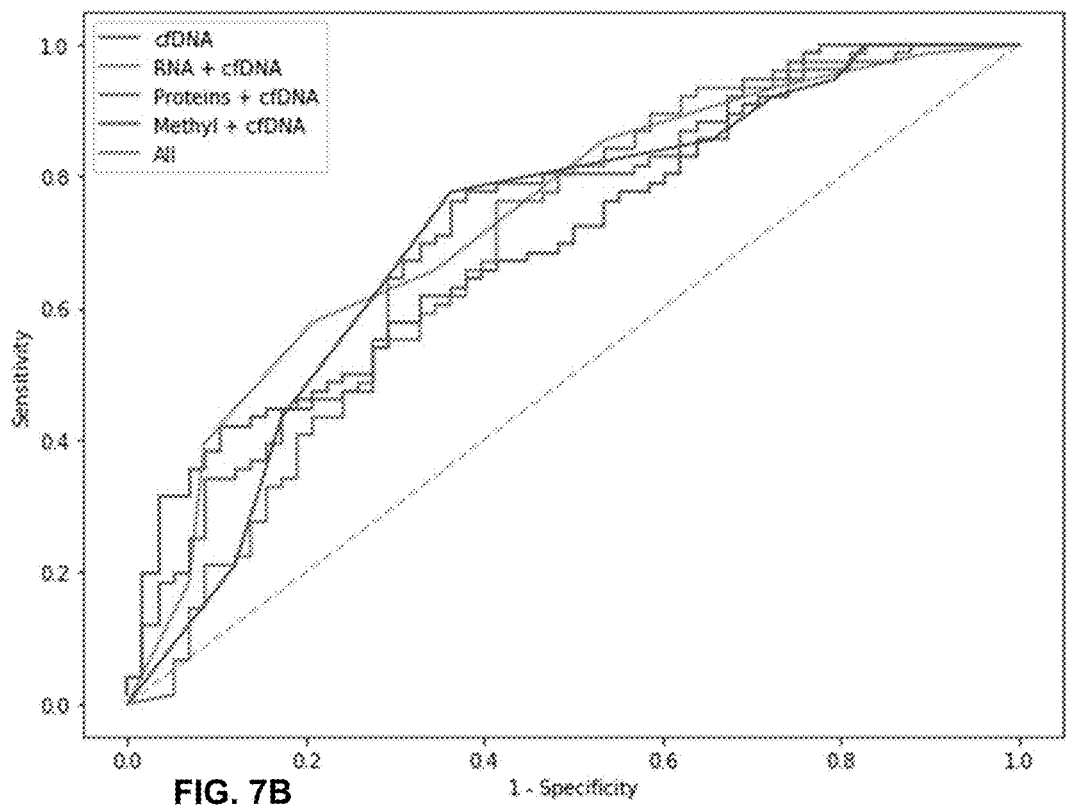
Figure 8A:
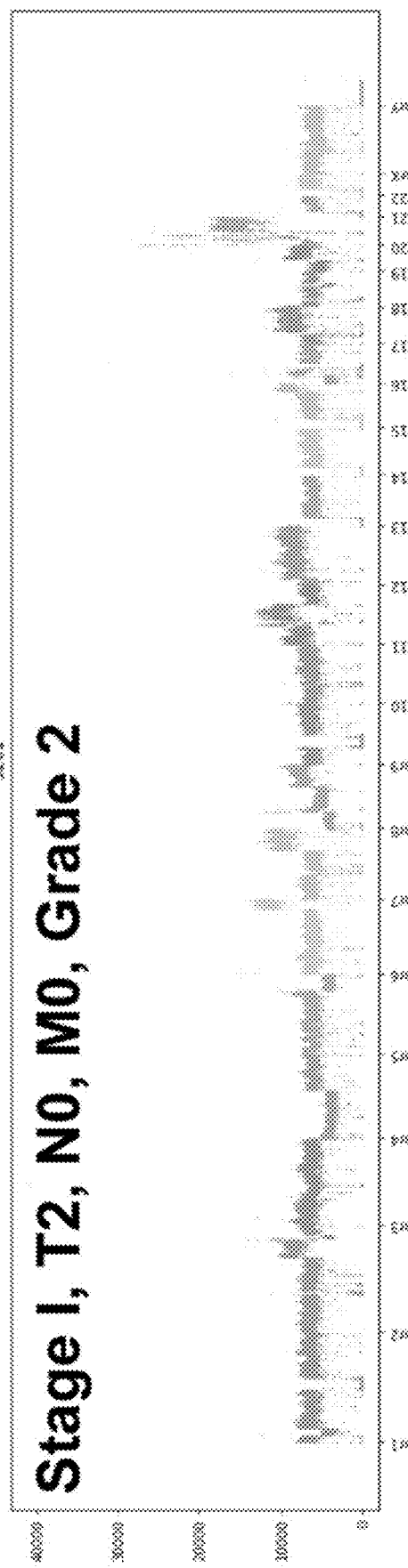
FIGS. 8A-8H show a distribution of tumor fraction cfDNA samples for individuals with high (>20%) tumor fraction based on cfDNA-seq data.
Figure 8B:
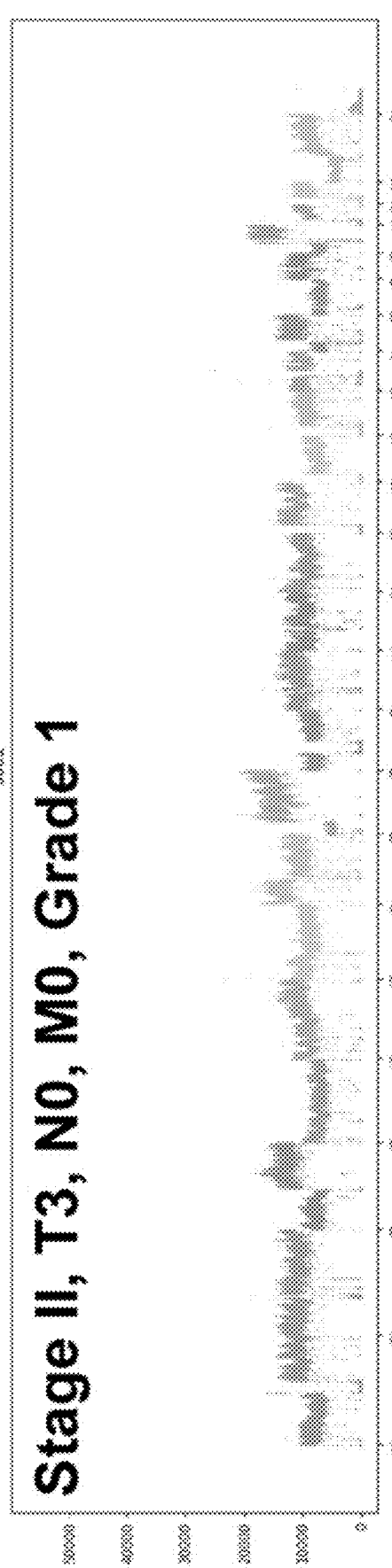
Figure 8C:
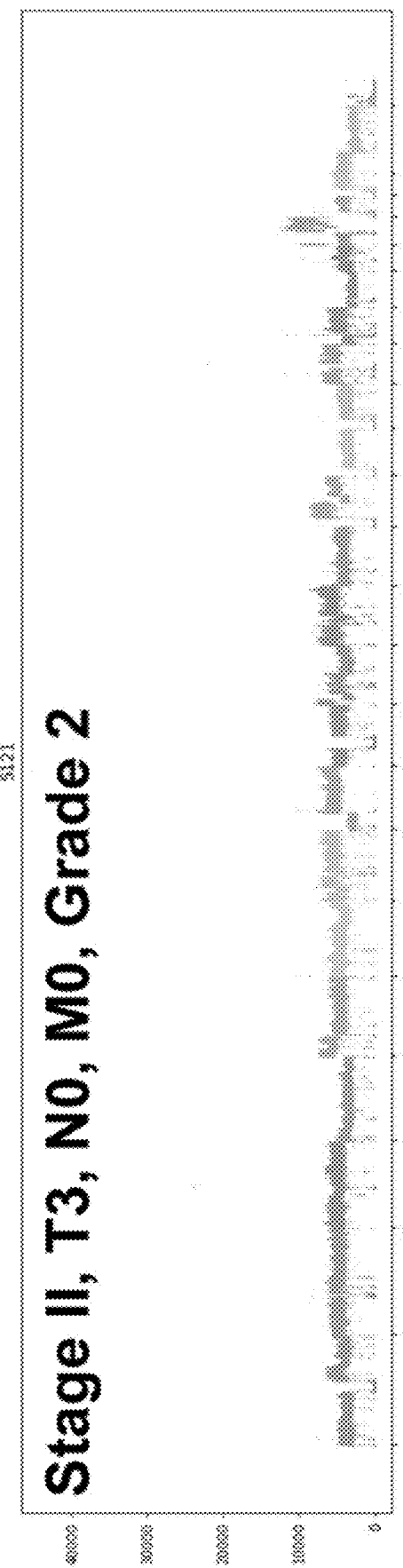
Figure 8D:
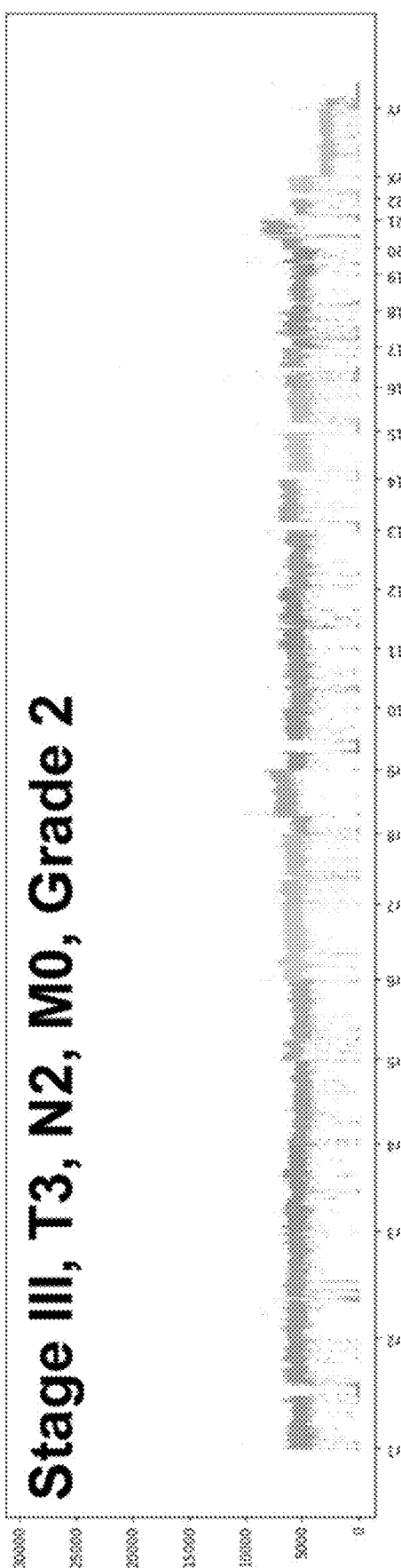
Figure 8E:
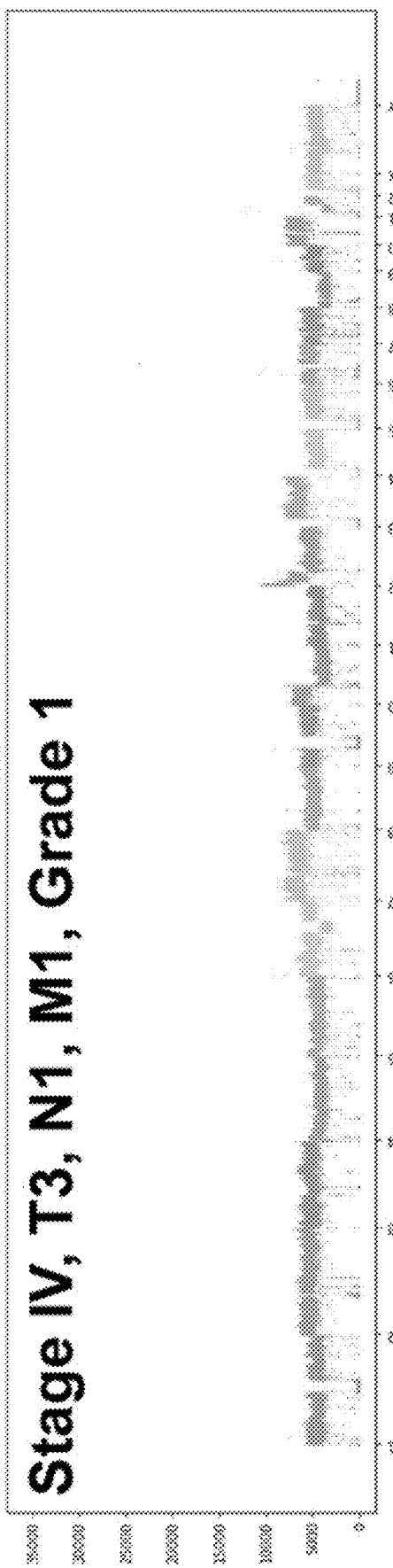
Figure 8F:
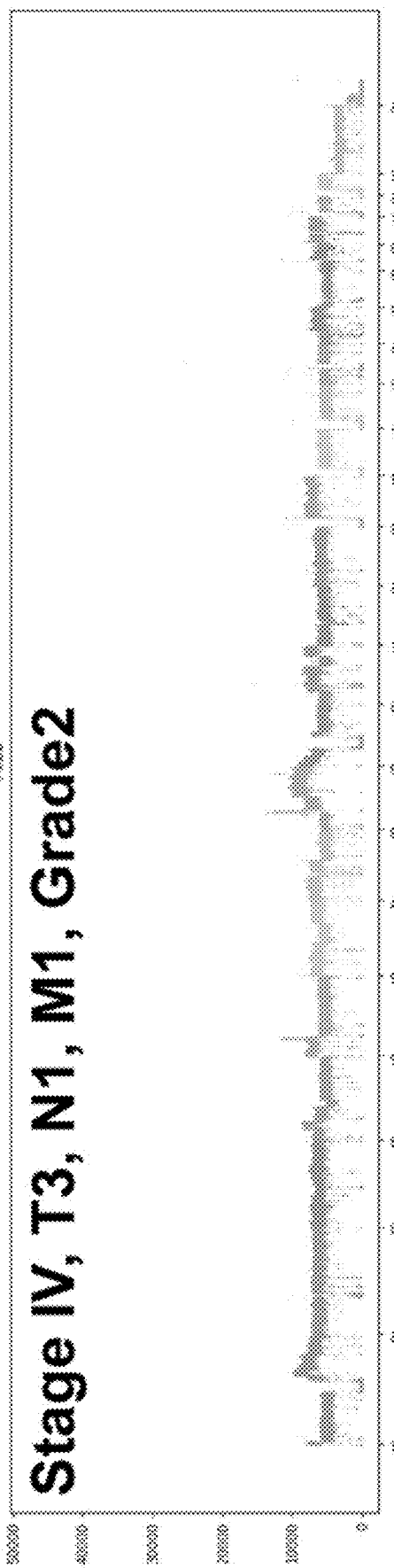
Figure 8G:
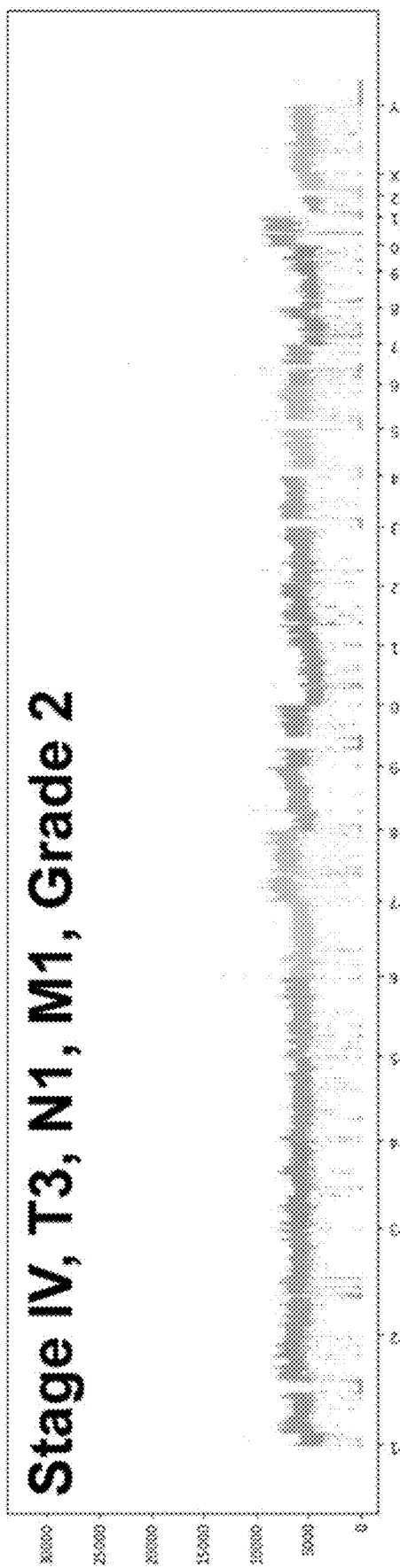
Figure 8H:
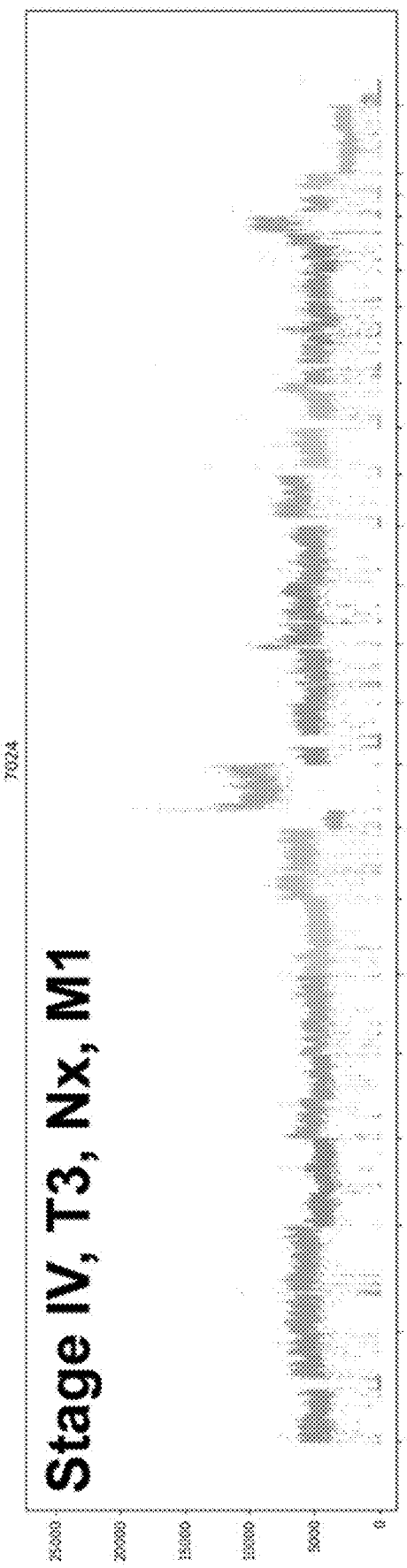

A 5× cross-validation was performed to obtain the AUC information for receiver operating characteristic curves in FIGS. 7A and 7B. The samples can be broken up into five different data sets, with training on four of the data sets and validation on the fifth data set. Sensitivity and specificity can be determined for a set of 4. Additionally, the assignment to sets can be updated with random seeds to provide further data. To determine sensitivity and specificity, the four classifications were reduced to 4, with healthy and benign polyps as one classification, and AA and CRC as the other classification.

FIG. 7A and FIG. 7B show classification performance for different analytes

B. Example 2: Analysis of Individual Assays for Classification of Biological Samples This example describes analysis of multiple analytes and multiple assays to distinguish between healthy individuals, AA and stages of CRC.

A blood sample was separated into different portions, and four assays of three classes of molecules were investigated. The classes of molecules were cell-free DNA, cell-free miRNA, and circulating proteins. Two assays were performed on the cf DNA.

De-identified blood samples were obtained from healthy individuals and individuals with benign polyps, advanced adenomas (AAs), and stage I-IV colorectal cancer (CRC). After plasma separation, multiple analytes were assayed as follows. First, cell-free DNA (cfDNA) content was assessed by low-coverage whole-genome sequencing (lcWGS) and whole-genome bisulfite sequencing (WGBS). Next, cell-free microRNA (cf-miRNA) was assessed by small-RNA sequencing. Finally, levels of circulating proteins and were measured by quantitative immunoassay.

Sequenced cfDNA, WGBS, and cf-miRNA reads were aligned to the human reference genome (hg38) and analyzed as follows. Further details are provided in the materials and methods section.

cfDNA (lcWGS): Fragments that aligned within annotated genomic regions were counted and normalized for depth of sequencing to produce a 30,000-dimensional vector per sample, each element corresponds to a count for a gene (e.g., number of reads aligning to that gene in a reference genome). Samples with high (>20%) tumor fraction were identified via manual inspection of large-scale CNV.

WGBS: Percentage of methylation was calculated per sample across LINE-1 CpGs and CpG sites in targeted genes (56 genes).

cf-miRNA: Fragments that aligned to annotated miRNA genomic regions were counted and normalized for depth of sequencing to produce a 1700-dimensional vector per sample.

Each of these sets of data can be filtered to identify measured values (e.g., reads aligned to a reference genome to get counts of reads for different genes). The measured values can be normalized. Further details on the normalization for each analyte is described in separate subsections for each analyte.

PCA analysis was performed for each analyte, and results are provided. Application of a machine learning model is provided in a separate section.

1. cf-DNA Low Coverage Whole Genome Sequencing

For a list of known genes having annotated regions, a sequence read count was determined for each of those annotated regions by counting the number of fragments aligned to that region. The read count for the genes can be normalized in various ways, e.g., using a global expectation that the genome is deployed; within-sample normalization; and a cross feature normalization. The cross feature normalization can refer to every one of those features averaging to specified value, e.g., 0, different negative values, one, or the range is 0 to 2. For cross feature normalization, the total reads from the sample is variable, and can thus depend on the preparation process and the sequencer loading process. The normalization can be to a constant number of reads, as part of a global normalization.

For a within-sample normalization, it is possible to normalize by some of the features or qualifying characteristics of some regions, in particular, for GC bias. Thus, the base pair makeup of each region can be different and used for normalization. And in some cases the number of GCs is significantly higher or lower than 50% and that has thermodynamic impact because the bases are more energetic and the processes are biased. Some regions provide more reads than expected because of biology artifacts of sample preparation in the lab. Thus, it may be necessary to correct for such biases by applying another kind of feature/feature transformation/normalization method.

FIGS. 8A-8H show a distribution of high tumor fraction samples (i.e. above 20%) as inferred by CNV, across clinical stage, indicating differences between healthy and normal. In this example, lcWGS of plasma cfDNA was able to identify CRC samples with high tumor fraction (>20%) on the basis of CNV across the genome. Moreover, high tumor fractions, while more frequent in late-stage CRC samples, were observed in some stage I and II samples. High tumor fractions were not observed in samples from healthy individuals or those with benign polyps or AAs.

FIGS. 8A-8H show CNV plots for individuals with high (>20%) tumor fraction based on cfDNA-seq data. Note that each plot in FIGS. 8A-8H corresponds to a histogram for a unique sample of the self-read DNA copy number. Note also that tumor fraction may be calculated by estimated from CNVs or using open source software such as ichor DNA. Table 3 shows distribution of high tumor fraction cfDNA samples across clinical stage.

TABLE 3

|  | Healthy | BP | AA | Stage I CRC | Stage II CRC | Stage III CRC | Stage IV CRC |
|---|---|---|---|---|---|---|---|
| N with high TF | 0 | 0 | 0 | 1 | 2 | 1 | 4 |
| Total N | 26 | 13 | 10 | 3 | 7 | 4 | 5 |

High tumor fraction samples do not necessarily correspond to samples clinically classified as late stage. In the figure, the total number of healthy people is 26. "BP" refers to benign polyps, "AA" refers to advanced adenoma, and "Chr" refers to chromosome.

2. Methylation

Differentially methylated regions (DMRs) are used for CpG sites. The regions can be dynamically assigned by discovery. It is possible to take a number of samples from different classes and discover which regions are the most differentially methylated between the different classifications. One then selects a subset to be differentially methylated and uses these for classification. The number of CpGs captured in the region is used. The regions may tend to be variable size. Accordingly, it is possible to perform a pre-discovery process that bundles a number of CPG sites together as a region. In this example, 56 genes and LINE1 elements (regions repeated across the genome) were studied. The percent methylation in these regions was investigated and used as features for training a machine learning model to perform classification. In this example, the classification makes use of essentially 57 features used for the PCA. The particular regions can be selected based on regions that had sufficient coverage through the samples.

Figure 9:
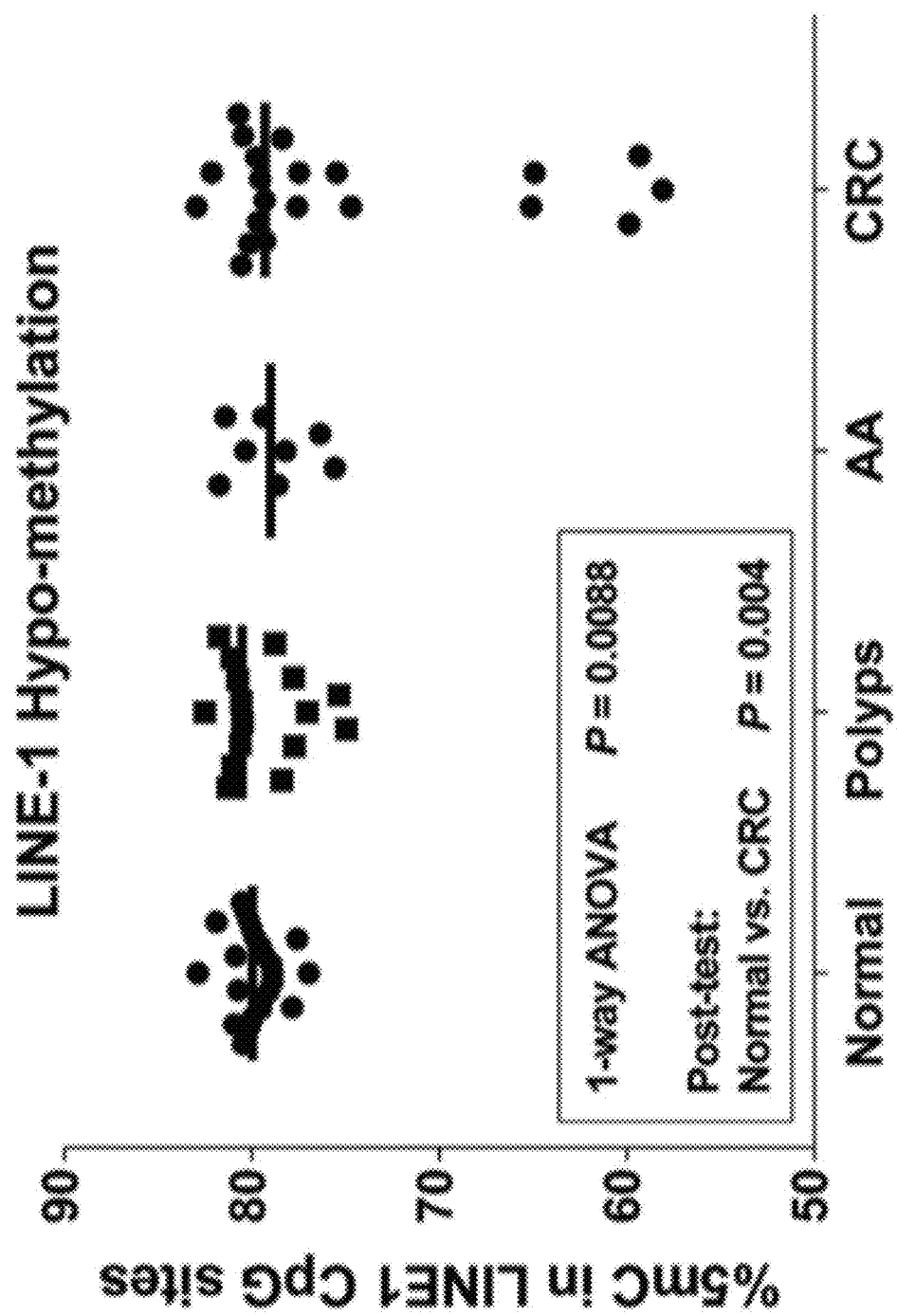
FIG. 9 shows CpG methylation analysis at LINE-1 Sites.

FIG. 9 shows CpG methylation analysis at LINE-1 Sites, indicating differences between healthy and normal samples. The figure shows methylation for all 57 regions used for the PCA. Each data point shown for the normal sample is for a different gene region and methylation.

In this example, genome-wide hypomethylation at LINE-1 CpG loci was only observed in individuals with CRC. Hypomethylation was not observed in samples without CRC, such as from healthy individuals or those with benign polyps or AAs. Note that each data point for the normal is for a different gene region and a methylation. In an example, all the reads that map to a region may be calculated. The system may determine whether the reads are positions are methylated and then sum the number of methylated CpG (e.g. C and G bases sequentially adjacent) and methylated CpG and calculate a ratio of the number of methylated CpG versus the number of methylated CpG.

In this example, significance was assessed by 1-way analysis of variance (ANOVA) followed by Sidak's multiple comparison test. Only significant adjusted P-values are shown. CpG hypomethylation of LINE-1 was only observed in CRC cases. Polyps (benign polyps), AA, CRC (stages I-IV). 5mC, 5-methylcytosine.

The percentage of DNA fragments aligned to sites and having methylation can be studied in the entire region of interest. For example, a gene region may have two CpG sites (e.g., C and G bases next to each other sequentially) for every, e.g., 100 reads aligning to the first CpG site and 90 reads aligning to the second CpG site, e.g., a total of 190. All the reads that map to that region are found and whether or not the reads are methylated is observed. Then the number of methylated CpGs is summed and a ratio of the number of methylated CpGs versus one of un-methylated CpGs is computed.

3. Micro-RNA

In this example, essentially every microRNA (miRNA) that was measurable (in this example, roughly 1700) was used as a feature. The measured values relate to the expression data for these miRNAs. Their transcripts are of a certain size, and each transcript is stored, and the number of miRNA found for each can be counted. For example, RNA sequences can be aligned to a reference miRNA sequence, e.g., a set of 1700 sequences corresponding to the known miRNA in the human transcriptome. Each miRNA found can be used as its own feature and everyone across all samples can become a feature set. Some samples have feature values that are 0, when there is no expression detected for that miRNA.

Figure 10:
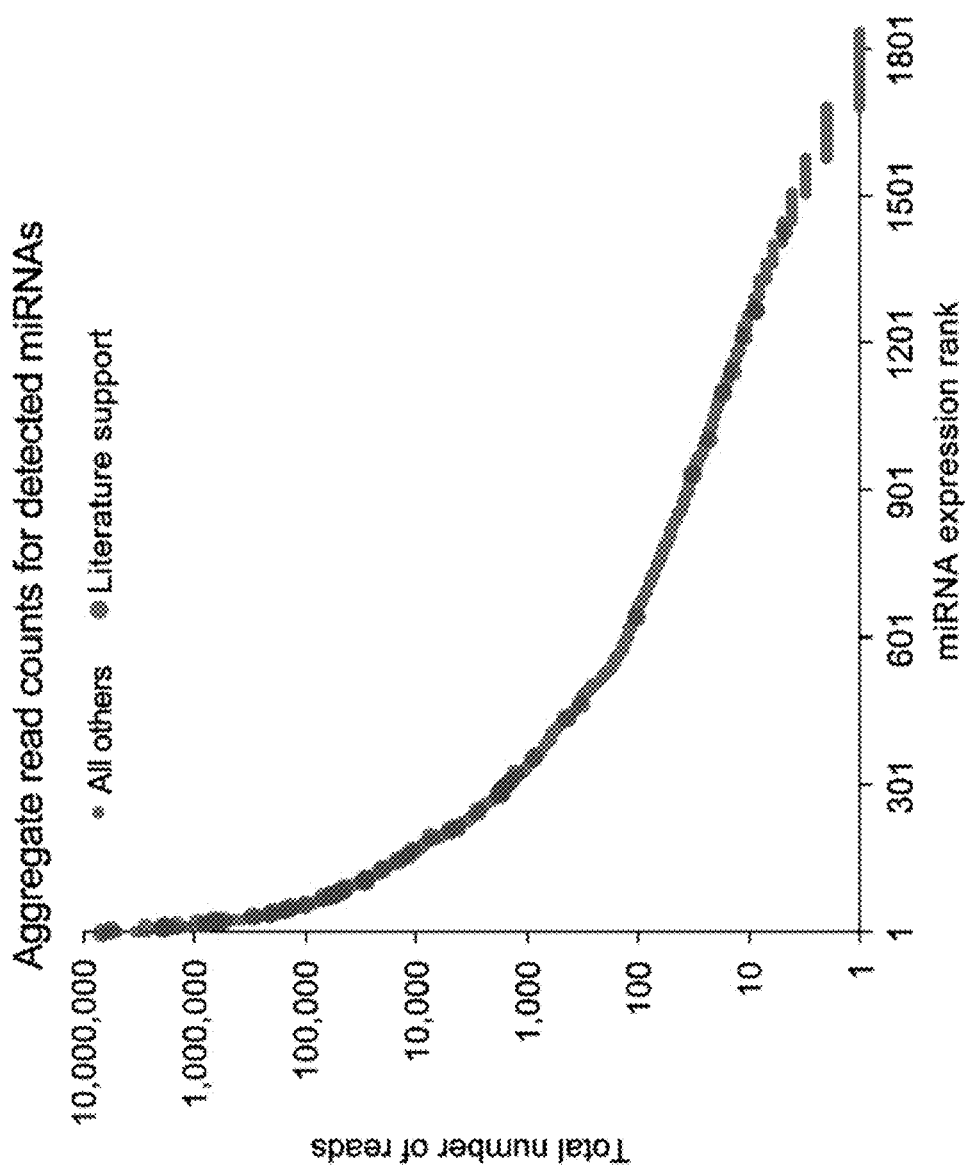
FIG. 10 shows cf-miRNA sequencing analysis.

FIG. 10 shows cf-miRNA Sequencing Analysis to characterize the microRNA. Shown are the number of reads mapping to each miRNA after pooling reads from all samples, rank ordered by expression. miRNAs indicated in red have been suggested as potential CRC biomarkers in the literature. Adapter-trimmed reads were mapped to mature human microRNA sequences (miRBase 21) using bowtie2. More than 1800 miRNAs were detected in plasma samples with at least 1 read, while 375 miRNAs were present at higher abundance (detected with an average of ≥10 reads per sample).

In an example, every sample is taken, and the reads are aggregated together. For each microRNA found in a sample, there may be numerous aggregate reads found. In this example, about 10 million aggregate reads were found to map to one single micro RNA; in aggregate, 300 micro RNAs were found with over 1,000 reads; about 600 were found with over 100 reads; 1,200 were found with 10 reads; and 1,800 or so with only a single read. Note that micro RNA with high expression rank may provide better markers, as a larger absolute change may result in a more reliable signal.

cf-miRNA profiles in individuals with CRC were discordant with those in healthy controls. In this example, miR-NAs suggested as potential CRC biomarkers in the literature tended to be present in higher abundance relative to other miRNAs.

4. Proteins

The protein data was normalized by a standard curve (14 proteins). Each one of the 14 proteins are essentially unique immunoassays, so each one has its own standard curve that typically recombinant protein in a very stable and optimized buffer. Thus, a standard curve is generated, which can be calculated in many ways. The concentration relationship is typically nonlinear. Then the sample is run and calculated based on the expected fluorescence concentration in the primary sample. The measured values can be triplicate measurements, but can be reduced to 14 individual values, e.g. by averaging or more complex statistical analysis.

Figure 11A:
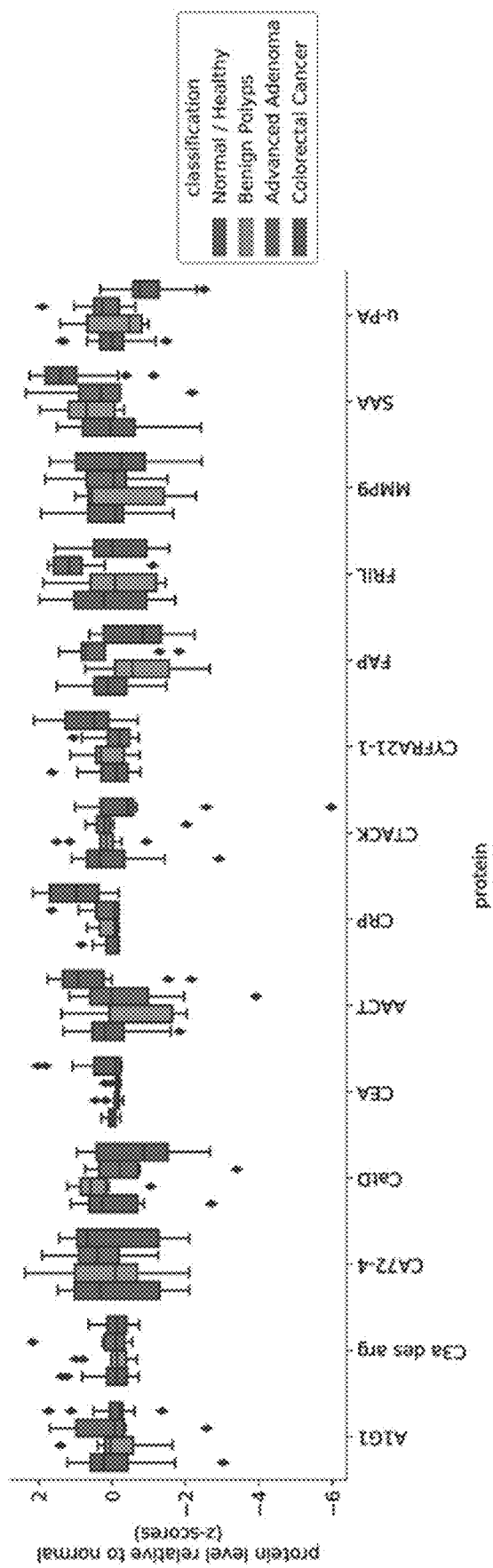
FIG. 11A shows circulating protein biomarker distribution.
Figures 11B, 11C, 11D:
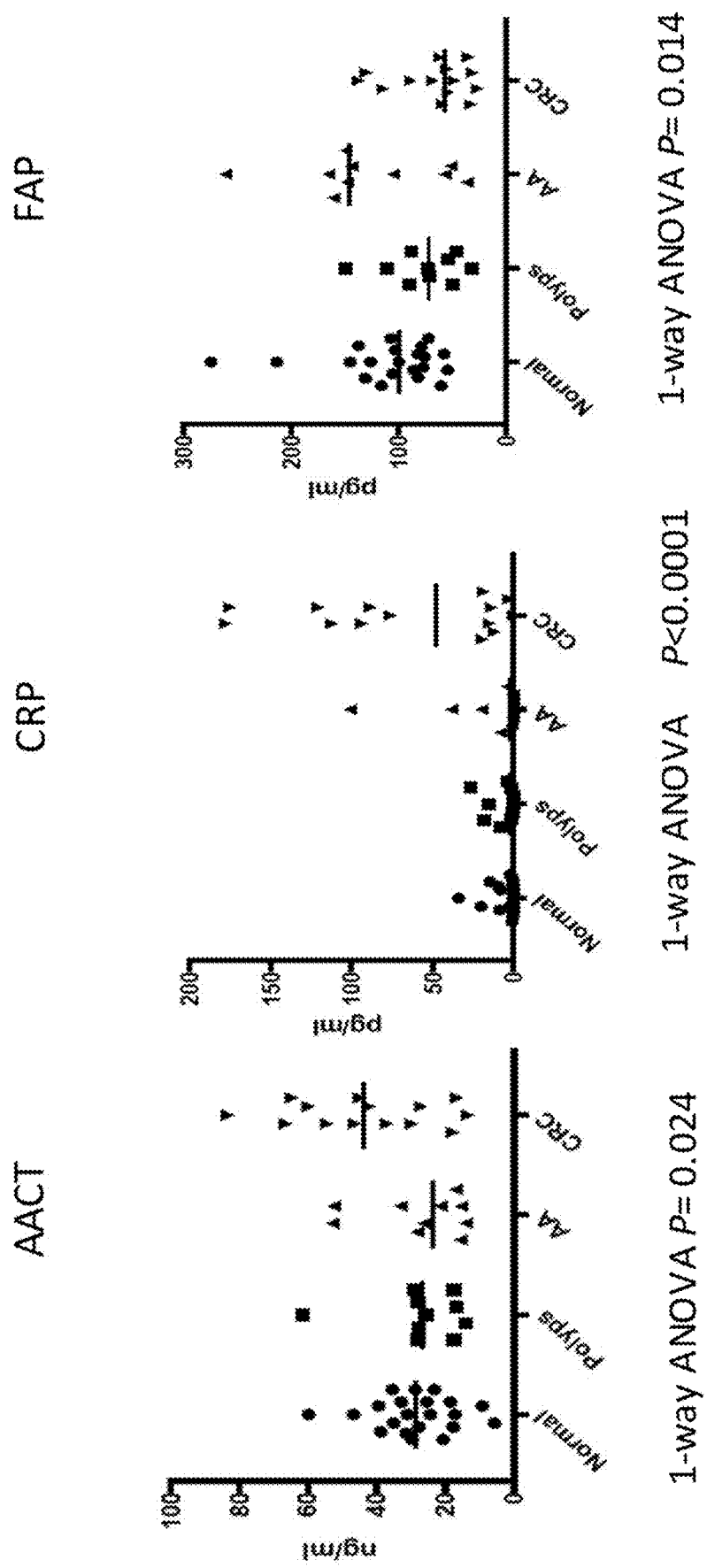
FIGS. 11B-11G show proteins which show significantly different levels across tissue types according to 1-way ANOVA followed by Sidak's multiple comparison test.
Figures 11E, 11F, 11G:
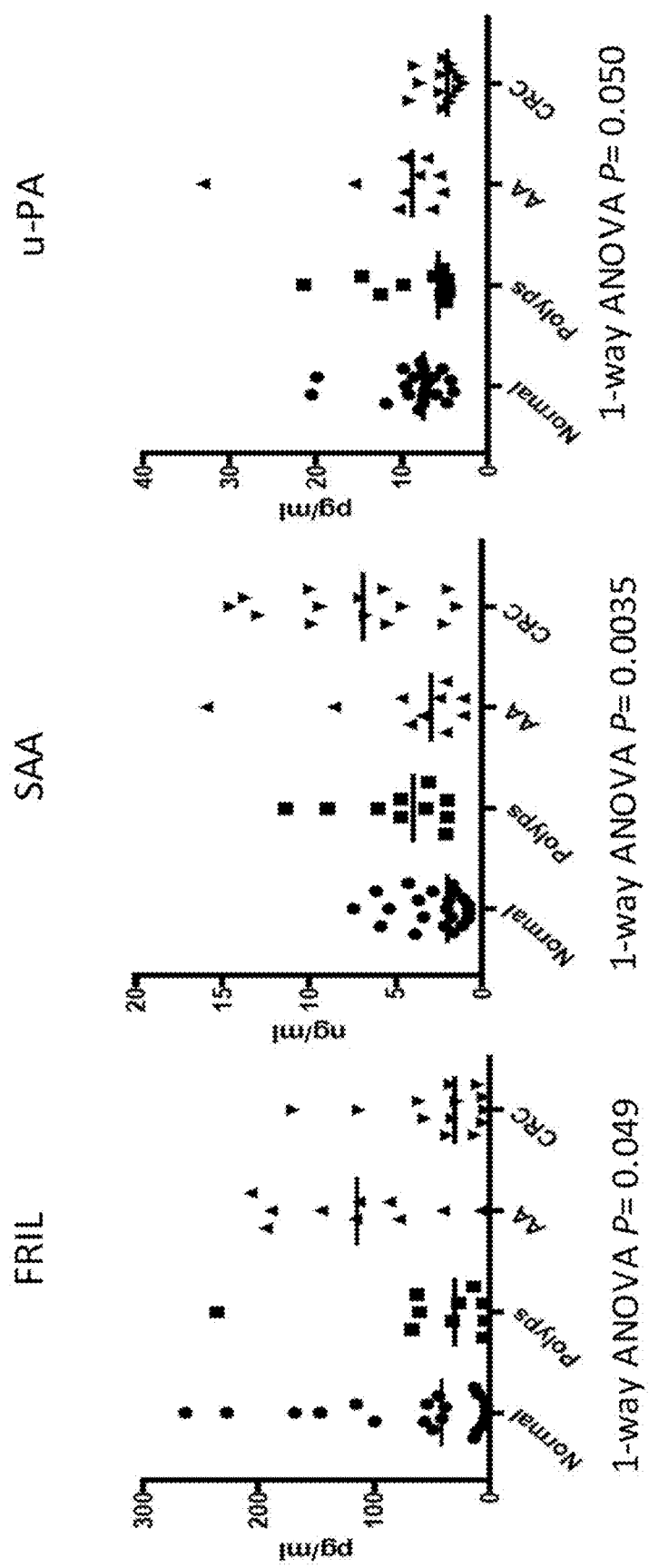

FIG. 11A shows circulating protein biomarker distribution. FIG. 11A shows boxplots indicating levels of all circulating proteins assayed, with outliers shown as diamonds. FIGS. 11B-11G show proteins which show significantly different levels across tissue types according to 1-way ANOVA followed by Sidak's multiple comparison test. Only significant adjusted P values are shown. Proteins measured using SIMOA (Quanterix): ATP-binding cassette transporter A1/G1 (A1G1), acylation stimulating protein (C3a des Arg), cancer antigen 72-4 (CA72-4), carcinoembryonic antigen (CEA), cytokeratin fragment 21-1 (CYFRA21-1), FRIL u-PA. Proteins measured by ELISA (Abcam): AACT, cathepsin D (CATD), CRP, cutaneous T-cell-attracting chemokine (CTACK), FAP, matrix metalloproeinase-9 (MMP9), SAA1.

In this example, in CRC samples, circulating levels of alpha-1-antichymotrypsin (AACT), C-reactive protein (CRP), and serum amyloid A (SAA) proteins were elevated, while urokinase-type plasminogen activator (u-PA) levels were lower compared with healthy controls. In AA samples, circulating levels of fibroblast activation protein (FAP) and Flt3 receptor-interacting lectin precursor (FRIL) proteins were elevated, while CRP levels were lower compared with CRC samples.

In this example, a distinction can be observed among some ANOVA plots. For example, CRP appears to be predictive. The FAP varies for the different ones. Accordingly, the multi analyte test can show an aggregate trend, whereas each one individually may be difficult to assess.

5. Dimensionality Reduction (e.g., PCA or Significant Difference)

Principal component analysis (PCA) was performed per analyte. In an example, the PCA is performed on the protein, the cell-free DNA, the methylation, and the microRNA data. Thus, four PCAs can be performed in that context.

In an example, all 14 proteins can be considered as a single analyte. For proteins, there are 14 measurements, thus 14 concentrations based on the individual fluorescence. These are vectorized with 14. The output of the PCA can be a component 1 that explains 31% of variation and component two that explains 17% of variation, etc. This can identify which proteins give the most variation.

For the lcWGS on cell-free DNA, a difference between a statistical value (e.g., mean, median, etc,) of the gene counts is used to identify genes with the most variance.

Figure 12B:
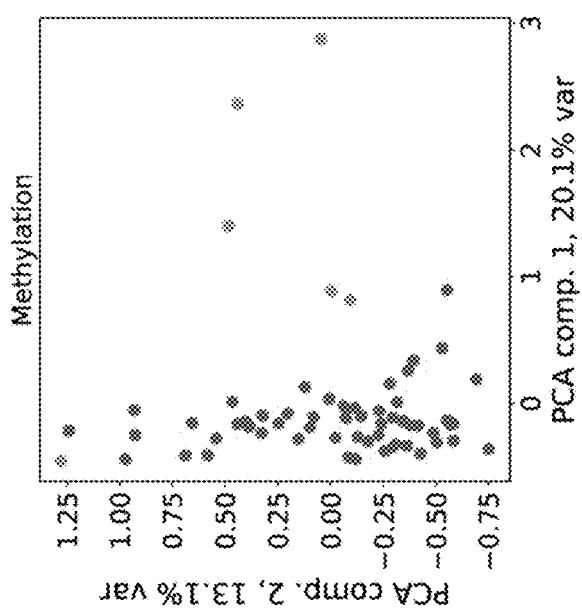
FIGS. 12A-12D show PCA of cfDNA, CpG methylation, cf-miRNA and protein counts as a function of tumor fraction.
Figure 12D:
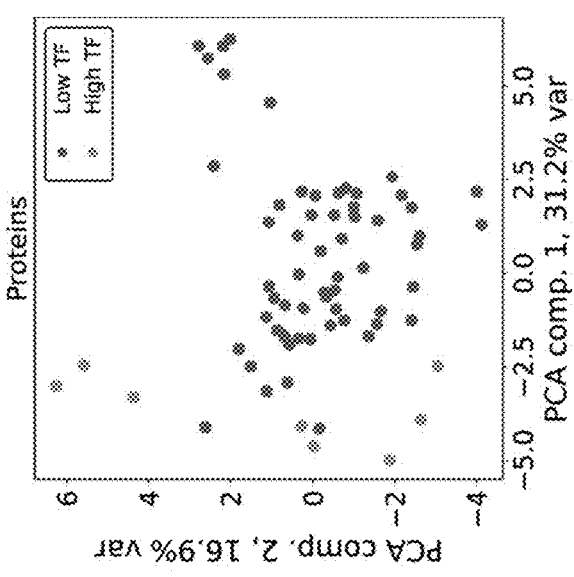
Figure 12A:
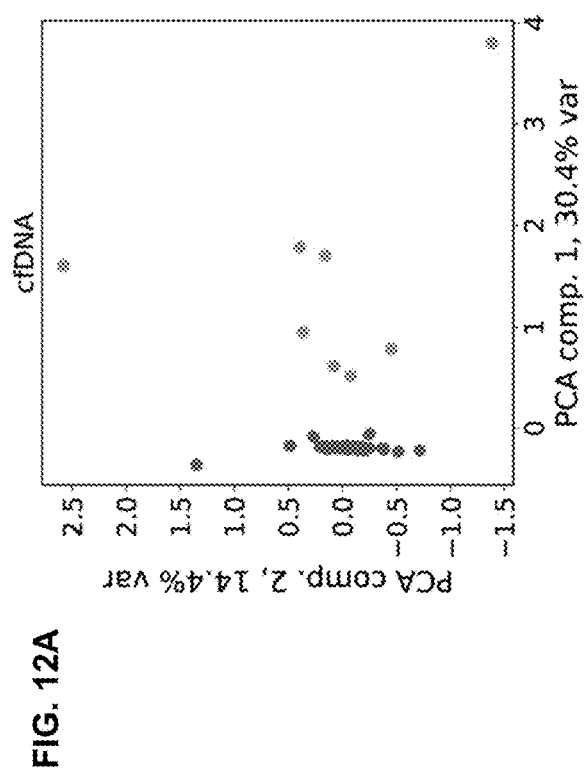
Figure 12C:
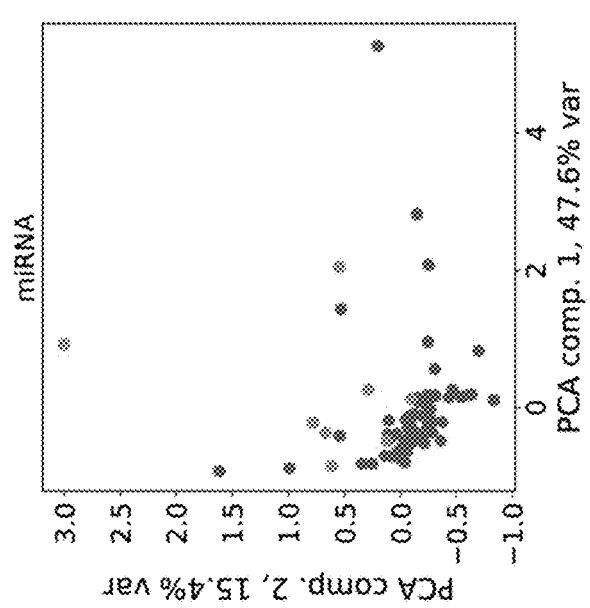
Figure 12F:
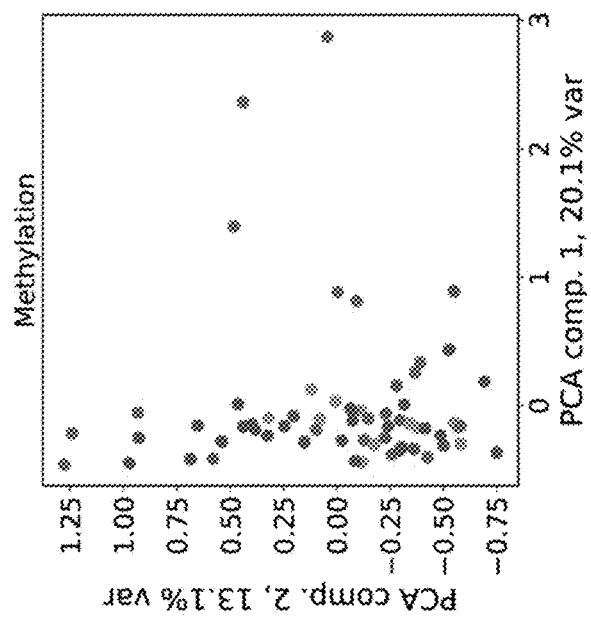
FIGS. 12E-12H show PCA of cfDNA, CpG methylation, cf-miRNA and protein counts as a function of patient diagnosis.
Figure 12H:
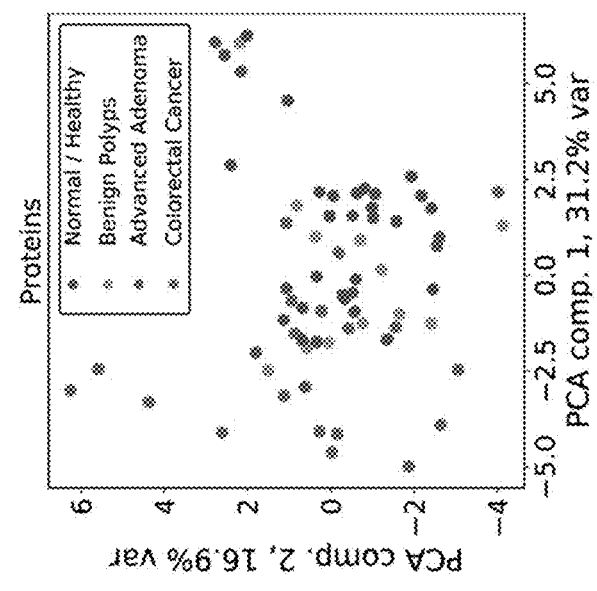
Figure 12E:
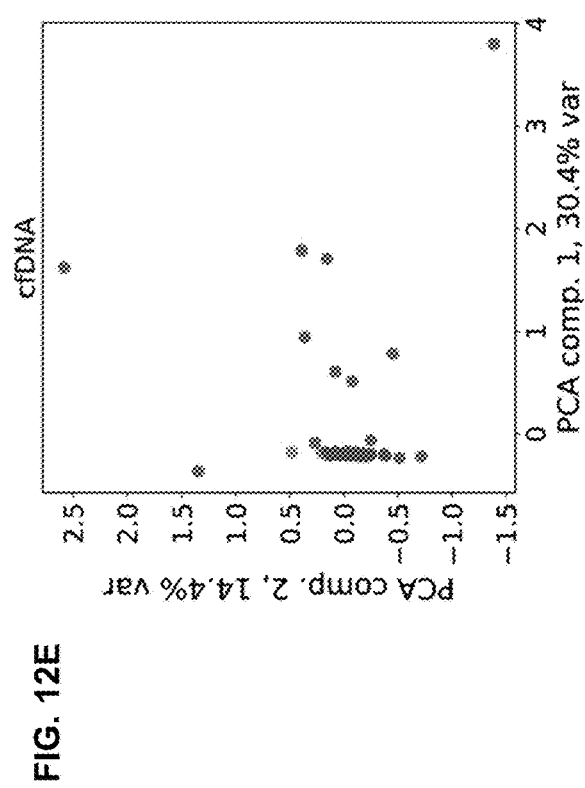
Figure 12G:
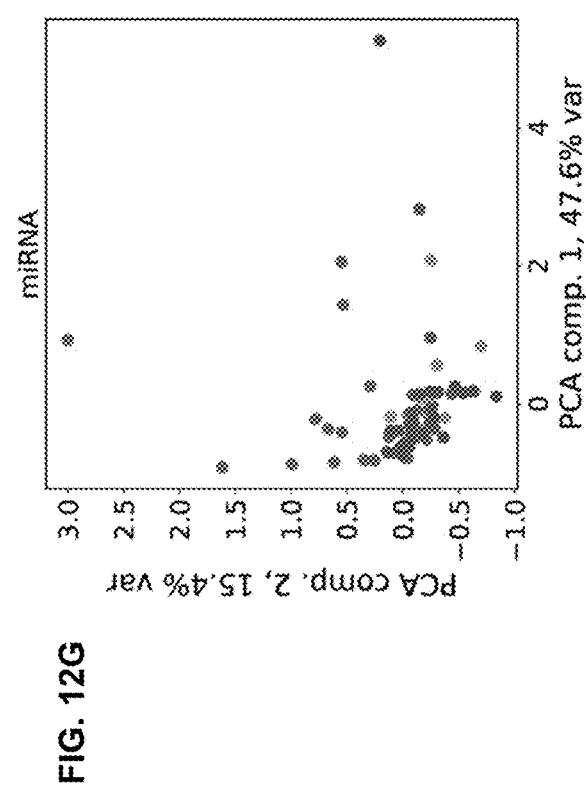

FIG. 12A shows the output of PCA analysis of cf-DNA, CpG methylation, cf-miRNA and protein counts as a function of tumor fraction. FIG. 12B shows PCA of cf-DNA, CpG methylation, cf-miRNA and protein counts as a function of analyte. High tumor fraction samples have consistently aberrant behavior across all 4 analytes investigated.

In the example of FIG. 12A, the PCA is used to separate distance between high and low tumor fraction. In FIG. 12B, it is sample classification (Normal, healthy, benign polyps, and colorectal cancer) for the different analytes. The disclosed system and methods can be used to maximize the differentiation between such classes. In this example, aberrant profiles across analytes were indicative of high TF (as estimated from cfDNA CNV), rather than cancer stage. Each dot shown corresponds to a separate sample; the PCA is the value for the highest component.

Various implementations may be used for dimensionality reduction. For dimensionality reduction, there are multiple different hypothesis tests can be used to calculate, e.g., significant differences and multiple different criteria used to set a threshold of how many to include. PCA or SVD (singular value decomposition) may be performed on the correlation matrix or the covariance matrix rather than on the data itself. Auto-encoding or variational auto-encoding can be used. Such filtering can filter out measured values (e.g., counts for regions) that have low variance 6. Conclusions lcWGS of plasma cfDNA was able to identify CRC samples with high tumor fraction (>20%) on the basis of copy number variation (CNV) across the genome. High tumor fractions, while more frequent in late-stage cancer samples, were observed in some stage I and II patients. Aberrant signals in each of the three other analytes—cf-miRNA profiles discordant with those in healthy controls, genome-wide hypomethylation at LINE1 (long interspersed nuclear element 1) CpG loci, and elevated levels of circulating carcinoembryonic antigen (CEA) and cytokeratin fragment 21-1 (CYFRA 21-1) proteins—were also observed in cancer patients. Strikingly, aberrant profiles across multiple analytes were indicative of high tumor fraction (as estimated from cfDNA CNV), rather than cancer stage.

These data suggest that tumor fraction is correlated with cancer stage, but has a large potential range, even in early stage samples. Previous literature on blood-based screens for detection of cancer has displayed discordance in the claimed ability of different single analytes to detect early stage cancer. tumor fraction may be able to explain the historical disagreement, as we found that aberrant profiles among cfDNA CpG methylation, cf-miRNA, and circulating protein levels were more strongly associated with high tumor fraction than with late stage. These findings suggest that some positive "early stage" detection results may in fact be "high tumor fraction" detection results. The results further demonstrate that assaying multiple analytes from a single sample may enable the development of classifiers that are reliable at low tumor fraction and for detecting pre-malignant or early-stage disease. Such multi-analyte classifiers are described below.

C. Example 3: Identification of Hi-C-Like Structure Using Covariance of Sequence Depth in Two Different Genomic Regions from cfDNA Across Multiple Samples This example describes a method of Identification of Hi-C-like structure at two different genomic regions from cfDNA in single sample to identify cell-type-of-origin as a feature for multianalyte-model generation.

Figure 13:
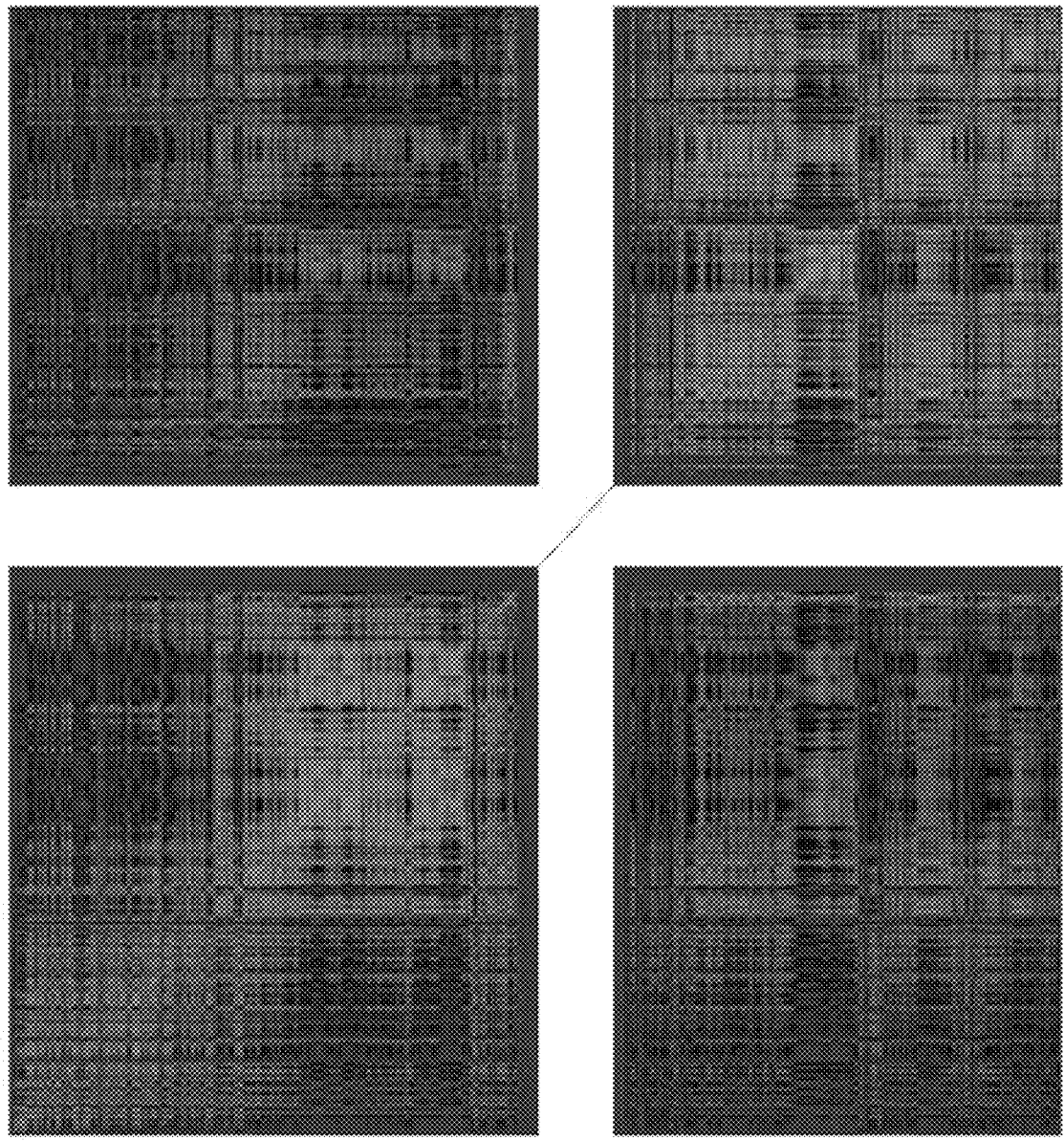
FIG. 13 shows a heatmap of chromosomal structure scores determined from the nuance structure of the correlation matrix generated using Pearson/Spearman/Kendall correlation of a region of the genome using cfDNA samples.
Figure 14:
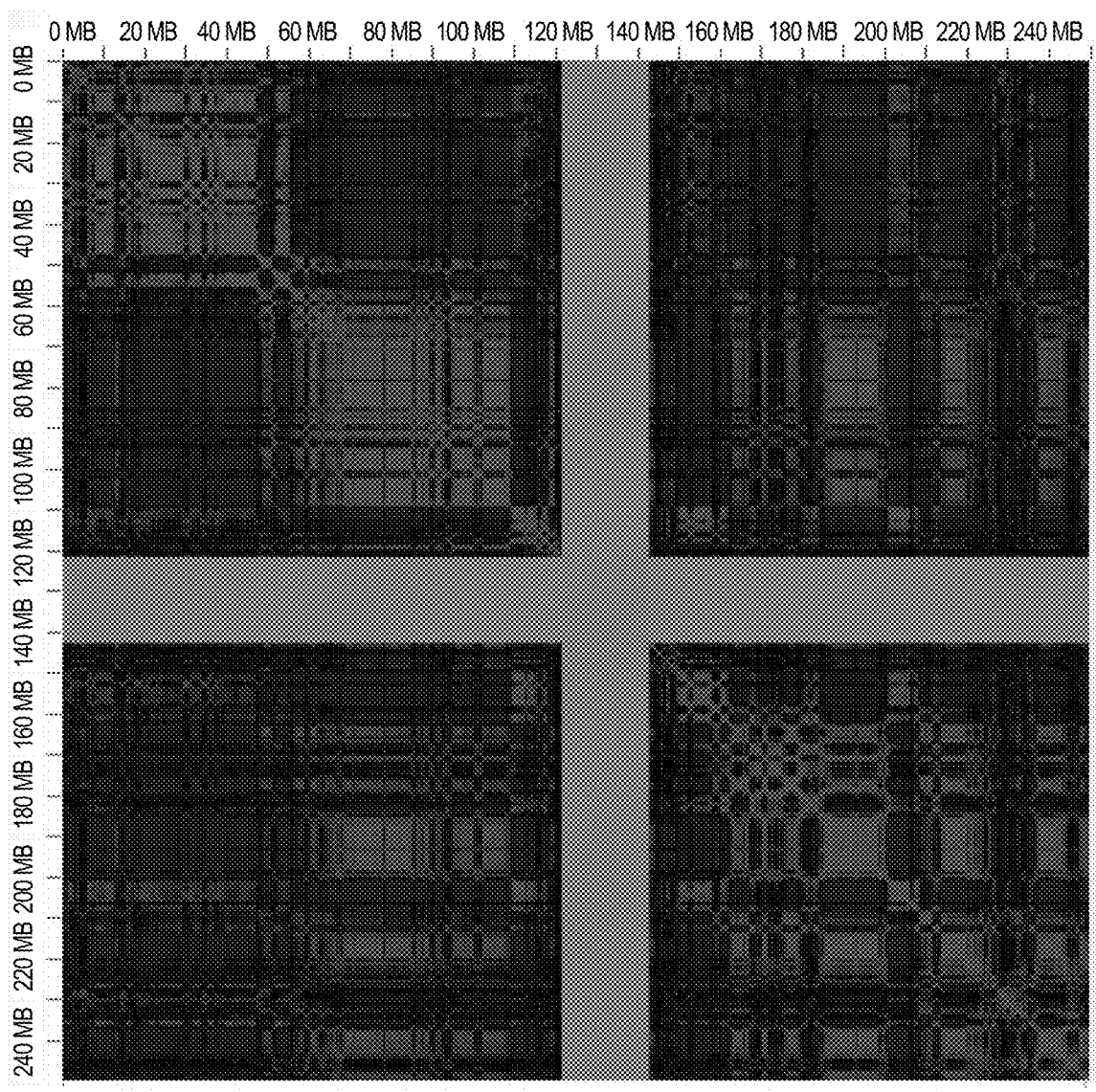
FIG. 14 shows a heatmap of chromosomal structure scores determined from Hi-C sequencing of the same region of the genome as in FIG. 13

The genome sequence of multiple cfDNA samples was segmented into non-overlapping bins of varying length (for example, 10-kb, 50-kb, and 1-Mb non-overlapping bins). The number of high-quality mapped fragments within each bin was then quantitated. The high-quality mapped fragments met a quality threshold. Pearson/Kendall/Spearman correlation was then used to calculate the correlation between pairs from the bins within the same chromosome or between different chromosomes. The structure score calculated from the nuance structure of the correlation matrix was used to generate a heatmap as shown in FIG. 13. A similar heatmap was generated using structure scores determined using Hi-C sequencing as shown in FIG. 14. The similarity of the two heatmaps suggests that the nuance structure determined using covariance was similar to the structure determined by Hi-C sequencing. Potential technical bias caused by GC bias, genomic DNA, and the correlation structure in MNase digestion was ruled out.

Genomic regions (larger bin size) were split into smaller bins and the Kolmogorov-Smirnov (KS) test was used to calculate the correlation between two larger bins. The KS test score provided information about the Hi-C-like structure, which can be used to distinguish cancer and control groups.

Two-dimensional segmentation (HiCseg) was used to segment and call domains in the correlation structure in cfDNA and Hi-C. The two approaches resulted in similar numbers of domains and highly overlapping domains.

Identification of cfDNA-specific co-releasing patterns. The covariance structure in cfDNA indicated that a mixed input signal pattern from multiple sources, including chromatin structure, genomic DNA, MNase digestions, and possible co-releasing pattern of cfDNA. Deep learning was used to remove signals from the other sources and only retain the potential co-releasing pattern of cfDNA.

Three-dimensional proximity of chromatin in cancer and non-cancer samples can be inferred from long-range spatial correlated fragmentation patterns. Fragmentation patterns of cfDNA from different genomic regions are not uniform and reflect local epigenetic signatures of the genome. There is high similarity between long-range epigenetic correlation structures and high order chromatin organization. Thus, long-range spatial correlated fragmentation patterns can reflect three-dimensional proximity of chromatin. A genome-wide map of in vivo high-order chromatin organization inferred from co-fragmentation patterns was generated using fragment length alone in cfDNA. Fragments generated from the endogenous physiological processes can reduce the likelihood of the technical variations associated with random ligation, restriction enzyme digestion, and biotin ligation during Hi-C library preparations. Sample collection and preprocessing: Retrospective human plasma samples (>0.27 mL) were acquired from 45 patients diagnosed with colon cancer (colorectal cancer), 49 patients diagnosed with lung cancer, and 19 patients diagnosed with melanoma. 100 samples from patients without a current cancer diagnosis were also acquired. In total, samples were collected from commercial biobanks from Southern and Northern Europe, and the United States. All samples were de-identified. Plasma samples were stored at −80° C. and thawed prior to use.

Cell-free DNA was extracted from 250 μL plasma (spiked with unique synthetic dsDNA fragments for sample tracking) using the MagMAX Cell-Free DNA Isolation Kit (Applied Biosystems) per manufacturer instructions. Paired-end sequencing libraries were prepared using the NEBNext Ultra II DNA Library Prep Kit (New England Biolabs) and sequenced on the Illumina NovaSeq 6000 Sequencing System with dual index across multiple S2 or S4 flowcells at 2×51 base pairs.

Whole genome sequencing data processing: Reads were de-multiplexed and aligned to the human genome (GRCh38 with decoys, alt contigs, and HLA contigs) using BWA-MEM 0.7.15. PCR-duplicate fragments were removed using unique molecular identifiers (UMIs). Contamination was assessed using a contamination model that marginalized over all possible genotypes and contamination fractions for common SNPs as identified by 1000 Genomes (IGSR).

Sequencing data were checked for quality and omitted from analysis if any of the following conditions were met: AT dropout >10 or GC dropout >2 (both computed via Picard 2.10.5). Any samples that were suspected of being contaminated because of expected allele fraction <0.99, unexpected genotype calls, or a failed negative control were manually inspected prior to inclusion in the data set. The adapter was trimmed by Atropos with default parameters. Only high quality reads with both ends uniquely mapped (having a mapping quality score of more than 60), properly paired, and not a PCR duplicate were used for all of the downstream analyses. Only autosomes were used in all downstream analyses.

Hi-C library preparation: In situ Hi-C library preparation of whole blood cells and neutrophils was performed by using Arima genomics service.

Hi-C data processing: Raw fastq files were uniformly processed through Juicerbox command line tools v1.5.6. Results having a mapping quality score of greater than 30 after filtering reads were used to generate a Pearson correlation matrix and compartment A/B. Principal component analysis (PCA) was calculated by PCA function at scikit-learn 0.19.1 in Python 3.5. The first principal component was used to segment the compartment. For each chromosome, compartments were grouped into two groups based on sign. The group of compartments with a lower mean value for gene density was defined as compartment B. The other group was defined as compartment A. Gene density was determined by gene number annotated by ensemble v84. The sequencing summary statistics and related metadata information are shown in TABLE 4.

calculated by a two-way KS test (ks_2samp function implemented in SciPy 1.1.0 with Python 3.6). P value was then converted to log10 scale. Pearson correlation for a particular paired bin was then calculated Sequence composition and mappability bias analysis: Mappability score was generated by GEM 17 for read length of 51 bp. G+C % was calculated by the gc5base track from UCSC genome browser. For each pair of 500-kb bins, G+C % and mappability was obtained from bin1 and bin2. A Gradient Boosting Machine (GBM) regression tree (GradientBoostingRegressor function implemented in scikit-learn 0.19.1 at Python 3.6) was then applied to regress out G+C % and mappability of each pixel of correlation coefficient score from the matrix of cfHi-C, gDNA, and Hi-C data. N_estimators was varied with depth=5 at different model complexities. Residual value after the regression was then used to calculate the correlation with whole blood cells (WBC) Hi-C data at the pixel level. The r2 value was calculated to measure the goodness-of-fit of the model.

Tissue-of-origin analysis in cfHi-C: To infer tissue of origin from cfHi-C data, the compartment of cfHi-C data (first PC on correlation matrix in cfHi-C) was modeled as a linear combination of the compartment in each of the reference Hi-C data (first PC on correlation matrix in cfHi-C). The eigenvalue was re-evaluated to ensure that compartment A was a positive number. Genomic regions with mappability of less than 0.75 were filtered out. Eigenvalues across cfHi-C and reference Hi-C panel were first transformed by quantile normalization. For each reference Hi-C dataset, only genomic bins that showed the highest eigenvalue to the rest of the reference Hi-C datasets (lowest when eigenvalue is negative) were used for the deconvolution analysis. The weights were constrained to sum up to 1 so that the weights can be interpreted as tissue contribution

TABLE 4

| Sample | Cell type | Sequenced Read Pairs | Alignable | Unique Reads | PCR Duplicates | Hi-C Contacts (mapQ >30) | Intra-chromosomal | Long Range (>20 Kb) |
|---|---|---|---|---|---|---|---|---|
| WBC (rep1) | Healthy primary cell | 497,515,422 | 399,546,659 | 360,941,621 | 37,159,056 | 281,540,814 | 212,861,951 | 130,109,640 |
| WBC (rep2) | Healthy primary cell | 504,116,676 | 404,185,417 | 370,323,116 | 32,765,071 | 291,948,221 | 215,483,948 | 135,398,173 |
| Neutrophil | Healthy primary cell | 1,964,564,641 | 1,604,729,787 | 1,368,283,218 | 227,593,030 | 1,056,873,797 | 778,621,055 | 462,518,953 |

Multiple-sample cfHi-C: 500-kb bins with mappability less than 0.75 were removed for the downstream analysis. Each 500-kb bin was first divided into 50-kb sub-bins. The median fragment length in each sub-bin was first summed up in the 500-kb bin and then normalized by the z-score method with the mean and the standard deviation of each chromosome and each sample. Pearson correlation was calculated between each paired bins across all the individuals.

Single-sample cfHi-C: 500-kb bins with a mappability of less than 0.75 were removed from the downstream analysis. The fragment length of all high-quality fragments in each 500-kb bin was then determined. The distribution similarity of fragment length within each pair of 500-kb bin was to cfDNA. Quadratic programming was used to solve the constrained optimization problem. To define tumor fraction, tissue contribution fractions from cancer were summed up.

ichorCNA analysis: ichorCNA v0.1.0 with default parameters was used to calculate the tumor fraction in each cfDNA WGS samples after normalizing to the group of the internal healthy samples.

Code and data availability: All the analysis codes were implemented in Python 3.6 and R 3.3.3. Publicly available data used in the study are shown in TABLE 5. Detailed summary statistics of fragment length at genomic bin level of each cfDNA sample.

TABLE 5

| Sample | Cell Type | Data type | Publications/Consortium |
|---|---|---|---|
| CD3+ T cell | Normal primary cell | Hi-C | NA |
| B cell (GM12878) | Normal Cell Line | Hi-C | PMID: 25497547 |
| Monocyte (THP-1) | Normal Cell Line | Hi-C | PMID: 28890333 |
| Erythroid Progenitor | Normal Cell Line | Hi-C | |
| HSPC | Normal Cell Line | Hi-C | |
| Endothelial cell of hepatic sinusoid | Normal liver | Hi-C | Encode |
| HEPG2 | Liver cancer cell line | Hi-C | Encode |
| Colon | Normal colon | Hi-C | PMID: 28985562 |
| HCT116 | Colon cancer cell line | Hi-C | Encode |
| DLD1 | Colon cancer cell line | Hi-C | Encode |
| Lung | Normal lung | Hi-C | Encode |
| A549 | Lung cancer cell line | Hi-C | Encode |
| NCI-H460 | Lung cancer cell line | Hi-C | Encode |
| HMEC | Normal breast epithelia cell line | Hi-C | Encode |
| T47D | Breast cancer cell line | Hi-C | Encode |
| RPMI-7951 | Melanoma cancer cell line | Hi-C | Encode |
| SK-MEL-5 | Melanoma cancer cell line | Hi-C | Encode |
| Genomic DNA | Whole blood | WGS | SRA |
| cfDNA | Circulating cfDNA | WGS | PMID: 26771485 |
| B cell (GM12878) | Normal Cell Line | DNas-seq | Encode |
| B cell (GM12878) | Normal Cell Line | WGBS | Encode |
| B cell (GM12878) | Normal Cell Line | H3K4me1, ChIP-seq | Encode |
| B cell (GM12878) | Normal Cell Line | H3K4me2, ChIP-seq | Encode |
| B cell (GM12878) | Normal Cell Line | H3K4me3, ChIP-seq | Encode |
| B cell (GM12878) | Normal Cell Line | H3K9ac, ChIP-seq | Encode |
| B cell (GM12878) | Normal Cell Line | H3K27ac, ChIP-seq | Encode |
| B cell (GM12878) | Normal Cell Line | H2AFZ, ChIP-seq | Encode |
| B cell (GM12878) | Normal Cell Line | H3K36me3, ChIP-seq | Encode |
| B cell (GM12878) | Normal Cell Line | H3K79me2, ChIP-seq | Encode |
| B cell (GM12878) | Normal Cell Line | H4K20me1, ChIP-seq | Encode |
| B cell (GM12878) | Normal Cell Line | H3K27me3, sChIP-eq | Encode |

Figures 15A, 15B, 15C:
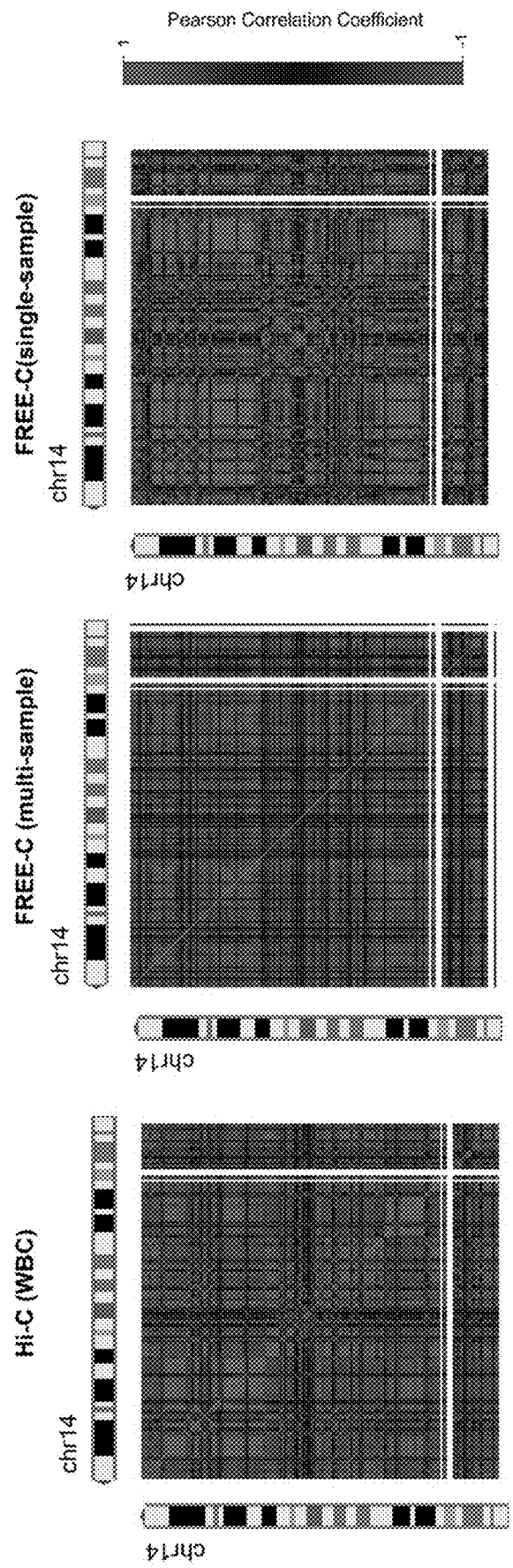
FIGS. 15A-15C show correlation maps generated from Hi-C, spatial correlated fragment length from multiple cfDNA samples, and spatial correlated fragment length distribution from a single cfDNA sample.
Figure 15D:
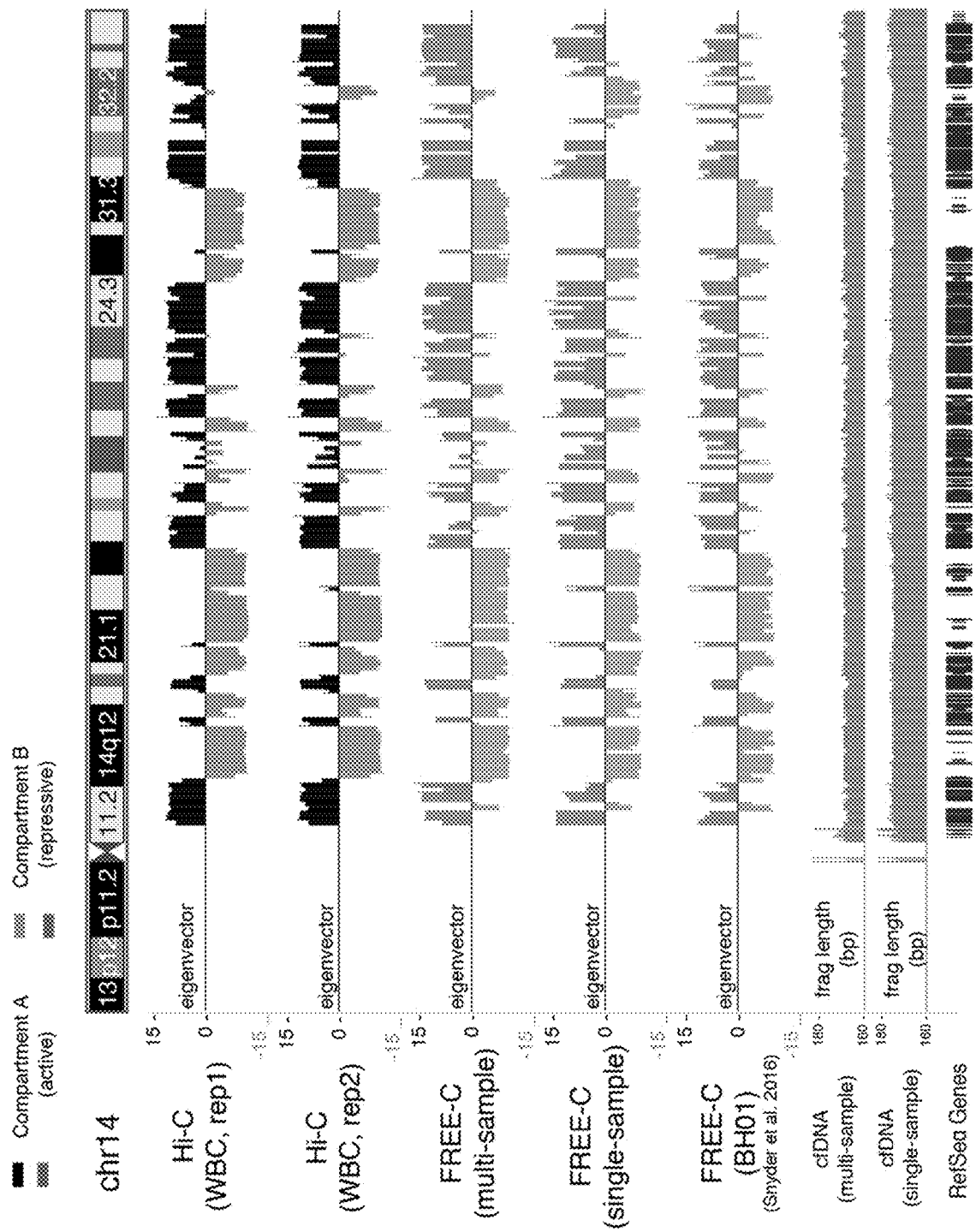
FIG. 15D shows genome browser tracks of compartment AB from Hi-C, multiple-sample cfDNA, and single-sample cfDNA.
Figure 15F:
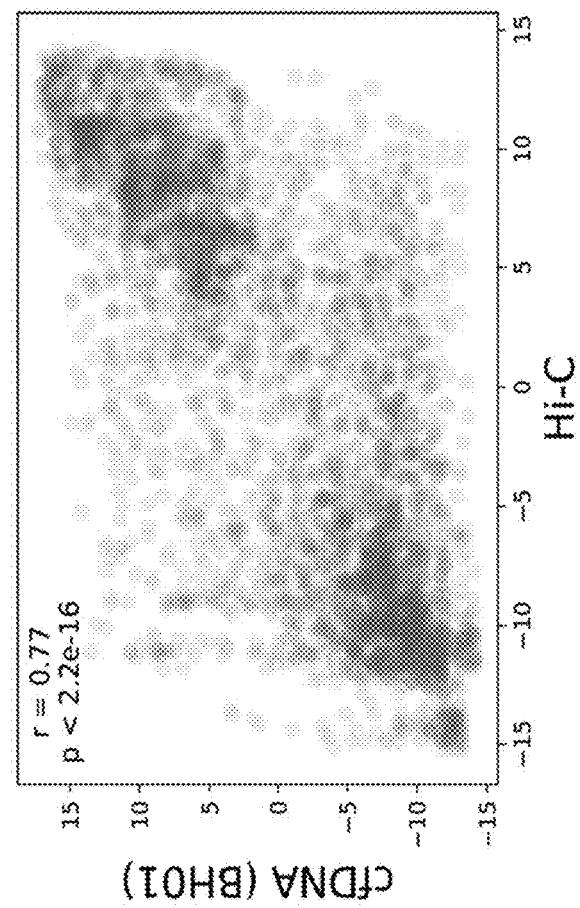
FIGS. 15E-F show scatter plots of the concordance at the compartment level between Hi-C, multiple-sample cfDNA (FIG. 15E), and single-sample cfDNA (FIG. 15F).
Figure 15E:
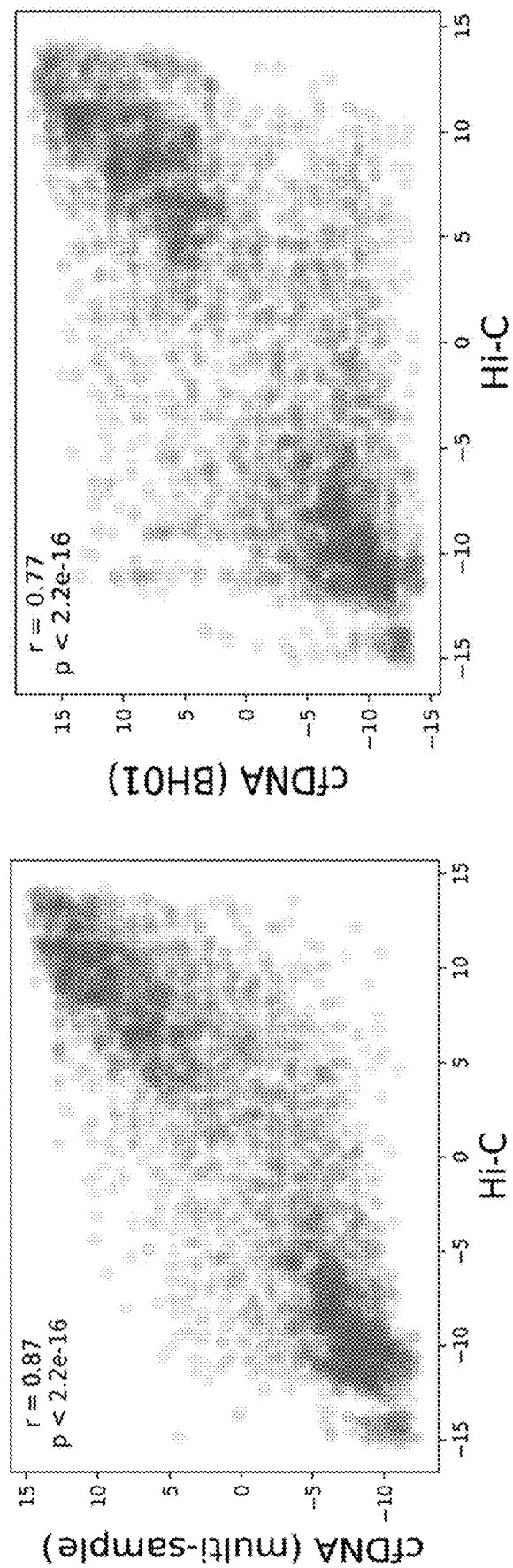

Paired-end whole genome sequencing (WGS) was performed on cfDNA from 568 different healthy individuals. For each sample, 395 million paired-end reads were obtained on average (approximately 12.8× coverage). After quality control and read filtering, 310 million high quality paired-end reads for each sample on average (approximately 10× coverage) were obtained. The autosome was divided into 500-kb, non-overlapping bins and the normalized fragmentation score was calculated from fragment length alone at each bin for each individual sample. The Pearson correlation coefficient was then calculated between each pair of bins at the normalized fragmentation score across all of the individuals. Similar patterns were found between the fragmentation correlation map of cfDNA and compartments of Hi-C experiments from whole blood cells (WBC) from two healthy individuals (FIGS. 15A-15D). FIGS. 15A-15C show correlation maps generated from Hi-C, spatial correlated fragment length from multiple cfDNA samples, and spatial correlated fragment length distribution from a single cfDNA sample. FIGS. 15D-15F show genome browser tracks of compartment A/B from Hi-C (WBC), multiple-sample cfDNA, and single-sample cfDNA. All comparisons were from chromosome 14 (chr14).

To quantify the degree of similarity, a Pearson correlation was calculated at the pixel level between Hi-C and inferred chromatin organization from cfDNA (genome-wide average Pearson r=0.76, p<2.2e-16). The pixel-level correlation coefficient shown in Hi-C was calculated from replicates of two different healthy individuals. The pixel-level correlation coefficient shown in cfDNA (multiple-sample FIG. 15E and single-sample FIG. 15F) was calculated by correlation with WBC individual 2.

Compartment A/B at Hi-C data and inferred chromatin organization from cfDNA were further called. There was higher concordance between Hi-C and inferred chromatin organization from cfDNA at the compartment level (Pearson r=0.89, p<2.2e-16). Compartment A/B called from Hi-C were largely overlapped with the results from cfDNA (hypergeometric test p<2.2e-16). This approach is referred to as cfHi-C.

Figure 16A:
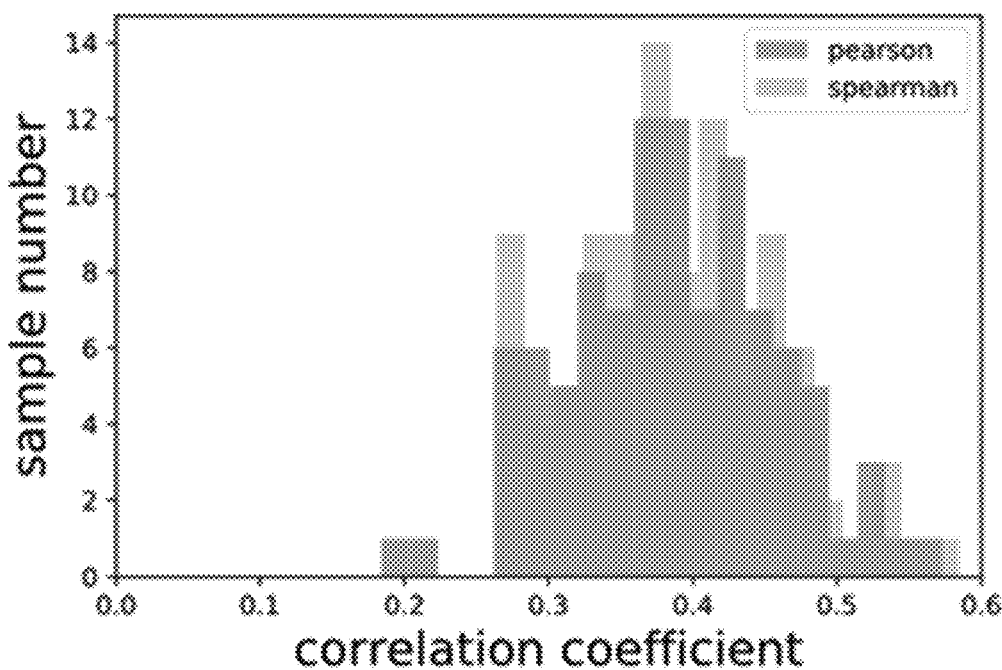
FIG. 16A shows the correlation between Hi-C and cfHi-C at the pixel level (500-kb bin).
Figure 16B:
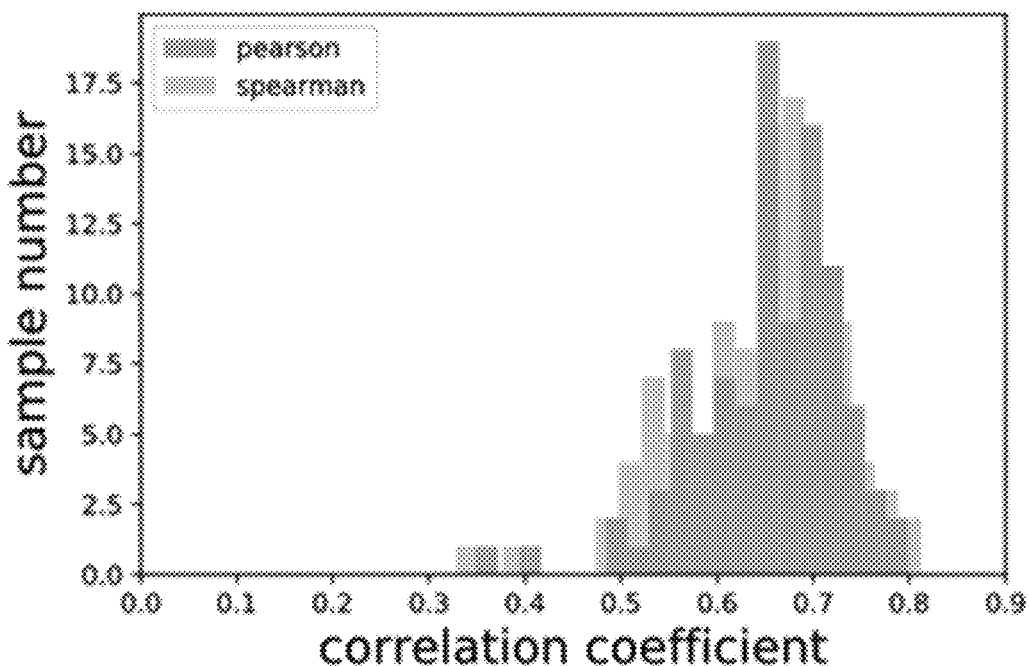
FIG. 16B shows the correlation between Hi-C and cfHi-C at the compartment level (500-kb bin).

To expand the application of cfHi-C to single-sample level, each 500-kb bin in each sample was divided into smaller 5-kb sub-bins and the Kolmogorov-Smirnov (KS) test was used to measure the similarity of fragmentation score distribution between each paired 500-kb bin. The KS test further confirmed high correlation between Hi-C and cfHi-C at both the pixel and compartment level (FIG. 16A and FIG. 16B). To rule out possible internal library preparation bias and sequencing bias caused by patterned flow cell technology in NovaSeq, the algorithm was replicated using publicly available external cfDNA dataset generated by the HiSeq 2000 platform (BH01). Similar patterns in the healthy cfDNA sample were observed using this dataset (FIG. 15D).

To rule out possible technical bias caused by sequence composition, Locally Weighted Scatterplot Smoothing (LOWESS) method was applied to normalize fragment length in each bin with the mean G+C % value. After regressing out G+C %, high similarity between Hi-C in WBC and multiple-sample cfHi-C was observed (Pearson correlation r=0.57, p<2.2e-16 FIG. 17A and FIG. 17B).

Figure 17E:
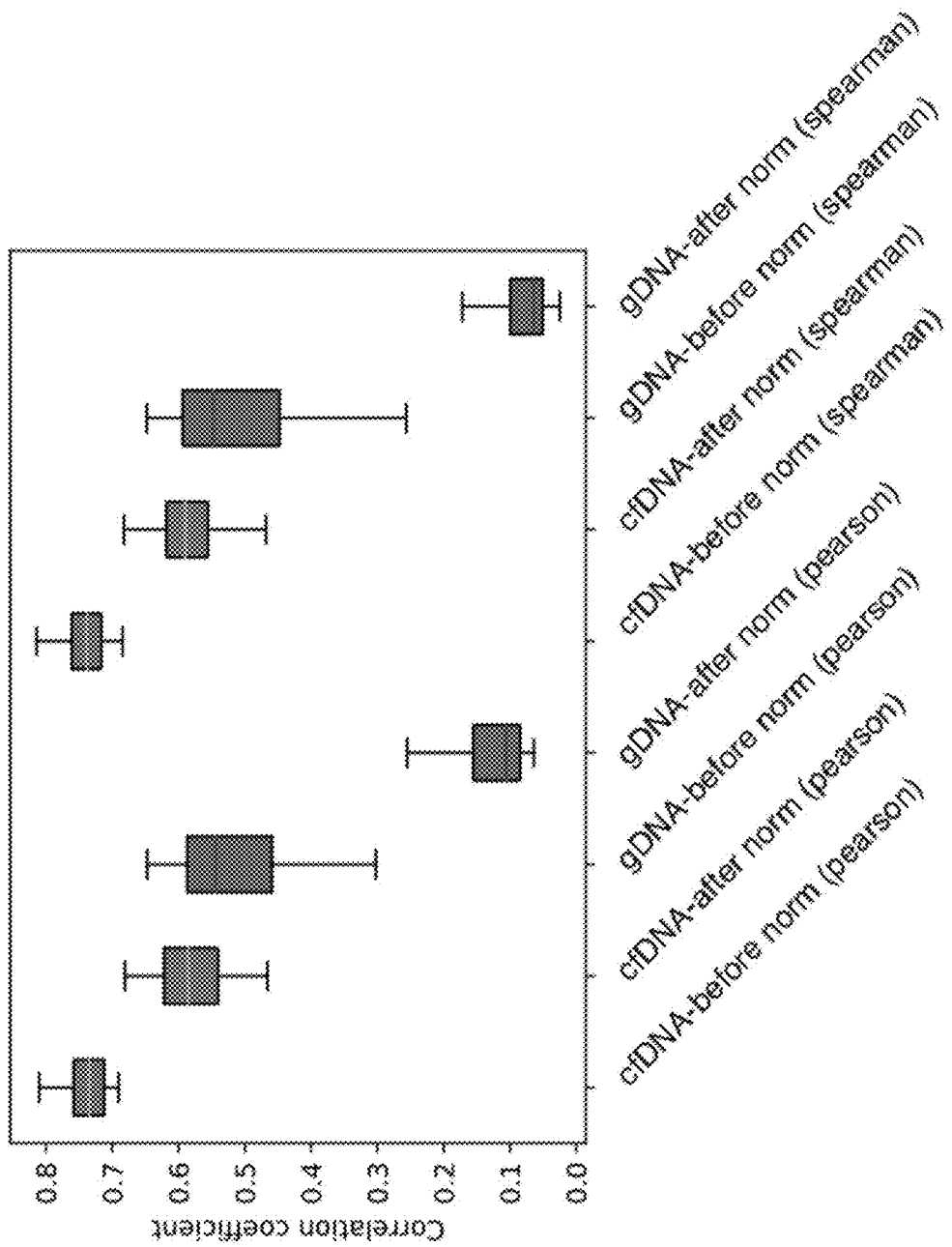
FIG. 17E shows a boxplot of pixel-level correlation (Pearson and Spearman) with Hi-C (WBC, rep2) across all of the chromosomes represented in FIGS. 17A-17D.

As a negative control, the same step was repeated using genomic DNA (gDNA) from primary white blood cells from 120 individuals. Again, there was relatively high similarity between Hi-C and gDNA before regressed out G+C % (Pearson correlation r=0.40, p<2.2e-16; FIG. 17C and FIG. 17D). However, after normalizing by G+C % in the gDNA, low residual similarity between Hi-C and gDNA was observed (Pearson correlation r=0.15, p<2.2e-16; FIG. 17D) and the Hi-C-like block structure was no longer observed. FIG. 17E shows a boxplot of pixel-level correlation (Pearson and Spearman) with Hi-C (WBC, rep2) across all of the chromosomes represented in FIGS. 17A-17D.

Figure 18A:
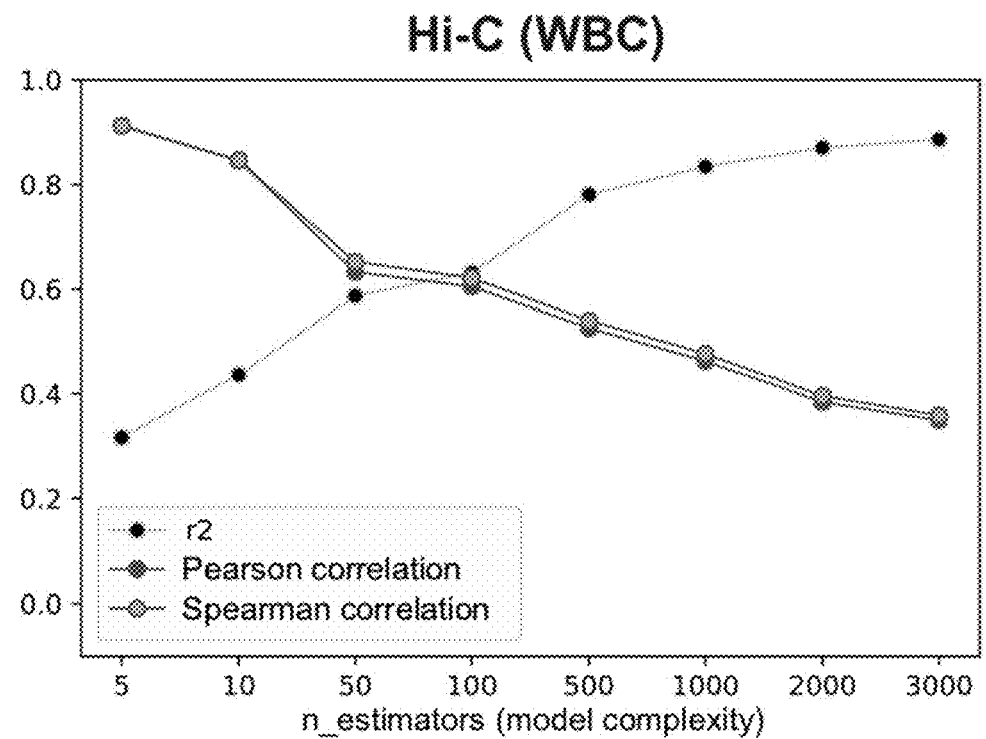
FIG. 18A shows G+C % and mappability bias analysis in two-dimensional space from multiple-sample cfHi-C.
Figure 18B:
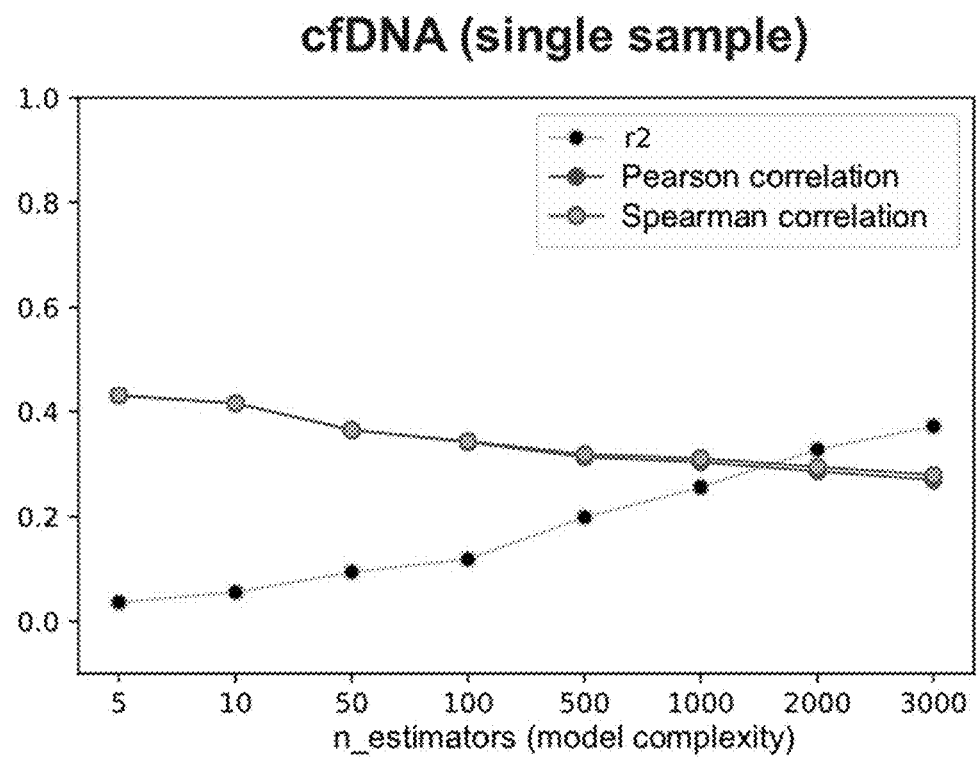
FIG. 18B shows G+C % and mappability bias analysis in two-dimensional space from single sample cfHi-C.

To elucidate the effect of G+C % and mappability in two-dimensional space, GBM regression tree was applied on cfHi-C. For each pixel on the cfHi-C matrix, two G+C % and mappability values at the interacted pair bin were obtained and then the G+C % and mappability from the signal at each pixel of the cfHi-C matrix were regressed out. After regressing out the bias of G+C % and mappability, significant residual similarity between Hi-C in WBC and both multiple-sample (Pearson correlation r=0.28, p<2.2e-16, n_estimator=500; FIG. 18A) and single-sample cfHi-C (Pearson correlation r=0.36, p<2.2e-16, n_estimator=500; FIG. 18B) was observed.

Figure 18C:
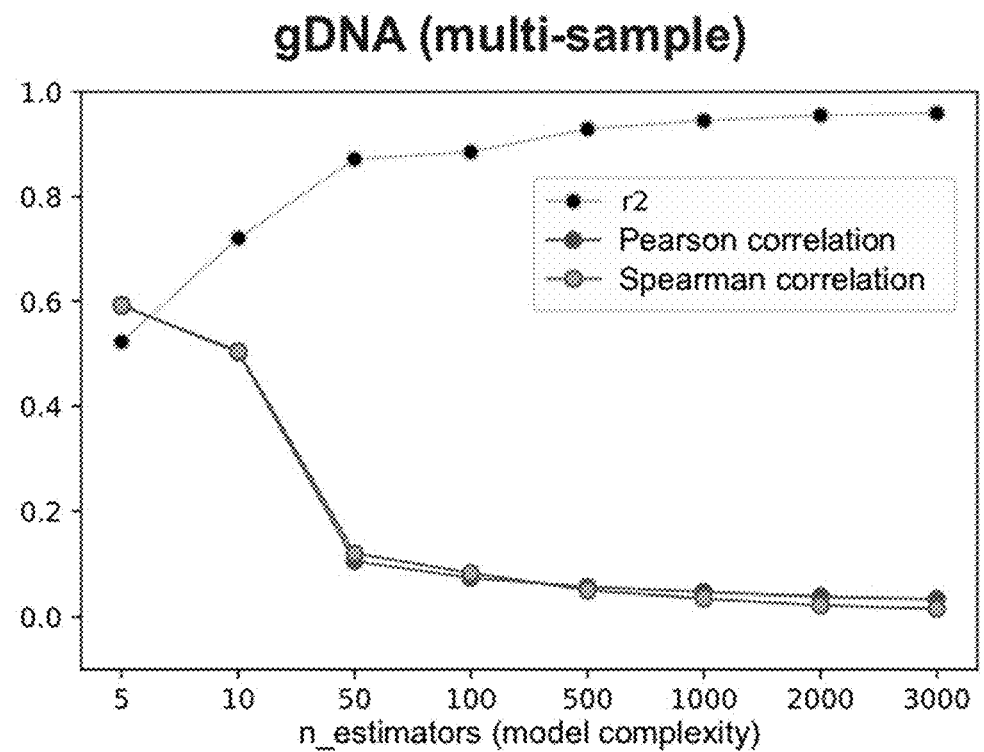
FIG. 18C shows G+C % and mappability bias analysis in two-dimensional space from multiple-sample genomic DNA.
Figure 18D:
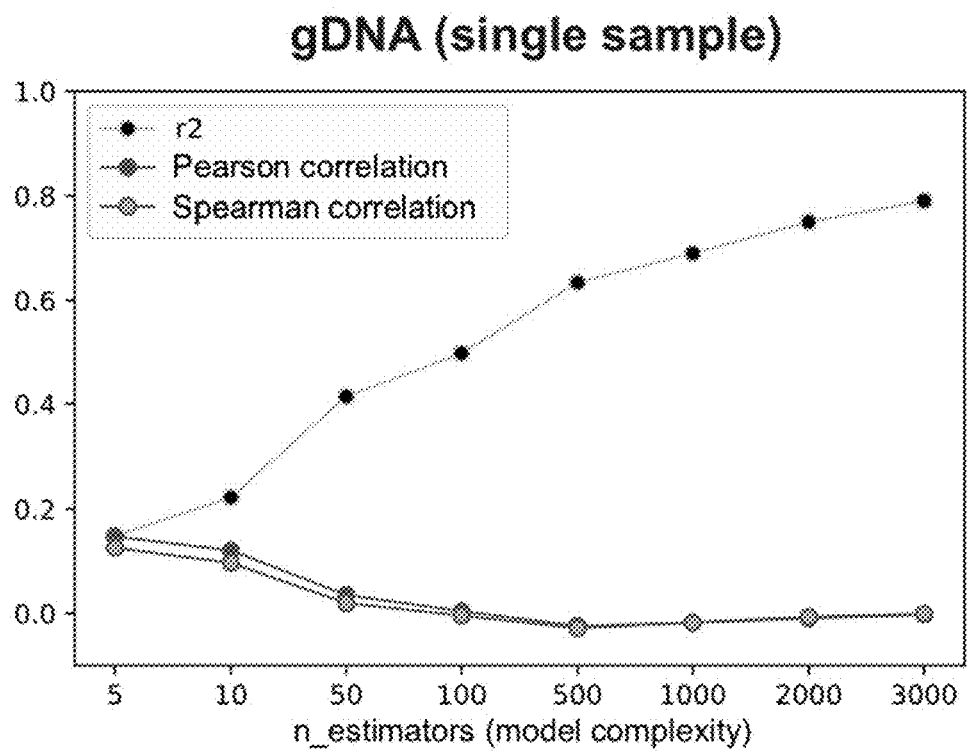
FIG. 18D shows G+C % and mappability bias analysis in two-dimensional space from single sample genomic DNA.
Figure 18E:
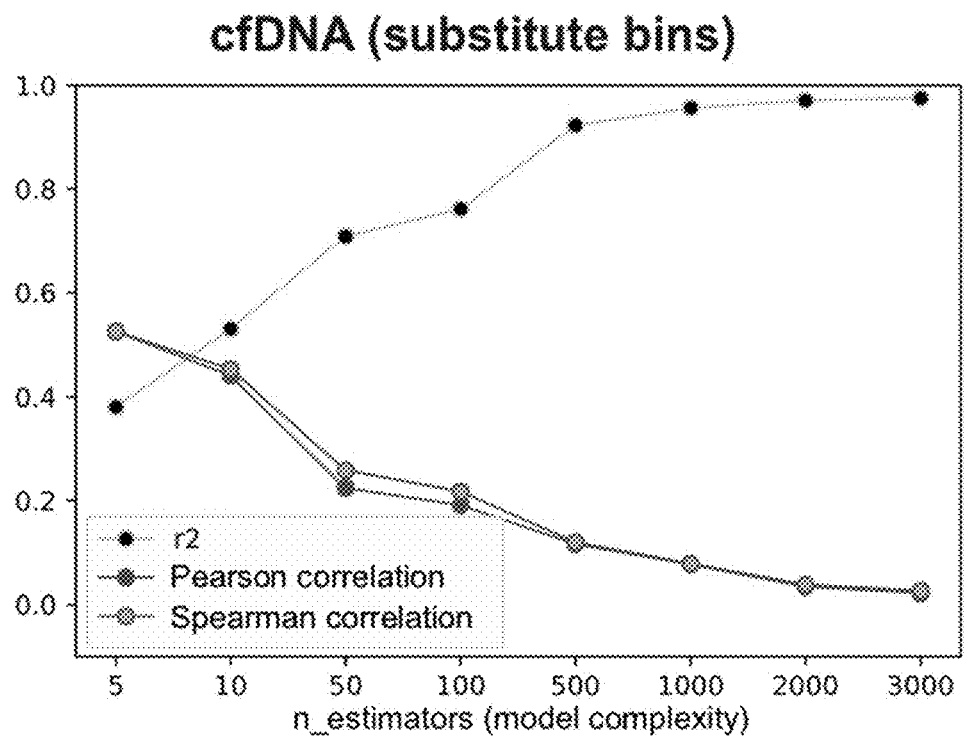
FIG. 18E shows G+C % and mappability bias analysis in two-dimensional space from multiple-sample cfHi-C.

In the negative control using gDNA, the residual similarity between Hi-C in WBC and both multiple-sample (Pearson correlation r=0.009, p=0.0002; FIG. 18C) and single-sample gDNA (Pearson correlation r=−0.03, p<2.2e-16; FIG. 18D) was not observed in the same range of model complexity. Further, for each paired bin in cfDNA, one of the bins was substituted with a random bin from another chromosome with the same G+C % and mappability, and the co-fragmentation score was recalculated. By using the same GBM regression tree approach on the simulated cfHi-C matrix, a significantly lower residual similarity with Hi-C was observed in the same range of model complexity (Pearson correlation r=0.13, p<2.2e-16; FIG. 18E).

Figure 18F:
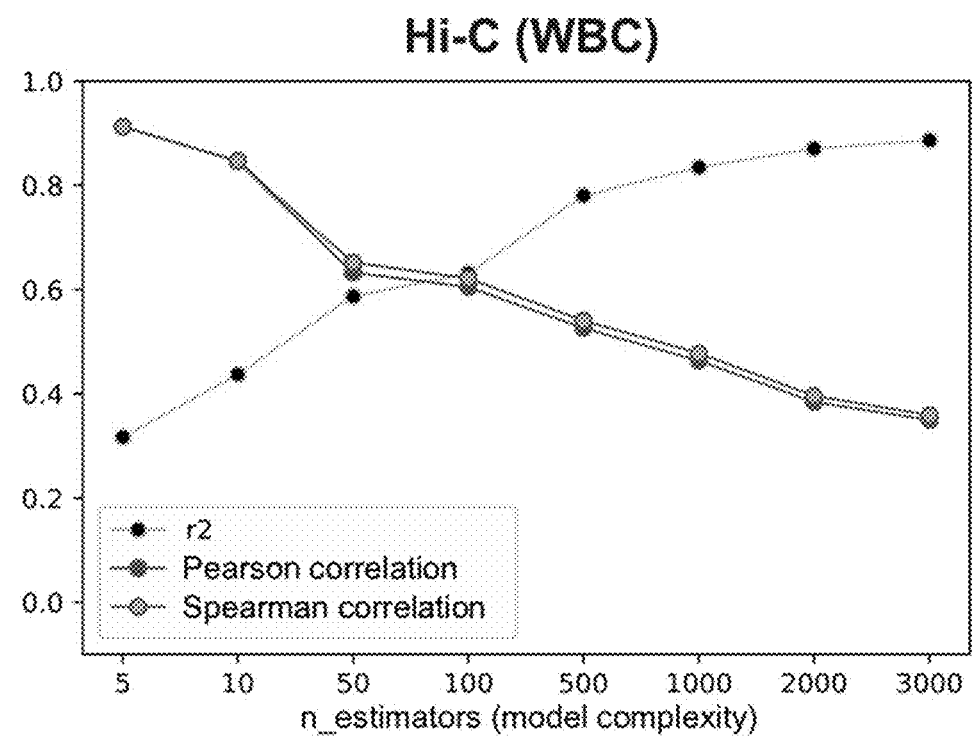
FIG. 18F shows G+C % and mappability bias analysis in two-dimensional space from Hi-C (WBC).

To demonstrate that the model retained biological signal after regressing out G+C % and mappability, the same regression tree approach was applied on WBC Hi-C from another individual (rep1). The high similarity was still observed with the replicate (Pearson correlation r=0.53, p<2.2e-16; FIG. 18F).

To explore the model complexity effect on the analysis, the regression tree was repeated with a different model complexity (n_estimator). The correlation with Hi-C was difficult to remove even with high model complexity using multiple-sample cfHi-C, single-sample cfHi-C, and Hi-C from another individual. This phenomenon did not occur with the negative control samples, such as multiple-sample gDNA, single-sample gDNA, and cfHi-C with permuted bins.

Figure 19A:
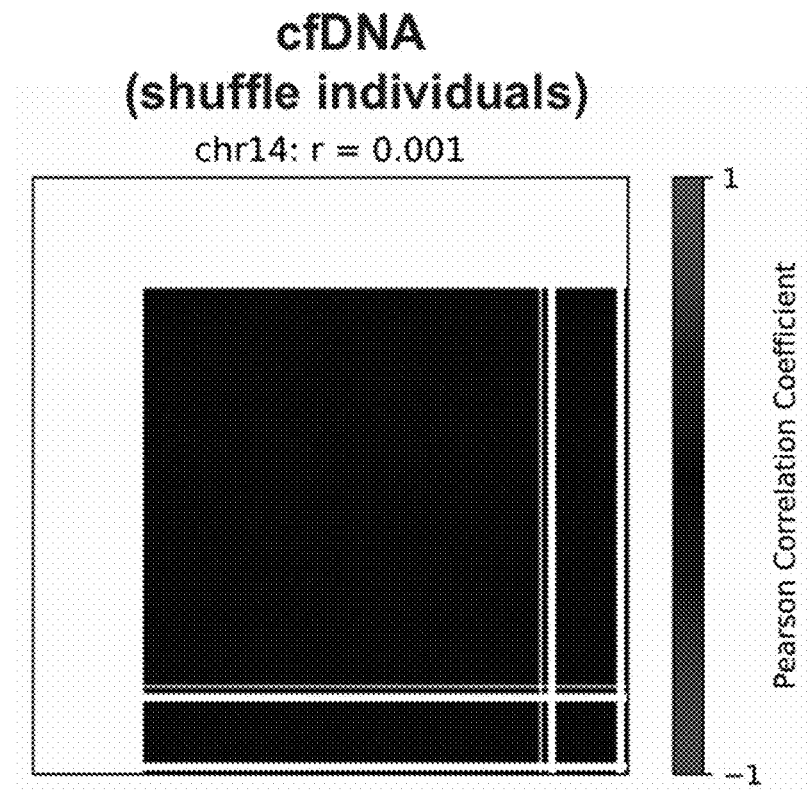
FIG. 19A shows a heatmap of multiple-sample cfHi-C in which one paired bins is randomly shuffled from any other individuals (chr14).
Figure 19B:
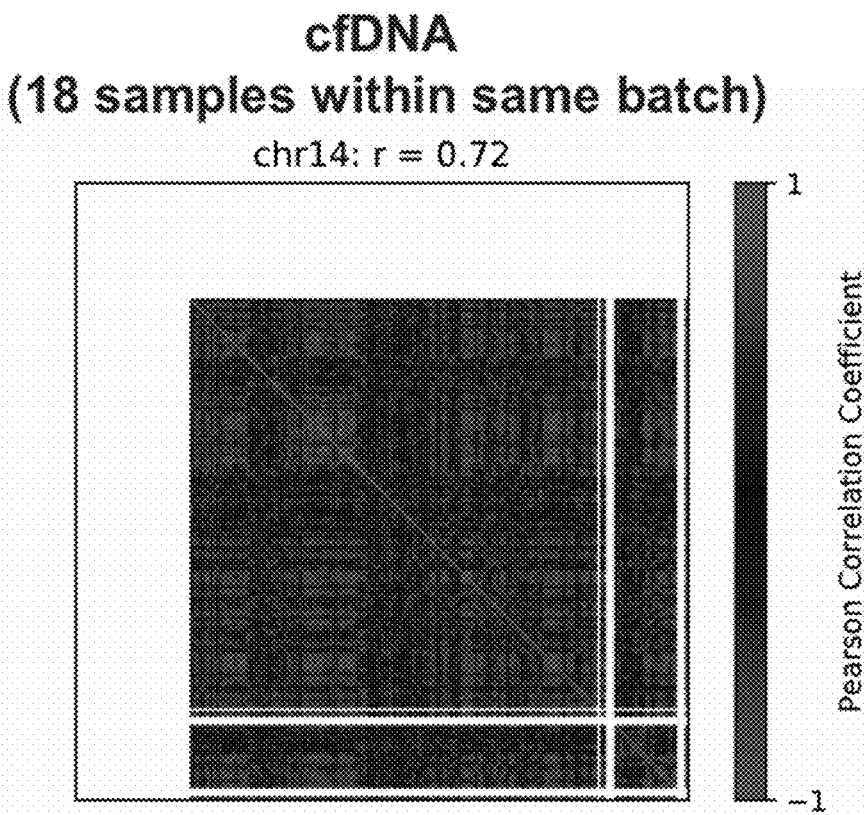
FIG. 19B shows a heatmap of multiple-sample cfHi-C on samples from the same batch as FIG. 19A (11 samples; chr14).
Figure 19C:
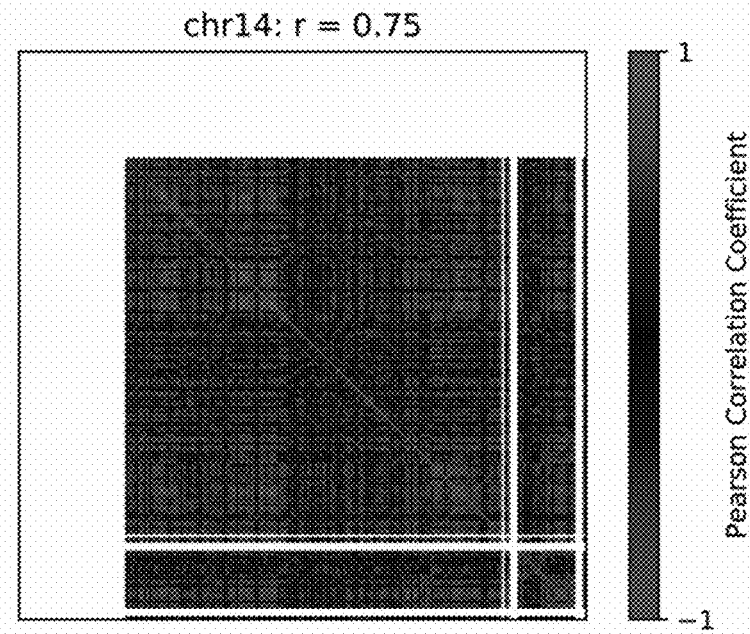
FIG. 19C shows a heatmap of multiple-sample cfHi-C on samples with the same sample size as FIG. 19B (11 samples; chr14).
Figure 19D:
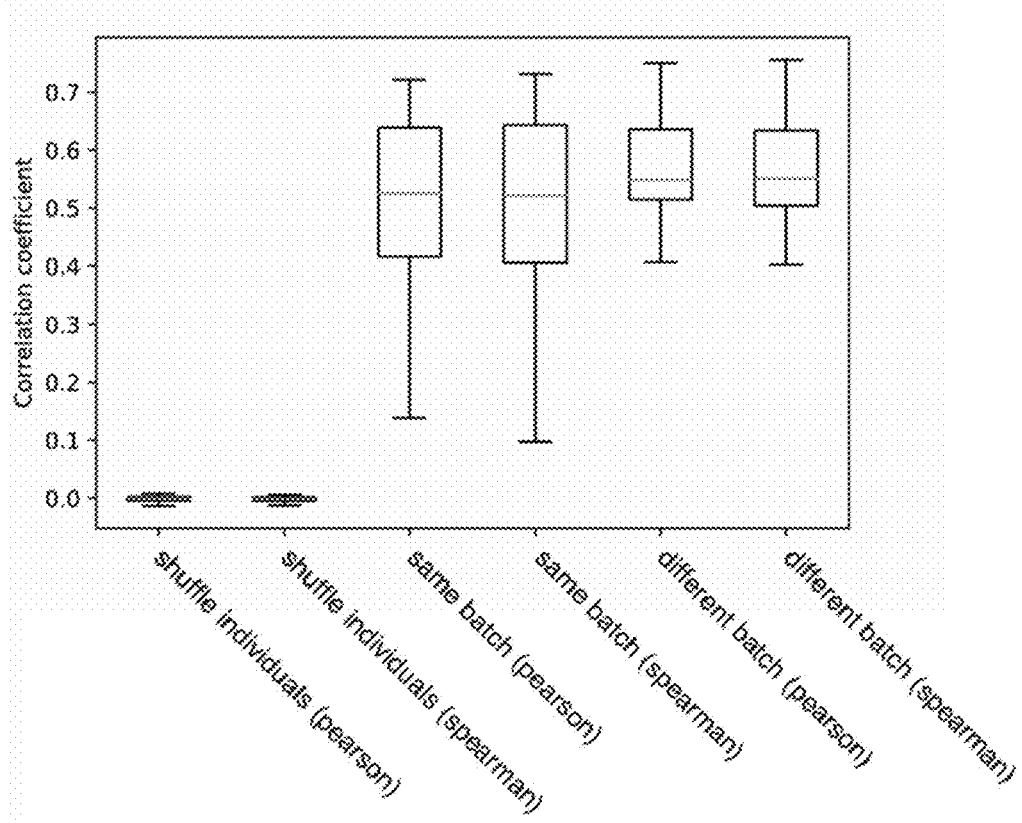
FIG. 19D shows a boxplot of pixel-level correlation with Hi-C (WBC, rep2) across all chromosomes represented in FIGS. 19A-19C.
Figure 20A:
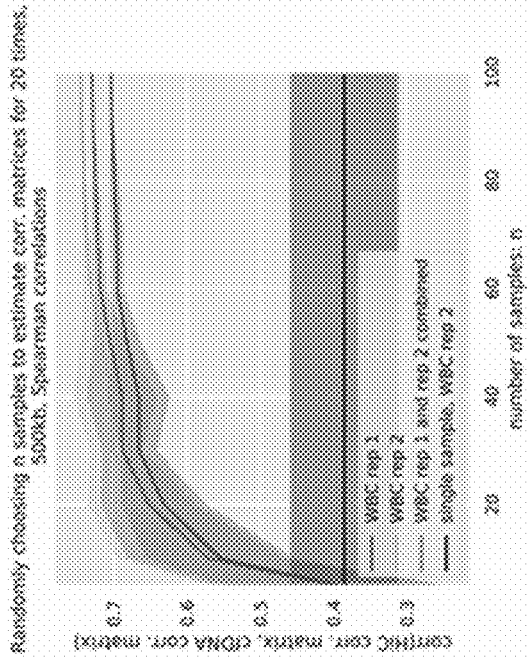
FIG. 20A shows a Pearson correlation between Hi-C (WBC, rep1) and multiple-sample cfHi-C at different sample sizes.
Figure 20B:
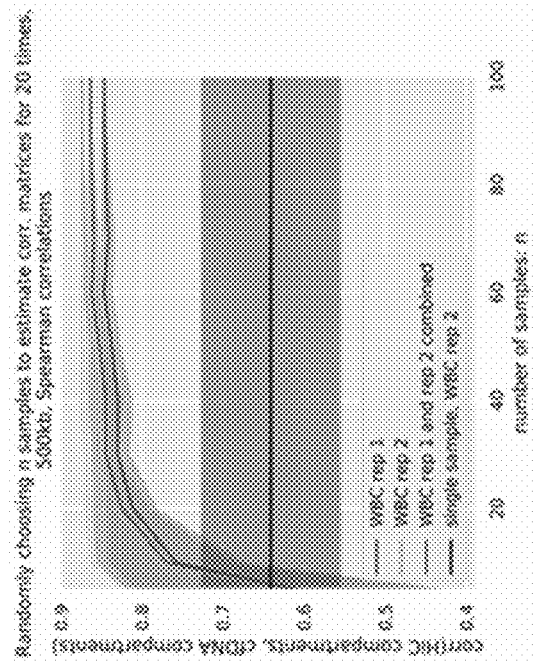
FIG. 20B shows a Spearman correlation between Hi-C (WBC, rep1) and multiple-sample cfHi-C at different sample sizes.
Figure 20C:
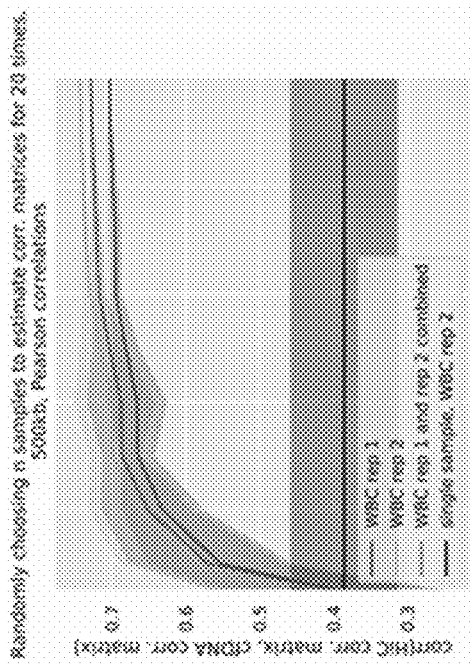
FIG. 20C shows a Pearson correlation between Hi-C (WBC, rep2) and multiple-sample cfHi-C at different sample sizes.
Figure 20D:
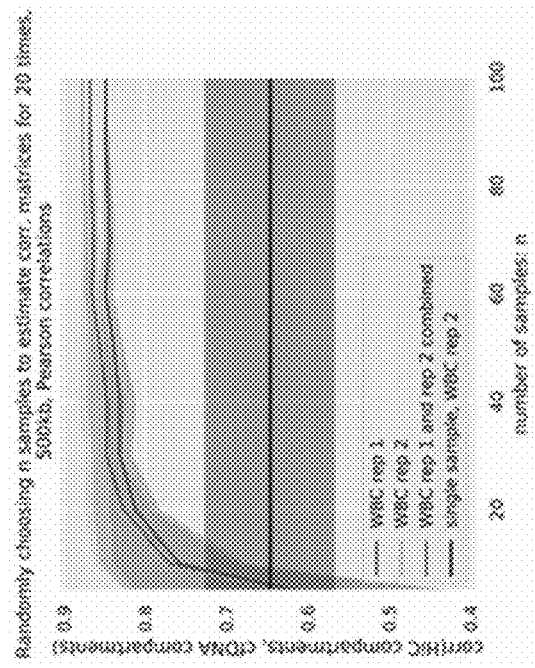
FIG. 20D shows a Spearman correlation between Hi-C (WBC, rep2) and multiple-sample cfHi-C at different sample sizes.
Figure 21B:
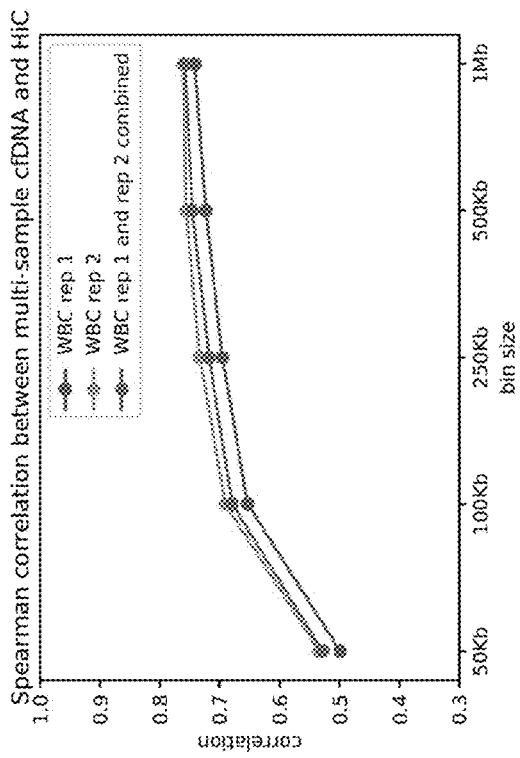
FIG. 21B shows a Spearman correlation at the pixel level between Hi-C and multiple-sample cfHi-C at different bin sizes.
Figure 21D:
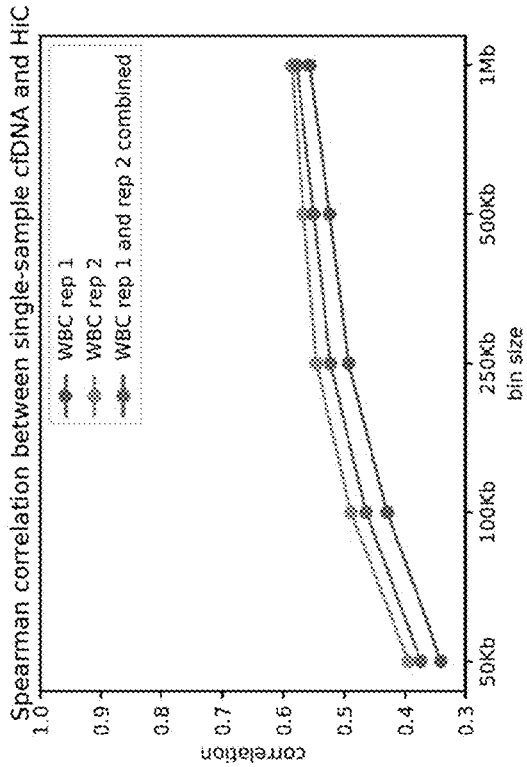
FIG. 21D shows a Spearman correlation at the pixel level between Hi-C and single-sample cfHi-C at different bin sizes.
Figure 21A:
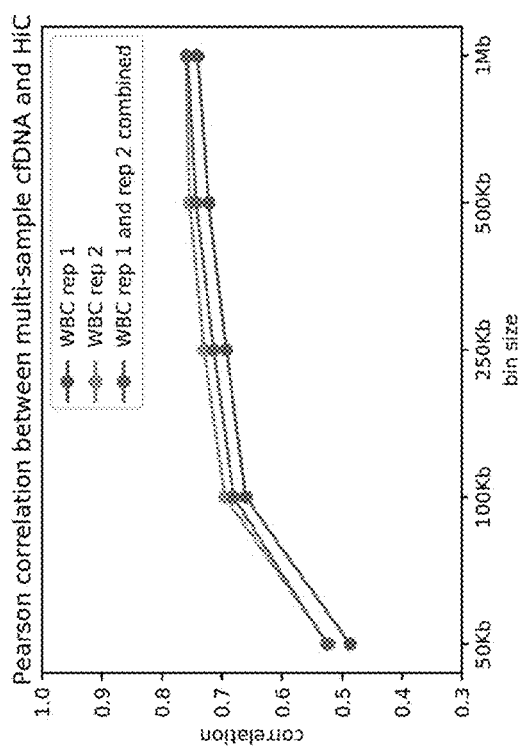
FIG. 21A shows a Pearson correlation at the pixel level between Hi-C and multiple-sample cfHi-C at different bin sizes.
Figure 21C:
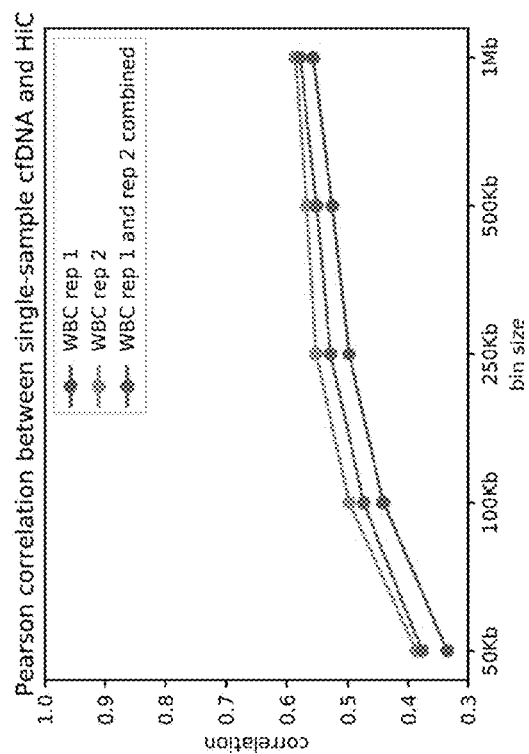
FIG. 21C shows a Pearson correlation at the pixel level between Hi-C and single-sample cfHi-C at different bin sizes.
Figure 21E:
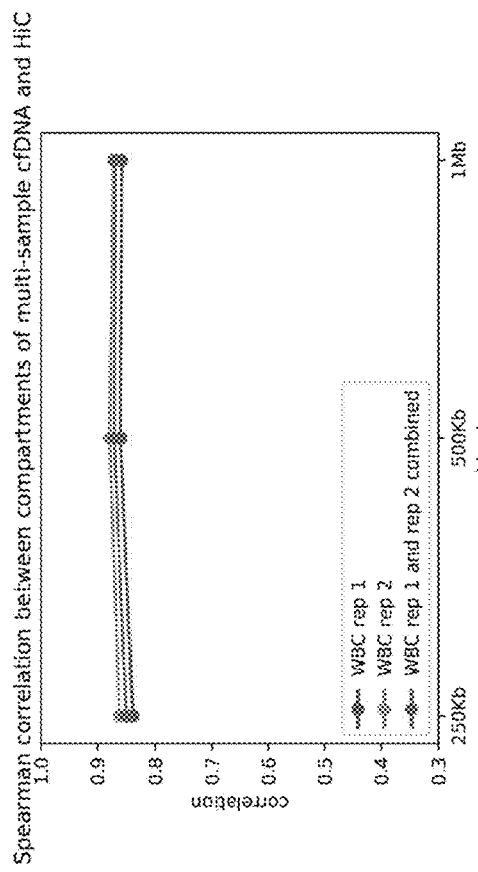
FIG. 21E shows a Pearson correlation at the compartment level between Hi-C and multiple sample cfHi-C at different bin sizes.
Figure 21F:
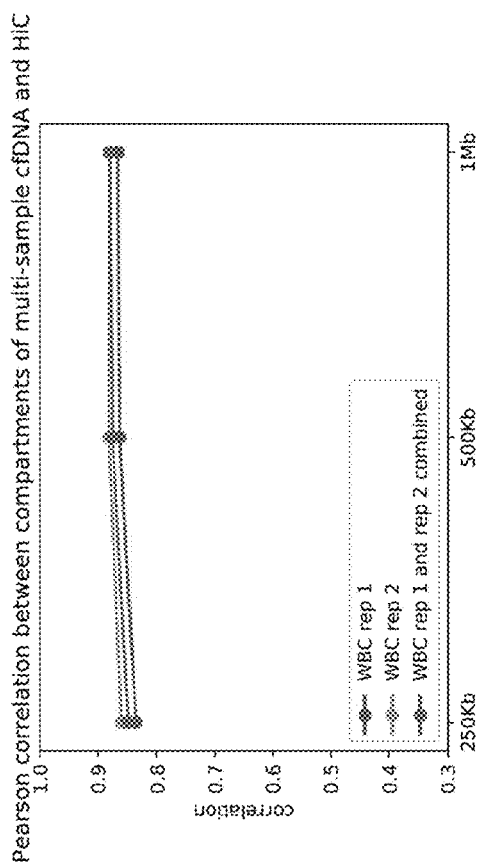
FIG. 21F shows a Spearman correlation at the compartment level between Hi-C and multiple sample cfHi-C at different bin sizes.
Figure 21G:
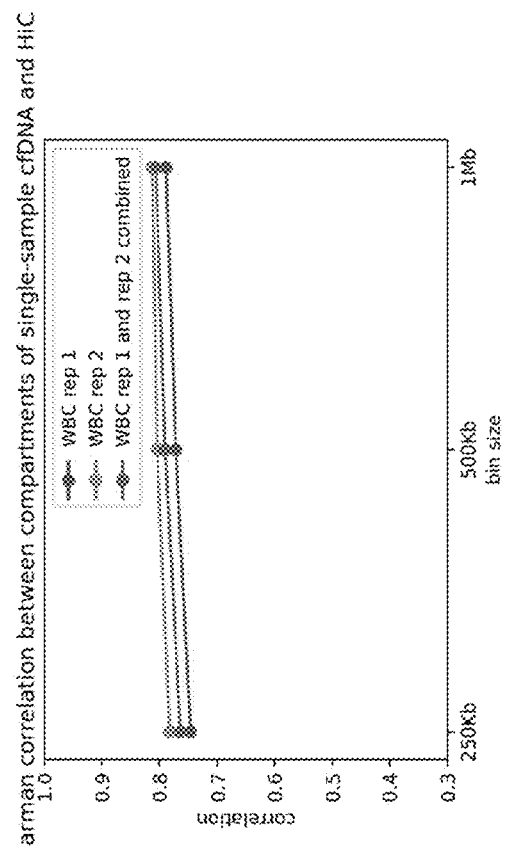
FIG. 21G shows a Pearson correlation at the compartment level between Hi-C and single sample cfHi-C at different bin sizes.
Figure 21H:
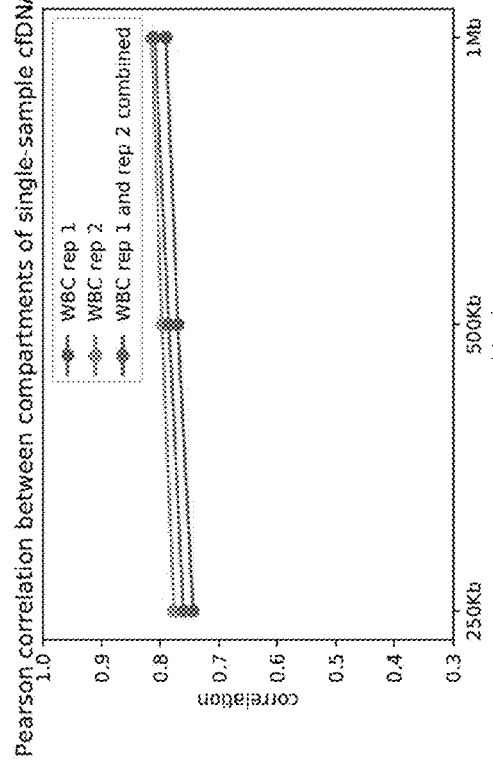
FIG. 21H shows a Spearman correlation at the compartment level between Hi-C and single sample cfHi-C at different bin sizes.

To rule out the possibility that the co-fragmentation pattern observed in multiple-sample cfHi-C was due to the batch defect during sequencing and library preparation, one bin was randomly shuffled across individuals for each paired bin in cfHi-C. As expected, the correlation with Hi-C was not observed (Pearson correlation r=−0.0002, p=0.74; FIG. 19A and FIG. 19D). A multiple-sample cfHi-C matrix from samples within the same batch (18 samples) was generated. High correlation was observed between Hi-C at the pixel level (Pearson correlation r=0.60, p<2.2e-16; FIG. 19B and FIG. 19D) and samples downsampled to the same size (Pearson correlation r=0.63, p<2.2e-16; FIG. 19C and FIG. 19D).

To test the robustness of this approach, the data at different sample sizes were randomly sub-sampled for multiple-sample cfHi-C. With a sample size of 10, a correlation coefficient of approximately 0.55 at the pixel level and 0.7 at the compartment level with WBC Hi-C was achieved. Saturation with a sample size of more than 80 was achieved (FIG. 20A-20D).

To understand the effect of bin size, the same procedure was repeated on different bin sizes. High concordance with Hi-C experiment at different resolutions was consistently observed (FIG. 21A-21H).

Figure 22A:
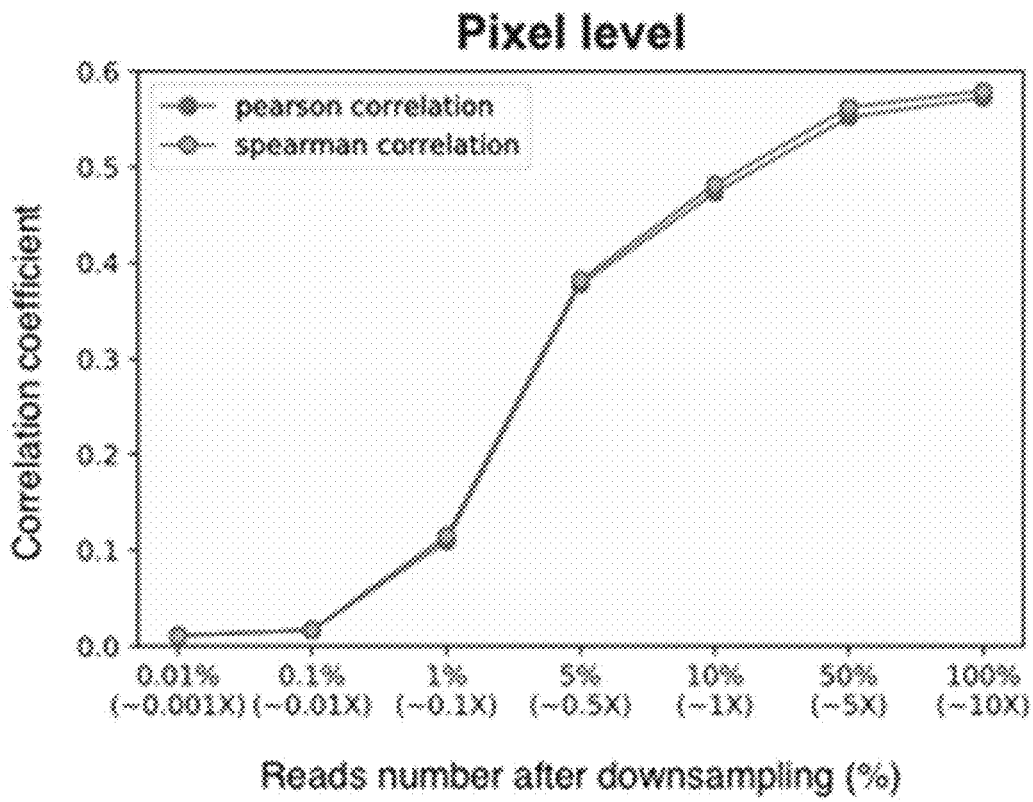
FIG. 22A shows Pearson and Spearman correlation at the pixel level between Hi-C and single-sample cfHi-C at different reads number after downsampling.
Figure 22B:
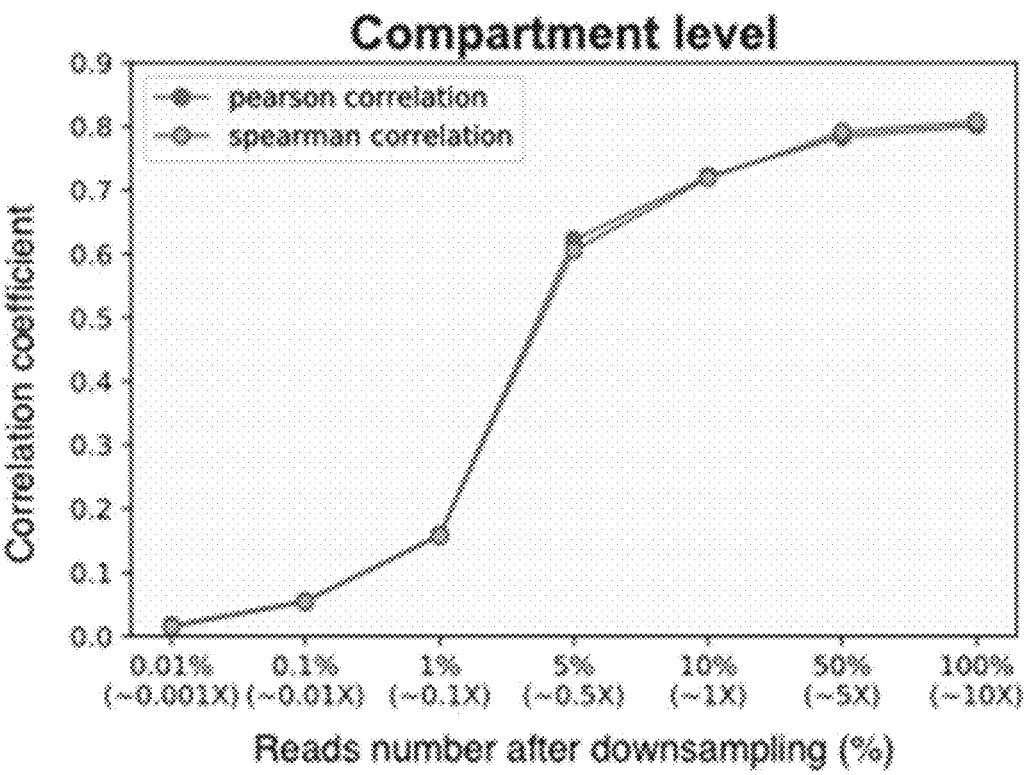
FIG. 22B shows Pearson and Spearman correlation at the compartment level between Hi-C and single-sample cfHi-C at different reads number after downsampling.

To elucidate the effect of sequencing depth in single-sample cfHi-C, the fragment number was downsampled into different sizes. Even with ~0.7× coverage, a correlation coefficient of approximately 0.45 at the pixel level and 0.7 at the compartment level with WBC Hi-C was still achieved (FIG. 22A and FIG. 22B).

Figure 23B:
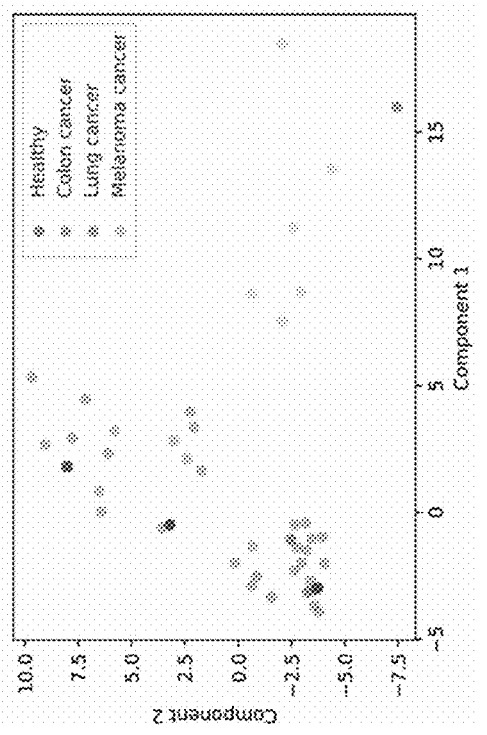
FIGS. 23B to 23F show CCA of healthy samples and high tumor fraction samples from colon cancer, lung cancer, and melanoma.
Figure 23D:
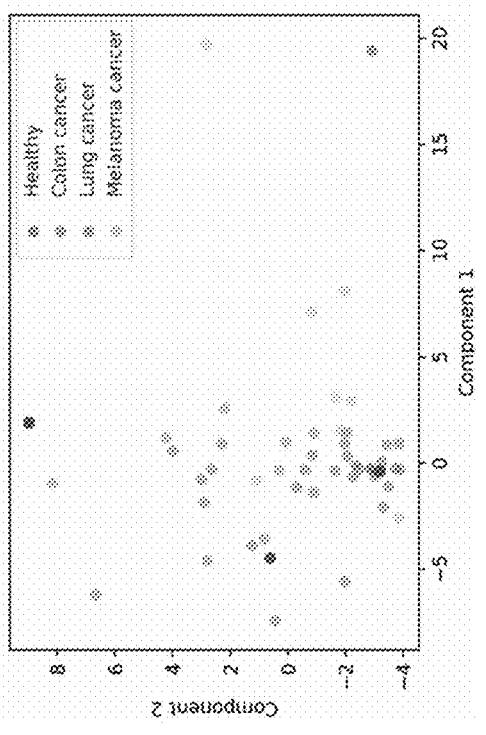
Figure 23A:
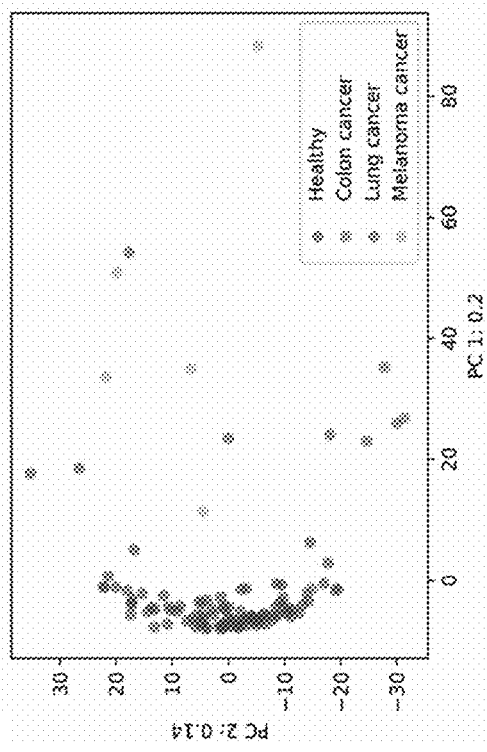
FIG. 23A shows a Kernel PCA (RBF kernel) of healthy samples and high tumor fraction samples from colon cancer, lung cancer, and melanoma.
Figure 23C:
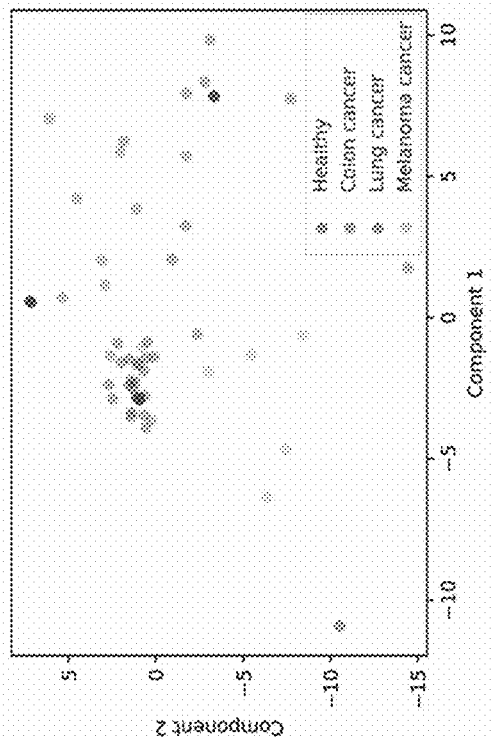
Figure 23E:
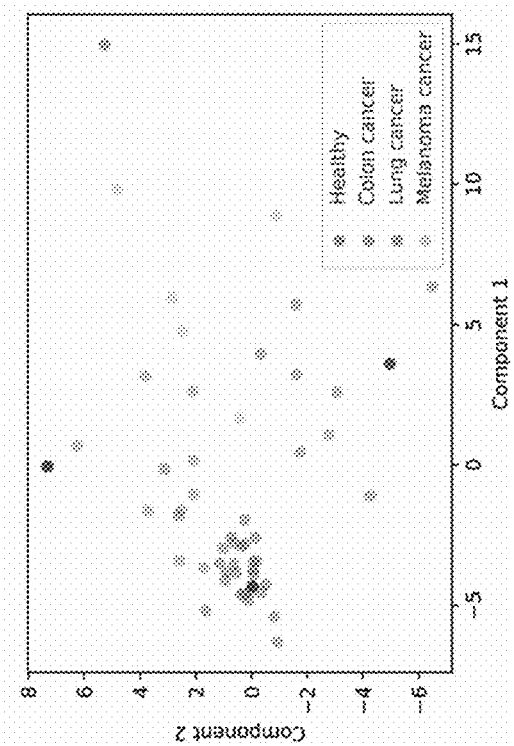
Figure 23F:
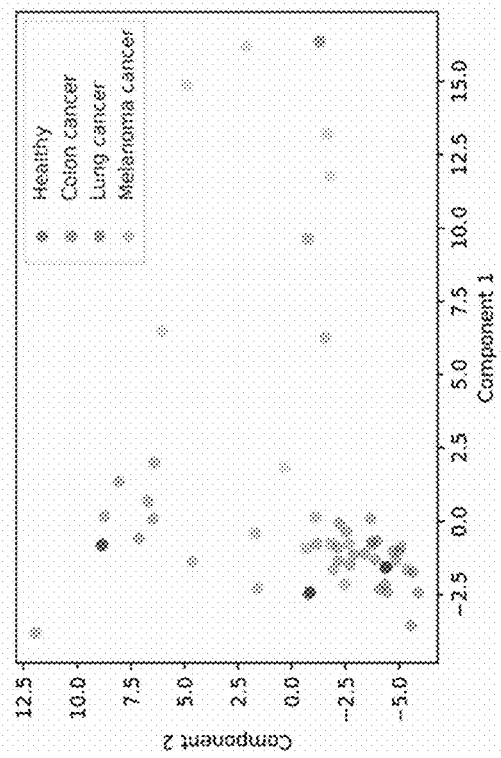

To determine whether the observed cfHi-C signal varies at different pathological conditions, additional WGS was generated at similar sequencing depth on cfDNA obtained from 45 colorectal cancer, 48 lung cancer, and 19 melanoma cancer patients. After standardizing the eigenvalue at the compartment level across all cfHi-C samples, principal component analysis (PCA) was applied to all of the healthy samples and selected cancer samples containing high tumor fraction (tumor fraction>=0.2, estimated by ichorCNA). Even at 500-kb resolution, separation was observed among the healthy and different type of cancer samples (FIG. 23A). By further applying semi-supervised dimensionality reduction method, Canonical Correlation Analysis (CCA), clear separation was observed among the healthy and cancer samples (FIGS. 23B-23F).

Figure 24:
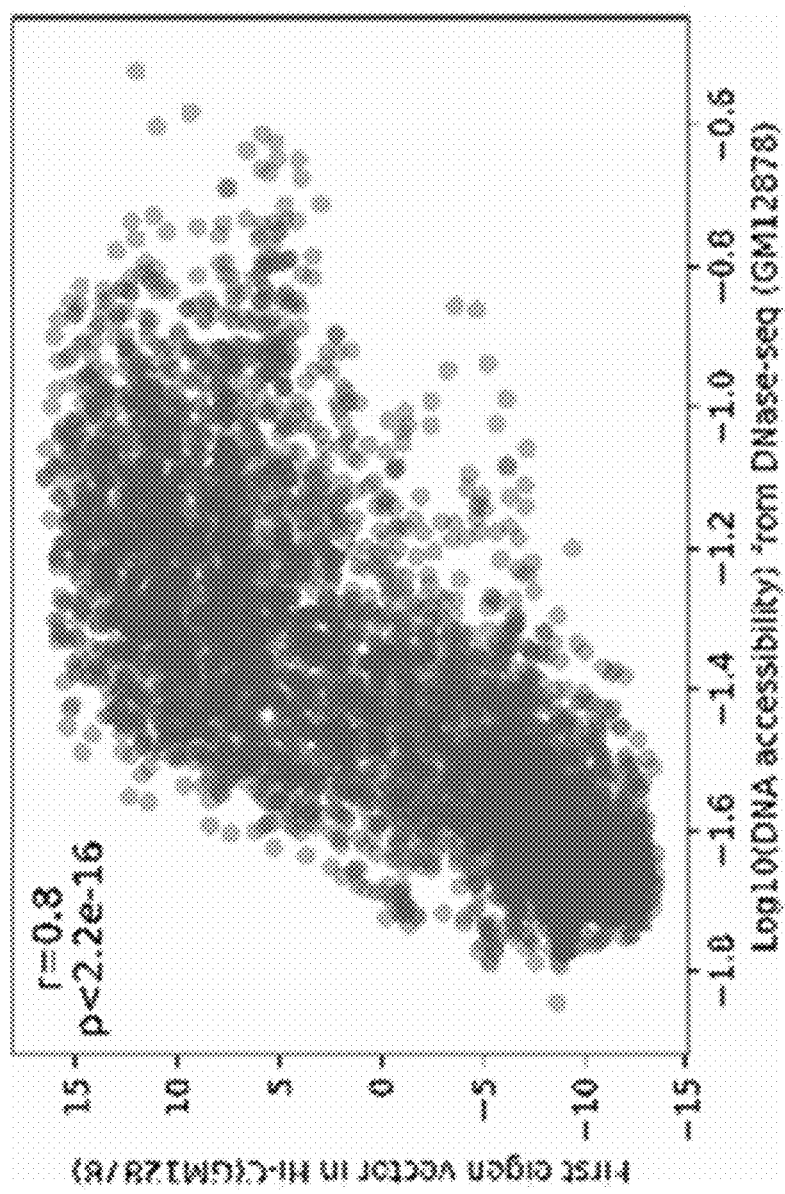
FIG. 24 shows a correlation map between DNA accessibility and compartment-level eigenvalue from Hi-C from the same cell type (GM12878).

To determine whether in vivo chromatin organization measured through cfDNA may be used to infer the cell types contributing to cfDNA in healthy individuals and patients with cancer, the amplitude of eigenvalue observed in Hi-C data was correlated with the amplitude of open/close status in the chromosome. A significantly high correlation between the signal strength of DNase-seq and eigenvalue in Hi-C compartment was observed at 500-kb resolution from GM12878 (Pearson correlation r=0.8, p<2.2e-16; FIG. 24). This observation suggested that the eigenvalue at the compartment level may be further used to quantify the openness of the chromosome.

To generate the reference Hi-C panel for the tissue-of-origin analysis, Hi-C data from 18 different cell types were uniformly processed from different pathological and healthy conditions. To determine whether correlation patterns were cell-specific, in situ Hi-C data were generated from neutrophil cells with 1.96 billion paired reads and 1.06 billion high-quality contacts (mapping quality score>30). Using a quantile-normalized eigenvalue at cell-type specific compartments identified from the reference Hi-C panel, approximately 80% cfDNA were detected from different types of white blood cells and almost no cfDNA were detected from cancer cells in cfHi-C (FIGS. 25A-25C). In contrast to the healthy samples, an increased fraction of cancer components from the relevant cell types was observed in colorectal cancer, lung cancer, and melanoma samples using cfHi-C (FIGS. 25A and 25B).

To rule out possible artifacts during library preparation and sequencing, the procedure was replicated using publicly available cfDNA WGS data from healthy individuals, colorectal cancer, squamous cell lung cancer, small cell lung adenocarcinoma, and breast cancer samples. Similar results were observed (FIGS. 25A and 25B).

Figure 26:
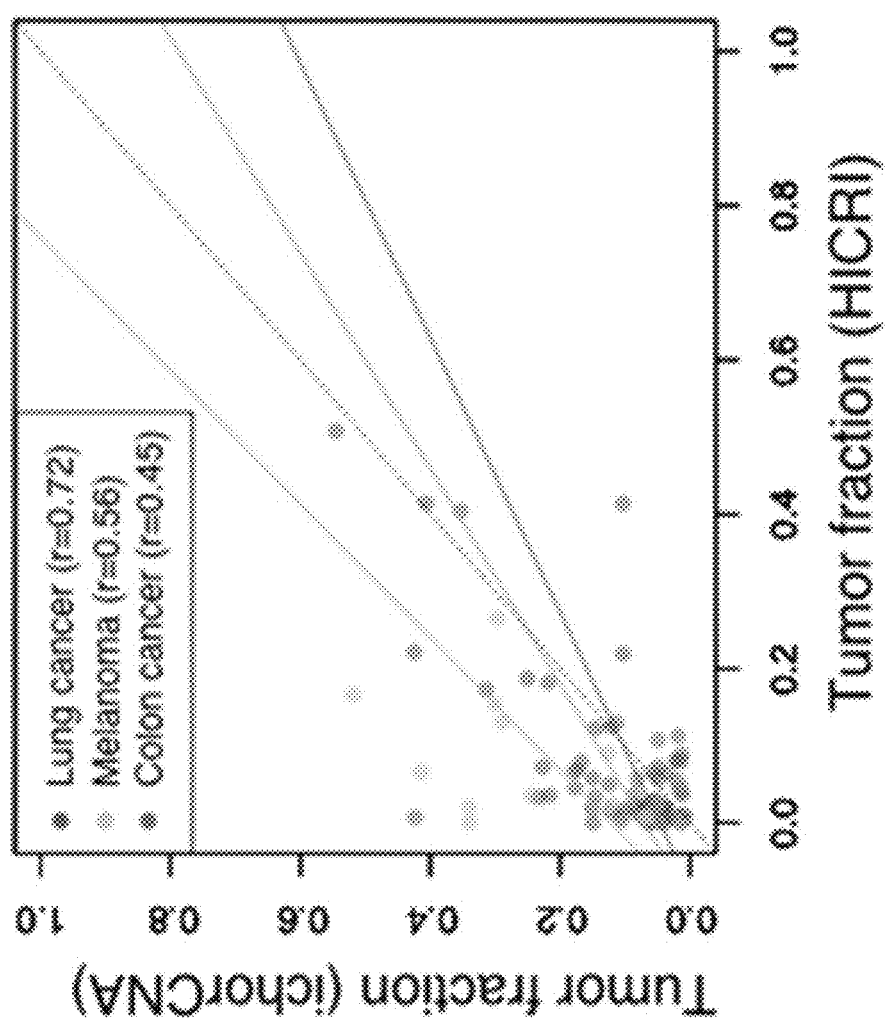
FIG. 26 shows a comparison between tumor fractions from ichorCNA and tumor fractions from cfHi-C by only using genomic regions with no CNV changes for lung cancer, melanoma, and colon cancer.

To quantify the accuracy of the approach, tumor fraction estimated by cfHi-C was compared to that estimated by ichorCNA. ichorCNA is an orthogonal method for estimating tumor fraction by coverage using copy number variations (CNV) in cfDNA. Similar low tumor fraction was observed in healthy individuals (tumor fraction median=0.00, mean=0.02; FIG. 25C) and significant high concordance with ichorCNA was observed in different cancer patients (FIG. 26).

To avoid confounding CNV from late-stage cancer, genomic regions with any significant CNV signals for the tissue-of-origin analysis were excluded. The results were still largely the same as the results prior to exclusions of late-stage cancer samples.

If long-range, spatial correlated fragmentation patterns observed in cfDNA are mainly affected by the epigenetic landscape, similar two-dimensional Hi-C-like patterns may be observed with different epigenetic signals. To test this hypothesis at the single-sample level, the modified KS test was used to determine the similarity between paired bins at different epigenetic signals from GM12878. High concordance was observed with the Hi-C experiment from the same cell type using DNase-seq, methylation level from whole-genome bisulfite sequencing (WGBS), H3K4me1 ChIP-seq, and H3K4me2 ChIP-seq. This observation suggests that inferred "virtual compartments" from these epigenetic marks is a comprehensive reference panel for performing nuance tissue-of-origin analysis.

In conclusion, these analyses demonstrate the potential of using cfDNA as a biomarker to monitor the longitudinal changes of in vivo chromatin organization and cell type compositions for different clinical conditions.

D. Example 4: Detection of Colorectal Cancer, Breast Cancer, Pancreatic Cancer, or Liver Cancer This example describes using perform predictive analytics using artificial intelligence based approaches to analyze acquired cfDNA data from a subject (to generate an output of diagnosis of the subject having a cancer (e.g., colorectal cancer, breast cancer or liver cancer or pancreatic cancer).

Retrospective human plasma samples were acquired from 937 patients diagnosed with colorectal cancer (CRC), 116 patients diagnosed with breast cancer, 26 patients diagnosed with liver cancer, and 76 patients diagnosed with pancreatic cancer. In addition, a set of 605 control samples were acquired from patients without a current cancer diagnosis (but potentially with other comorbidities or undiagnosed cancer), of which 127 had confirmed negative colonoscopies. In total, samples were collected from 11 institutions and commercial biobanks from Southern and Northern Europe and the United States. All samples were de-identified.

Control samples for the CRC model include all samples except the liver control samples, (n=524). Control samples in the breast cancer model (n=123) included samples from the same institutions contributing breast cancer samples. The liver cancer samples originate from a case control study with 25 matched control samples; the control samples are actually HBV positive but negative for cancer. Pancreatic cancer samples and corresponding controls also were obtained from a single institution; of the 66 controls, 45 of the control samples have some non-cancerous pathologies including pancreatitis, CBD stones, benign strictures, pseudocysts, etc.

Each patient's age, gender, and cancer stage (when available) were obtained for each sample. Plasma samples collected from each patient were stored at −80° C. and thawed prior to use.

Cell-free DNA was extracted from 250 μL plasma (spiked with unique synthetic double stranded DNA (dsDNA) fragments for sample tracking) using the MagMAX Cell-Free DNA Isolation Kit (Applied Biosystems), per manufacturer instructions. Paired-end sequencing libraries were prepared using the NEBNext Ultra II DNA Library Prep Kit (New England Biolabs), including polymerase chain reaction (PCR) amplification and unique molecular identifiers (UMIs), and sequenced using an Illumina NovaSeq 6000 Sequencing System across multiple S2 or S4 flow cells at 2×5 1 base pairs to a minimum of 400 million reads (median=636 million reads), except for liver cancer samples that were sequenced to a minimum of 4 million reads (median=28 million reads).

Obtained sequencing reads were de-multiplexed, adapter trimmed, and aligned to a human reference genome (GRCh38 with decoys, alt contigs, and HLA contigs) using a Burrows Wheeler aligner (BWA-MEM 0.7.15). PCR duplicate fragments were removed using fragment endpoints or unique molecular identifiers (UMIs) when present.

For all samples except the liver cancer experiment, sequencing data were checked for quality and excluded from further analysis if any of the following conditions were met: an AT dropout of greater than about 10 (computed via Piccard 2.10.5), a GC dropout of greater than about 2 (computed via Piccard 2.10.5), or a sequencing depth of less than about 10×. Additionally, samples in which the relative counts in sex chromosomes which were not consistent with the annotated gender were removed from further processing and discarded. Further, any samples that were suspected of being contaminated (e.g., because of expected allele fraction less than about 0.99, unexpected genotype calls, or batches with a contaminated negative control) were manually inspected prior to inclusion in the data set.

A cfDNA "profile" was created for each sample by counting the number of fragments that aligned to each putative protein-coding region of the genome. This type of data representation can capture at least two types of signals: (1) somatic CNV s (where gene regions provide a sampling of the genome, enabling the capture of any consistent large-scale amplifications or deletions); and (2) epigenetic changes in the immune system represented in cfDNA by variable nucleosome protection causing observed changes in coverage.

A set of functional regions of the human genome, comprising putatively protein-coding gene regions (with the genomic coordinate range including both intrans and exons), was annotated in the sequencing data. The annotations for the protein-encoding gene regions ("gene" regions) were obtained from the Comprehensive HUman Expressed Sequences (CHESS) project (v1.0). A feature set was generated from the annotated human genome regions, comprising vectors of counts of cfDNA fragments corresponding to a set of genomic regions. The feature set was obtained by counting a number of cfDNA fragments having a mapping quality of at least 60 that overlapped with each of the annotated gene regions by at least one base, thereby producing a "gene feature" set (D=24,152, covering 1352 Mb) for each sample.

Featurized vectors of counts were preprocessed via the following transformations. First, counts of cfDNA fragments corresponding to sex chromosomes were removed (only autosomes were kept). Second, counts of cfDNA fragments corresponding to poor-quality genomic bins were removed. Third, features were normalized for their length. Poor quality genomic bins were identified by having any of: a mean mappability across a bin of less than about 0.75, a GC percentage of less than about 30% or greater than about 70%, or a reference-genome N content of greater than about 10%. Fourth, depth normalization was performed on the counts of cfDNA fragments. For per sample depth normalization, a trimmed mean was generated by removing the bottom and top ten percent of bins before calculating the mean of the counts across bins in a sample, and the trimmed mean was used as a scaling factor. GC correction was applied on the counts of cIDNA fragments, using a Loess regression correction to address GC bias. Following these filtering transformations, the resulting vector of gene features had a dimensionality of 17,582 features, covering 1172 Mb.

A cross-validation procedure may be performed as part of a machine learning technique to obtain an approximation of a model's performance on new, prospectively collected unseen data. Such an approximation may be obtained by sequentially training a model on a subset of the data and testing it on a held-out set of data, unseen by the model during training. A k-fold cross-validation procedure may be applied, which calls for randomly stratifying all the data into k groups (or folds) and testing each group on a model fitted to the other folds. This approach may be a common, tractable way to estimate generalization performance. However, if there is any confounding of class label with a known covariate, such "k-fold" cross-validation schemes may yield inflated performance issues that may not generalize to new datasets. The machine may learn to simply identify the batch and associated distribution of labels. This may lead to misleading results and poor generalizability because the classifier learns erroneous associations between class label and the confounding factor within the training set, and incorrectly applies in the test set. Cross-validation performance can overestimate generalization performance because the test set can have the same confounders, but a prospective set without the confounding factor may not work, leading to a large generalization error.

Such issues may be mitigated by performing a "k-batch" validation, which is stratified such that the test set contains only unseen elements of the confounding factor. Such "k-batch" validation may provide a more robust assessment of generalization performance for data that is processed at different time points. This effect may be mitigated by performing a validation that is stratified so that the test set contains only unseen elements of the confounding factor. Since short term effects may be observed that co-occur with samples processed on the same batch (e.g., specific GC bias profiles), the cross-validation may comprise stratification by batches instead of random stratification. That is, any sample in the test set may not come from a batch that was also seen in training. Such an approach may be termed "k-batch," and validation in this manner may provide a more robust assessment of generalization performance for data on a new batch.

In addition, the sample collection and/or processing protocol may also represent sources of bias. Differences in protocols can result in major variation in the data. Such variation can be roughly captured by grouping samples by the institution where the sample originated. To address this with k-batch, class labels of all samples from an institution in training can be balanced. For each sourcing institution in the training set of each fold, down sampling can be performed to achieve a matched ratio of cases to controls that originate from that institution. A cross validation can be deemed balanced if this down sampling is applied to the training data, and such a validation approach can be called "balanced k-batch."

In addition, k-batch cross-validation works well for controlling within batch biases, but there can also be process drift that occurs as samples are processed over an extended period of time (e.g., over several months, 1 year, 2 years, etc.). Similar to a time series split, the batches can be divided only after sorting them in time. Since the order of samples is still determined by batches, such a validation approach can be termed "ordered k-batch."

After preprocessing the feature sets, all 4 strategies of cross-validation were performed ("k-fold," "k-batch," "balanced k-batch," "ordered k-batch") on the data. All cross-validation strategies are used to train a model that tests each sample exactly once. This approach allows a direct comparison of the sets of models trained by different cross-validation techniques. In an ideal world with a perfect dataset and a perfect machine, all forms of cross-validation may yield identical results.

FIGS. 28A-28D illustrate training schemas fork-fold, k-batch, balanced k-batch, and ordered kbatch. Each square represents a single sample, with the fill color indicating class label, the border color representing a confounding factor like institution, and the number indicating processing batch. The held-out test set of samples is separated from the training set by a dashed line.

Figures 27A, 27B:
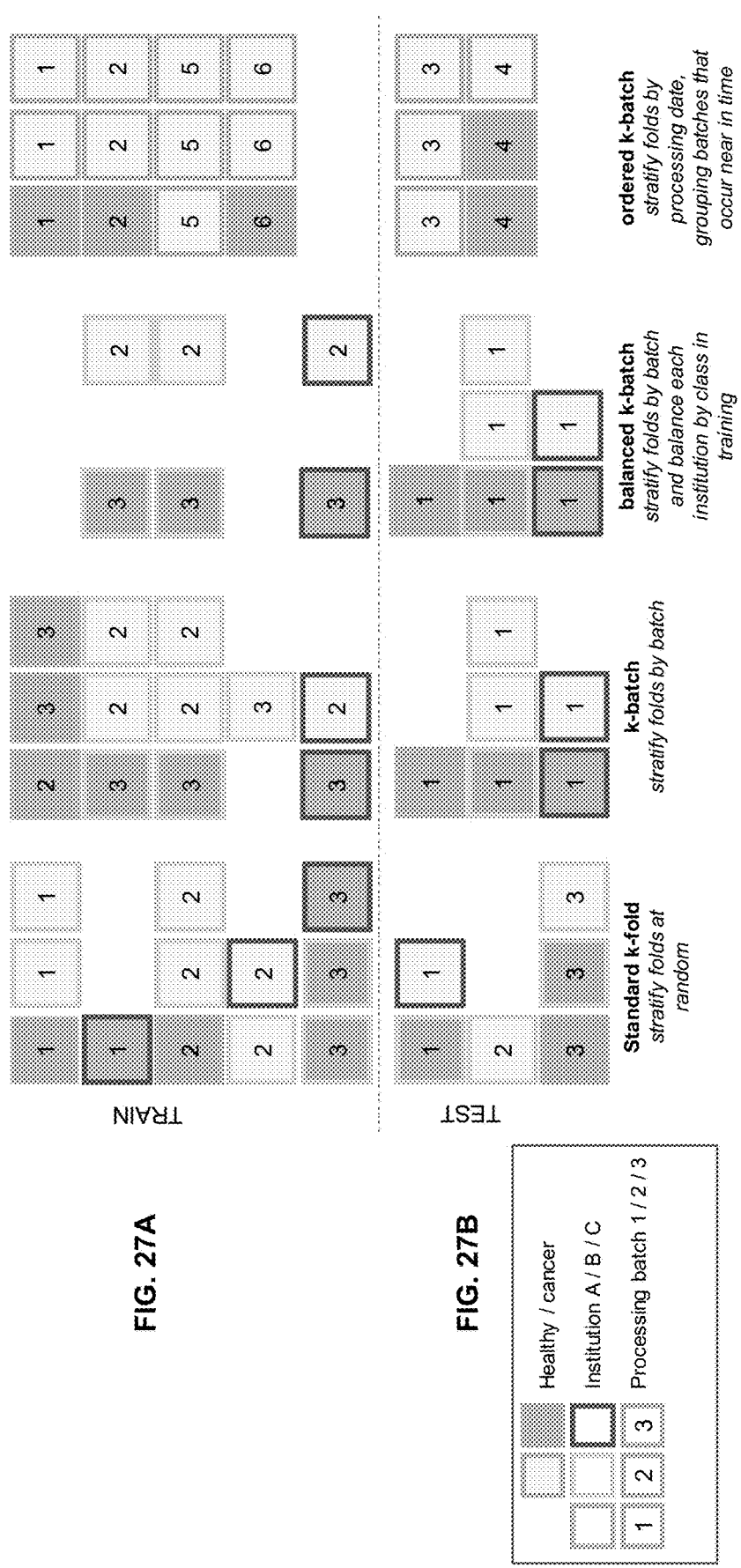
FIG. 27A shows training schemas fork-fold, k-batch, balanced k-batch, and ordered k-batch.
FIG. 27B shows a k-batch with institutional downsampling scheme.

As an example, the k-batch with institutional downsampling scheme may be applied to CRC classifier training (FIG. 27A). Training sets can be balanced across sets of retrospective patients from each institution. Folds may be constructed in terms of sequencing batch, as discussed above, where 10% of the batches are randomly held out as a test set, and training is performed on the remaining 90% of the batches. Within each fold, confounding arising from potential differences in pre-analytical processing procedures can be eliminated by downsampling the input training samples to ensure equal class-balance across each sample source. In other words, for a given sample source, if 70% of the training samples were CRC samples, CRC examples from this source institution are downsampled to achieve a 50% class split between CRC and control examples.

For model training, a series of transformations were fitted on the training data and applied to the test data. Outliers (e.g., any values above the 99th percentile of the training data, per feature) were replaced with the 99th percentile of observed feature values. The data were standardized by subtracting the per-feature mean and dividing by the standard deviation. A targeted set of methods to reduce the dimensionality of the input feature vectors was compared, including performing singular value decomposition on the input data and truncating to the top 1500 components; performing principal component analysis (e.g., similarly truncating to the top 1500 components); or applying no dimensionality reduction step and passing standardized features directly to the classifier. The transformed data was provided as input into a targeted set of classifiers, including logistic regression and support vector machines (SVM). Random search using an internal validation set of 20% of the training data was used in each fold to optimize classifier hyperparameters, including regularization constants and (for radial basis function SVM) the kernel bandwidth.

Mean AUC across the test folds are reported along with standard deviation. The observed sensitivities and specificities were reported as the mean across the test folds with each threshold set corresponding to 85% specificity within IU samples of that test fold. Confidence intervals for sensitivities and AUCs were obtained with resampled bootstrapping.

To understand the impact of individual features on classification, a sweep was performed over levels of L1 logistic regression regularization (using LASSO) with no prior dimensionality reduction. L1 regularization penalizes weight coefficients within a logistic regression model by the absolute value of their magnitude and allows for the identification of a sparse feature set. The level of regularization at which classification performance was closest to performance with the best performing classification pipeline was identified. A set of important sparse gene features was identified by intersecting genes common to multiple folds across multiple experiments. With the set of important sparse features, the distributions of preprocessed read counts across the two primary class distributions of CRC and control samples were examined and compared to distributions of copy number in that segment (as called by IchorCNA) in each gene region. Genes that are significant in distributions of copy number between two populations may be indicative of copy number variants (CNVs), while insignificant differences can indicate other biological mechanisms.

Paired-end whole-genome sequencing (WGS) was performed on plasma DNA samples obtained from 937 control subjects and 524 patients diagnosed with CRC. The population as a whole was approximately equally split by sex (54% female, 46% male). The CRC patient population included 85% early-stage (stage I and stage II) samples, as shown in Table 6. In all reported analyses, while models were trained on all available samples, the performance results were limited to samples from patients within the age range of 50 to 84 years old, to be consistent with the intended use populations examined in commercially-available CRC screening tests. The resulting control sample population skewed younger (median age=61 years old, interquartile range [IQR]=56-67 years old) than the cancer sample population (median age=67, IQR=60-74 years old, p<0.01, Mann-Whitney U-test).

TABLE 6

Number of healthy and cancer samples used for CRC experiments (by stage, gender and age)

| CRC | | Cancer (n = 937) | Control (n = 524) |
|---|---|---|---|
| Gender | Female n, (%) | 433 (46%) | 361 (69%) |
| | Male n, (%) | 504 (54%) | 163 (31%) |
| Stage | I | 297 | |
| | II | 496 | |
| | III | 110 | |
| | IV | 9 | |
| | Unknown | 25 | |
| Age | Median/IQR | Median age: 60.0 | Median age: 67.0 |
| | | IQR: 53.0-66.0 | IQR: 60.0-75.0 |

A k-fold cross-validation procedure was examined to assess generalizability of model performance. With k=10 folds, the top methods after random search of hyperparameters were principal component analysis (PCA) over the entire training set into a support vector machine (SVM). Other methods were also within error bounds of this model and may be used in alternative examples. This method achieved a mean area-under-the curve (AUC) of 0.87 (with a 0.026 standard deviation across folds), with a mean sensitivity of 77% (with a 0.059 standard deviation across folds) at an 85% specificity of IU samples, as shown in Table 7.

TABLE 7

CRC performance by cross-validation procedure in the intended use population

| Validation | AUC mean ± std | Sensitivity at 85% Specificity |
|---|---|---|
| k-fold | 0.87 ± 0.026 | 77% ± 5.9% |
| k-batch | 0.84 ± 0.033 | 70% ± 8.6% |
| Balanced k-batch | 0.81 ± 0.044 | 61% ± 11% |
| Ordered k-batch | 0.81 ± 0.10 | 62% ± 19% |

To assess generalizability to new data, a variety of validation schemes that explored possible confounders were evaluated (as shown in FIG. 27B), including k-batch, balanced k-batch and timeline k-batch, which are various ways to control for possible short-term, institutional, or long-term biases, respectively. These forms of validation were performed with the same method chosen in the previously described k-fold experiment. The number of folds (e.g., k=10) is constant across all procedures.

First, batch effects which can cause significant confounding were assessed, especially when the number of batches is low. With the same methods of PCA and a random search over SVM, the k-batch cross-validation achieved a mean AUC of 0.84 (with a 0.33 standard deviation across folds) with a mean sensitivity of 70% at 85% specificity (Table 7), which is similar to k-fold performance.

Because retrospective samples from different institutions may have been subject to different pre-analytical processing and storage conditions, a balanced k-fold validation was also evaluated, where institutions are sampled to a uniform distribution of cancer vs. non-cancer for that institution in the training data (e.g., Institution A has an equal number of cancer samples and noncancer samples in a training dataset). Even though the training data was significantly reduced by this approach (an average of 654.6 samples per fold in training, versus 1314.9 samples per fold with kfold or k-batch), this procedure still achieved a mean AUC of 0.83 (with a 0.018 standard deviation across folds) with a mean sensitivity of 66% at 85% specificity (Table 7).

Finally, an approach to assess longer term process drift was conducted using a timeline kbatch, which was performed by splitting samples by process date and grouping samples processed near in time to each other in the same fold. Using this strategy, any information learned about the technical process in the range of training dates may not generalize to the test dates. This technique achieved a mean AUC of 0.81 (with a 0.10 standard deviation across folds) with a mean sensitivity of 62% at 85% specificity (Table 7).

Figure 28A:
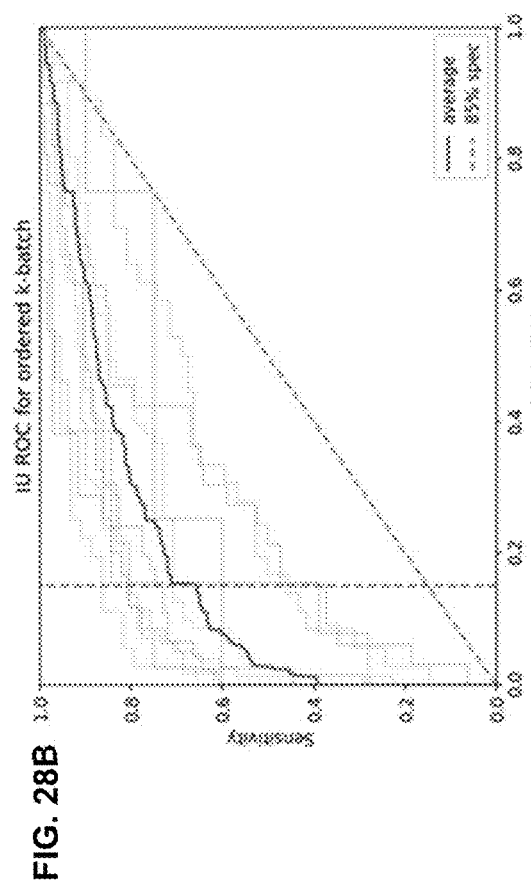
FIGS. 28A-28D show examples of receiver operating characteristic (ROC) curves for all validation approaches evaluated (e.g., k-fold, k-batch, balanced k-batch, and ordered k-batch) for cancer detection.
Figure 28B:
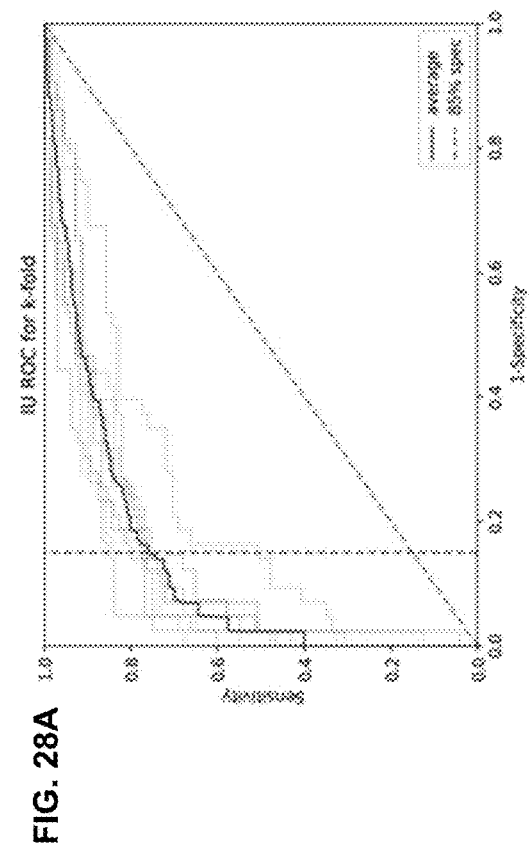
Figure 28C:
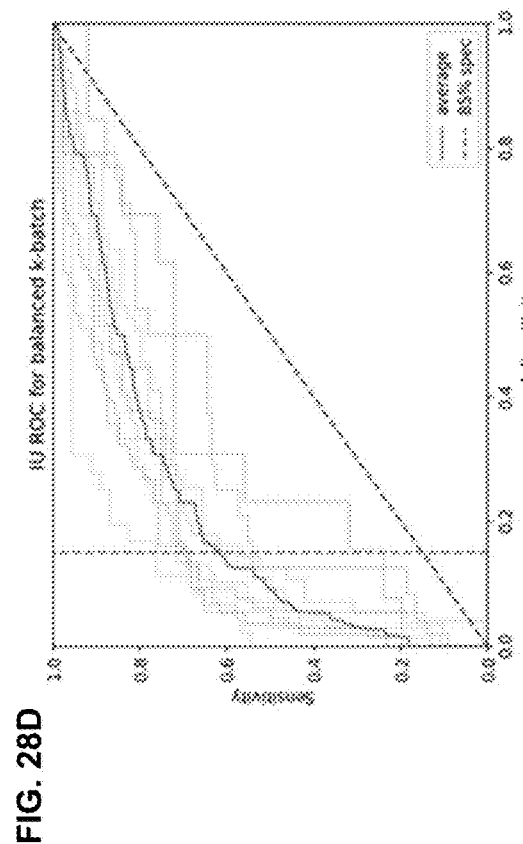
Figure 28D:
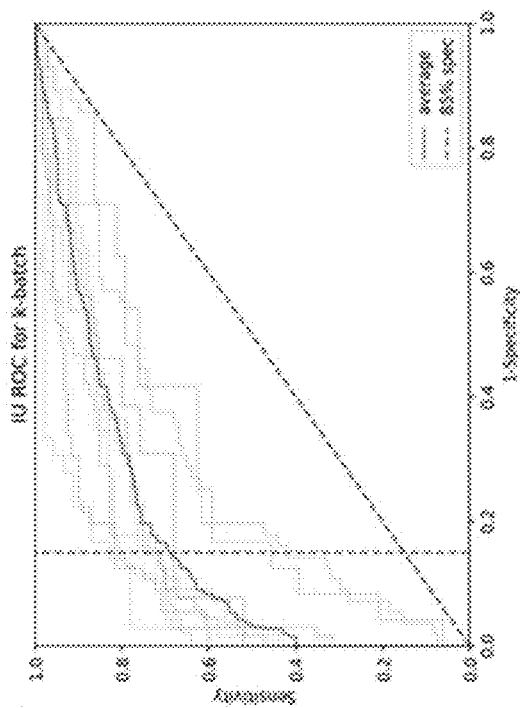
Figure 28E:
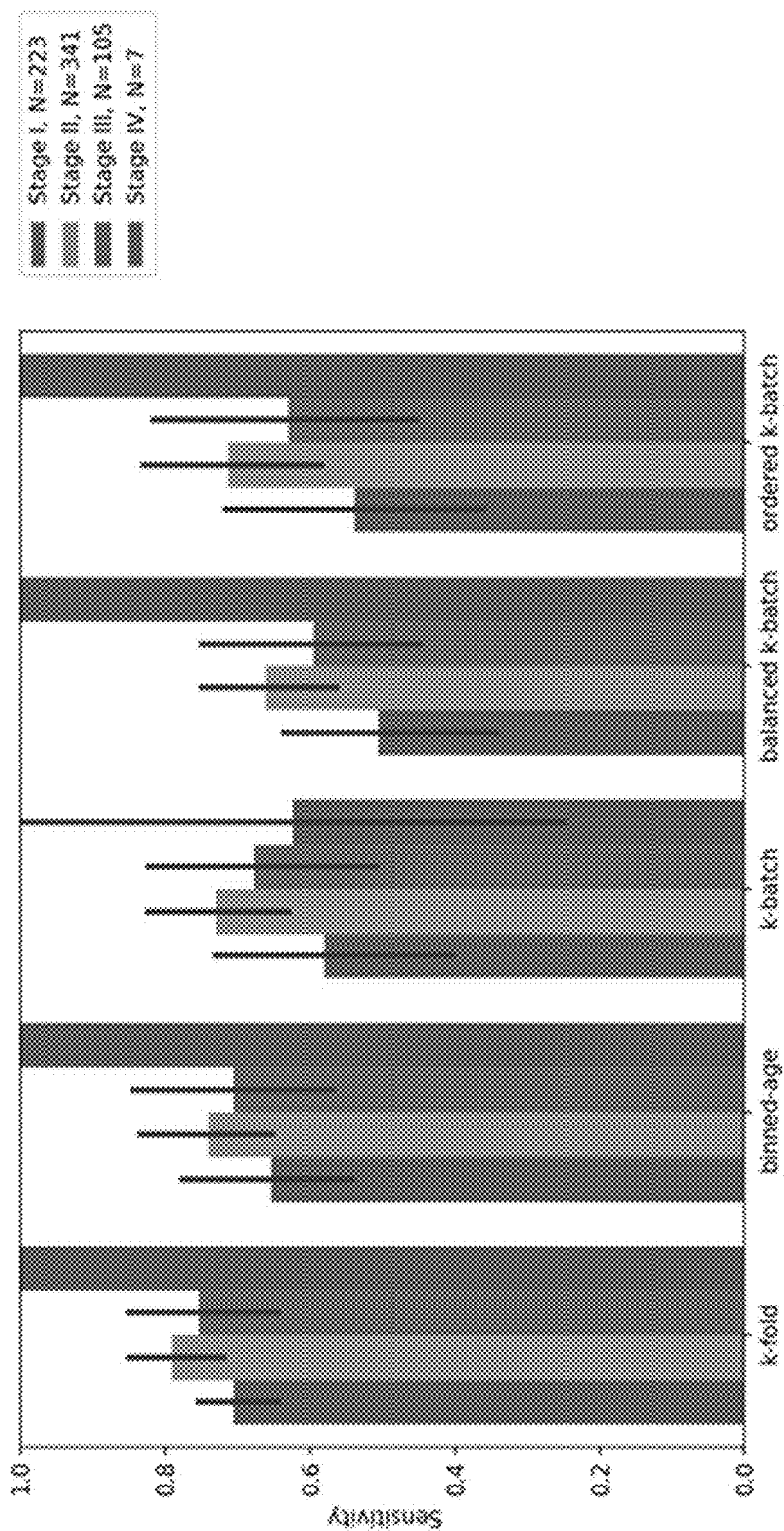
FIG. 28E shows sensitivity by CRC stage across all validation approaches evaluated.

In order to begin to understand the obtained models, performance was analyzed for each validation method, over various populations within the data. FIGS. 28A-28D show examples of receiver operating characteristic (ROC) curves for all validation approaches evaluated (e.g., k-fold, k-batch, balanced k-batch, and ordered k-batch) for cancer detection. Within each validation method, consistent sensitivity was achieved across stages I through III (within confidence intervals), and stage IV samples were consistently classified correctly (FIG. 28E, showing sensitivity by CRC stage across all validation approaches evaluated). This may not be surprising since late-stage cancers may be relatively easy to distinguish due to the large number of observed CNV s. Further, performance was observed to be comparable across validation types to the general trend of overall AUC.

Figure 28F:
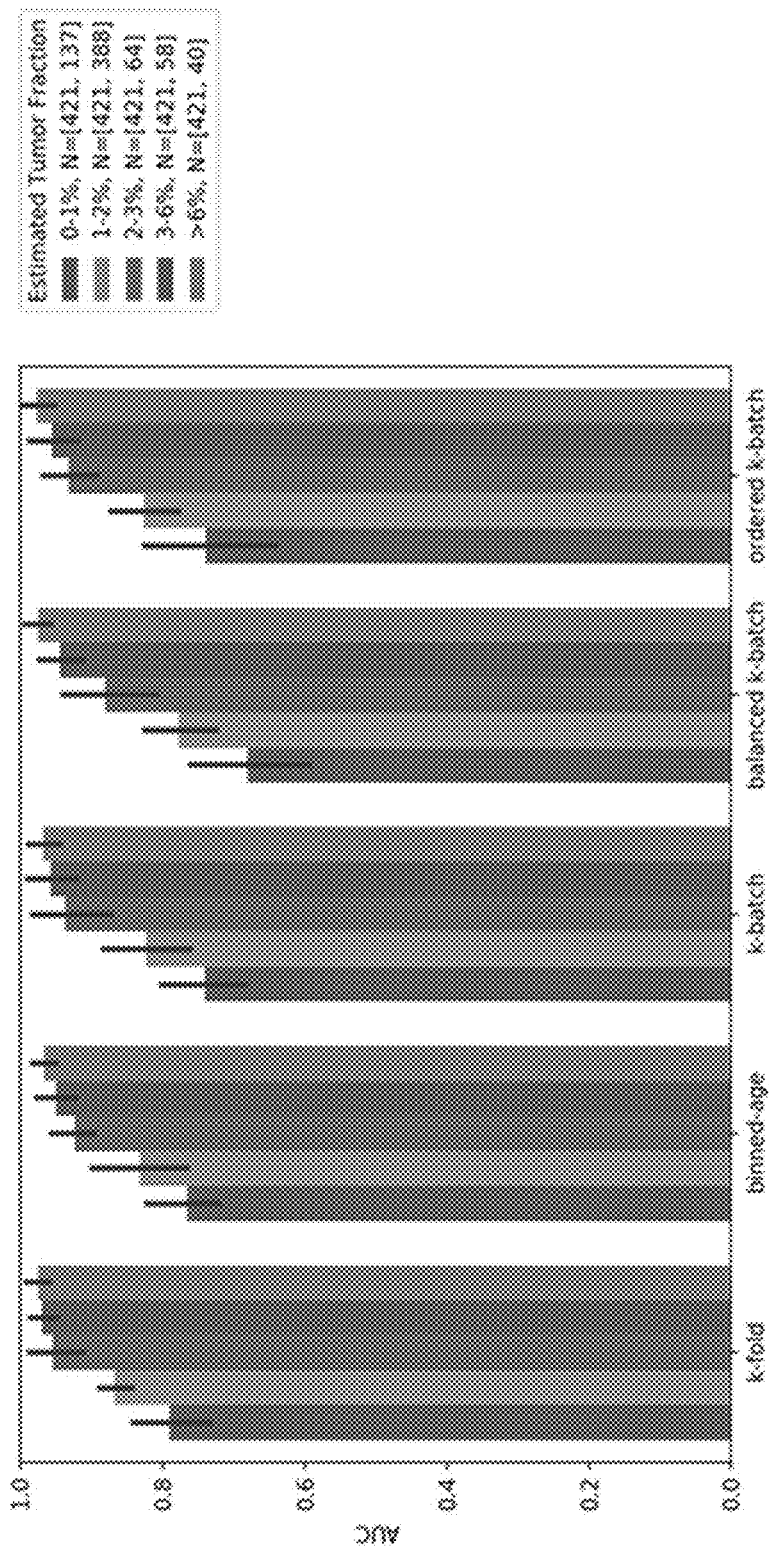
FIG. 28F shows AUC by IchorCNA-estimated tumor fraction across all validation approaches evaluated.

Next, tumor fraction was analyzed separately from clinical staging. In order to estimate tumor fraction, a hidden Markov model (IchorCNA) that iteratively estimates tumor fraction and CNV segmentations for each sample was used. Performance was evaluated within various bins of tumor fraction, in which cancer and control samples were found to overlap with estimated tumor fraction below about 2% (FIG. 28F).

If the tumor fraction values alone were used to predict cancer, an AUC of 63% may be achieved over the IU population, which is lower than all validation methods. Again, consistent performance was observed within cross-validation procedures across ranges of tumor fraction (FIG. 28F, showing AUC by IchorCNA-estimated tumor fraction across all validation approaches evaluated), except within the high tumor fraction bin (greater than about 6%) where there are a small number of control samples with very high tumor fraction (e.g., which may possibly be label swaps).

Figure 28G:
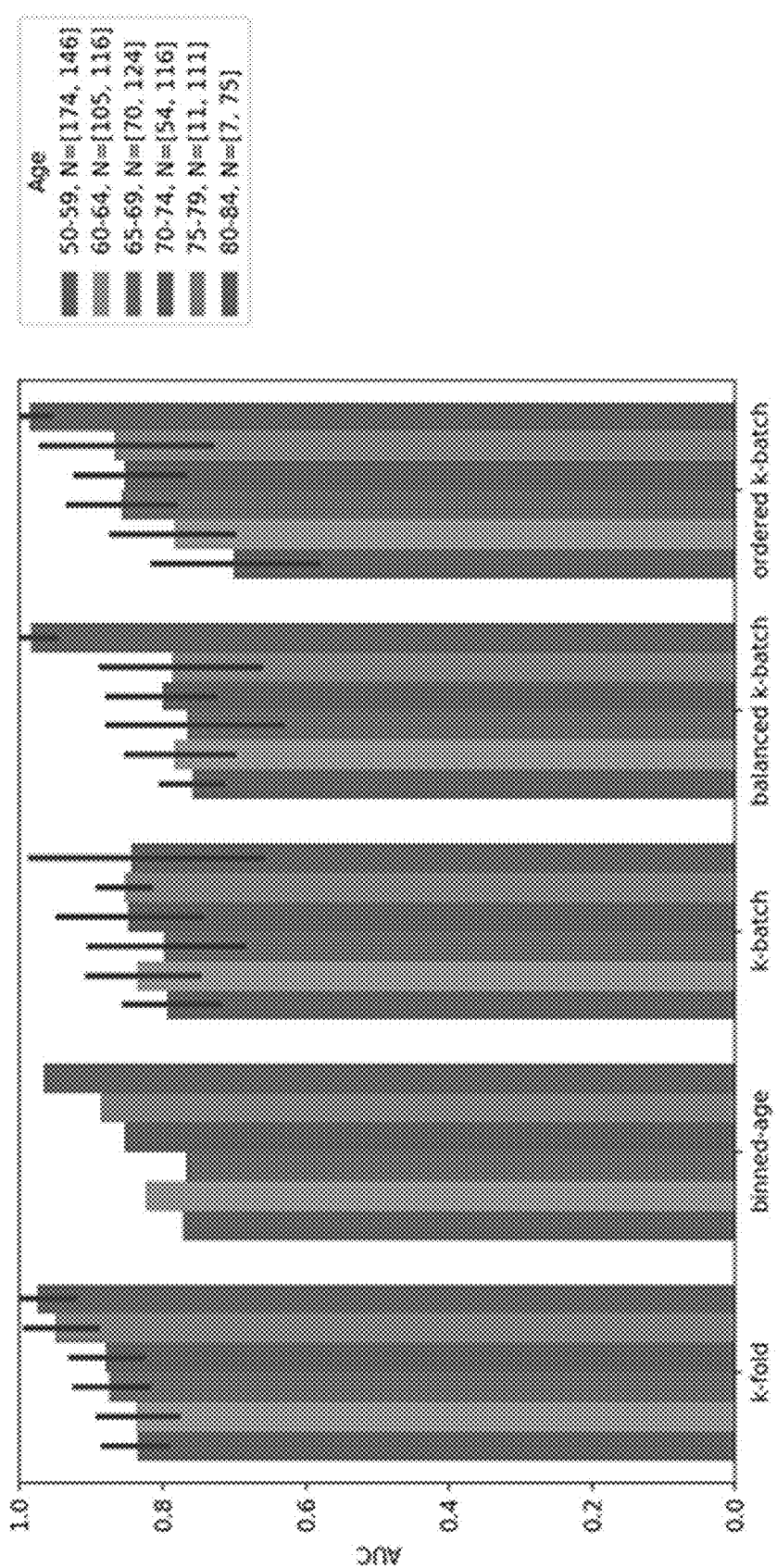
FIG. 28G shows AUC by age bins across all validation approaches evaluated.

Since age may be a known confounder and class balance in gender is uneven (Table 6), a classifier's ability to predict cancer on just age and gender was assessed, among the samples for which the data is available. The resulting performance is a mean AUC of 0.75, which confirms the general notion that cancer is an age-related disease and is reflected in the population of our data. The AUC performance increases with older age bands (FIG. 28G, showing AUC by age bins across all validation approaches evaluated). Here a diversity in performance characteristics is observed, which suggests the distributions of age populations in these folds are very different.

Figure 28H:
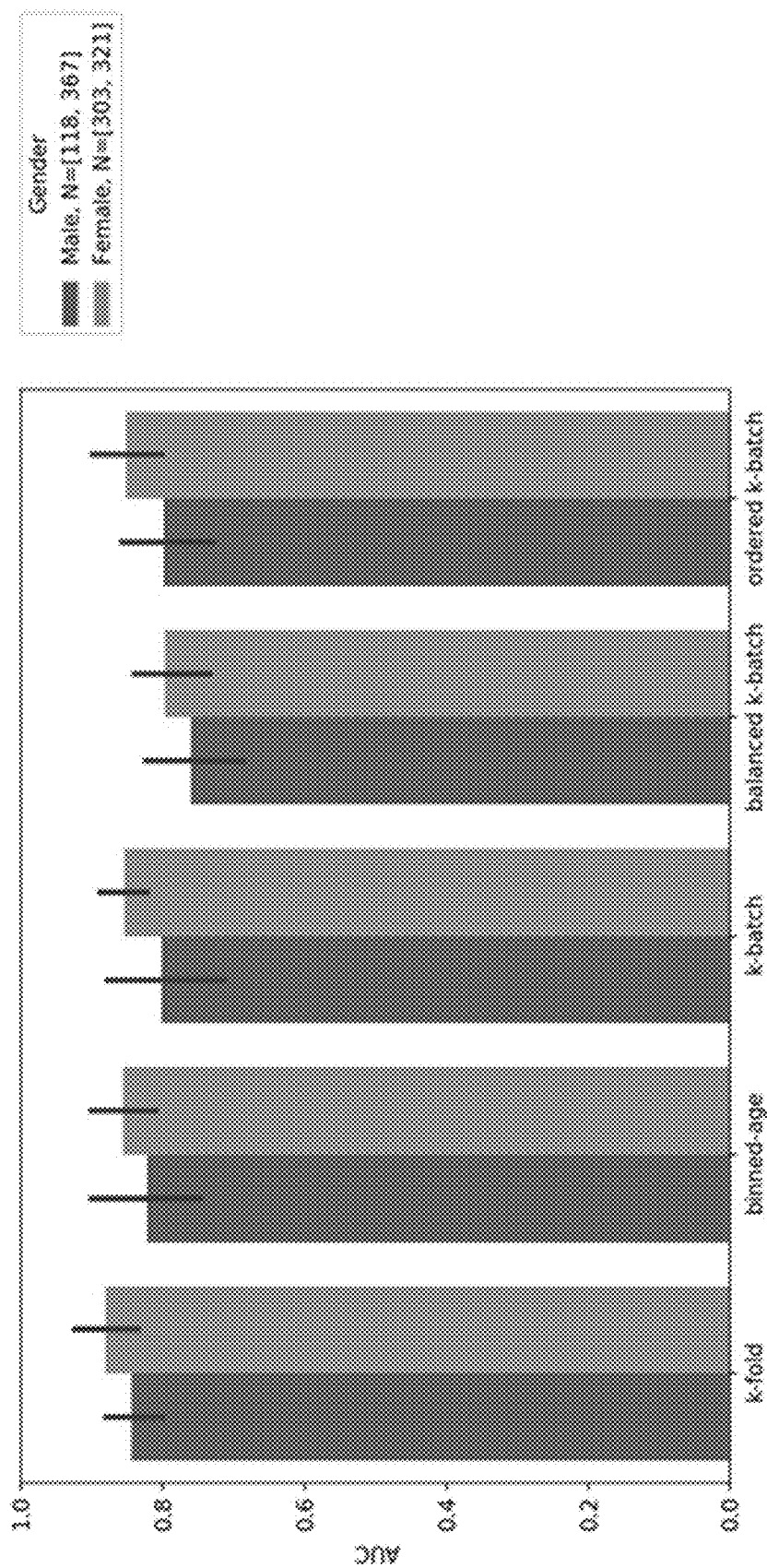
FIG. 28H shows AUC by gender bins across all validation approaches evaluated.
Figure 29A:
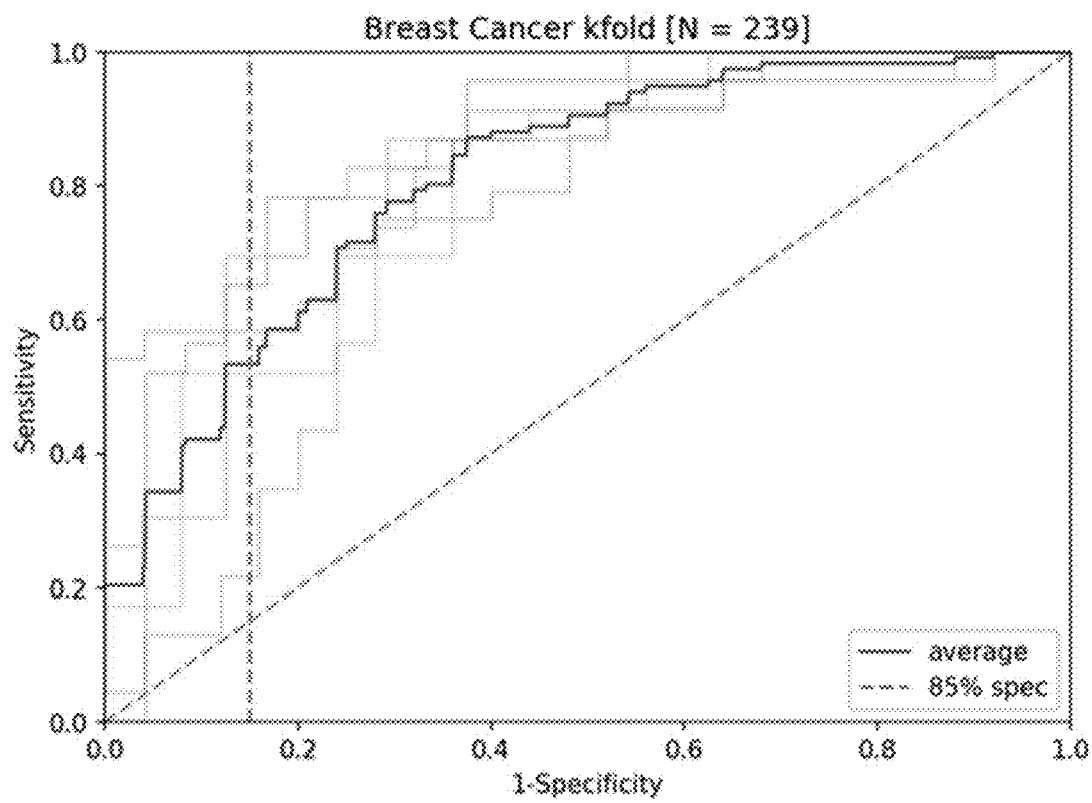
FIGS. 29A-29B show classification performance in cross validation (ROC curves) for breast cancer.
Figure 29B:
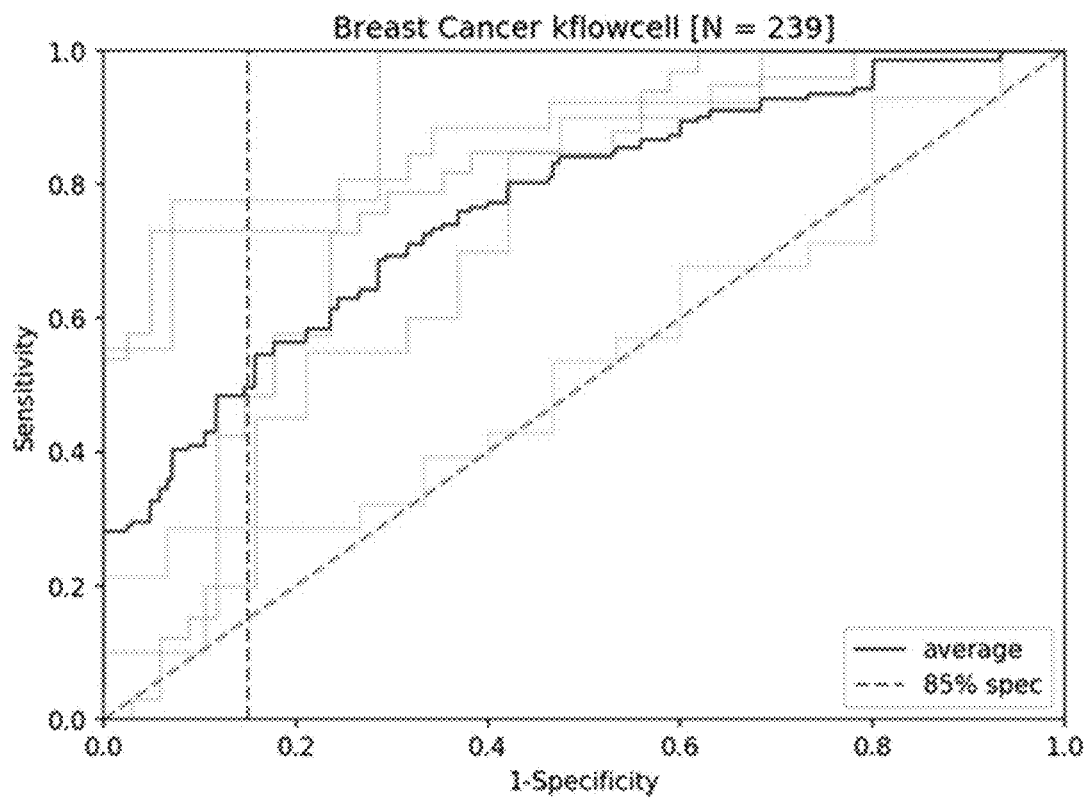
Figure 29C:
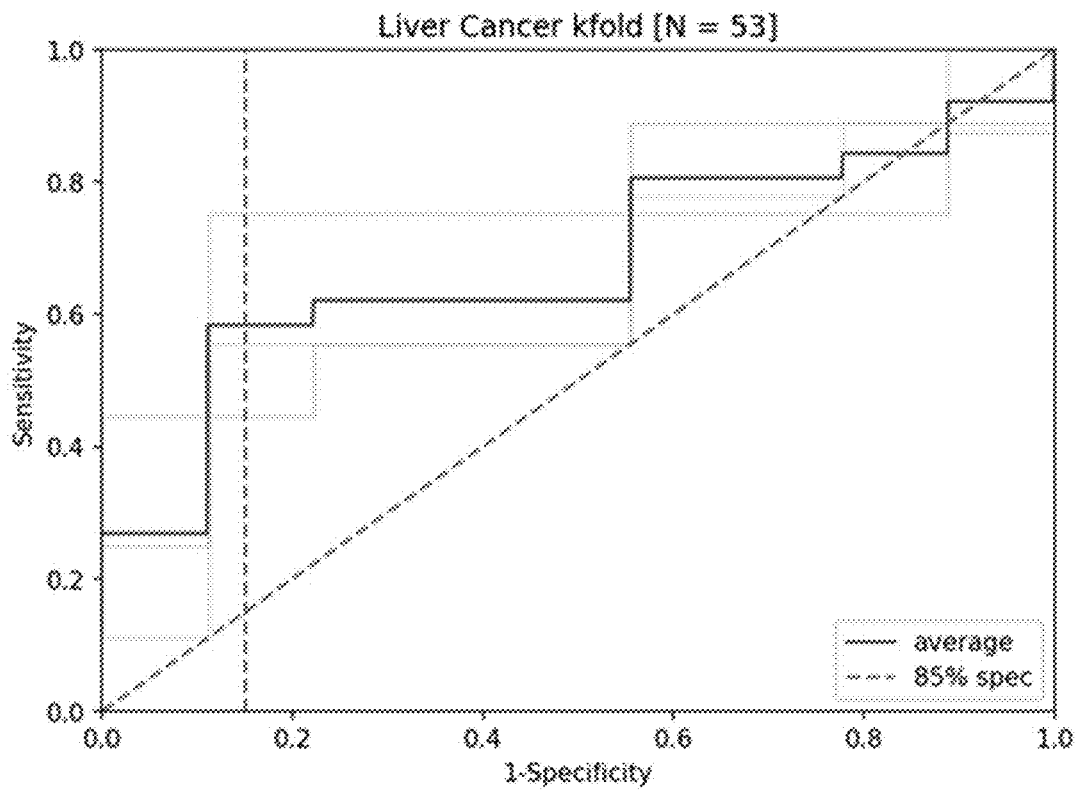
FIGS. 29C-29D show classification performance in cross validation (ROC curves) for liver cancer.
Figure 29D:
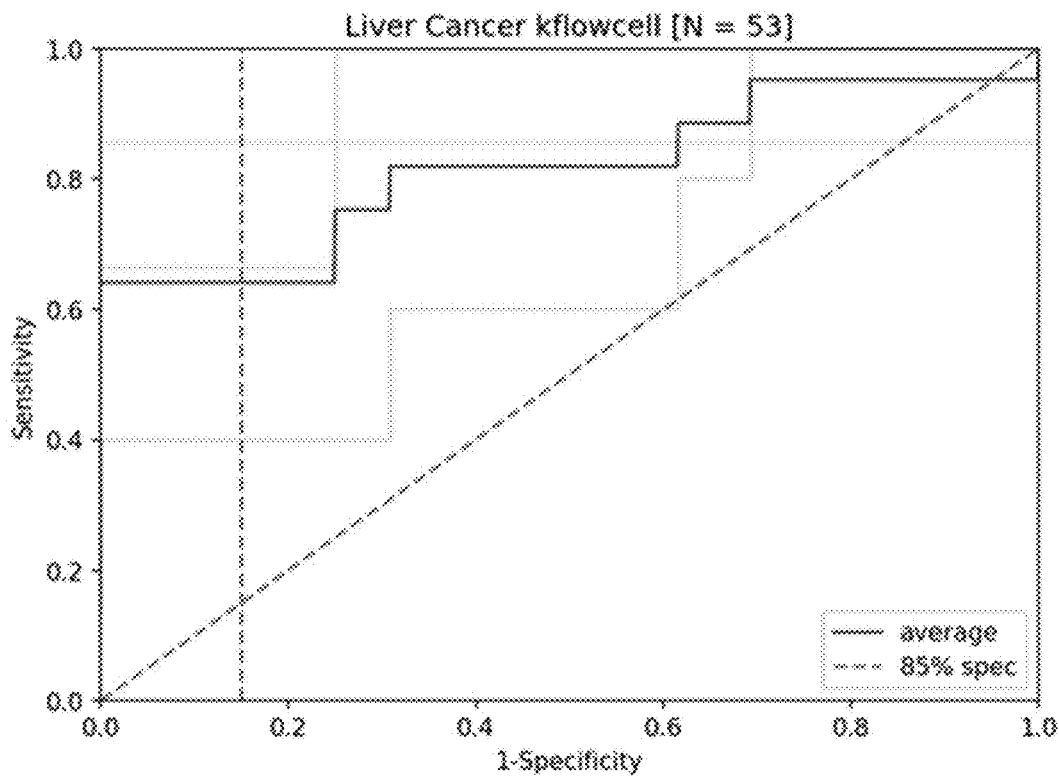
Figure 29E:
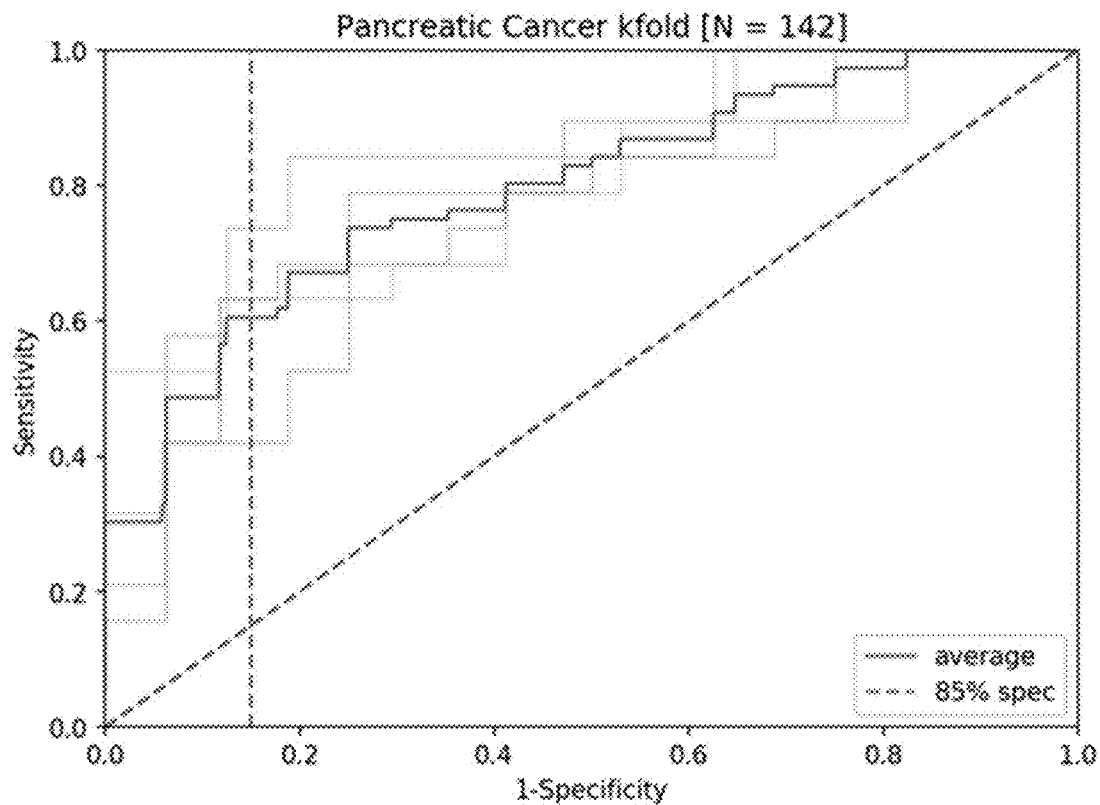
FIGS. 29E-29F show classification performance in cross validation (ROC curves) for pancreatic cancer.
Figure 29F:
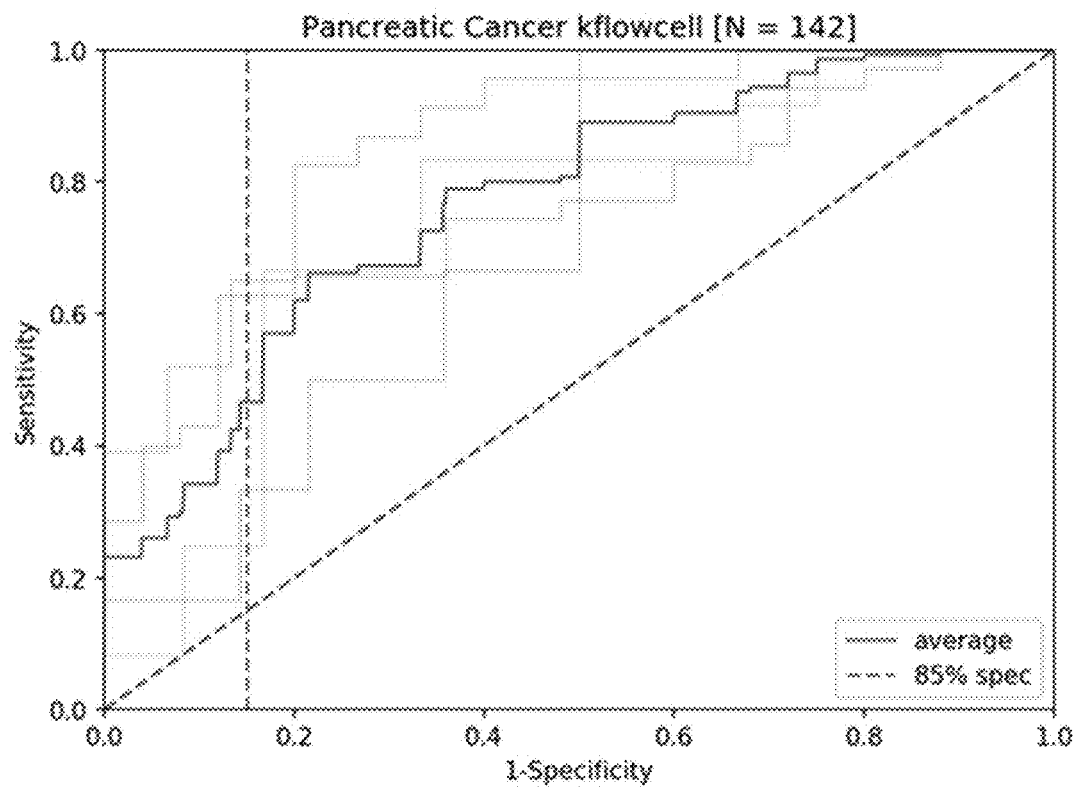

Performance across genders is comparable across validation types (FIG. 28H, showing AUC by gender across all validation approaches evaluated), with little or no difference across different validations. While the performance on female samples exceeds that of the male samples, this observation may be an artifact of having more female samples in the dataset, therefore suggesting that that age is a stronger confounder than gender.

To estimate which input features contribute to the classifier's ability to predict cancer class, a model designed to capture sparse signals was trained. Using k-fold cross validation, a sweep over regularization coefficient was performed, and five sparse models were discovered with performance similar to those of the initial set of experiments. The inverse of L1 regularization strength, C, for the five models ranged from 0.022 to 0.071, and the mean AUCs for the five models ranged from 0.80 to 0.82. A set of features was identified with corresponding learned weighting coefficients having an absolute value greater than zero across seven or more folds of learned classifiers. The intersection of the five experiments yielded 29 genes listed in Table 8, which may be considered "highly important features" toward a cancer-detecting classifier.

TABLE 8

| Gene | Seqname | CNV p-value | Feature p-value |
|---|---|---|---|
| CCR3 | chr3 | 4.59E−12 | 9.17E−11 |
| CD4 | chr12 | 1.68E−01 | 1.24E−05 |
| CTBP2 | chr10 | 1.70E+01 | 6.67E−11 |
| CTSD | chr11 |  | 1.98E−01 |
| ENHO | chr21 | 1.91E+01 | 5.10E−10 |
| EVA1C | chr6 | 5.47E−01 | 4.38E−08 |
| GSTA3 | chr6 | 1.35E+01 | 1.78E−07 |
| HIST1H2AK | chr5 | 7.43E+00 | 2.04E−03 |
| IK | chr7 | 7.98E−01 | 2.28E−07 |
| IRF5 | chr7 | 5.46E−10 | 2.19E−09 |
| KLF14 | chr1 | 1.96E−12 | 1.41E−07 |
| KMO | chr3 | 1.79E+01 | 4.36E−07 |
| KY | chr3 | 7.13E−04 | 2.36E−20 |
| LGALS3 | chr14 | 1.75E−06 | 5.94E−13 |
| LOC100130520 | chr17 | 1.75E+00 | 1.08E−10 |
| LOC105376906 | chr19 | 5.76E−09 | 5.27E−08 |
| MCAT | chr22 | 2.48E−07 | 5.88E−11 |
| NEDD8 | chr14 | 2.19E−06 | 2.73E−11 |
| NSMCE1 | chr16 | 3.71E−01 | 1.27E−06 |

Of the features of Table 8, nearly all had univariate significant differences (p<0.05, Bonferroni corrected) between CRC and healthy samples. In addition, copy number distributions were compared at each of these gene sites between the cancer and control samples, as called by IchorCNA. Of the highly important features, only 10 had significant differences in CNVs, and matched with significant features with univariate differences (p<0.05, Bonferroni corrected) More significant CNV p-values may indicate differences CNV between cancer and control samples for that gene region. These ten sites may be picking up CNVs very well, while the other sites may be picking up other changes. These changes may be either changes in CNV that are not detected by IchorCNA, or changes that are a result of other biological mechanisms. Some of the genes may be indicative of markers beyond CRC-related genes, as immune genes appear in the list of highly important features.

Figure 30:
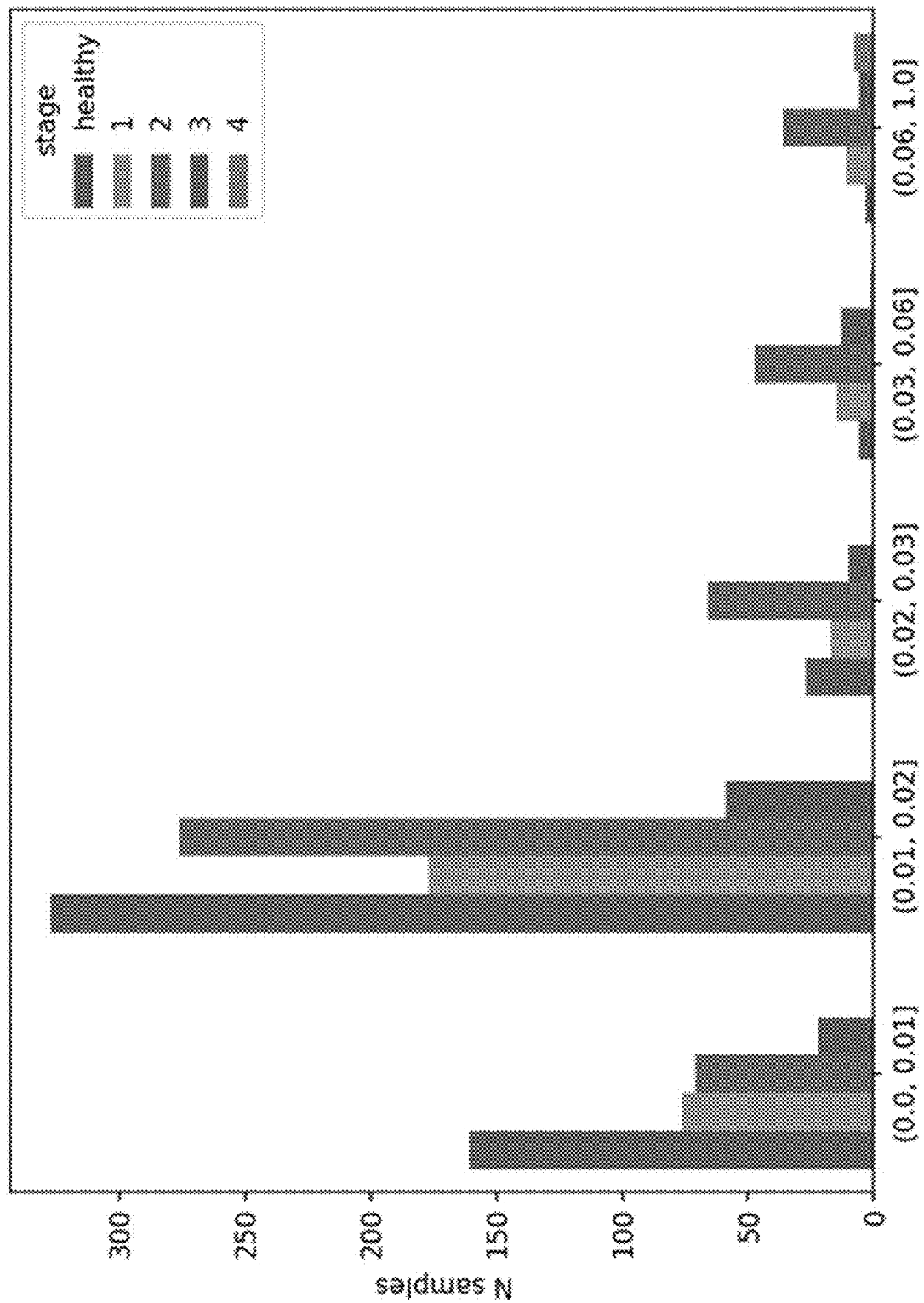
FIG. 30 shows a distribution of estimated tumor fraction (TF) by class.
Figure 31A:
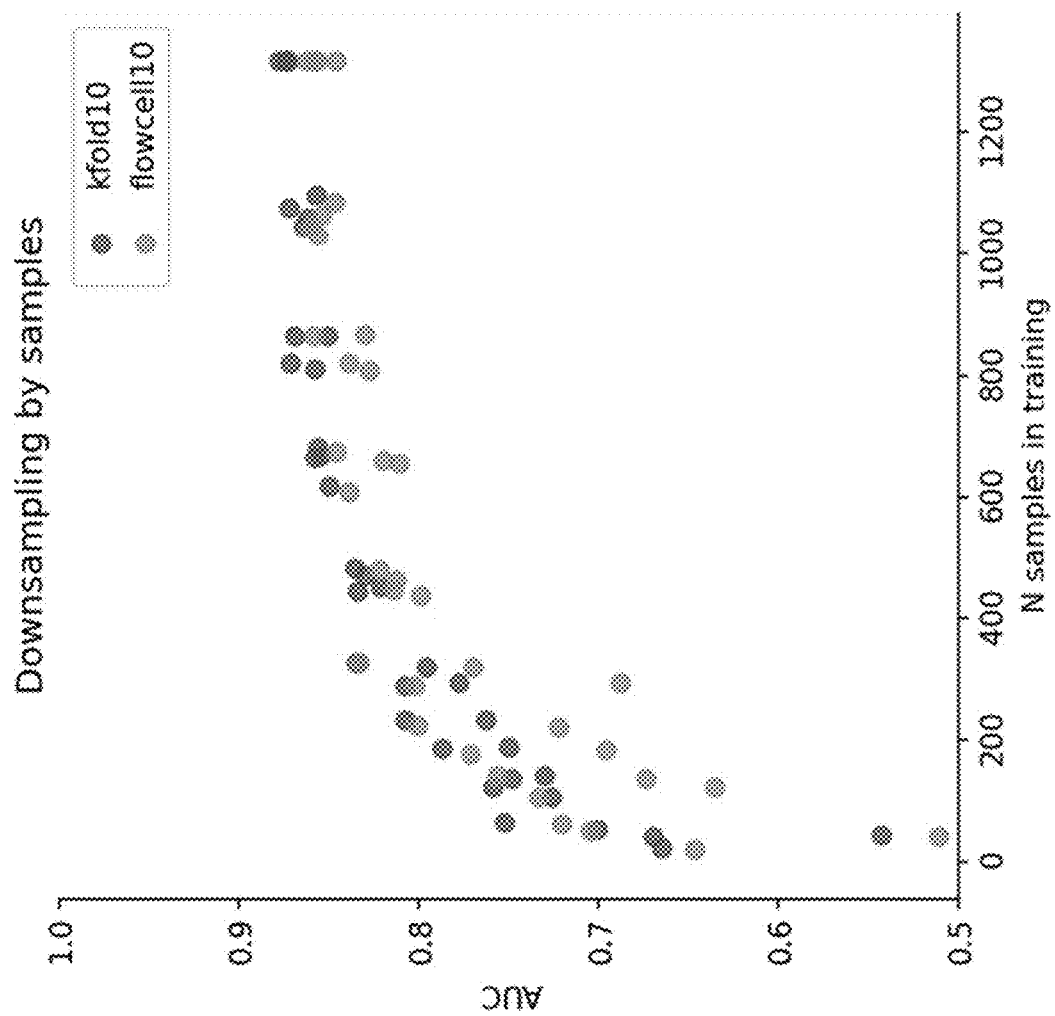
FIG. 31A shows the AUC performance of CRC classification when the training set of each fold is downsampled either as a percentage of samples.
Figure 31B:
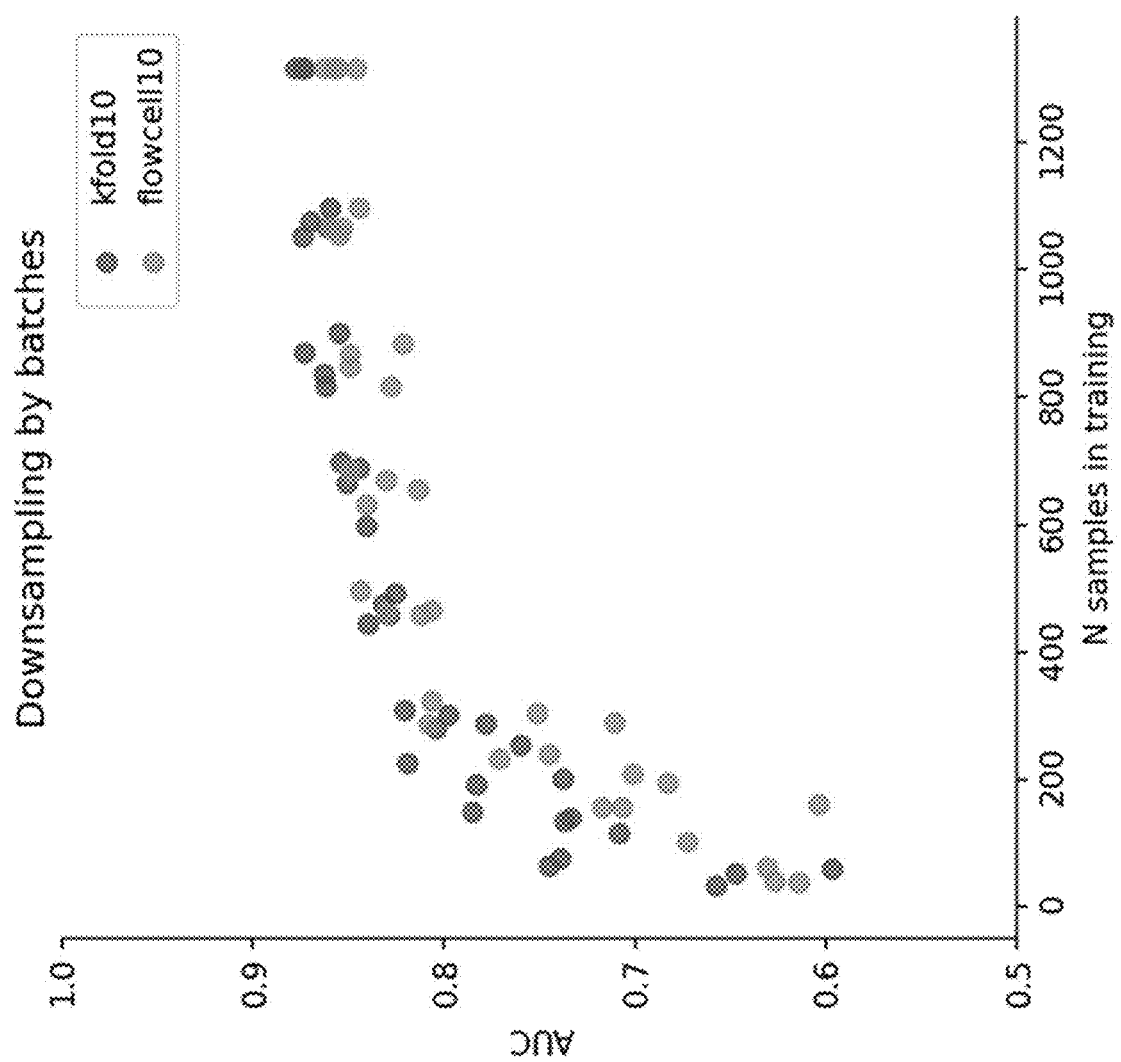
FIG. 31B shows the AUC performance of CRC classification when the training set of each fold is downsampled either as a percentage of samples or as a percentage of batches.
Figure 32A:
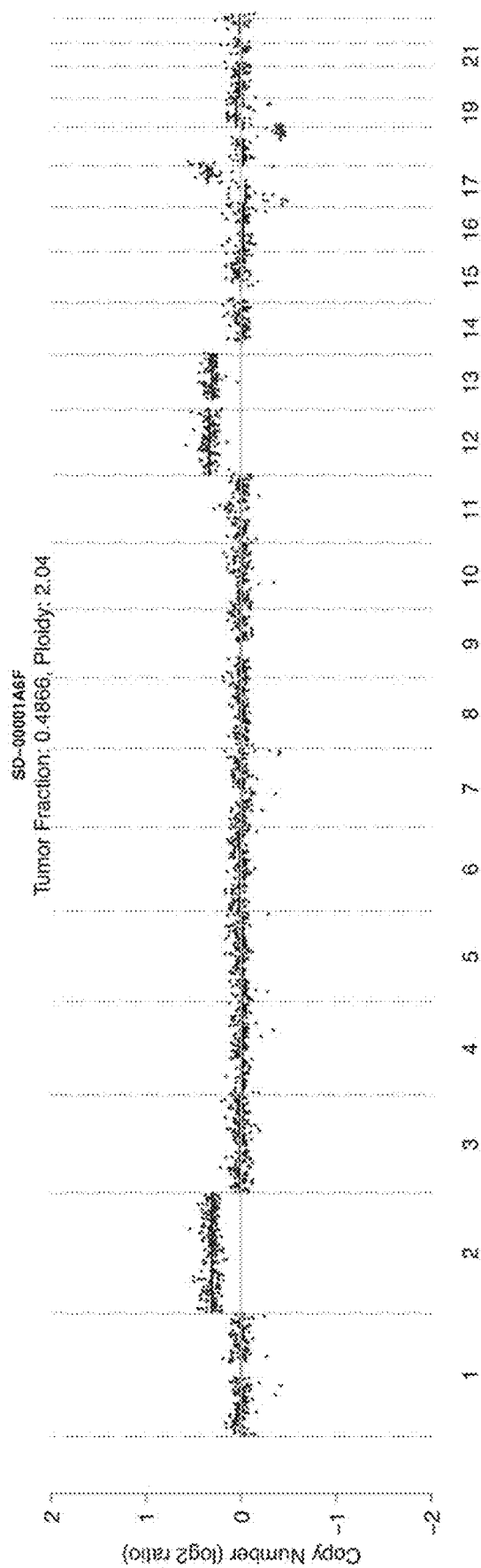
FIGS. 32A-32C show examples of healthy samples with high tumor fraction.
Figure 32B:
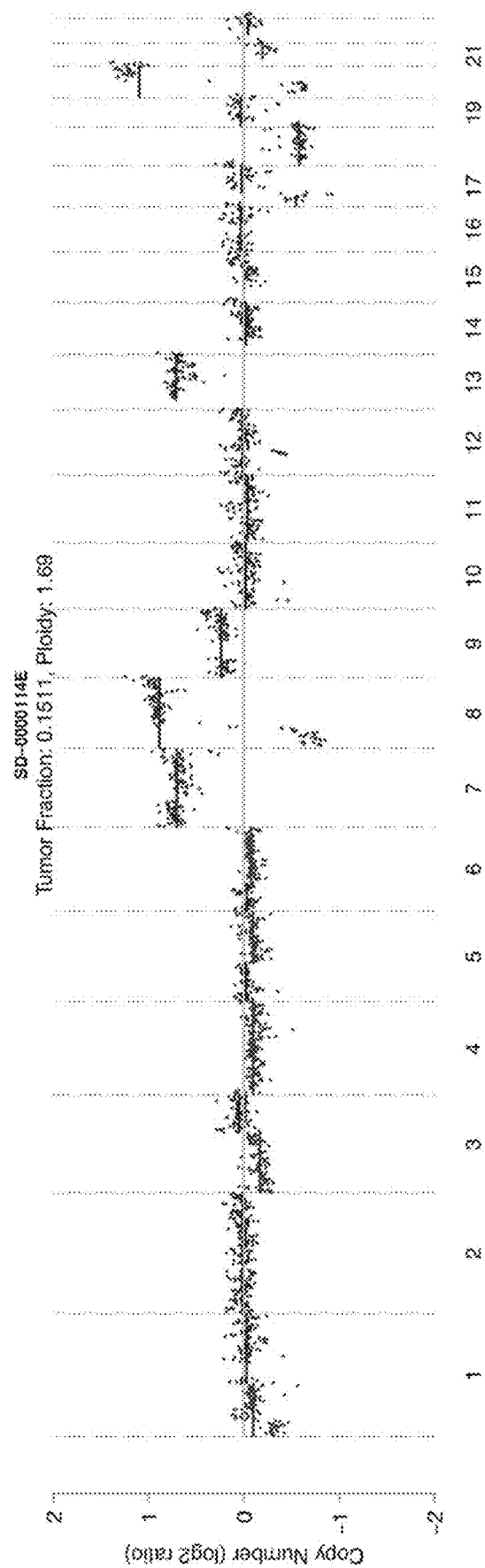
Figure 32C:
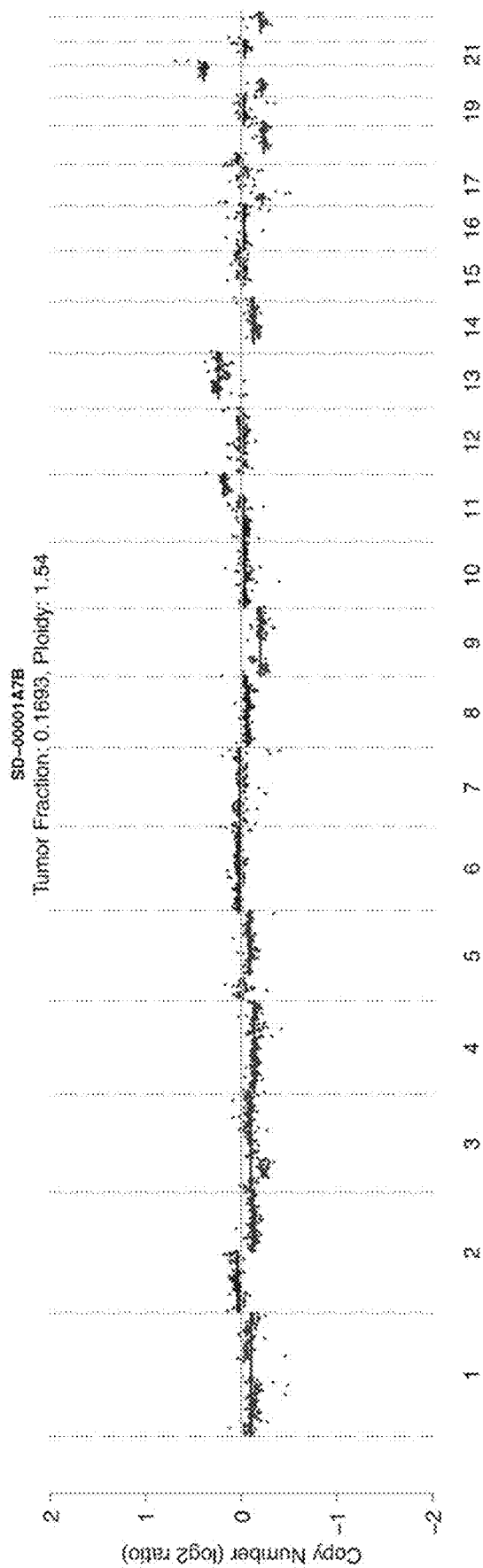

As an example of the use of such highly important features, a classifier can be programmed or configured to analyze quantitative measures (e.g., counts) of cfNA sequencing reads obtained from a sample of a subject at each of a plurality of genomic regions comprising at least about 10 distinct regions, at least about 20 distinct regions, at least about 30 distinct regions, at least about 40 distinct regions, at least about 50 distinct regions, at least about 60 distinct regions, at least about 70 distinct regions, or at least about 75 distinct regions of the group of highly important features in order to detect a cancer (e.g., colorectal cancer, breast cancer, pancreatic cancer, or liver cancer) in the subject. In addition to evaluating CRC detection, the same sequencing protocol was evaluated on plasma cfDNA samples obtained from patients diagnosed with pancreatic cancer (n=126), breast cancer (n=116), and liver cancer (n=26) with institution-matched control patients (FIGS. 29A-29F, showing classification performance in cross validation (ROC curves) for breast cancer, liver cancer, and pancreatic cancer, respectively). The majority of breast cancer samples also skewed towards early-stage cancer: 73% of breast cancer samples were stage I or stage II (with 1.7% breast cancer samples lacking stage information). All liver cancer and pancreatic cancer samples lacked stage information. The same classification framework as described above was applied, except the number of folds was scaled to the data size (Table 9). Although the results are lower, they appear to be unreasonable given the smaller number of samples in these experiments. FIG. 30 shows a distribution of estimated tumor fraction by class, and FIGS. 31A and 31B show the AUC performance of CRC classification when the training set of each fold is downsampled either as a percentage of samples or as a percentage of batches, respectively. Similar drops in performance are observed when the data are trained with comparable numbers within the CRC experiment. FIGS. 32A-32C show examples of healthy samples with high tumor fraction.

TABLE 9

Cross-validation results of breast cancer, liver cancer, and pancreatic cancer
Cancer k = Validation AUC mean ± std with Sensitivity at 85%

| Cancer | K = | Validation Method | AUC mean ± std | Sensitivity at 85% Specificity |
|---|---|---|---|---|
| Breast | 5 | K-fold | 0.81 ± 0.039 | 53% ± 19% |
|  |  | K-batch | 0.77 ± 0.13 | 50% ± 26% |
| Liver | 3 | K-fold | 0.68 ± 0.027 | 58% ± 15% |
|  |  | K-batch | 0.82 ± 0.1 | 64% ± 23% |
| Pancreatic | 4 | K-fold | 0.8 ± 0.03 | 61% ± 13% |
|  |  | K-batch | 0.77 ± 0.058 | 47% ± 20% |

The results demonstrate excellent performance of early-stage (e.g., stage I and stage II) cancer detection from the blood. Machine learning techniques were applied to a large collection of cohorts of early-stage CRC cfDNA samples from an international pool of sample sources, to effectively learn the relationship between a patient's cfDNA profile and cancer diagnosis, with a sensitivity of about 62-77% at a specificity of 85% in rigorously-defined out-of-sample evaluations. In addition, similar levels of predictive performance were achieved when the same machine learning technique was applied to cohorts of cfDNA samples obtained from patients with breast, pancreatic, and liver cancer, with sensitivities ranging from 47% to 64% at a specificity of 85%. Despite the sizeable number of samples included in these analyses, classification performance can continue to increase with additional samples, suggesting that even without further methodological advances, cancer detection performance may be expected to improve with further sample collection. The results are also consistent with previous studies, with several identified important features having putative relationships with cancer.

When performing the learning and validation approach (as shown above) to conduct biomarker discovery using retrospective samples, it may be important to control for confounding factors. In general, differences in pre-analytical processing (e.g., centrifugation speed, collection tube type, number of freeze-thaw cycles) as well as analytical processing (e.g., library preparation batch, sequencing run), if confounded with class label, can provide misleading generalization results. For example, if processing variables are not properly accounted for, it is possible to achieve much higher validation metrics of predictive performance in a cancer-control dataset (e.g., an AUC of 87% AUC may be observed in a standard k-fold cross-validation approach, as compared to an AUC of 84% in a balanced k-batch approach (or another approach which incorporates a more rigorous accounting of generalization performance). In general, although statistical approaches generally may not be immune to confounding effects, a high-dimensional genome-wide machine learning approach may be particularly susceptible to such confounding effects if not properly accounted for.

While such processing effects can be somewhat mitigated computationally, a robust experimental design may be a highly effective method of ensuring generalizable results, with the minimization of the mutual information between class label and any potential noise-inducing variable (e.g., minimization of confounding). In retrospective studies, and even in large prospective collection studies, such randomization may not always be possible, given the large number of potential important covariates. In such cases, techniques such as enforcing class balance across known confounding variables, robust cross-validation stratification during learning, or computational approaches to normalize out potential covariates may be appropriately used. Techniques such as the approach of downsampling to ensure class balance by sample source and out-of-sample validation by library preparation processing batch can provide more realistic assessments of a method's generalizability to new data.

A cfDNA count-profile representation of the input cfDNA may serve as an unbiased representation of the available signal in the blood (compared to, for example, a mutation-based or methylation-assay approach), allowing the capture of both signals directly from the tumor (e.g., CNV s) as well as those from non-tumor sources, such as changes in immunological epigenetic cellular states from, for example, the circulating immune system or tumor microenvironment. The success of this approach, given the expected low tumor fraction in early-stage cancer patients, may suggest that cfDNA can be used as a derived epigenetic cellular signal to capture changes in physiologic states.

In predominantly early-stage population, tumor fraction (as estimated through CNV calls) may not necessarily correspond to clinical cancer stage. There is evidence that the count-profile approach uses a diversity of signals in the models with a set of highly important gene features, which includes genes with common CNV sites (e.g., IRF5 and KLF14 on the 7q32 arm) and genes that are insignificant for CNV but important to the immune and colon systems (e.g., CD4, WNTI, and STATI).

Further, because such signals are distributed across the genome and may require relatively low sequencing depth in comparison to extremely high-depth targeted sequencing (e.g., at least about 1,000×, at least about 5,000×, at least about 10,000×, at least about 20,000×, at least about 30,000×, at least about 40,000×, at least about 50,000×, or at least about 60,000× sequencing depth) to detect ctDNA mutations, a cfDNA approach may be more practical and thus advantageous in terms of sample volumes required.

Early stage colorectal cancer was detected in human plasma samples using artificial intelligence and whole-genome sequencing of cell-free DNA human plasma samples were acquired from 797 patients diagnosed with colorectal cancer (CRC) at varying stages (e.g. stages I-IV and unknown) as shown in Table 10. In addition, a set of 456 control samples were acquired from subjects without a current cancer diagnosis. Samples were collected from academic medical centers and commercial biobanks. All samples were de-identified.

Cell-free DNA was extracted from 250 μL plasma. Paired-end sequencing libraries were prepared and sequenced using an Illumina NovaSeq 6000 Sequencing System to a minimum of 400 million reads (median=636 million reads).

Reads aligning to annotated protein-coding genes were extracted, and read counts were normalized to account for variability in read depth, sequence-content bias, and technical batch effects.

TABLE 10

Clinical characteristics and demographics of patients with CRC and non-cancer controls

|  | CRC N = 797 | Control N = 456 | Total Samples N = 1253 |
|---|---|---|---|
| Control N (%) | | | |
| Female | 377 (47%) | 279 (61%) | 656 (52%) |
| Male | 411 (52%) | 122 (27%) | 533 (43%) |
| Unknown | 9 (1%) | 55 (12%) | 64 (5%) |
| Stage N (%) | | | |
| I | 239 (30%) | N/A | N/A |
| II | 417 (52%) | | |
| III | 114 (14%) | | |
| IV | 10 (1%) | | |
| Unknown | 17 (2%) | | |
| Age (yrs) | | | |
| Median (IQR) | 69 (61-77) | 59 (61-77) | 65 (57-74) |

Figure 34A:
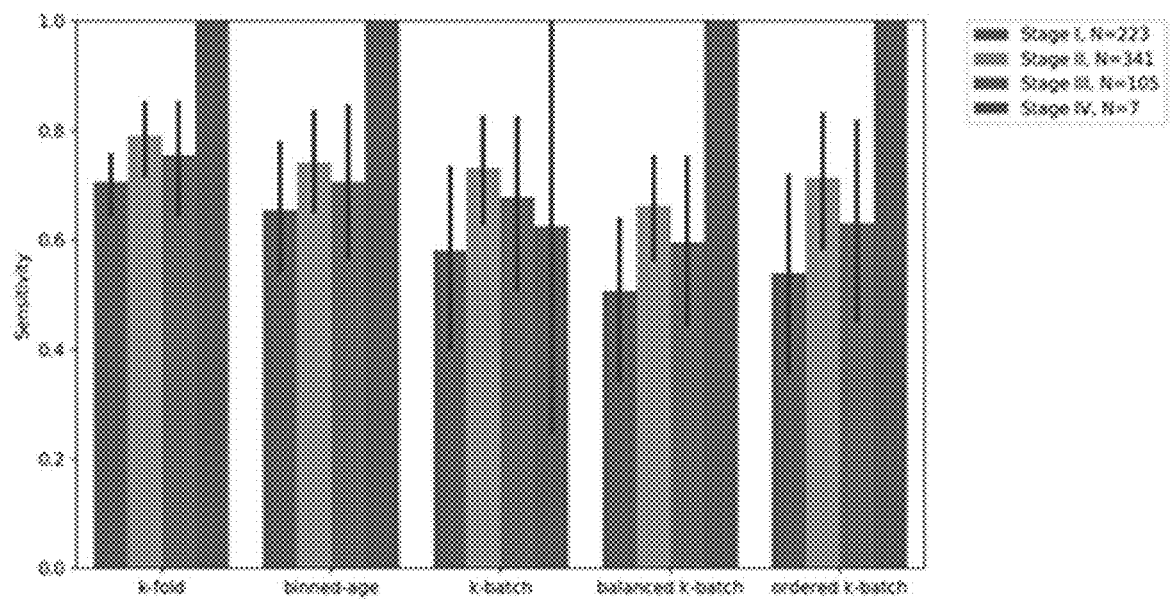
FIG. 34A shows sensitivity by CRC stage in patients aged 50-84.

Machine learning models were trained using different cross-validation techniques including standard k-fold, k-batch, and balanced k-batch (FIG. 34A). All methods were trained on kfold, and the best performing method was chosen to train models for the other cross-validation procedures.

Figures 33A, 33B:
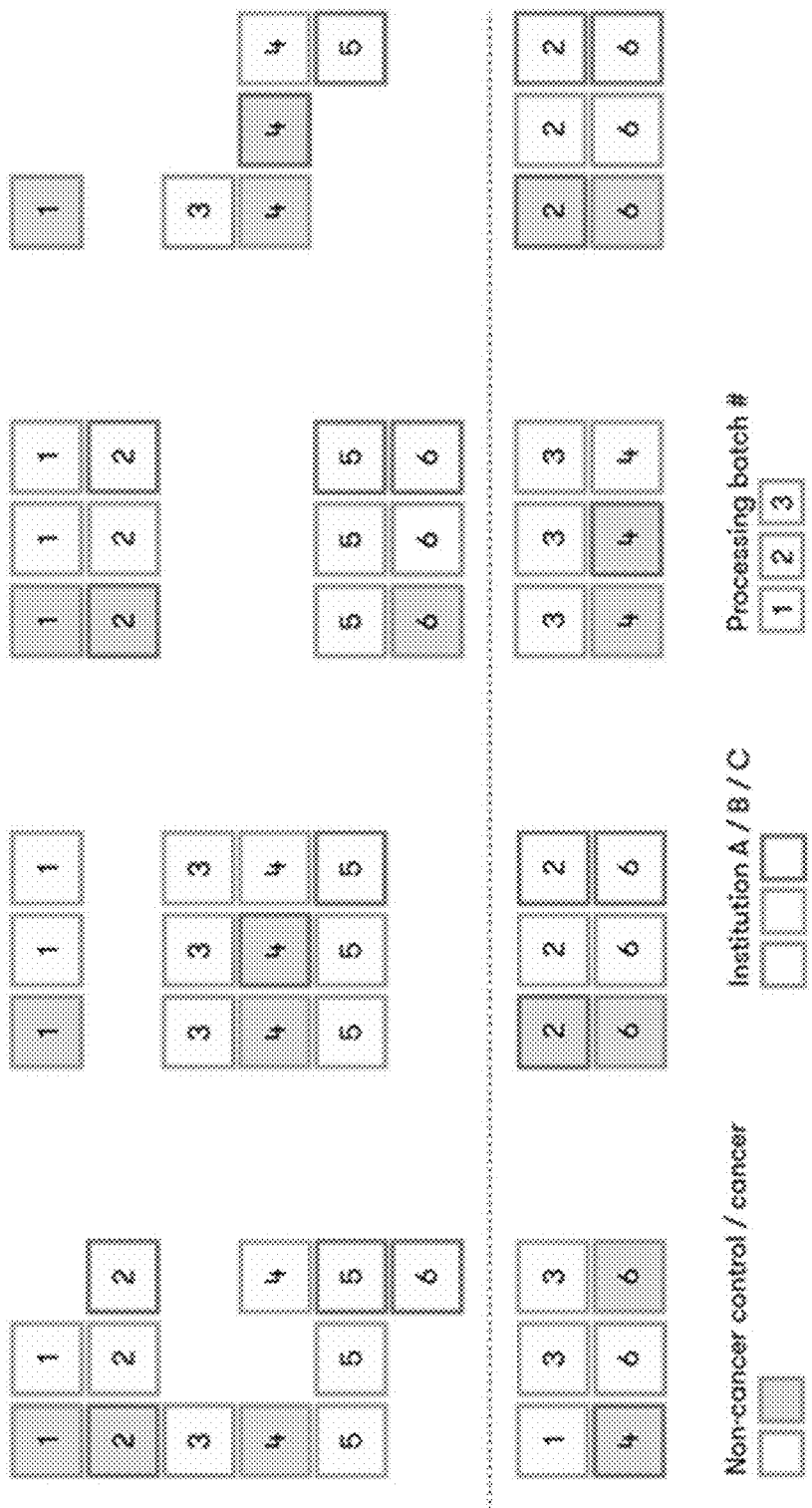
FIG. 33A shows k-fold model training methods and cross-validation procedures.
FIG. 33B shows training schemas fork-fold, k-batch, and balanced k-batch.

FIG. 34A illustrates training schemas fork-fold, k-batch, and balanced k-batch. Each square represents a single sample, with the fill color indicating class label (CRC or non-cancer control), the border color representing the institution of origin, and the number indicating processing batch. The held-out test set of samples (FIG. 33B) is separated from the training set by a dashed line.

Figure 34B:
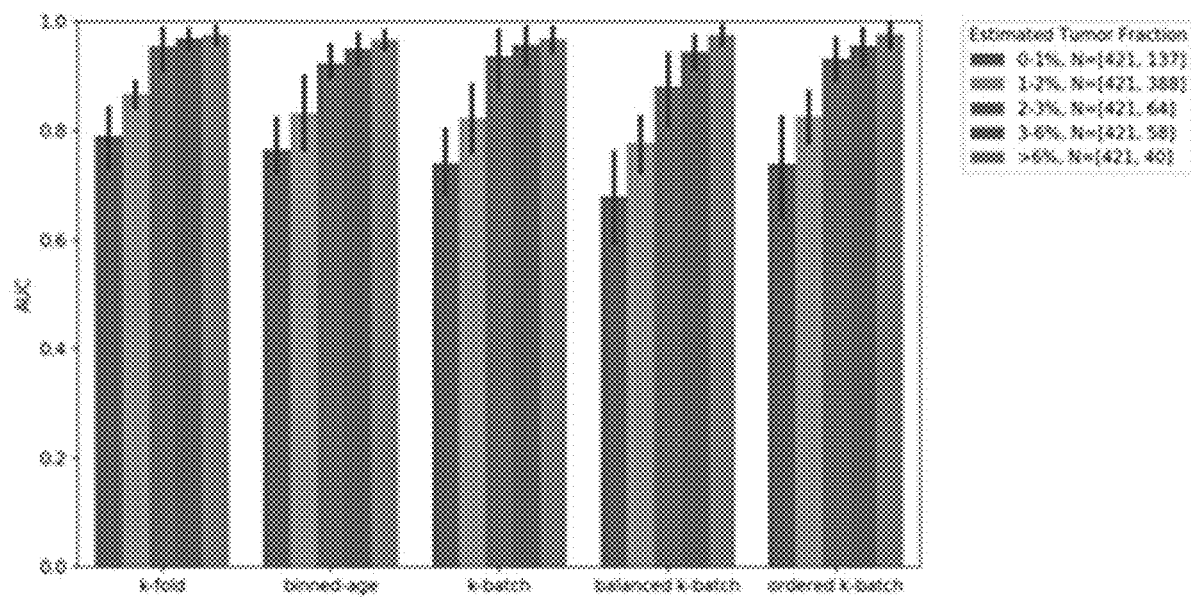
FIG. 34B shows sensitivity by tumor fraction in patients aged 50-84.

Classification performance for CRC within the intended-use age range (50-84) across all validation methods. FIGS. 34A and 34B show CRC sensitivity by CRC stage or tumor fraction, respectively In FIG. 34A, threshold for sensitivity was defined at 85% specificity in each test fold. N is number of samples for each stage. CI=95% bootstrap confidence interval. 82% of samples were from patients with early-stage CRC (stages I and II). All validation methods achieved approximately equivalent sensitivity across stages I through III based on confidence intervals. Stage IV cancer was always correctly classified.

In FIG. 34B, threshold for sensitivity was defined at 85% specificity in each test fold. N is number of CRC samples. Tumor fraction is the proportion of cfDNA derived from tumor tissue (e.g., ctDNA/cfDNA) and was estimated using IchorCNA. CI=95% bootstrap confidence interval.

Figure 34C:
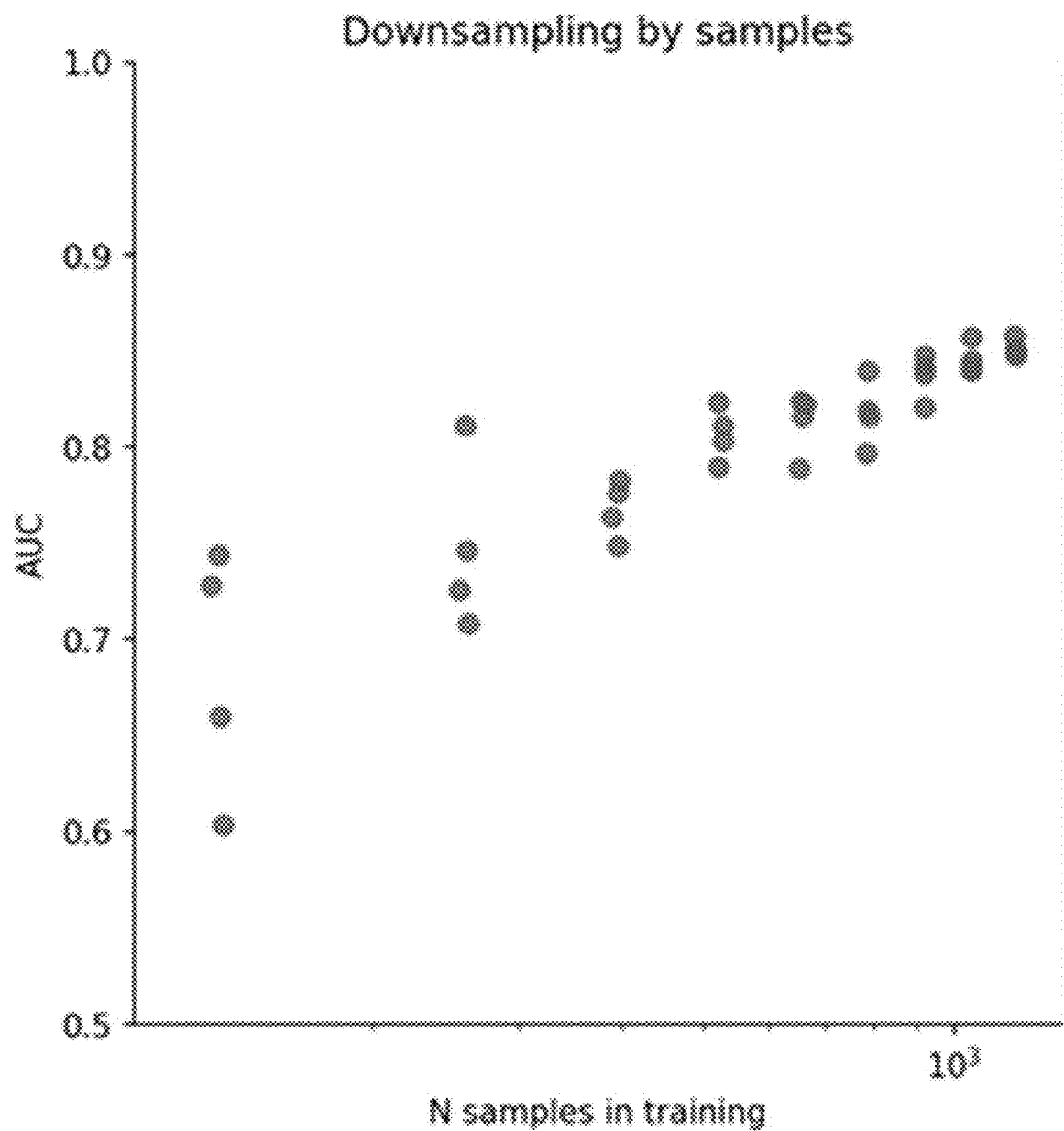
FIG. 34C shows the AUC performance of CRC classification between total number of samples.

FIG. 34C shows the AUC performance of CRC classification when the training set of each fold is downsampled. Classifier performance continued to improve with the addition of more training samples.

Table 11 shows classification performance in cross-validation (ROC curves) in patients aged 50-84. Batch-to-batch technical variability was evaluated using k-batch validation. Institution specific differences in population or sample handling were evaluated using balanced k-batch validation. Sensitivity increased with increasing tumor fraction across all validation methods. AUC for IchorCNA-estimated tumor fraction alone was 0.63, which was lower than results from the ML model under any cross-validation scheme.

TABLE 11

CRC performance by cross-validation procedure in patients aged 50-84

| Validation Method | Average Training Set Size (N) | Mean AUC (95% CI) | Mean Sensitivity at 85% Specificity (95% CI) |
| --- | --- | --- | --- |
| K-fold | 1128 | 0.89 (0.87-0.91) | 82% (78-85%) |
| K-batch | 1128 | 0.89 (0.87-0.91) | 80% (76-85%) |
| Balanced k-batch | 592 | 0.86 (0.83-0.89) | 75% (68-81%) |

AUC = area under the receiver operating characteristic curve;
CI = 95% bootstrap confidence interval;
SD = standard deviation.

A prototype blood-based CRC screening test using cfDNA and machine learning achieved high sensitivity and specificity in a predominantly early-stage CRC cohort (stages I and II). Classifier performance suggests contributions from both tumor and non-tumor (e.g., immune) derived signals. Assessing genome-wide cfDNA profiles at moderate depth of coverage enables the use of low-volume plasma samples. Cross-validation methods highlighted the importance of similar confounder analyses for retrospective (and prospective) studies.

E. Example 5: A Gene Expression Prediction Model that Uses cfDNA Fragment Coverage and Length to Predict which Genes are Highly or Lowly Expressed in cfDNA-Producing Cells This example describes methods for generating predictions of the expression or chromatin state of a gene, for example, by analyzing cfDNA profiles using one or more convolutional neural networks (CNNs). Such methods are useful in a multi-analyte platform for classification of individuals with and without colorectal cancer (CRC). The expression of a gene can be controlled by access of the cell's machinery to the transcription start site (TSS). Access to the TSS can be determined the state of the chromatin on which the TSS is located. Chromatin state can be controlled through chromatin remodeling, which can condense (close) or loosen (open) TSSs. A closed TSS results in decreased gene expression while an open TSS results in increased gene expression. Identifying changes in the chromatin state of genes can serve as a method to identify the presence of a disease in a subject De-identified plasma samples from patients with colorectal cancer (n=532) and non-cancer controls (n=234) were obtained from academic medical centers and commercial biobanks. The plasma samples were separated based on CRC stage information as follows: stage I (n=169), stage II (n=256), stage III (n=97), stage IV (n=6) and unknown stage information (n=4). A prediction model was trained to determine if a gene is "on" or "off" in cfDNA. The model was trained on average expression of stable genes from external datasets. Knowledge from pre-trained model was used to train a disease prediction model. A separate gene set was used to fix the previous model to plausibly change expression state between cancer and non-cancer.

Figure 35:
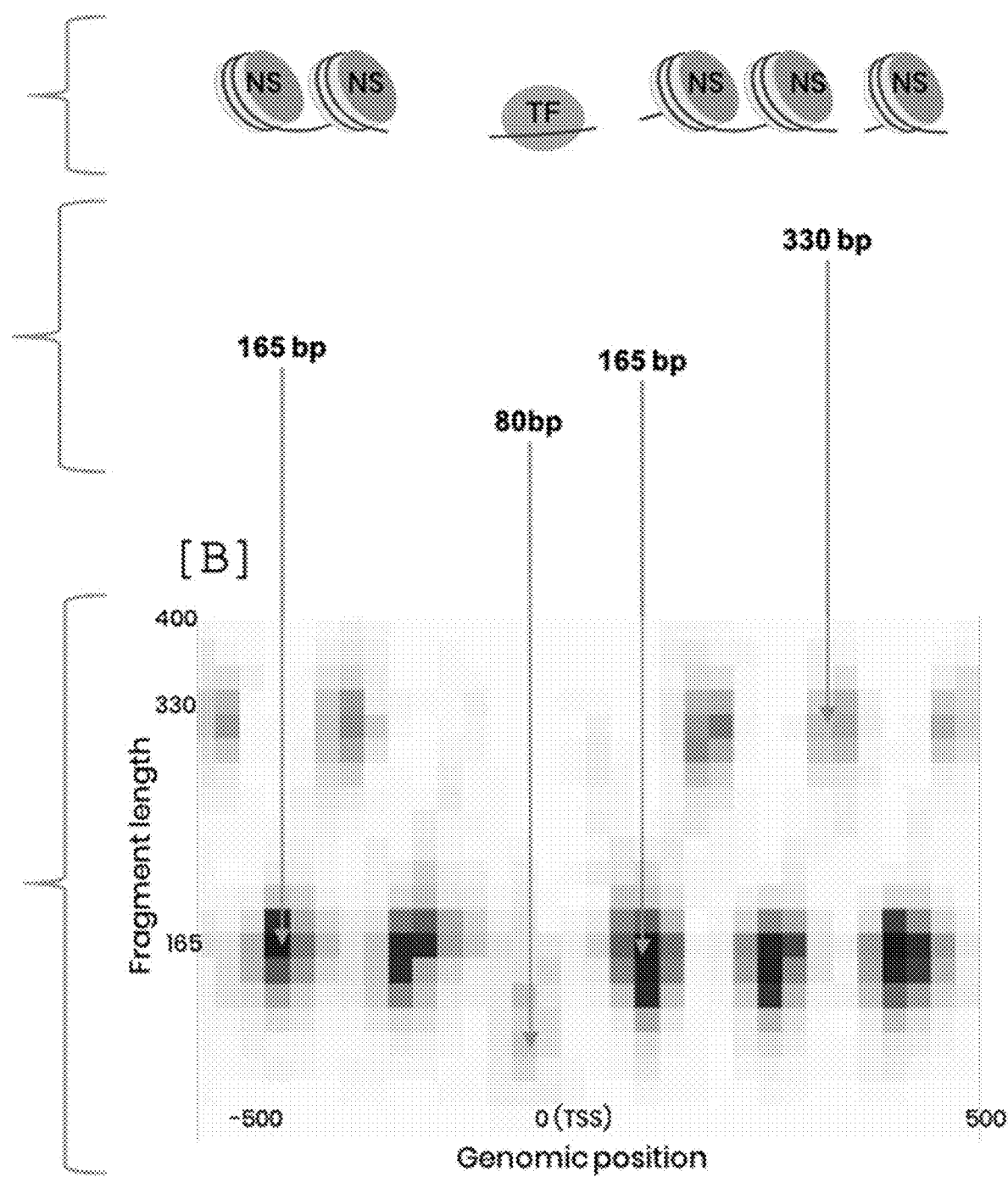
FIG. 35 shows a schematic of V-plots derived from cfDNA capture protein-DNA associations, showing chromatin architecture and transcriptional state. TF=Transcription Factor (small footprint region protected), NS=Nucleosome (large region protected, full wraps of DNA)
Figure 36A:
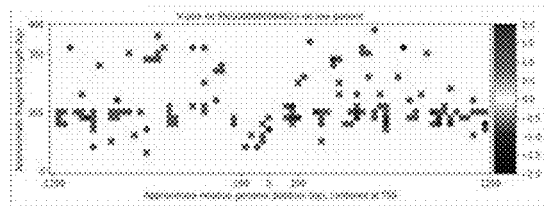
FIGS. 36A-36G show cfDNA derived V-plots around TSS regions used to predict gene expression.
Figure 36C:
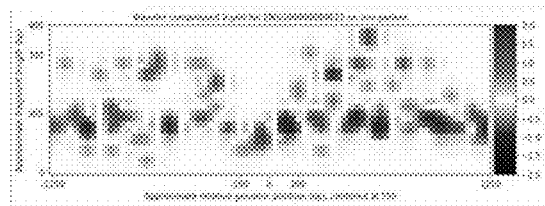
Figure 36B:
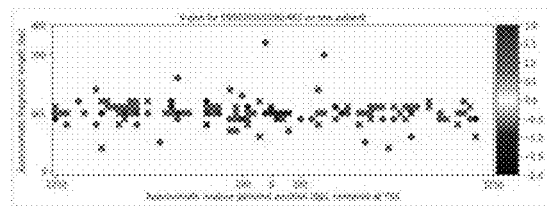
Figure 36D:
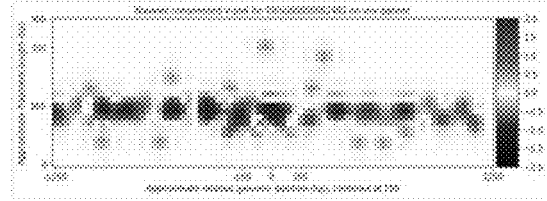
Figure 36E:
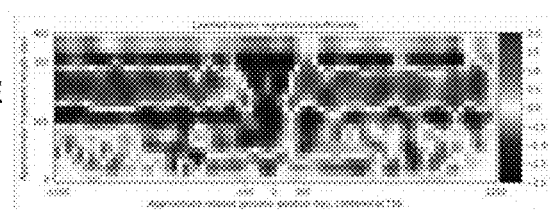
Figure 36F:
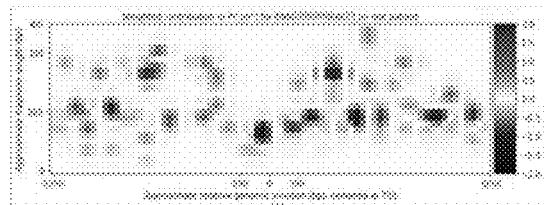
Figure 36G:
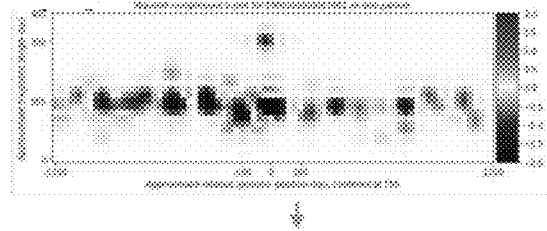

V-plots are derived from cfDNA capture protein-DNA associations, showing chromatin architecture and transcriptional state. Footprinting was performed to show cfDNA corresponds to regions of the genome protected by proteins. Raw sequencing data: Paired-end sequencing of cfDNA provides fragment lengths and recovers protected fragments of DNA. Average V-plot of an expressed ("on") gene: DNA-protein binding location and binding-site size can be inferred from fragment length and location (genomic position) of sequenced cfDNA fragments. Each pixel in the V-plot is colored by the number of fragments with a particular length (Y axis) have a midpoint at this position (X axis). Darker colors indicate a greater number of fragments. (FIG. 35)

Input V-Plot shows a rich but sparse representation of cfDNA fragment position and size in a TSS region for a gene. Wavelet compression and smoothing is applied to reduce complexity while preserving the key parts of the signal. Learned logistic regression coefficients: red regions generally provide evidence for a gene being "on" while blue regions generally provide evidence for a gene being "off". Applying these coefficients to the data, regions that contribute to higher P("on") are shown as red while regions that contribute to lower P("on") are blue. (FIGS. 36A-36G) In addition to categorizing on and off gene expression, the presence or absence of accessible chromatin was measured by ATAC-seq in two cell populations of blood, one much more abundant than the other. This method was still able to differentiate cfDNA regions with monocyte specific ATAC-seq peaks from pDC specific peaks. These peaks are not limited to any particular function and can include TSSs as well as other kinds of distal enhancers, for example.

TABLE 12

| Method AUC (+/− SD) | Blood constitutive TSS <0.1 FPKM vs >25 FPKM | Blood constitutive TSS <0.1 FPKM vs >1 FPKM | Monocytes (~6% of WBCs) vs pDCs (<1% of WBCs) specific ATAC peaks |
| --- | --- | --- | --- |
| 2D Wavelet | 0.98 ± 0.01 | 0.95 ± 0.02 | 0.75 ± 0.03 |
| V-plot CNN | 0.98 ± 0.01 | 0.95 ± 0.02 | 0.71 ± 0.04 |
| 2D Wavelet (downsampled) | 0.97 ± 0.01 | 0.93 ± 0.01 | 0.72 ± 0.02 |
| Normalized TSS coverage | 0.95 ± 0.02 | 0.91 ± 0.02 | 0.66 ± 0.05 |

Figure 37:
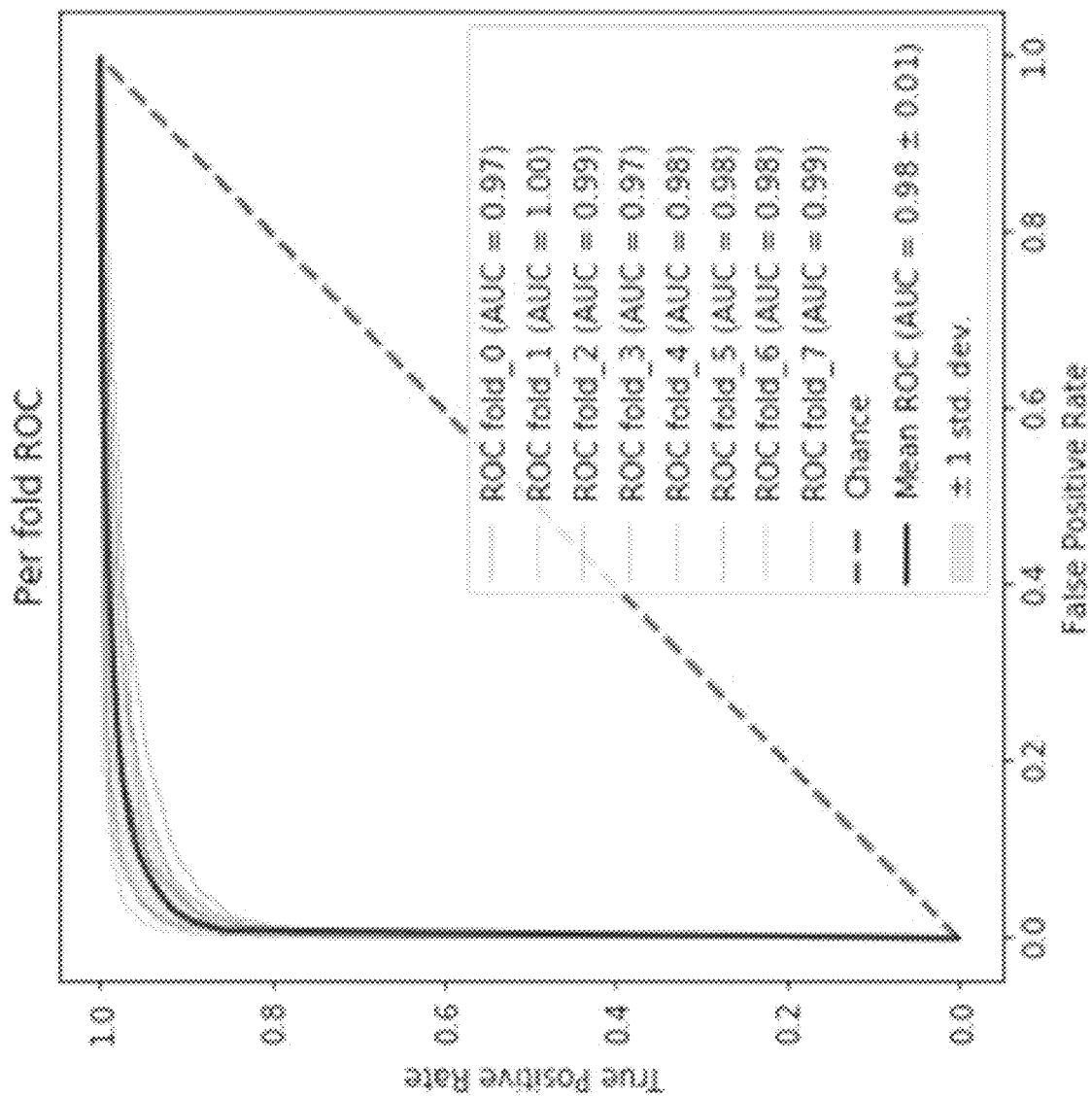
FIG. 37 shows classifiers using representations of fragment length and location accurately categorize on and off genes using different cutoffs
Figure 38B:
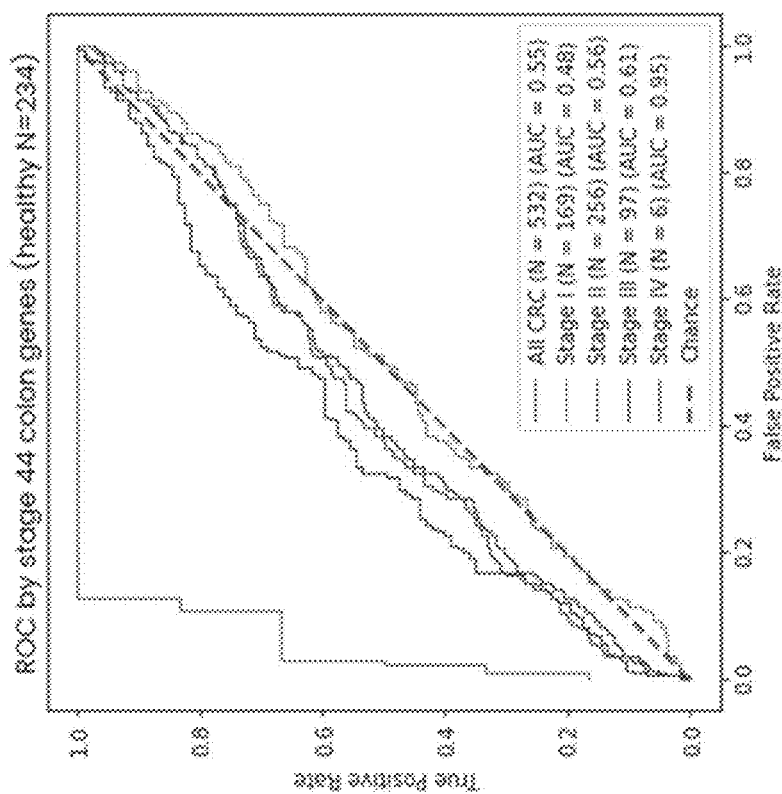
FIGS. 38A-38C show the classification accuracy using a tumor-targeted gene set by stage and estimated tumor fraction. IchorCNA-based tumor fraction estimates (ITF) increase with stage but most stage I-III CRC have low estimated ITF (<1%) (FIG. 38A). Performance increases by stage, most notably at stage IV (FIG. 38B). Performance increases most strongly with tumor fraction (FIG. 38C)
Figure 38A:
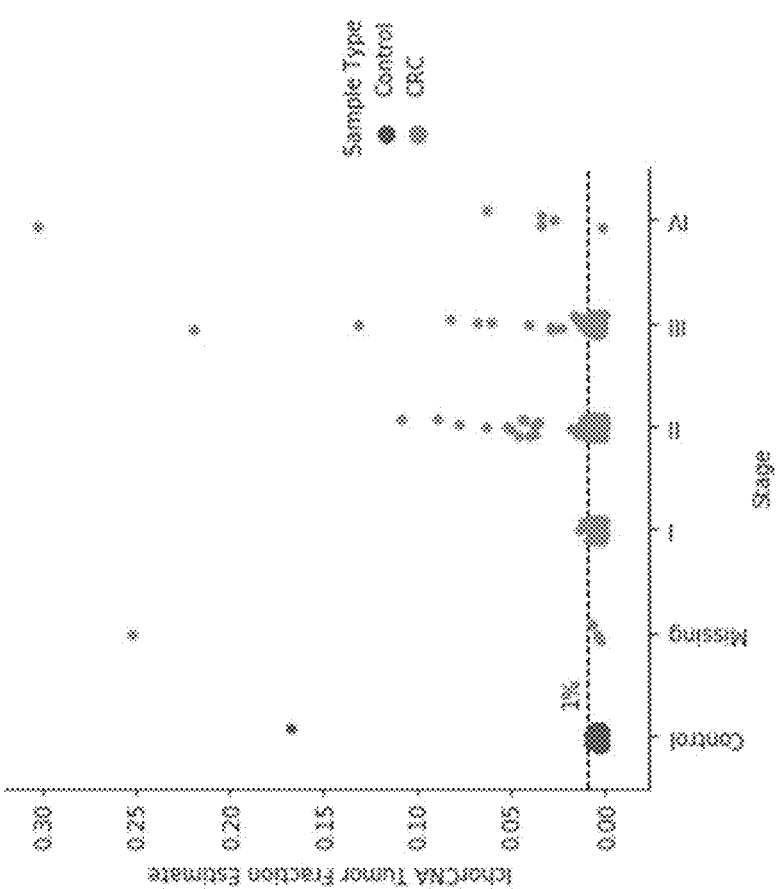
Figure 38C:
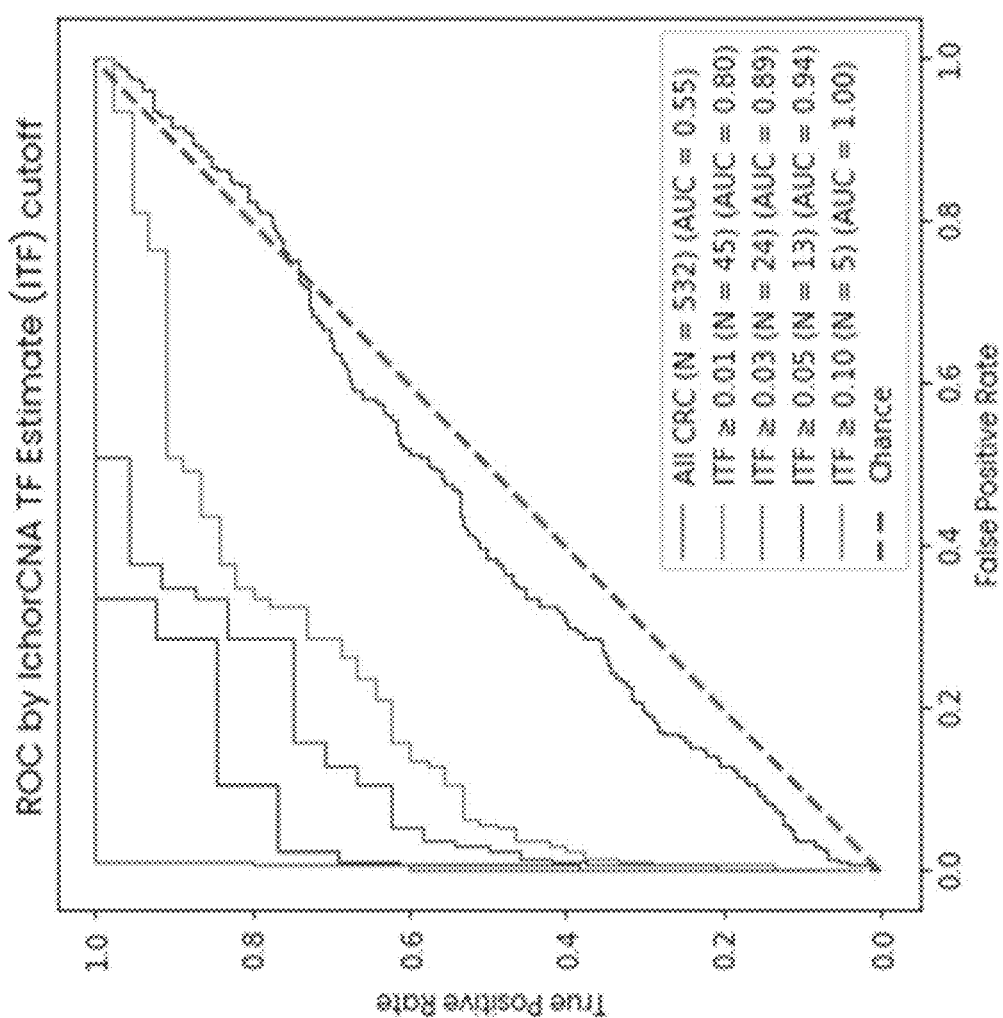

Normalized TSS coverage only uses normalized fragment counts in "on" vs "off" genes to predict expression. The "on" genes have lower coverage (are less protected by nucleosomes) than "off" genes (1). (FIG. 37) FPKM—a normalized RNA-seq measurement of relative expression Fragments Per Kilobase of transcript per Million mapped reads; pDC—Plasmacytoid Dendritic Cell; ROC—receiver operating characteristic; AUC—area under the receiver operating characteristic curve Classification accuracy was evaluated using a tumor-targeted gene set by stage and tumor fraction was estimated. For this approach we used 44 genes expressed in colon and not in blood cells as measured in roadmap were used. Colon genes were assumed to be expressed in colon cancer, as well as adjacent healthy colon tissue, which does not contribute substantial quantities of material to cfDNA in healthy individuals. (FIGS. 38A-38C)

Figure 39A:
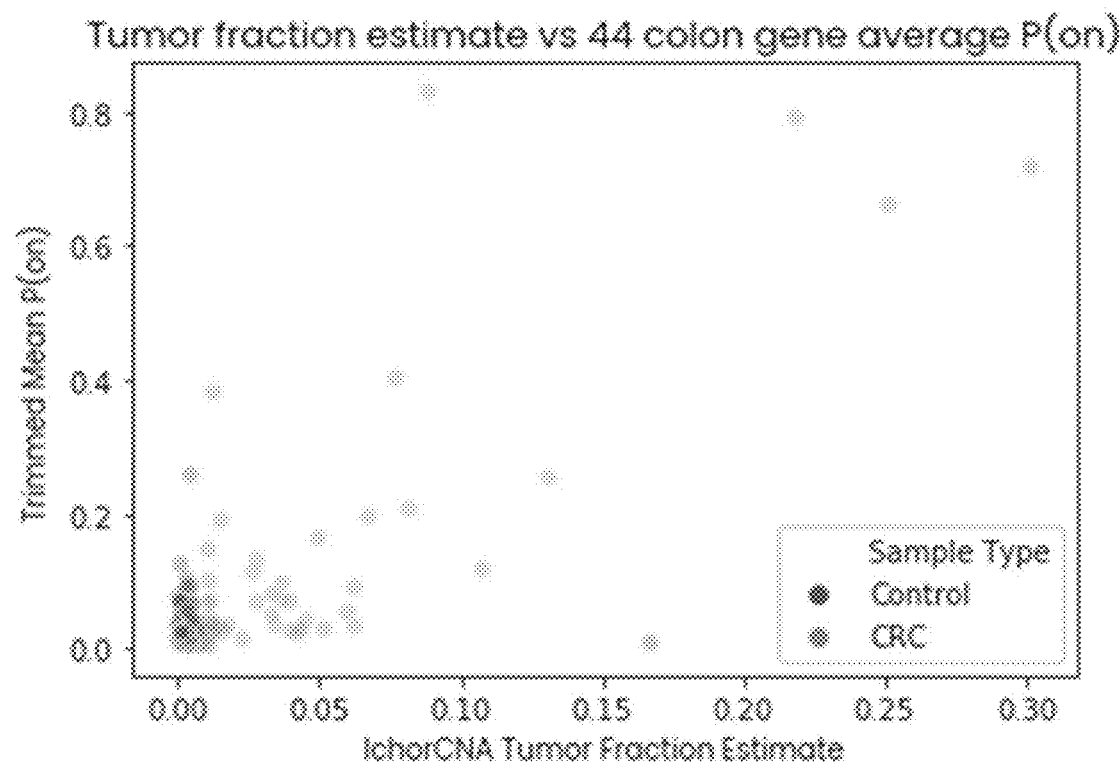
FIG. 39A shows tumor fraction estimate vs a 44-colon gene average P(on).
Figure 39B:
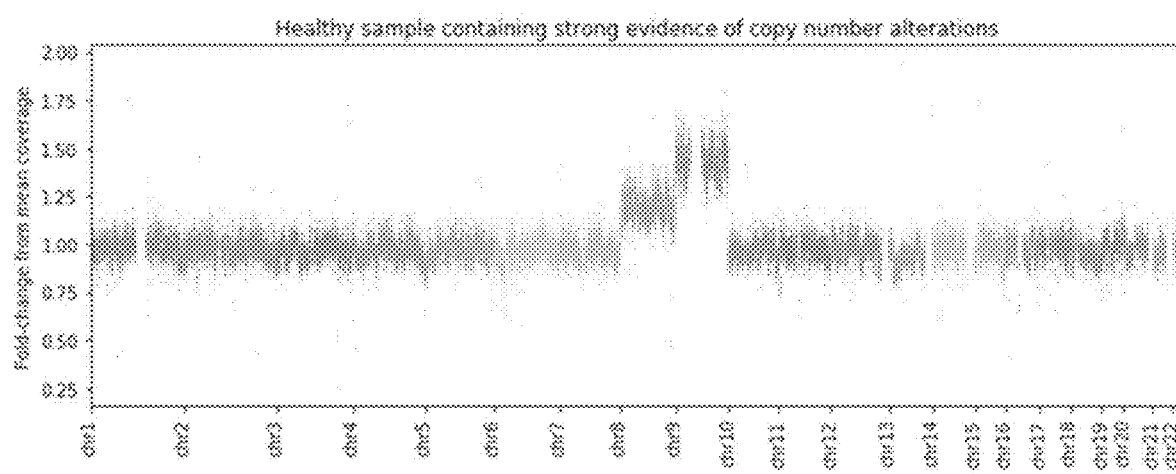
FIG. 39B fold-change from mean coverage is shown for a healthy sample containing strong evidence of copy number alternations in chr8 and chr9.

Average gene expression prediction was shown to augment CNV based tumor fraction estimation. A high tumor fraction non-cancer control displayed a low average probability of expression P (on) of the 44 colon genes, differentiating it from high tumor fraction CRC samples (FIG. 39A). These copy number changes may be either germline, or somatic and not originating from the tumor, but from other non-cancerous cells in the body (FIG. 39B). While preferred examples have been shown and described herein, it will be obvious to those having ordinary skill in the art that such examples are provided by way of example only. Numerous variations, changes, and substitutions will now occur to those having ordinary skill in the art without departing from the invention. It should be understood that various alternatives to the examples described herein can be employed in practicing the disclosure. It is intended that the following claims define the scope and that methods and structures within the scope of these claims and their equivalents be covered thereby.

XI. COMPUTER SYSTEM

Any of the computer systems or circuits mentioned herein may utilize any suitable number of subsystems. The subsystems can be connected via a system bus 75. As examples, subsystems can include input/output (I/O) devices, system memory, storage device(s), and network adapter(s) (e.g. Ethernet, Wi-Fi, etc.), which can be used to connect a computer system other devices (e.g., an engine control unit). System memory and/or storage device(s) may embody a computer readable medium.

A computer system can include a plurality of the same components or subsystems, e.g., connected together by external interface, by an internal interface, or via removable storage devices that can be connected and removed from one component to another component. In some embodiments, computer systems, subsystem, or apparatuses can communicate over a network.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method of screening an individual for a colorectal advanced adenoma, the method comprising:
   a) assaying a plurality of classes of molecules in a biological sample from the individual using a plurality of assays, wherein the assaying provides a plurality of sets of measured values representative of the plurality of classes of molecules, the biological sample being whole blood, plasma, or serum, wherein the plurality of classes of molecules includes a first class of nucleic acids endogenous to the individual and a second class of polyamino acids endogenous to the individual, wherein the first class of nucleic acids is cell-free DNA (cfDNA), wherein a first assay is applied to the cfDNA molecules to obtain a first set of measured values, and wherein a second assay is applied to the polyamino acids to obtain a second set of measured values, and wherein the first assay applied to the cfDNA molecules includes methylation sequencing;
   b) identifying a set of features corresponding to properties of each of the plurality of classes of molecules to be input to a machine learning model;
   c) preparing a feature vector of feature values from the plurality of sets of measured values representative of the plurality of classes of molecules, each feature value corresponding to a feature of the set of features and including one or more measured values, wherein the feature vector includes at least one feature value obtained using each set of the plurality of sets of measured values representative of the plurality of classes of molecules;
   d) loading, into a memory of a computer system, the machine learning model, the machine learning model trained using training vectors obtained from training biological samples, a first subset of the training biological samples identified as having the colorectal advanced adenoma and a second subset of the training biological samples identified as not having the colorectal advanced adenoma; and
   e) inputting the feature vector into the machine learning model to obtain an output classification of whether the individual has the colorectal advanced adenoma.

2. The method of claim 1, wherein the second class of polyamino acids is peptides, proteins, autoantibodies or fragments thereof.

3. The method of claim 1, wherein the plurality of classes of molecules include the second class being autoantibodies and a third class of circulating proteins.

4. The method of claim 1, wherein the plurality of assays include at least two of: whole-genome sequencing (WGS), whole-genome bisulfite sequencing (WGSB), enzymatic methyl sequencing, quantitative immunoassay, enzyme-linked immunosorbent assay-(ELISA), protein microarray, mass spectrometry, low-coverage Whole-Genome Sequencing (1cWGS), selective tagging 5mC sequencing, CNV calling, tumor fraction (TF) estimation, LINE-1 CpG methylation, 56 genes CpG methylation, cf-Protein Immuno-Quant ELISAs, single molecule array (SIMOA), and cf-miRNA sequencing, and cell type or cell phenotype mixture proportions derived from any of the above assays.

5. The method of claim 4, wherein the plurality of assays include whole-genome bisulfite or enzymatic methyl sequencing that include the methylation sequencing.

6. The method of claim 1, wherein the machine learning model is trained and constructed according to one or more of: linear discriminant analysis (LDA), partial least squares (PLS), random forest, k-nearest neighbor (KNN), support vector machine (SVM) with radial basis function kernel (SVMRadial), SVM with linear basis function kernel (SVM-Linear), SVM with polynomial basis function kernel (SVM-Poly), decision trees, multilayer perceptron, mixture of experts, sparse factor analysis, hierarchical decomposition, and combinations of linear algebra routines and statistics.

7. The method of claim 1, wherein the biological sample is a plasma sample, and wherein the measured values include methylation patterns of the cell-free DNA found in the plasma sample.

* * * * *